US012453770B2

(12) United States Patent
Tavernier et al.

(10) Patent No.: US 12,453,770 B2
(45) **Date of Patent: *Oct. 28, 2025**

(54) CLEC9A BINDING AGENTS

(71) Applicants: Orionis Biosciences BV, Ghent (BE); VIB VZW, Ghent (BE); Universiteit Gent, Ghent (BE)

(72) Inventors: Jan Tavernier, Balegem (BE); Nikolai Kley, Newton, MA (US); Anje Cauwels, Merelbeke (BE); Sarah Gerlo, Ghent (BE)

(73) Assignees: Orionis Biosciences BV, Ghent (BE); VIB VZW, Ghent (BE); Universiteit Gent, Ghent (BE)

( * ) Notice: Subject to any disclaimer, the term of this patent is extended or adjusted under 35 U.S.C. 154(b) by 1206 days.

This patent is subject to a terminal disclaimer.

(21) Appl. No.: 17/222,043

(22) Filed: Apr. 5, 2021

(65) Prior Publication Data

US 2022/0356253 A1 Nov. 10, 2022

Related U.S. Application Data

(63) Continuation of application No. 16/075,318, filed as application No. PCT/EP2017/052544 on Feb. 6, 2017, now Pat. No. 11,001,631.

(60) Provisional application No. 62/411,805, filed on Oct. 24, 2016, provisional application No. 62/353,607, filed on Jun. 23, 2016, provisional application No. 62/335,965, filed on May 13, 2016, provisional application No. 62/335,979, filed on May 13, 2016, provisional application No. 62/335,968, filed on May 13, 2016, provisional application No. 62/335,880, filed on May 13, 2016, provisional application No. 62/336,030, filed on May 13, 2016, provisional application No. 62/291,769, filed on Feb. 5, 2016, provisional application No. 62/291,772, filed on Feb. 5, 2016, provisional application No. 62/291,779, filed on Feb. 5, 2016, provisional application No. 62/291,776, filed on Feb. 5, 2016, provisional application No. 62/291,774, filed on Feb. 5, 2016.

(51) Int. Cl.

| | |
|---|---|
| ***A61K 39/395*** | (2006.01) |
| ***A61K 38/00*** | (2006.01) |
| ***A61P 35/00*** | (2006.01) |
| ***C07K 16/00*** | (2006.01) |
| ***C07K 16/28*** | (2006.01) |
| *A61K 39/00* | (2006.01) |
| *C07K 14/56* | (2006.01) |
| *C07K 14/715* | (2006.01) |
| *C07K 16/24* | (2006.01) |

(52) U.S. Cl.

CPC ............ *A61K 39/395* (2013.01); *A61K 38/00* (2013.01); *A61P 35/00* (2018.01); *C07K 16/00* (2013.01); *C07K 16/2851* (2013.01); *A61K 2039/505* (2013.01); *A61K 2039/57* (2013.01); *C07K 14/56* (2013.01); *C07K 14/7156* (2013.01); *C07K 16/249* (2013.01); *C07K 16/2815* (2013.01); *C07K 16/2818* (2013.01); *C07K 16/2827* (2013.01); *C07K 16/2887* (2013.01); *C07K 2317/22* (2013.01); *C07K 2317/24* (2013.01); *C07K 2317/31* (2013.01); *C07K 2317/33* (2013.01); *C07K 2317/569* (2013.01); *C07K 2317/622* (2013.01); *C07K 2317/66* (2013.01); *C07K 2317/74* (2013.01); *C07K 2317/90* (2013.01); *C07K 2317/92* (2013.01); *C07K 2319/00* (2013.01); *C07K 2319/02* (2013.01); *C07K 2319/33* (2013.01); *C07K 2319/735* (2013.01); *C07K 2319/74* (2013.01); *Y02A 50/30* (2018.01)

(58) Field of Classification Search

None

See application file for complete search history.

(56) References Cited

U.S. PATENT DOCUMENTS

| | | | | |
|---|---|---|---|---|
| 5,595,756 | A * | 1/1997 | Bally | A61K 9/1272 264/4.1 |
| 5,914,254 | A | 6/1999 | Mascarenhas et al. | |
| 8,580,266 | B2 * | 11/2013 | Sancho-Madrid | A61K 39/0011 424/178.1 |
| 8,980,267 | B2 | 3/2015 | Grewal et al. | |
| 9,139,634 | B2 | 9/2015 | Morrison et al. | |
| 9,534,056 | B2 | 1/2017 | Grewal et al. | |
| 11,001,631 | B2 * | 5/2021 | Tavernier | A61K 39/395 |

(Continued)

FOREIGN PATENT DOCUMENTS

| | | | |
|---|---|---|---|
| RU | 2011127226 | A | 1/2013 |
| WO | 9102754 | A1 | 3/1991 |

(Continued)

OTHER PUBLICATIONS

Sporn et al, "Chemoprevention of Cancer," Carcinogenesis, vol. 21 (2000), 525-530 (Year: 2000).*

(Continued)

*Primary Examiner* — Brian Gangle
*Assistant Examiner* — Andrea K McCollum
(74) *Attorney, Agent, or Firm* — Morgan, Lewis & Bockius LLP

(57) ABSTRACT

The present invention relates, in part, to agents that bind C-type lectin domain containing 9A (Clec9A) and their use as diagnostic and therapeutic agents. The present invention further relates to pharmaceutical compositions comprising the Clec9A binding agents and their use in the treatment of various diseases.

11 Claims, 27 Drawing Sheets

Specification includes a Sequence Listing.

(56) References Cited

U.S. PATENT DOCUMENTS

| | | | | |
|---|---|---|---|---|
| 2010/0172868 | A1 | 7/2010 | Morrison et al. | |
| 2010/0297076 | A1 | 11/2010 | Morrison et al. | |
| 2011/0020273 | A1 | 1/2011 | Chang et al. | |
| 2011/0081341 | A1 | 4/2011 | Honjo et al. | |
| 2011/0104112 | A1 | 5/2011 | Morrison et al. | |
| 2011/0224407 | A1 | 9/2011 | Langer et al. | |
| 2011/0274658 | A1 | 11/2011 | Silver et al. | |
| 2013/0183298 | A1 | 7/2013 | Le et al. | |
| 2013/0230517 | A1 | 9/2013 | Grewal et al. | |
| 2014/0271462 | A1 | 9/2014 | Ho et al. | |
| 2014/0348789 | A1 | 11/2014 | Tavernier et al. | |
| 2015/0139951 | A1 | 5/2015 | Grewal et al. | |
| 2015/0265721 | A1 * | 9/2015 | Lahoud .................. | C07K 14/47 435/375 |
| 2015/0313965 | A1 | 11/2015 | Pogue et al. | |

FOREIGN PATENT DOCUMENTS

| | | | | |
|---|---|---|---|---|
| WO | 2003033720 | A2 | 4/2003 | |
| WO | 2006053883 | A1 | 5/2006 | |
| WO | 2006115800 | A2 | 11/2006 | |
| WO | 2008014612 | A1 | 2/2008 | |
| WO | 2008124086 | A2 | 10/2008 | |
| WO | 2009003145 | A1 | 12/2008 | |
| WO | WO 2009013484 | A1 | 1/2009 | |
| WO | 2009039409 | A1 | 3/2009 | |
| WO | 2010036918 | A2 | 4/2010 | |
| WO | 2010066740 | A1 | 6/2010 | |
| WO | 2011020783 | A2 | 2/2011 | |
| WO | 2011029870 | A1 | 3/2011 | |
| WO | 2012170072 | A1 | 12/2012 | |
| WO | WO-2013053008 | A2 * | 4/2013 | ............. A61P 37/00 |
| WO | 2013059885 | A2 | 5/2013 | |
| WO | 2013107791 | A1 | 7/2013 | |
| WO | 2013134138 | A1 | 9/2013 | |
| WO | WO 2013/163689 | A1 | 11/2013 | |
| WO | 2015007520 | A1 | 1/2015 | |
| WO | 2015007536 | A1 | 1/2015 | |
| WO | 2015007542 | A1 | 1/2015 | |
| WO | 2015007903 | A1 | 1/2015 | |
| WO | WO 2015018528 | A1 | 2/2015 | |
| WO | 2017077382 | A1 | 5/2017 | |

OTHER PUBLICATIONS

Auerbach et al (Cancer and Metastasis Reviews, 2000, 19: 167-172) (Year: 2000).*
Gura T (Science, 1997, 278(5340): 1041-1042 (Year: 1997).*
Hogenesch et al (J Control Release. Dec. 10, 2012; 164(2): 183-186.) (Year: 2012).*
Hait (Nature Reviews/Drug Discovery, 2010, 9, pp. 253-254) (Year: 2010).*
Gravanis et al. (Chin Clin Oncol, 2014, 3, pp. 1-5) (Year: 2014).*
Beans (PNAS 2018; 115(50): 12539-12543) (Year: 2018).*
Idoyaga et al., "Comparable T helper 1 (Thl) and CD8 T-cell immunity by targeting HIV gag p24 to CD8 dendritic cells within antibodies to Langerin, DEC205, and Clec9A," PNAS, vol. 108, No. 6, Jan. 24, 2011, pp. 2384-2389.
International Search Report in PCT/EP2017/052544 mailed Jun. 6, 2017, 16 pages.
Kircheis, et al., "Biological activity of mutants of human tumour necrosis factor-alpha," Immunology, Jul. 1, 1992, pp. 433-438.
Lahoud et al., "Targeting Antigen to Mouse Dendritic Cells via Clec9A Induces Potent CD4 T Cell Responses Biased toward a Follicular Helper Phenotype," The Journal of Immunology, vol. 187, No. 2, Jul. 15, 2011, pp. 842-850.
Minn, "Interferons and the Immunogenic Effects of Cancer Therapy," Trends In Immunology, vol. 36, No. 11, Nov. 1, 2015, pp. 725-737.
Picco et al., "Targeting DNGR-1 (CLEC9A) with antibody/MUC1 peptide conjugates as a vaccine for carcinomas", European Journal of Immunology, vol. 44, No. 7, Apr. 17, 2014, pp. 1947-1955.
Puskas, et al., "Development of an attenuated interleukin-2 fusion protein than can be activated by tumour-expressed proteases," Immunology, vol. 133, No. 2, Jun. 23, 2011, pp. 206-220.
Sancho et al., "Identification of a dendritic cell receptor that couples sensing of necrosis to immunity", Nature, Nature Publishing Group, United Kingdom, vol. 458, No. 7240, Apr. 16, 2009, pp. 899-903.
Zitvogel et al., "Type I interferons in anticancer immunity," The Journal of Immunology, vol. 15, No. 7, Jun. 1, 2015, pp. 405-414.
Acres, B., et al., "Fusokine Interleukin-2/Interleukin-18, a Novel Potent Innate and Adaptive Immune Stimulator with Decreased Toxicity", Cancer Res., vol. 65, No. 20, (2005), pp. 9536-9546.
Baba, M., et al., "Identification of CCR6, the Specific Receptor for a Novel Lymphocyte-Directed CC Chemokine LARC", The Journal of Biological Chemistry vol. 272, No. 23, (1997), pp. 14893-14898.
Bork "Powers and Pitfalls in Sequence Analysis: The 70% Hurdle", Genome Research, vol. 10 (2000), pp. 398-400.
Bork et al., "Go hunting in sequence databases but watch out for the traps." Trends in Genetics vol. 12 (1996), pp. 425-427.
Boschert et al., Single chain TNF derivatives with individually mutated receptor binding sites reveal differential stoichiometry of ligand receptor complex formation for TNFR1 and TNER2. Cellular Signalling 22 (7):1088-1096, 2010.
Bremer et al., Superior activity of fusion protein scFvRit:sFasL over cotreatment with rituximab and Fas agonists. Cancer Res. 68:597-604, 2008.
Camacho, N.P., et al., "Structure of an Interleukin-1β Mutant With Reduced Bioactivity Shows Multiple Subtle Changes in Conformation That Affect Protein-Protein Recognition", Biochemistry, vol. 32, No. 34, (1993), pp. 8749-8757.
Coulstock, E., et al., "Liver-Targeting of Interferon-Alpha with Tissue Specific Domain Antibodies." PLOS One, vol. 8, No. 2, (2013), pp. 1-11.
De Bruyn, M., et al., "Antibody-Based Fusion Proteins to Target Death Receptors in Cancer", Cancer Letters, vol. 332, (2013), pp. 175-183.
Deffar et al., "Nanobodies—The New Concept in Antibody Engineering" African Journal of Biotechnology, 2009, vol. 8 No. 12, pp. 2645-2652.
Dijkmans, R., et al., "Murine Interferon-γ/Interleukin-1 Fusion Proteins Used as Antigens for the Generation of Hybridomas Producing Monoclonal Anti-Interleukin-1 Antibodies", Cytokine, vol. 3, No. 2, (1991), pp. 134-140.
Dimitrov, D. S., "Engineered CH2 Domains (Nanoantibodies)", mAbs, Landes Bioscience, vol. 1, No. 1, (2009), pp. 26-28.
Frey, K., et al., "Antibody-Based Targeting of Interferon-Alpha to the Tumor Neovasculature: A Critical Evaluation", Integrative Biology, vol. 3, (2011), p. 468-478.
Garlanda et al., "The Interleukin-1 Family: Back to the Future", Immunity, Dec. 12, 2013, 39(6) 1003-1018.
Holler, N., et al: "Two Adjacent Trimeric Fas Ligands are Required for Fas Signaling and Formation of a Death-Inducing Signaling Complex", Molecular and Cellular Biology, vol. 23, No. 4, (2003), pp. 1428-1440.
Huang, T., et al., "A Trimeric Anti-HER2/neu ScFv and Tumor Necrosis Factor-[alpha] Fusion Protein Induces HER2/Neu Signaling and Facilitates Repair of Injured Epithelia", The Journal of Pharmacology and Experimental Therapeutics, vol. 316, No. 3, (2006), pp. 983-991.
Krippner-Heidenreich, A., et al: "Single-Chain TNF, a TNF Derivative with Enhanced Stability and Antitumoral Activity", The Journal of Immunology, vol. 180, (2008), pp. 8176-8183.
Masci, P. et al., "New and Modified Interferon alfas: Preclinical and Clinical Data", Current Oncology Reports, vol. 5, (2003), pp. 108-113.
Ngo et al., "Computational Complexity, Protein Structure Prediction, and the Levinthal Paradox. The Protein Folding Problem and Tertiary Structure Prediction", Edited by: Mertz et al., (Birkhauser, Boston), (1994), pp. 492-495.
Pan, M., et al., "Mutation of the IFNAR-1 Receptor Binding Site of Human IFN-[alpha]2 Generates Type I IFN Competitive Antagonists", Biochemistry, vol. 47, (2008), pp. 12018-12027.

(56) References Cited

OTHER PUBLICATIONS

Patris, et al., “Nanoimmunoassay onto a screen printed electrode for HER2 breast cancer biomarker determination”, Talanta, 2014, vol. 130 pp. 164-170.
Penafuerte, C., et al., “The Human Ortholog of Granulocyte Macrophage Colony-Stimulating Factor and Interleukin-2 Fusion Protein Induces Potent Ex Vivo Natural Killer Cell Activation and Maturation”, Cancer Res, vol. 69, No. 23, (2009), pp. 9020-9028.
Rafei, M., et al., “A MCP1 Fusokine with CCR2-Specific Tumoricidal Activity”, Molecular Cancer, vol. 10, No. 121, (2011), pp. 1-11.
Rafei, M., et al., “An Engineered GM-CSF-CCL2 Fusokine Is A Potent Inhibitor of CCR2-Driven Inflammation as Demonstrated in a Murine Model of Inflammatory Arthritis”, The Journal of Immunology, vol. 183, (2009), pp. 1759-1766.
Roisman, LC., et al., “Structure of the Interferon-Receptor Complex Determined by Distant Constraints from Double Mutant Cycles and Flexible Docking”, PNAS, vol. 98, No. 23, (2001), pp. 13231-13236.
Rovero S et al., “Insertion of the DNA for the 163-171 Peptide of IL 1β Enables a DNA Vaccine Encoding p185neu to Inhibit Mammary Carcinogenesis in Her-2/neu Transgenic BALB/c Mice”, Gene Therapy, vol. 8, (2001), pp. 447-452.
Schutyser, E., et al., “The CC Chemokine CCL20 and its Receptor CCR6”, Cytokine & Growth Factor Reviews, vol. 14, (2003), pp. 409-426.
Vaneycken, et al., “Preclinical Screening of Anti-HER2 Nanobodies for Molecular Imaging of Breast Cancer”, The FASEB Journal, 2011, vol. 25, pp. 2433-2446.
Weber, H., et al., “Single Amino Acid Changes that Render Human IFN-[alpha]2 Biologically Active on Mouse Cells”, The EMBO Journal, vol. 6, No. 3, (1987), pp. 591-598.
Wells, “Additivity of mutational effects in proteins.” Biochemistry, vol. 29, No. 37, (1990), pp. 8509-8517.
Wesolowski et al., “Single Domain Antibodies: Promising Experimental and Therapeutic Tools in Infection and Immunity”, Med Microbiol Immunol. 2009, vol. 198 pp. 157-174.
Barbara, J A et al., “Dissociation of TNF-alpha cytotoxic and proinflammatory activities by p55 receptor- and p75 receptor-selective TNF-alpha mutants,” EMBO Journal, vol. 13, No. 4, (1994) pp. 843-850.
Garcin, Genevieve et al., “High Efficiency cell-specific targeting of cytokine activity,” Nature Communications, vol. 5, No. 8 (2014).
Loetscher, H et al., “Human Tumor Necrosis Factor alpha (TNFalpha) Mutants with Exclusive Specificity for the 55-kDa or 75-kDa TNF Receptors,” Journal of Biological Chemistry, American Society For Biochemistry and Molecular Biology, US, vol. 268, No. 35 (1993) pp. 26350-26357.
Caminschi et al., “Antibody responses initiated by Clec9A-bearing dendritic cells in normal and Batf3-/- mice,” Molecular Immunology 50, 2012.
Li et al., “Antibodies targeting Clec9A promote strong humoral immunity without adjuvant in mice and non-human primates,” Eur. J. Immunol. 45, 2015.

* cited by examiner

FIGURE 3 (CONTINUED)

```
                                        360         *        380         *        400         *
SEQ ID NO:297   R1CHCL23 : GTCACCGTCTCCAGCGGCCGCTACCCGTACGACGTTCCGGACTACGGTTCCGGCCGAGCATAG : 399
SEQ ID NO:298   R2CHCL18 : GTCACCGTCTCCAGCGGCCGCTACCCGTACGACGTTCCGGACTACGGTTCCGGCCGAGCATAG : 399
SEQ ID NO:299   R2CHCL22 : GTCACCGTCTCCAGCGGCCGCTACCCGTACGACGTTCCGGACTACGGTTCCGGCCGAGCATAG : 399
SEQ ID NO:300   R2CHCL49 : GTCACCGTCTCCAGCGGCCGCTACCCGTACGACGTTCCGGACTACGGTTCCGGCCGAGCATAG : 399
SEQ ID NO:301   R2CHCL53 : GTCACCGTCTCCAGCGGCCGCTACCCGTACGACGTTCCGGACTACGGTTCCGGCCGAGCATAG : 399
SEQ ID NO:302   R2CHCL25 : GTCACCGTCTCCAGCGGCCGCTACCCGTACGACGTTCCGGACTACGGTTCCGGCCGAGCATAG : 399
SEQ ID NO:303   R1CHCL27 : GTCACCGTCTCCAGCGGCCGCTACCCGTACGACGTTCCGGACTACGGTTCCGGCCGAGCATAG : 393
SEQ ID NO:304   R1CHCL82 : GTCACCGTCTCCAGCGGCCGCTACCCGTACGACGTTCCGGACTACGGTTCCGGCCGAGCATAG : 399
SEQ ID NO:305   R2CHCL10 : GTCACCGTCTCCAGCGGCCGCTACCCGTACGACGTTCCGGACTACGGTTCCGGCCGAGCATAG : 399
SEQ ID NO:306   R1CHCL34 : GTCACCGTCTCCAGCGGCCGCTACCCGTACGACGTTCCGGACTACGGTTCCGGCCGAGCATAG : 399
SEQ ID NO:307   R2CHCL3  : GTCACCGTCTCCAGCGGCCGCTACCCGTACGACGTTCCGGACTACGGTTCCGGCCGAGCATAG : 396
SEQ ID NO:308   R1CHCL50 : GTCACCGTCTCCAGCGGCCGCTACCCGTACGACGTTCCGGACTACGGTTCCGGCCGAGCATAG : 393
SEQ ID NO:309   R2CHCL8  : GTCACCGTCTCCAGCGGCCGCTACCCGTACGACGTTCCGGACTACGGTTCCGGCCGAGCATAG : 393
SEQ ID NO:310   R1CHCL21 : GTCACCGTCTCCAGCGGCCGCTACCCGTACGACGTTCCGGACTACGGTTCCGGCCGAGCATAG : 393
SEQ ID NO:311   R2CHCL87 : GTCACCGTCTCCAGCGGCCGCTACCCGTACGACGTTCCGGACTACGGTTCCGGCCGAGCATAG : 393
SEQ ID NO:312   R2CHCL24 : GTCACCGTCTCCAGCGGCCGCTACCCGTACGACGTTCCGGACTACGGTTCCGGCCGAGCATAG : 411
SEQ ID NO:313   R2CHCL38 : GTCACCGTCTCCAGCGGCCGCTACCCGTACGACGTTCCGGACTACGGTTCCGGCCGAGCATAG : 393
SEQ ID NO:314   R1CHCL16 : GTCACCGTCTCCAGCGGCCGCTACCCGTACGACGTTCCGGACTACGGTTCCGGCCGAGCATAG : 393
SEQ ID NO:315   R1CHCL56 : GTCACCGTCTCCAGCGGCCGCTACCCGTACGACGTTCCGGACTACGGTTCCGGCCGAGCATAG : 396
SEQ ID NO:316   R2CHCL69 : GTCACCGTCTCCAGCGGCCGCTACCCGTACGACGTTCCGGACTACGGTTCCGGCCGAGCATAG : 396
SEQ ID NO:317   R2CHCL32 : GTCACCGTCTCCAGCGGCCGCTACCCGTACGACGTTCCGGACTACGGTTCCGGCCGAGCATAG : 396
SEQ ID NO:318   R2CHCL14 : GTCACCGTCTCCAGCGGCCGCTACCCGTACGACGTTCCGGACTACGGTTCCGGCCGAGCATAG : 384
SEQ ID NO:319   R2CHCL42 : GTCACCGTCTCCAGCGGCCGCTACCCGTACGACGTTCCGGACTACGGTTCCGGCCGAGCATAG : 384
SEQ ID NO:320   R2CHCL13 : GTCACCGTCTCCAGCGGCCGCTACCCGTACGACGTTCCGGACTACGGTTCCGGCCGAGCATAG : 384
SEQ ID NO:321   R2CHCL41 : GTCACCGTCTCCAGCGGCCGCTACCCGTACGACGTTCCGGACTACGGTTCCGGCCGAGCATAG : 384
SEQ ID NO:322   R2CHCL94 : GTCACCGTCTCCAGCGGCCGCTACCCGTACGACGTTCCGGACTACGGTTCCGGCCGAGCATAG : 384
SEQ ID NO: 323  R2CHCL27 : GTCACCGTCTCCAGCGGCCGCTACCCGTACGACGTTCCGGACTACGGTTCCGGCCGAGCATAG : 384
```

FIGURE 4 (CONTINUED)

| | | | |
|---|---|---|---|
| | | | 120 |
| SEQ ID NO:59 | R2CHCL8 | : | VTVSS |
| SEQ ID NO:60 | R1CHCL50 | : | VTVSS |
| SEQ ID NO:61 | R1CHCL21 | : | VTVSS |
| SEQ ID NO:62 | R2CHCL87 | : | VTVSS |
| SEQ ID NO:63 | R2CHCL24 | : | VTVSS |
| SEQ ID NO:64 | R2CHCL38 | : | VTVSS |
| SEQ ID NO:65 | R1CHCL16 | : | VTVSS |
| SEQ ID NO:66 | R2CHCL10 | : | VTVSS |
| SEQ ID NO:67 | R1CHCL34 | : | VTVSS |
| SEQ ID NO:68 | R1CHCL82 | : | VTVSS |
| SEQ ID NO:69 | R2CHCL3 | : | VTVSS |
| SEQ ID NO:70 | R2CHCL69 | : | VTVSS |
| SEQ ID NO:71 | R1CHCL56 | : | VTVSS |
| SEQ ID NO:72 | R2CHCL32 | : | VTVSS |
| SEQ ID NO:73 | R2CHCL49 | : | VTVSS |
| SEQ ID NO:74 | R2CHCL53 | : | VTVSS |
| SEQ ID NO:75 | R2CHCL22 | : | VTVSS |
| SEQ ID NO:76 | R2CHCL25 | : | VTVSS |
| SEQ ID NO:77 | R2CHCL18 | : | VTVSS |
| SEQ ID NO:78 | R1CHCL23 | : | VTVSS |
| SEQ ID NO:79 | R1CHCL27 | : | VTVSS |
| SEQ ID NO:80 | R2CHCL13 | : | VTVSS |
| SEQ ID NO:81 | R2CHCL14 | : | VTVSS |
| SEQ ID NO:82 | R2CHCL42 | : | VTVSS |
| SEQ ID NO:83 | R2CHCL41 | : | VTVSS |
| SEQ ID NO:84 | R2CHCL94 | : | VTVSS |
| SEQ ID NO:85 | R2CHCL27 | : | VTVSS |

FIGURE 5

| Group | Member(s) |
|---|---|
| 1 | R1CHCL21, R1CHCL50, R2CHCL8, R2CHCL87 |
| 2 | R2CHCL24 |
| 3 | R2CHCL38 |
| 4 | R1CHCL16 |
| 5 | R1CHCL34, R1CHCL82, R2CHCL10 |
| 6 | R2CHCL3 |
| 7 | R1CHCL56, R2CHCL32, R2CHCL69 |
| 8 | R1CHCL23, R2CHCL18, R2CHCL22, R2CHCL25, R2CHCL49, R2CHCL53 |
| 9 | R1CHCL27 |
| 10 | R2CHCL13, R2CHCL14, R2CHCL41, R2CHCL42, R2CHCL94 |
| 11 | R2CHCL27 |

A.

B.

A.

B.

SEQUENCE LISTING

```
<160> NUMBER OF SEQ ID NOS: 324

<210> SEQ ID NO 1
<211> LENGTH: 235
<212> TYPE: PRT
<213> ORGANISM: Artificial Sequence
<220> FEATURE:
<223> OTHER INFORMATION: Synthetic polymer.

<400> SEQUENCE: 1

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125
```

-continued

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 2
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 2

Gly Ser Ile Ser Ser Ile Asn Val Met Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 3

Gly Ser Phe Ser Ser Ile Asn Val Met Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 4

Gly Ser Ile Ser Ser Ile Asn Ile Met Gly
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 5

Gly Ser Ile Ser Ser Ile Asn Ile Met Gly
1               5                   10

<210> SEQ ID NO 6
<211> LENGTH: 10
<212> TYPE: PRT
<213> ORGANISM: Artificial Sequence -continued
<220> FEATURE:
<223> OTHER INFORMATION: Synthetic Sequence

<400> SEQUENCE: 6

Val Ser Ile Phe Ser Ile Asn Ala Met Gly
1 5 10

<210> SEQ ID NO 7
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 7

Gly Ser Ile Phe Ser Leu Asn Ala Met Gly
1 5 10

<210> SEQ ID NO 8
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 8

Gly Arg Thr Ile Ser Asn Tyr Asp Met Ala
1 5 10

<210> SEQ ID NO 9
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 9

Gly Arg Thr Phe Thr Thr Ser Leu Met Gln
1 5 10

<210> SEQ ID NO 10
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 10

Glu Arg Asn Leu Arg Ile Tyr Asp Met Ala
1 5 10

<210> SEQ ID NO 11
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 11

Glu Arg Asn Leu Arg Ser Tyr Asp Met Ala
1 5 10

<210> SEQ ID NO 12
<211> LENGTH: 10
<212> TYPE: PRT
<213> ORGANISM: Artificial Sequence
<220> FEATURE:

-continued

<223> OTHER INFORMATION: Synthetic Sequence

<400> SEQUENCE: 12

Gly Leu Thr Phe Ser Asn Tyr His Met Gly
1 5 10

<210> SEQ ID NO 13
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 13

Gly Leu Thr Phe Ser Ser Tyr His Met Gly
1 5 10

<210> SEQ ID NO 14
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 14

Gly Leu Thr Phe Ser Arg Tyr His Met Gly
1 5 10

<210> SEQ ID NO 15
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 15

Gly Leu Thr Leu Ser Ser Tyr Tyr Ile Ala
1 5 10

<210> SEQ ID NO 16
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 16

Gly Leu Thr Phe Ser Ser Tyr Tyr Thr Gly
1 5 10

<210> SEQ ID NO 17
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 17

Gly Leu Thr Leu Ser Ser Tyr His Met Gly
1 5 10

<210> SEQ ID NO 18
<211> LENGTH: 10
<212> TYPE: PRT
<213> ORGANISM: Artificial Sequence
<220> FEATURE:
<223> OTHER INFORMATION: Synthetic Sequence -continued

<400> SEQUENCE: 18

Gly Arg Thr Ser Ser Pro Tyr Val Thr Gly
1 5 10

<210> SEQ ID NO 19
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 19

Gly Phe Thr Phe Ser Gly Tyr Val Met Ser
1 5 10

<210> SEQ ID NO 20
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 20

Gly Phe Thr Phe Ser Gly Tyr Val Met Thr
1 5 10

<210> SEQ ID NO 21
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 21

Gly Phe Thr Phe Ser Gly Tyr Leu Met Ser
1 5 10

<210> SEQ ID NO 22
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 22

Arg Ile Thr Asn Leu Gly Leu Pro Asn Tyr Ala Asp Trp Leu Lys Asp
1 5 10 15

<210> SEQ ID NO 23
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 23

Arg Ile Thr Asn Leu Gly Leu Pro Asn Tyr Ala Asp Ser Val Thr Gly
1 5 10 15

<210> SEQ ID NO 24
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 24

Arg Ile Thr Asn Ile Gly Leu Pro Asn Tyr Ala Asp Ser Val Lys Gly
1 5 10 15

<210> SEQ ID NO 25
<211> LENGTH: 16
<212> TYPE: PRT
<213> ORGANISM: Artificial Sequence
<220> FEATURE:
<223> OTHER INFORMATION: Synthetic polymer.

<400> SEQUENCE: 25

Arg Ile Thr Asn Leu Gly Leu Pro Asn Tyr Ala Asp Ser Val Glu Gly
1 5 10 15

<210> SEQ ID NO 26
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 26

Ala Ile Thr Ser Gly Gly Arg Val Val Tyr Ser Asp Ser Val Lys Gly
1 5 10 15

<210> SEQ ID NO 27
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 27

Ala Ile Thr Ser Gly Gly Arg Thr Ala Tyr Ala Asp Ser Val Lys Gly
1 5 10 15

<210> SEQ ID NO 28
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 28

His Ile Thr Ser Asp Gly Arg Ile Val Tyr Ala Asp Pro Val Lys Gly
1 5 10 15

<210> SEQ ID NO 29
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 29

Arg Ile Ser Gly Ser Gly Asp Arg Thr Asp Tyr Ala Asp Ser Val Lys
1 5 10 15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 30

Ser Ile Thr Trp Ser Thr Gly Asn Thr His Tyr Ala Asp Ser Val Lys
1 5 10 15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 31

Val Ile Ser Ser Ser Gly Asp Ser Thr His Tyr Ser Asp Phe Val Lys
1 5 10 15

Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 32

Val Ile Thr Ser Ser Gly Asp Ser Thr His Tyr Ser Asp Phe Val Lys
1 5 10 15

Gly

<210> SEQ ID NO 33
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 33

Gln Ile Thr Trp Ser Asp Ala Ser Ile Tyr Tyr Ala Gly Ser Val Lys
1 5 10 15

Gly

<210> SEQ ID NO 34
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 34

Gln Ile Thr Trp Ser Asp Thr Ser Ile Tyr Tyr Ala Gly Ser Val Lys
1 5 10 15

Gly

<210> SEQ ID NO 35
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 35

Gln Ile Thr Trp Ser Asp Gly Thr Thr Tyr Tyr Pro Gly Ser Val Lys 1 5 10 15

Gly

<210> SEQ ID NO 36
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 36

Gln Ile Arg Trp Ser Asp Asp Ser Thr Tyr Tyr Pro Gly Ser Val Lys
1 5 10 15

Gly

<210> SEQ ID NO 37
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 37

Gln Ile Ser Trp Ser Asp Asp Ser Thr Tyr Tyr Ala Asp Ser Val Lys
1 5 10 15

Gly

<210> SEQ ID NO 38
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 38

Thr Val Ser Trp Gly Gly Val Thr Tyr Tyr Ala Asp Ser Val Lys Gly
1 5 10 15

<210> SEQ ID NO 39
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 39

Ser Ile Gly Ser Gly Gly Gly Tyr Pro Ser Tyr Thr Asp Ser Val Glu
1 5 10 15

Gly

<210> SEQ ID NO 40
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 40

Ser Ile Gly Ser Gly Gly Gly Tyr Pro Ser Tyr Thr Gly Ser Val Glu
1 5 10 15

Gly

<210> SEQ ID NO 41

<211> LENGTH: 17
<212> TYPE: PRT
<213> ORGANISM: Artificial Sequence
<220> FEATURE:
<223> OTHER INFORMATION: Synthetic Sequence

<400> SEQUENCE: 41

His Ile Gly Ser Gly Gly Gly Tyr Pro Ser Tyr Thr Asp Ser Val Gln
1 5 10 15

Gly

<210> SEQ ID NO 42
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 42

His Ile Gly Ser Gly Gly Gly His Ala Thr Tyr Thr Asp Ser Val Glu
1 5 10 15

Gly

<210> SEQ ID NO 43
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 43

Thr Ile Gly Ser Gly Gly Gly Ile Thr Ser Tyr Ala Asp Ser Val Lys
1 5 10 15

Gly

<210> SEQ ID NO 44
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 44

Val Ala Leu Ser Ala Glu Tyr
1 5

<210> SEQ ID NO 45
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 45

Val Ala Leu Lys Ala Glu Tyr
1 5

<210> SEQ ID NO 46
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 46

Val Gly Leu Lys Ala Glu Tyr
1 5

<210> SEQ ID NO 47
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 47

Lys Thr Lys Ser Ala Val Leu Phe Gly Gly Met Asp Tyr
1 5 10

<210> SEQ ID NO 48
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 48

Tyr Ile Arg Gly Glu Asp Tyr
1 5

<210> SEQ ID NO 49
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 49

Lys His Tyr Ala Ser Asn Tyr
1 5

<210> SEQ ID NO 50
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 50

Gln Asp Phe Gly Ser Pro Ser Phe
1 5

<210> SEQ ID NO 51
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 51

Gln Asp Phe Arg Ser Pro Asp Phe
1 5

<210> SEQ ID NO 52
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 52

Gln Ile Phe Gly Ser Pro Asn Phe 1 5

<210> SEQ ID NO 53
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 53

Leu Ala Ile His Gly Asp Tyr
1 5

<210> SEQ ID NO 54
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 54

Asn Gln Ile Arg Gln Trp Pro
1 5

<210> SEQ ID NO 55
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 55

Asn Ser Ile Arg Gln Trp Pro
1 5

<210> SEQ ID NO 56
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 56

Asn Ala Ile Arg Gln Trp Pro
1 5

<210> SEQ ID NO 57
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 57

Arg Lys Val Gly Gly Pro Asp Tyr
1 5

<210> SEQ ID NO 58
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 58

Asn Thr Phe Gly Asn Val Tyr
1 5

<210> SEQ ID NO 59
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 59

```
Gln Val Gln Leu Val Glu Ser Gly Gly Gly Leu Val His Pro Gly Gly
1               5                   10                  15

Ser Leu Arg Leu Ser Cys Ala Ala Ser Gly Ser Ile Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Trp Leu Lys
    50                  55                  60

Asp Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Leu Val Ala Leu Ser Ala Glu Tyr Trp Gly Gln Gly Thr Gln Val Thr
            100                 105                 110

Val Ser Ser
        115
```

<210> SEQ ID NO 60
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 60

```
Gln Val Gln Leu Val Glu Ser Gly Gly Gly Leu Val His Pro Gly Gly
1               5                   10                  15

Ser Leu Arg Leu Ser Cys Ala Ala Ser Gly Ser Phe Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Ser Val Thr
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Leu Val Ala Leu Lys Ala Glu Tyr Trp Gly Gln Gly Thr Gln Val Thr
            100                 105                 110

Val Ser Ser
        115
```

<210> SEQ ID NO 61
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 61

```
Gln Val Gln Leu Val Glu Ser Gly Gly Gly Leu Val His Arg Gly Gly
1               5                   10                  15

Ser Leu Arg Leu Ser Cys Ala Ala Ser Gly Ser Ile Ser Ser Ile Asn
            20                  25                  30

Ile Met Gly Trp Tyr Arg Gln Ala Pro Gly Lys Glu Arg Glu Leu Val
        35                  40                  45

Ala Arg Ile Thr Asn Ile Gly Leu Pro Asn Tyr Ala Asp Ser Val Lys
    50                  55                  60

Gly Arg Phe Thr Ile Ser Arg Asp Asn Ala Lys Ser Thr Val Tyr Leu
65                  70                  75                  80

Gln Met Asn Ser Leu Asn Ala Glu Asp Thr Ala Val Tyr Tyr Cys Tyr
                85                  90                  95

Leu Val Ala Leu Lys Ala Glu Tyr Trp Gly Gln Gly Thr Gln Val Thr
            100                 105                 110

Val Ser Ser
        115
```

<210> SEQ ID NO 62
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 62

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Ser Val Glu
    50                  55                  60

Gly Arg Phe Thr Ile Ser Arg Asp Lys Asp Glu Asn Thr Val Tyr Leu
65                  70                  75                  80

Glu Met Asn Thr Leu Lys Pro Glu Asp Thr Ala Val Tyr Tyr Cys Tyr
                85                  90                  95

Leu Val Gly Leu Lys Ala Glu Tyr Trp Gly Gln Gly Thr Gln Val Thr
            100                 105                 110

Val Ser Ser
        115
```

<210> SEQ ID NO 63
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 63

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ser Asp Ser Ile Asn
            20                  25                  30

Ala Met Gly Trp Tyr Arg Gln Ala Pro Gly Lys Glu Arg Glu Leu Val
        35                  40                  45

Ala Ala Ile Thr Ser Gly Gly Arg Val Val Tyr Ser Asp Ser Val Lys
    50                  55                  60
```

```
Gly Arg Gly Thr Ile Ser Arg Asp Asn Ala Lys Asn Thr Val Tyr Leu
65                  70                  75                  80

Gln Ile Ala Ser Leu Lys Pro Glu Asp Thr Ala Val Tyr Tyr Cys Asn
                85                  90                  95

Val Lys Thr Lys Ser Ala Val Leu Phe Gly Gly Met Asp Tyr Trp Gly
            100                 105                 110

Lys Gly Thr Gln Val Thr Val Ser Ser
        115                 120


<210> SEQ ID NO 64
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Val Ser Ile Phe Ser Ile Asn
            20                  25                  30

Ala Met Gly Trp Tyr Arg Gln Ala Pro Gly Lys Glu Arg Glu Leu Val
        35                  40                  45

Ala Ala Ile Thr Ser Gly Gly Arg Thr Ala Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asp Ser Leu Lys Pro Glu Asp Thr Asp Val Tyr Tyr Cys Lys
                85                  90                  95

Ala Tyr Ile Arg Gly Glu Asp Tyr Trp Gly Lys Gly Thr Gln Val Thr
            100                 105                 110

Val Ser Ser
        115


<210> SEQ ID NO 65
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 65

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Leu Asn
            20                  25                  30

Ala Met Gly Trp Tyr Arg Gln Ala Pro Gly Lys Glu Arg Glu Leu Val
        35                  40                  45

Ala His Ile Thr Ser Asp Gly Arg Ile Val Tyr Ala Asp Pro Val Lys
    50                  55                  60

Gly Arg Phe Thr Ile Ser Arg Val Asp Gly Lys Asn Met Val Thr Leu
65                  70                  75                  80

Gln Met Asn Ser Leu Lys Pro Glu Asp Thr Ala Val Tyr Tyr Cys Asn
                85                  90                  95

Ala Lys His Tyr Ala Ser Asn Tyr Trp Gly Gln Gly Thr Gln Val Thr
            100                 105                 110

Val Ser Ser
```

115

<210> SEQ ID NO 66
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 66

```
Gln Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Ile Ser Asn Tyr
            20                  25                  30

Asp Met Ala Trp Ser Arg Gln Ala Pro Gly Lys Glu Arg Glu Phe Val
        35                  40                  45

Ala Arg Ile Ser Gly Ser Gly Asp Arg Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Gln Ile Gln Asp Phe Gly Ser Pro Ser Phe Ser Gly Gln Gly Thr Gln
            100                 105                 110

Val Thr Val Ser Ser
        115
```

<210> SEQ ID NO 67
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 67

```
Asp Val Gln Leu Val Glu Ser Gly Gly Gly Ser Val Gln Ala Gly Gly
1               5                   10                  15

Ser Leu Arg Leu Ser Cys Ala Ala Ser Gly Arg Thr Ile Ser Asn Tyr
            20                  25                  30

Asp Met Ala Trp Ser Arg Gln Ala Pro Gly Lys Glu Arg Glu Phe Val
        35                  40                  45

Ala Arg Ile Ser Gly Ser Gly Asp Arg Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Gln Ile Gln Asp Phe Arg Ser Pro Asp Phe Trp Ser Gln Gly Thr Gln
            100                 105                 110

Val Thr Val Ser Ser
        115
```

<210> SEQ ID NO 68
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 68

```
Gln Val Gln Leu Val Glu Ser Gly Gly Glu Ser Val Gln Ala Gly Gly
1               5                   10                  15

Ser Leu Arg Leu Ser Cys Ala Ala Ser Gly Arg Thr Ile Ser Asn Tyr
            20                  25                  30

Asp Met Ala Trp Ser Arg Gln Ala Pro Gly Lys Glu Arg Glu Phe Val
        35                  40                  45

Ala Arg Ile Ser Gly Ser Gly Asp Arg Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Asn Cys
                85                  90                  95

Gln Thr Gln Ile Phe Gly Ser Pro Asn Phe Ser Gly Gln Gly Thr Gln
            100                 105                 110

Val Thr Val Ser Ser
        115
```

<210> SEQ ID NO 69
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 69

```
Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Thr Thr Ser
            20                  25                  30

Leu Met Gln Trp His Arg Gln Ala Pro Gly Lys Glu Arg Glu Phe Val
        35                  40                  45

Ala Ser Ile Thr Trp Ser Thr Gly Asn Thr His Tyr Ala Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Lys Pro Glu Asp Thr Ala Ile Tyr Thr Cys
                85                  90                  95

Arg Val Leu Ala Ile His Gly Asp Tyr Trp Gly Gln Gly Thr Gln Val
            100                 105                 110

Thr Val Ser Ser
        115
```

<210> SEQ ID NO 70
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 70

```
Asp Val Gln Leu Val Glu Ser Gly Gly Gly Leu Val Gln Ala Gly Asp
1               5                   10                  15

Ser Leu Arg Leu Ser Cys Ala Ala Ser Glu Arg Asn Leu Arg Ile Tyr
            20                  25                  30

Asp Met Ala Trp Tyr Arg Gln Ala Pro Gly Lys Glu Arg Glu Tyr Val
        35                  40                  45

Ala Val Ile Ser Ser Ser Gly Asp Ser Thr His Tyr Ser Asp Phe Val
```

```
    50                  55                  60

Lys Gly Arg Phe Thr Ile Ser Arg Asp Asn Ala Lys Asn Thr Val Ser
65                  70                  75                  80

Leu Gln Met Asp Ser Leu Lys Pro Glu Asp Thr Ala Phe Tyr Tyr Cys
                85                  90                  95

Asn Val Asn Gln Ile Arg Gln Trp Pro Trp Gly Gln Gly Thr Gln Val
            100                 105                 110

Thr Val Ser Ser
        115


<210> SEQ ID NO 71
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 71

Gln Val Gln Leu Val Glu Ser Gly Gly Gly Leu Val Gln Ala Gly Asp
1               5                   10                  15

Ser Leu Arg Leu Ser Cys Ala Ala Ser Glu Arg Asn Leu Arg Ile Tyr
            20                  25                  30

Asp Met Ala Trp Tyr Arg Gln Ala Pro Gly Lys Glu Arg Glu Tyr Val
        35                  40                  45

Ala Val Ile Ser Ser Ser Gly Asp Ser Thr His Tyr Ser Asp Phe Val
    50                  55                  60

Lys Gly Arg Phe Thr Ile Ser Arg Asp Asn Ala Lys Asn Thr Val Ser
65                  70                  75                  80

Leu Gln Met Asp Ser Leu Lys Pro Glu Asp Thr Ala Phe Tyr Tyr Cys
                85                  90                  95

Asn Val Asn Ser Ile Arg Gln Trp Pro Trp Gly Gln Gly Thr Gln Val
            100                 105                 110

Thr Val Ser Ser
        115


<210> SEQ ID NO 72
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 72

Gln Val Gln Leu Val Glu Ser Gly Gly Gly Leu Val Gln Ala Gly Asp
1               5                   10                  15

Ser Leu Arg Leu Ser Cys Thr Ala Ser Glu Arg Asn Leu Arg Ser Tyr
            20                  25                  30

Asp Met Ala Trp Trp Arg Gln Ala Pro Gly Lys Glu Arg Glu Tyr Val
        35                  40                  45

Ala Val Ile Thr Ser Ser Gly Asp Ser Thr His Tyr Ser Asp Phe Val
    50                  55                  60

Lys Gly Arg Phe Thr Ile Ser Arg Asp Asn Ala Lys Asn Thr Val Ser
65                  70                  75                  80

Leu Gln Met Asp Ser Leu Lys Pro Glu Asp Thr Ala Ser Tyr Tyr Cys
                85                  90                  95

Asn Val Asn Ala Ile Arg Gln Trp Pro Trp Gly Gln Gly Thr Gln Val
            100                 105                 110
```

Thr Val Ser Ser
115

<210> SEQ ID NO 73
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 73

Asp Val Gln Leu Val Glu Ser Gly Gly Gly Ser Val Gln Ala Gly Gly
1 5 10 15

Ser Leu Arg Leu Ser Cys Ala Ile Ser Gly Leu Thr Phe Ser Asn Tyr
20 25 30

His Met Gly Trp Tyr Arg Gln Ala Pro Gly Arg Glu Arg Glu Phe Val
35 40 45

Ala Gln Ile Thr Trp Ser Asp Ala Ser Ile Tyr Tyr Ala Gly Ser Val
50 55 60

Lys Gly Arg Phe Thr Ile Ser Arg Asp Asn Val Lys Asn Ile Val Tyr
65 70 75 80

Leu Gln Ile Asp Asn Leu Lys Pro Glu Asp Thr Ala Ile Tyr Tyr Cys
85 90 95

Asp Ala Arg Lys Val Gly Gly Pro Asp Tyr Trp Gly Gln Gly Thr Gln
100 105 110

Val Thr Val Ser Ser
115

<210> SEQ ID NO 74
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 74

Gln Val Gln Leu Val Glu Ser Gly Gly Gly Leu Val Gln Ala Gly Gly
1 5 10 15

Ser Leu Thr Leu Ser Cys Ala Ile Ser Gly Leu Thr Phe Ser Ser Tyr
20 25 30

His Met Gly Trp Tyr Arg Gln Ala Pro Gly Arg Glu Arg Glu Phe Val
35 40 45

Ala Gln Ile Thr Trp Ser Asp Thr Ser Ile Tyr Tyr Ala Gly Ser Val
50 55 60

Lys Gly Arg Phe Thr Ile Ser Arg Asp Asn Val Lys Asn Ile Val Tyr
65 70 75 80

Leu Gln Ile Asp Asn Leu Lys Pro Glu Asp Thr Ala Ile Tyr Tyr Cys
85 90 95

Asp Ala Arg Lys Val Gly Gly Pro Asp Tyr Trp Gly Gln Gly Thr Gln
100 105 110

Val Thr Val Ser Ser
115

<210> SEQ ID NO 75
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 75

Asp Val Gln Leu Val Glu Ser Gly Gly Gly Leu Val Gln Ala Gly Gly
1 5 10 15

Ser Leu Arg Leu Ser Cys Ala Ile Ser Gly Leu Thr Phe Ser Arg Tyr
20 25 30

His Met Gly Trp Tyr Arg Gln Ala Pro Gly Arg Glu Arg Glu Phe Val
35 40 45

Ala Gln Ile Thr Trp Ser Asp Gly Thr Thr Tyr Tyr Pro Gly Ser Val
50 55 60

Lys Gly Arg Phe Thr Ile Ser Arg Asp Asn Ala Arg Asn Thr Val Tyr
65 70 75 80

Leu Gln Ile Asp Asn Leu Lys Pro Glu Asp Thr Ala Ile Tyr Tyr Cys
85 90 95

Asp Ala Arg Lys Val Gly Gly Pro Asp Tyr Trp Gly Gln Gly Thr Gln
100 105 110

Val Thr Val Ser Ser
115

<210> SEQ ID NO 76
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 76

Gln Val Gln Leu Val Glu Ser Gly Gly Gly Leu Val Gln Ala Gly Gly
1 5 10 15

Ser Leu Arg Leu Ser Cys Ala Thr Ser Gly Leu Thr Leu Ser Ser Tyr
20 25 30

Tyr Ile Ala Trp Tyr Arg Gln Ala Pro Gly Arg Glu Arg Glu Phe Val
35 40 45

Ala Gln Ile Arg Trp Ser Asp Asp Ser Thr Tyr Tyr Pro Gly Ser Val
50 55 60

Lys Gly Arg Phe Thr Ile Ser Arg Asp Asn Ala Arg Asn Thr Val Tyr
65 70 75 80

Leu Arg Met Asp Asn Leu Lys Pro Glu Asp Thr Ala Arg Tyr Tyr Cys
85 90 95

Asp Ala Arg Lys Val Gly Gly Pro Asp Tyr Trp Gly Gln Gly Thr Gln
100 105 110

Val Thr Val Ser Ser
115

<210> SEQ ID NO 77
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 77

Asp Val Gln Leu Val Glu Ser Gly Gly Gly Leu Val Gln Ala Gly Gly
1 5 10 15

Ser Leu Arg Leu Ser Cys Ala Thr Ser Gly Leu Thr Phe Ser Ser Tyr
20 25 30

Tyr Thr Gly Trp Tyr Arg Gln Ala Pro Gly Arg Glu Arg Glu Phe Val
35 40 45

```
Ala Gln Ile Ser Trp Ser Asp Asp Ser Thr Tyr Tyr Ala Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Asn Leu Lys Pro Gly Asp Thr Ala Ile Tyr Tyr Cys
                85                  90                  95

Asp Ala Arg Lys Val Gly Gly Pro Asp Tyr Trp Gly Gln Gly Thr Gln
            100                 105                 110

Val Thr Val Ser Ser
        115
```

<210> SEQ ID NO 78
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 78

```
Asp Val Gln Leu Val Glu Ser Gly Gly Gly Leu Val Gln Ala Gly Gly
1               5                   10                  15

Ser Leu Arg Leu Ser Cys Ala Thr Ser Gly Leu Thr Leu Ser Ser Tyr
            20                  25                  30

His Met Gly Trp Tyr Arg Gln Ala Pro Gly Arg Glu Arg Glu Phe Val
        35                  40                  45

Ala Gln Ile Ser Trp Ser Asp Asp Ser Thr Tyr Tyr Ala Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Asn Leu Lys Pro Glu Asp Thr Ala Ile Tyr Tyr Cys
                85                  90                  95

Asp Ala Arg Lys Val Gly Gly Pro Asp Tyr Trp Gly Gln Gly Thr Gln
            100                 105                 110

Val Thr Val Ser Ser
        115
```

<210> SEQ ID NO 79
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 79

```
Asp Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Pro Tyr
            20                  25                  30

Val Thr Gly Trp Tyr Arg Gln Thr Pro Gly Lys Glu Arg Glu Pro Val
        35                  40                  45

Ala Thr Val Ser Trp Gly Gly Val Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ala Leu Lys Pro Glu Asp Thr Ala Ile Tyr Tyr Cys Asn
                85                  90                  95

Val Asn Thr Phe Gly Asn Val Tyr Trp Gly Gln Gly Thr Gln Val Thr
            100                 105                 110
```

```
Val Ser Ser
        115


<210> SEQ ID NO 80
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 80

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Val Met Ser Trp Val Arg Gln Ala Pro Gly Lys Gly Leu Glu Trp Val
        35                  40                  45

Ala Ser Ile Gly Ser Gly Gly Gly Tyr Pro Ser Tyr Thr Asp Ser Val
    50                  55                  60

Glu Gly Arg Phe Thr Ile Ser Arg Asp Asn Ala Lys Asn Thr Leu Tyr
65                  70                  75                  80

Leu Leu Met Asp Asn Leu Lys Pro Asp Asp Thr Ala Val Tyr Tyr Cys
                85                  90                  95

Glu Met Leu Gly Arg Arg Gly Gln Gly Thr Gln Val Thr Val Ser Ser
            100                 105                 110


<210> SEQ ID NO 81
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 81

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Val Met Ser Trp Val Arg Gln Ala Pro Gly Lys Gly Leu Glu Trp Val
        35                  40                  45

Ala Ser Ile Gly Ser Gly Gly Gly Tyr Pro Ser Tyr Thr Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Asn Leu Lys Pro Asp Asp Thr Ala Val Tyr Tyr Cys
                85                  90                  95

Glu Met Leu Gly Arg Arg Gly Gln Gly Thr Gln Val Thr Val Ser Ser
            100                 105                 110


<210> SEQ ID NO 82
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 82

Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Gly Tyr
            20                  25                  30

Val Met Ser Trp Val Arg Gln Ala Pro Gly Lys Gly Leu Glu Trp Val
        35                  40                  45

Ala Ser Ile Gly Ser Gly Gly Gly Tyr Pro Ser Tyr Thr Gly Ser Val
    50                  55                  60

Glu Gly Arg Phe Thr Ile Ser Arg Asp Asn Ala Lys Asn Thr Leu Tyr
65                  70                  75                  80

Leu Leu Met Asn Asn Leu Lys Pro Asp Asp Thr Ala Val Tyr Tyr Cys
                85                  90                  95

Glu Met Leu Gly Arg Arg Gly Gln Gly Thr Gln Val Thr Val Ser Ser
            100                 105                 110


<210> SEQ ID NO 83
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Val Met Ser Trp Val Arg Gln Ala Pro Gly Lys Gly Leu Glu Trp Val
        35                  40                  45

Ala His Ile Gly Ser Gly Gly Gly Tyr Pro Ser Tyr Thr Asp Ser Val
    50                  55                  60

Gln Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Val Tyr Tyr Cys
                85                  90                  95

Glu Met Leu Gly Arg Arg Gly Gln Gly Thr Gln Val Thr Val Ser Ser
            100                 105                 110


<210> SEQ ID NO 84
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 84

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Val Met Thr Trp Val Arg Gln Ala Pro Gly Lys Gly Leu Glu Trp Val
        35                  40                  45

Ala His Ile Gly Ser Gly Gly Gly His Ala Thr Tyr Thr Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Asn Leu Lys Ala Glu Asp Thr Ala Val Tyr Tyr Cys
                85                  90                  95

Glu Phe Leu Gly Arg Arg Gly Gln Gly Thr Gln Val Thr Val Ser Ser
            100                 105                 110
```

<210> SEQ ID NO 85
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 85

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Gly Tyr
20 25 30

Leu Met Ser Trp Val Arg Gln Ala Pro Gly Lys Gly Leu Glu Trp Val
35 40 45

Ala Thr Ile Gly Ser Gly Gly Gly Ile Thr Ser Tyr Ala Asp Ser Val
50 55 60

Lys Gly Arg Phe Thr Ile Ser Arg Asp Asn Ala Lys Asn Thr Leu Tyr
65 70 75 80

Leu Gln Met Asn Asn Leu Lys His Glu Asp Thr Ala Val Tyr Tyr Cys
85 90 95

Glu Thr Val Ile Lys Arg Gly Gln Gly Thr Gln Val Thr Val Ser Ser
100 105 110

<210> SEQ ID NO 86
<211> LENGTH: 165
<212> TYPE: PRT
<213> ORGANISM: Artificial Sequence
<220> FEATURE:
<223> OTHER INFORMATION: Synthetic Sequence

<400> SEQUENCE: 86

Cys Asp Leu Pro Gln Thr His Ser Leu Gly Ser Arg Arg Thr Leu Met
1 5 10 15

Leu Leu Ala Gln Met Arg Lys Ile Ser Leu Phe Ser Cys Leu Lys Asp
20 25 30

Arg His Asp Phe Gly Phe Pro Gln Glu Glu Phe Gly Asn Gln Phe Gln
35 40 45

Lys Ala Glu Thr Ile Pro Val Leu His Glu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Val Ile Gln Gly Val Gly Val Thr Glu Thr Pro Leu Met Lys
100 105 110

Glu Asp Ser Ile Leu Ala Val Arg Lys Tyr Phe Gln Arg Ile Thr Leu
115 120 125

Tyr Leu Lys Glu Lys Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

Leu Arg Ser Lys Glu
165

<210> SEQ ID NO 87
<211> LENGTH: 165
<212> TYPE: PRT

<213> ORGANISM: Artificial Sequence
<220> FEATURE:
<223> OTHER INFORMATION: Synthetic Sequence

<400> SEQUENCE: 87

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 88
<211> LENGTH: 157
<212> TYPE: PRT
<213> ORGANISM: Artificial Sequence
<220> FEATURE:
<223> OTHER INFORMATION: Synthetic Sequence

<400> SEQUENCE: 88

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 89
<211> LENGTH: 171
<212> TYPE: PRT
<213> ORGANISM: Artificial Sequence
<220> FEATURE:
<223> OTHER INFORMATION: Synthetic Sequence

<400> SEQUENCE: 89

```
Leu Pro Gly Val Gly Leu Thr Pro Ser Ala Ala Gln Thr Ala Arg Gln
1               5                   10                  15

His Pro Lys Met His Leu Ala His Ser Asn Leu Lys Pro Ala Ala His
            20                  25                  30

Leu Ile Gly Asp Pro Ser Lys Gln Asn Ser Leu Leu Trp Arg Ala Asn
        35                  40                  45

Thr Asp Arg Ala Phe Leu Gln Asp Gly Phe Ser Leu Ser Asn Asn Ser
    50                  55                  60

Leu Leu Val Pro Thr Ser Gly Ile Tyr Phe Val Tyr Ser Gln Val Val
65                  70                  75                  80

Phe Ser Gly Lys Ala Tyr Ser Pro Lys Ala Thr Ser Ser Pro Leu Tyr
                85                  90                  95

Leu Ala His Glu Val Gln Leu Phe Ser Ser Gln Tyr Pro Phe His Val
            100                 105                 110

Pro Leu Leu Ser Ser Gln Lys Met Val Tyr Pro Gly Leu Gln Glu Pro
        115                 120                 125

Trp Leu His Ser Met Tyr His Gly Ala Ala Phe Gln Leu Thr Gln Gly
    130                 135                 140

Asp Gln Leu Ser Thr His Thr Asp Gly Ile Pro His Leu Val Leu Ser
145                 150                 155                 160

Pro Ser Thr Val Phe Phe Gly Ala Phe Ala Leu
                165                 170
```

<210> SEQ ID NO 90
<211> LENGTH: 281
<212> TYPE: PRT
<213> ORGANISM: Artificial Sequence
<220> FEATURE:
<223> OTHER INFORMATION: Synthetic Sequence

<400> SEQUENCE: 90

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140
```

```
Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 91
<211> LENGTH: 153
<212> TYPE: PRT
<213> ORGANISM: Artificial Sequence
<220> FEATURE:
<223> OTHER INFORMATION: Synthetic Sequence

<400> SEQUENCE: 91

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150


<210> SEQ ID NO 92
<211> LENGTH: 133
<212> TYPE: PRT
<213> ORGANISM: Artificial Sequence
<220> FEATURE:
<223> OTHER INFORMATION: Synthetic Sequence

<400> SEQUENCE: 92

Ala Pro Thr Ser Ser Ser Thr Lys Lys Thr Gln Leu Gln Leu Glu His
```

-continued

```
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

```
<210> SEQ ID NO 93
<211> LENGTH: 129
<212> TYPE: PRT
<213> ORGANISM: Artificial Sequence
<220> FEATURE:
<223> OTHER INFORMATION: Synthetic Sequence

<400> SEQUENCE: 93

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser
```

```
<210> SEQ ID NO 94
<211> LENGTH: 185
<212> TYPE: PRT
<213> ORGANISM: Artificial Sequence
<220> FEATURE:
<223> OTHER INFORMATION: Synthetic Sequence

<400> SEQUENCE: 94

Ala Pro Val Pro Pro Gly Glu Asp Ser Lys Asp Val Ala Ala Pro His
1               5                   10                  15

Arg Gln Pro Leu Thr Ser Ser Glu Arg Ile Asp Lys Gln Ile Arg Tyr
            20                  25                  30

Ile Leu Asp Gly Ile Ser Ala Leu Arg Lys Glu Thr Cys Asn Lys Ser
```

35 40 45

Asn Met Cys Glu Ser Ser Lys Glu Ala Leu Ala Glu Asn Asn Leu Asn
50 55 60

Leu Pro Lys Met Ala Glu Lys Asp Gly Cys Phe Gln Ser Gly Phe Asn
65 70 75 80

Glu Glu Thr Cys Leu Val Lys Ile Ile Thr Gly Leu Leu Glu Phe Glu
85 90 95

Val Tyr Leu Glu Tyr Leu Gln Asn Arg Phe Glu Ser Ser Glu Glu Gln
100 105 110

Ala Arg Ala Val Gln Met Ser Thr Lys Val Leu Ile Gln Phe Leu Gln
115 120 125

Lys Lys Ala Lys Asn Leu Asp Ala Ile Thr Thr Pro Asp Pro Thr Thr
130 135 140

Asn Ala Ser Leu Thr Thr Lys Leu Gln Ala Gln Asn Gln Trp Leu Gln
145 150 155 160

Asp Met Thr Thr His Leu Ile Leu Arg Ser Phe Lys Glu Phe Leu Gln
165 170 175

Ser Ser Leu Arg Ala Leu Arg Gln Met
180 185

<210> SEQ ID NO 95
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 95

Ser Pro Gly Pro Val Pro Pro Ser Thr Ala Leu Arg Glu Leu Ile Glu
1 5 10 15

Glu Leu Val Asn Ile Thr Gln Asn Gln Lys Ala Pro Leu Cys Asn Gly
20 25 30

Ser Met Val Trp Ser Ile Asn Leu Thr Ala Gly Met Tyr Cys Ala Ala
35 40 45

Leu Glu Ser Leu Ile Asn Val Ser Gly Cys Ser Ala Ile Glu Lys Thr
50 55 60

Gln Arg Met Leu Ser Gly Phe Cys Pro His Lys Val Ser Ala Gly Gln
65 70 75 80

Phe Ser Ser Leu His Val Arg Asp Thr Lys Ile Glu Val Ala Gln Phe
85 90 95

Val Lys Asp Leu Leu Leu His Leu Lys Lys Leu Phe Arg Glu Gly Arg
100 105 110

Phe Asn

<210> SEQ ID NO 96
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 96

Met Ala Ala Glu Pro Val Glu Asp Asn Cys Ile Asn Phe Val Ala Met
1 5 10 15

Lys Phe Ile Asp Asn Thr Leu Tyr Phe Ile Ala Glu Asp Asp Glu Asn
20 25 30

Leu Glu Ser Asp Tyr Phe Gly Lys Leu Glu Ser Lys Leu Ser Val Ile

-continued

```
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp Leu


<210> SEQ ID NO 97
<211> LENGTH: 270
<212> TYPE: PRT
<213> ORGANISM: Artificial Sequence
<220> FEATURE:
<223> OTHER INFORMATION: Synthetic Sequence

<400> SEQUENCE: 97

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205
```

Glu Lys Pro Leu Pro Asp Gln Ala Phe Phe Val Leu His Asn Met His
210 215 220

Ser Asn Cys Val Ser Phe Glu Cys Lys Thr Asp Pro Gly Val Phe Ile
225 230 235 240

Gly Val Lys Asp Asn His Leu Ala Leu Ile Lys Val Asp Ser Ser Glu
245 250 255

Asn Leu Cys Thr Glu Asn Ile Leu Phe Lys Leu Ser Glu Thr
260 265 270

<210> SEQ ID NO 98
<211> LENGTH: 447
<212> TYPE: PRT
<213> ORGANISM: Artificial Sequence
<220> FEATURE:
<223> OTHER INFORMATION: Synthetic Sequence

<400> SEQUENCE: 98

Gln Val Gln Leu Val Gln Ser Gly Val Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met Tyr Trp Val Arg Gln Ala Pro Gly Gln Gly Leu Glu Trp Met
35 40 45

Gly Gly Ile Asn Pro Ser Asn Gly Gly Thr Asn Phe Asn Glu Lys Phe
50 55 60

Lys Asn Arg Val Thr Leu Thr Thr Asp Ser Ser Thr Thr Thr Ala Tyr
65 70 75 80

Met Glu Leu Lys Ser Leu Gln Phe Asp Asp Thr Ala Val Tyr Tyr Cys
85 90 95

Ala Arg Arg Asp Tyr Arg Phe Asp Met Gly Phe Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 99
<211> LENGTH: 218
<212> TYPE: PRT
<213> ORGANISM: Artificial Sequence
<220> FEATURE:
<223> OTHER INFORMATION: Synthetic Sequence

<400> SEQUENCE: 99

Glu Ile Val Leu Thr Gln Ser Pro Ala Thr Leu Ser Leu Ser Pro Gly
1 5 10 15

Glu Arg Ala Thr Leu Ser Cys Arg Ala Ser Lys Gly Val Ser Thr Ser
20 25 30

Gly Tyr Ser Tyr Leu His Trp Tyr Gln Gln Lys Pro Gly Gln Ala Pro
35 40 45

Arg Leu Leu Ile Tyr Leu Ala Ser Tyr Leu Glu Ser Gly Val Pro Ala
50 55 60

Arg Phe Ser Gly Ser Gly Ser Gly Thr Asp Phe Thr Leu Thr Ile Ser
65 70 75 80

Ser Leu Glu Pro Glu Asp Phe Ala Val Tyr Tyr Cys Gln His Ser Arg
85 90 95

Asp Leu Pro Leu Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 100
<211> LENGTH: 440
<212> TYPE: PRT
<213> ORGANISM: Artificial Sequence
<220> FEATURE:
<223> OTHER INFORMATION: Synthetic Sequence

<400> SEQUENCE: 100

Gln Val Gln Leu Val Glu Ser Gly Gly Gly Val Val Gln Pro Gly Arg
1 5 10 15

Ser Leu Arg Leu Asp Cys Lys Ala Ser Gly Ile Thr Phe Ser Asn Ser
20 25 30

Gly Met His Trp Val Arg Gln Ala Pro Gly Lys Gly Leu Glu Trp Val
35 40 45

Ala Val Ile Trp Tyr Asp Gly Ser Lys Arg Tyr Tyr Ala Asp Ser Val
50 55 60

Lys Gly Arg Phe Thr Ile Ser Arg Asp Asn Ser Lys Asn Thr Leu Phe
65 70 75 80

Leu Gln Met Asn Ser Leu Arg Ala Glu Asp Thr Ala Val Tyr Tyr Cys
85 90 95

Ala Thr Asn Asp Asp Tyr Trp Gly Gln Gly Thr Leu Val Thr Val Ser
100 105 110

Ser Ala Ser Thr Lys Gly Pro Ser Val Phe Pro Leu Ala Pro Cys Ser
115 120 125

Arg Ser Thr Ser Glu Ser Thr Ala Ala Leu Gly Cys Leu Val Lys Asp
130 135 140

Tyr Phe Pro Glu Pro Val Thr Val Ser Trp Asn Ser Gly Ala Leu Thr
145 150 155 160

Ser Gly Val His Thr Phe Pro Ala Val Leu Gln Ser Ser Gly Leu Tyr
165 170 175

Ser Leu Ser Ser Val Val Thr Val Pro Ser Ser Ser Leu Gly Thr Lys
180 185 190

Thr Tyr Thr Cys Asn Val Asp His Lys Pro Ser Asn Thr Lys Val Asp
195 200 205

Lys Arg Val Glu Ser Lys Tyr Gly Pro Pro Cys Pro Pro Cys Pro Ala
210 215 220

Pro Glu Phe Leu Gly Gly Pro Ser Val Phe Leu Phe Pro Pro Lys Pro
225 230 235 240

Lys Asp Thr Leu Met Ile Ser Arg Thr Pro Glu Val Thr Cys Val Val
245 250 255

Val Asp Val Ser Gln Glu Asp Pro Glu Val Gln Phe Asn Trp Tyr Val
260 265 270

Asp Gly Val Glu Val His Asn Ala Lys Thr Lys Pro Arg Glu Glu Gln
275 280 285

Phe Asn Ser Thr Tyr Arg Val Val Ser Val Leu Thr Val Leu His Gln
290 295 300

Asp Trp Leu Asn Gly Lys Glu Tyr Lys Cys Lys Val Ser Asn Lys Gly
305 310 315 320

Leu Pro Ser Ser Ile Glu Lys Thr Ile Ser Lys Ala Lys Gly Gln Pro
325 330 335

Arg Glu Pro Gln Val Tyr Thr Leu Pro Pro Ser Gln Glu Glu Met Thr
340 345 350

Lys Asn Gln Val Ser Leu Thr Cys Leu Val Lys Gly Phe Tyr Pro Ser
355 360 365

```
Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 101
<211> LENGTH: 214
<212> TYPE: PRT
<213> ORGANISM: Artificial Sequence
<220> FEATURE:
<223> OTHER INFORMATION: Synthetic Sequence

<400> SEQUENCE: 101

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 102
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 102

Glu Ile Val Leu Thr Gln Ser Pro Ser Ser Leu Ser Ala Ser Val Gly
```

```
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105


<210> SEQ ID NO 103
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 103

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105


<210> SEQ ID NO 104
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 104

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95
```

Phe Gly Gly Gly Thr Lys Leu Glu Ile Lys
            100                 105

<210> SEQ ID NO 105
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 105

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 106
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 106

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Ser Phe Ser Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Trp Gly Gln Gly Thr Leu
            100                 105                 110

Val Thr Val Ser Ser
        115

<210> SEQ ID NO 107
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 107

Gln Val Gln Leu Val Gln Ser Gly Ser Glu Leu Lys Lys Pro Gly Ala

```
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Val Gly Tyr Asp Ala Leu Asp Tyr Trp Gly Gln Gly Thr Leu
            100                 105                 110

Val Thr Val Ser Ser
        115


<210> SEQ ID NO 108
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 108

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115


<210> SEQ ID NO 109
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 109

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60
```

-continued

```
Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115


<210> SEQ ID NO 110
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 110

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Asp Ser Gly Glu Ser Thr Tyr Ala Glu Glu Phe
    50                  55                  60

Lys Gly Arg Phe Ala Phe Ser Leu Asp Thr Ser Val Asn Thr Ala Tyr
65                  70                  75                  80

Leu Gln Ile Thr Ser Leu Asn Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser
        115


<210> SEQ ID NO 111
<211> LENGTH: 254
<212> TYPE: PRT
<213> ORGANISM: Artificial Sequence
<220> FEATURE:
<223> OTHER INFORMATION: Synthetic Sequence

<400> SEQUENCE: 111

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125
```

```
Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr Trp Leu Leu His Ile Phe Ile
        195                 200                 205

Pro Phe Cys Ile Ile Ala Phe Ile Phe Ile Ala Thr Val Ile Ala Leu
    210                 215                 220

Arg Lys Gln Leu Cys Gln Lys Leu Tyr Ser Ser Lys Asp Thr Thr Lys
225                 230                 235                 240

Arg Pro Val Thr Thr Thr Lys Arg Glu Val Asn Ser Ala Ile
                245                 250


<210> SEQ ID NO 112
<211> LENGTH: 453
<212> TYPE: PRT
<213> ORGANISM: Artificial Sequence
<220> FEATURE:
<223> OTHER INFORMATION: Synthetic Sequence

<400> SEQUENCE: 112

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Glu Pro Lys
    210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 113
<211> LENGTH: 29
<212> TYPE: PRT
<213> ORGANISM: Artificial Sequence
<220> FEATURE:
<223> OTHER INFORMATION: Synthetic Sequence
<220> FEATURE:
<221> NAME/KEY: BRANCHED
<222> LOCATION: (9)..(15)
<223> OTHER INFORMATION: SNTSESFK(SNTSESF)FRVTQLAPKAQIKE

<400> SEQUENCE: 113

Ser Asn Thr Ser Glu Ser Phe Lys Ser Asn Thr Ser Glu Ser Phe Phe
1               5                   10                  15

Arg Val Thr Gln Leu Ala Pro Lys Ala Gln Ile Lys Glu
            20                  25


<210> SEQ ID NO 114
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 114

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30
```

-continued

```
Tyr Met Asn Trp Val Lys Gln Ser His Gly Lys Ser Leu Glu Trp Ile
        35                  40                  45

Gly Asn Ile Asn Pro Tyr Asn Gly Gly Thr Thr Tyr Asn Gln Lys Phe
    50                  55                  60

Lys Gly Lys Ala Thr Leu Thr Val Asp Lys Ser Ser Arg Thr Ala Tyr
65                  70                  75                  80

Met Glu Ile Asn Ser Leu Thr Ser Glu Asp Ser Ala Val Tyr Tyr Cys
                85                  90                  95

Ala Arg Gly Arg Ile Tyr Asp Gly Ser Leu Asp Tyr Trp Gly Gln Gly
            100                 105                 110

Thr Ala Leu Thr Val Ser Ser
        115


<210> SEQ ID NO 115
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 115

Asp Ile Gln Met Thr Gln Phe Pro Ser Ser Leu Cys Ala Ser Gln Gly
1               5                   10                  15

Gly Lys Val Thr Val Thr Cys Lys Ala Ser Gln Asp Ile Asn Asn Tyr
            20                  25                  30

Met Ala Trp Tyr Gln His Lys Pro Gly Lys Gly Pro Arg Leu Leu Ile
        35                  40                  45

His Tyr Thr Ser Thr Leu Leu Ser Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys
            100                 105


<210> SEQ ID NO 116
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 116

Gln Val Gln Leu Gln Gln Ser Gly Ala Glu Leu Ala Lys Pro Gly Ala
1               5                   10                  15

Ser Val Arg Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly His Ile Asn Pro Ser Ser Gly Phe Thr Thr Tyr Asn Gln Asn Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Tyr Glu Asp Ser Ala Val Tyr Phe Cys
                85                  90                  95

Ala Arg Glu Asp Tyr Asp Val Asp Tyr Trp Gly Gln Gly Thr Thr Leu
            100                 105                 110
```

```
Thr Val Ser Ser
        115


<210> SEQ ID NO 117
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 117

Asp Ile Val Met Thr Gln Ser Gln Lys Phe Met Ser Thr Ser Val Gly
1               5                   10                  15

Asp Arg Val Ser Val Thr Cys Lys Ala Ser Gln Ser Val Asp Thr Asn
            20                  25                  30

Val Ala Trp Tyr Gln Gln Lys Pro Gly Gln Ser Pro Lys Ala Leu Ile
        35                  40                  45

Phe Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Ser Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Ser Gly Thr Lys Leu Glu Ile Lys
            100                 105


<210> SEQ ID NO 118
<211> LENGTH: 122
<212> TYPE: PRT
<213> ORGANISM: Artificial Sequence
<220> FEATURE:
<223> OTHER INFORMATION: Synthetic Sequence

<400> SEQUENCE: 118

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Tyr Thr Ile Tyr Tyr Thr Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Tyr Gly Ser Phe Tyr Glu Tyr Tyr Phe Asp Tyr Trp
            100                 105                 110

Gly Gln Gly Thr Thr Leu Thr Val Ser Ser
        115                 120


<210> SEQ ID NO 119
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 119
```

-continued

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys
            100                 105


<210> SEQ ID NO 120
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 120

Glu Val Gln Leu Val Glu Ser Gly Gly Gly Leu Val Gln Ala Gly Lys
1               5                   10                  15

Ser Leu Arg Leu Ser Cys Ala Ala Ser Gly Ser Ile Phe Ser Ile His
            20                  25                  30

Ala Met Gly Trp Phe Arg Gln Ala Pro Gly Lys Glu Arg Glu Phe Val
        35                  40                  45

Ala Ala Ile Thr Trp Ser Gly Gly Ile Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Asp Arg Ala Glu Ser Ser Trp Tyr Asp Tyr Trp Gly Gln Gly
            100                 105                 110

Thr Gln Val Thr Val Ser Ser
        115


<210> SEQ ID NO 121
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 121

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ala Ser Ile His
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Ile Tyr Tyr Cys
                85                  90                  95

Ala Gly Asp Lys His Gln Ser Ser Trp Tyr Asp Tyr Trp Gly Gln Gly
            100                 105                 110

Thr Gln Val Thr Val Ser Ser
        115


<210> SEQ ID NO 122
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 122

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser Ile His
            20                  25                  30

Ala Met Gly Trp Phe Arg Gln Ala Pro Gly Lys Glu Arg Glu Phe Val
        35                  40                  45

Ala Ala Ile Thr Trp Ser Gly Gly Ile Thr Tyr Tyr Ala Asp Ser Leu
    50                  55                  60

Lys Gly Arg Phe Thr Ile Ser Arg Asp Asn Ala Lys Asn Thr Gly Tyr
65                  70                  75                  80

Leu Gln Met Asn Ser Leu Lys Pro Glu Asp Thr Ala Ile Tyr Tyr Cys
                85                  90                  95

Ala Ala Asp Arg Ala Gln Ser Ser Trp Tyr Asp Tyr Trp Gly Gln Gly
            100                 105                 110

Thr Gln Val Thr Val Ser Ser
        115


<210> SEQ ID NO 123
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 123

Glu Val Gln Leu Val Glu Ser Gly Gly Gly Leu Val Gln Ala Gly Gly
1               5                   10                  15

Ser Leu Gly Leu Ser Cys Ala Ala Ser Gly Ser Ile Phe Ser Ile Asn
            20                  25                  30

Ala Met Ala Trp Phe Arg Gln Ala Pro Gly Lys Glu Arg Glu Phe Val
        35                  40                  45

Ala Leu Ile Ser Trp Ser Gly Gly Ser Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Asp Arg Val Asp Ser Asn Trp Tyr Asp Tyr Trp Gly Gln Gly
            100                 105                 110

Thr Gln Val Thr Val Ser Ser
        115
```

<210> SEQ ID NO 124
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 124

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Ser Gly
            20                  25                  30

Thr Met Gly Trp Phe Arg Arg Ala Pro Gly Lys Glu Arg Glu Phe Val
        35                  40                  45

Ala Ser Ile Pro Trp Ser Gly Gly Arg Ile Tyr Tyr Ala Asp Ser Val
    50                  55                  60

Lys Gly Arg Phe Thr Ile Ser Arg Asp Asn Ala Gln Asn Thr Val Tyr
65                  70                  75                  80

Leu Gln Met Asn Ser Leu Lys Pro Glu Asp Thr Ala Val Tyr Tyr Cys
                85                  90                  95

Ala Val Lys Glu Arg Ser Thr Gly Trp Asp Phe Ala Ser Trp Gly Gln
            100                 105                 110

Cys Thr Gln Val Thr Val Ser Ser
        115                 120

<210> SEQ ID NO 125
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 125

Gln Val Gln Leu Val Gln Ser Gly Ala Glu Leu Lys Gln Pro Gly Ala
1               5                   10                  15

Ser Val Lys Met Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Ser Val Thr Val Ser Ser
        115                 120

<210> SEQ ID NO 126
<211> LENGTH: 122
<212> TYPE: PRT
<213> ORGANISM: Artificial Sequence
<220> FEATURE:
<223> OTHER INFORMATION: Synthetic Sequence

<400> SEQUENCE: 126

Gln Val Gln Leu Val Gln Ser Gly Ala Glu Val Lys Gln Pro Gly Ala
1               5                   10                  15

```
Ser Val Lys Met Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Asp
                85                  90                  95

Cys Ala Arg Trp Arg Asp Ser Ser Gly Tyr His Ala Met Asp Tyr Trp
            100                 105                 110

Gly Gln Gly Thr Ser Val Thr Val Ser Ser
        115                 120


<210> SEQ ID NO 127
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 127

Gln Val Gln Leu Val Gln Ser Gly His Glu Val Lys Gln Pro Gly Ala
1               5                   10                  15

Ser Val Lys Met Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Leu Val Thr Val Ser Ser
        115                 120


<210> SEQ ID NO 128
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 128

Gln Val Gln Leu Val Gln Ser Gly His Glu Val Lys Gln Pro Gly Ala
1               5                   10                  15

Ser Val Lys Met Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Arg Ala Thr Leu Thr Ala Asp Lys Ser Thr Ser Thr Ala Tyr
```

```
65                  70                  75                  80

Met Glu Leu Ser Ser Leu Arg Ser Glu Asp Thr Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Leu Val Thr Val Ser Ser
        115                 120


<210> SEQ ID NO 129
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 129

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Leu Val Thr Val Ser Ser
        115                 120


<210> SEQ ID NO 130
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 130

Asp Ile Val Leu Thr Gln Ser Pro Ala Ser Leu Thr Leu Ser Pro Gly
1               5                   10                  15

Gln Arg Leu Thr Ile Ser Cys Arg Ala Ser Gln Ser Val Ser Thr Ser
            20                  25                  30

Gly Tyr Ser Tyr Met His Trp Tyr Gln Gln Lys Pro Asp Gln Ser Pro
        35                  40                  45

Lys Leu Leu Ile Lys Phe Gly Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Glu Glu Asp Phe Ala Thr Tyr Tyr Cys Gln His Ser Trp
                85                  90                  95

Glu Ile Pro Tyr Thr Phe Gly Gln Gly Thr Lys Leu Glu Ile Lys
            100                 105                 110


<210> SEQ ID NO 131
<211> LENGTH: 111
```

<212> TYPE: PRT
<213> ORGANISM: Artificial Sequence
<220> FEATURE:
<223> OTHER INFORMATION: Synthetic Sequence

<400> SEQUENCE: 131

```
Asp Ile Val Leu Thr Gln Ser Pro Ala Thr Leu Ser Leu Ser Pro Gly
1               5                   10                  15

Gln Arg Leu Thr Ile Ser Cys Arg Ala Ser Gln Ser Val Ser Thr Ser
            20                  25                  30

Gly Tyr Ser Tyr Met His Trp Tyr Gln Gln Lys Pro Asp Gln Ser Pro
        35                  40                  45

Lys Leu Leu Ile Lys Phe Gly Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln His Ser Trp
                85                  90                  95

Glu Ile Pro Tyr Thr Phe Gly Gln Gly Thr Lys Leu Glu Ile Lys
            100                 105                 110
```

<210> SEQ ID NO 132
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 132

```
Glu Ile Val Leu Thr Gln Ser Pro Ala Thr Leu Ser Leu Ser Pro Gly
1               5                   10                  15

Gln Arg Leu Thr Ile Ser Cys Arg Ala Ser Gln Ser Val Ser Thr Ser
            20                  25                  30

Gly Tyr Ser Tyr Met His Trp Tyr Gln Gln Lys Pro Asp Gln Ser Pro
        35                  40                  45

Lys Leu Leu Ile Lys Phe Gly Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln His Ser Trp
                85                  90                  95

Glu Ile Pro Tyr Thr Phe Gly Gln Gly Thr Lys Leu Glu Ile Lys
            100                 105                 110
```

<210> SEQ ID NO 133
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 133

```
Asp Ile Val Leu Thr Gln Ser Pro Ala Thr Leu Ser Leu Ser Pro Gly
1               5                   10                  15

Gln Arg Leu Thr Ile Ser Cys Arg Ala Ser Gln Ser Val Ser Thr Ser
            20                  25                  30

Gly Tyr Ser Tyr Met His Trp Tyr Gln Gln Lys Pro Asp Gln Ser Pro
        35                  40                  45

Lys Leu Leu Ile Lys Phe Gly Ser Asn Leu Glu Ser Gly Ile Pro Ala
```

-continued

```
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Glu Ile Pro Tyr Thr Phe Gly Gln Gly Thr Lys Leu Glu Ile Lys
            100                 105                 110


<210> SEQ ID NO 134
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 134

Glu Val Gln Leu Val Glu Ser Gly Gly Gly Leu Val Gln Ala Gly Lys
1               5                   10                  15

Ser Leu Arg Leu Ser Cys Ala Ala Ser Gly Ser Ile Phe Ser Ile His
            20                  25                  30

Ala Met Gly Trp Phe Arg Gln Ala Pro Gly Lys Glu Arg Glu Phe Val
        35                  40                  45

Ala Ala Ile Thr Trp Ser Gly Gly Ile Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Asp Arg Ala Glu Ser Ser Trp Tyr Asp Tyr Trp Gly Gln Gly
            100                 105                 110

Thr Gln Val Thr Val Ser Ser
        115


<210> SEQ ID NO 135
<211> LENGTH: 451
<212> TYPE: PRT
<213> ORGANISM: Artificial Sequence
<220> FEATURE:
<223> OTHER INFORMATION: Synthetic Sequence

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125
```

-continued

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 136
<211> LENGTH: 215
<212> TYPE: PRT
<213> ORGANISM: Artificial Sequence
<220> FEATURE:
<223> OTHER INFORMATION: Synthetic Sequence

<400> SEQUENCE: 136

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30
```

```
Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 137
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 137

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120
```

<210> SEQ ID NO 138
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 138

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Arg Val Ser Ser Ser
20 25 30

Tyr Leu Ala Trp Tyr Gln Gln Lys Pro Gly Gln Ala Pro Arg Leu Leu
35 40 45

Ile Tyr Asp Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Leu Pro
85 90 95

Trp Thr Phe Gly Gln Gly Thr Lys Val Glu Ile Lys
100 105

<210> SEQ ID NO 139
<211> LENGTH: 448
<212> TYPE: PRT
<213> ORGANISM: Artificial Sequence
<220> FEATURE:
<223> OTHER INFORMATION: Synthetic Sequence

<400> SEQUENCE: 139

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

-continued

```
Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 140
<211> LENGTH: 214
<212> TYPE: PRT
<213> ORGANISM: Artificial Sequence
<220> FEATURE:
<223> OTHER INFORMATION: Synthetic Sequence

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 141
<211> LENGTH: 450
<212> TYPE: PRT
<213> ORGANISM: Artificial Sequence
<220> FEATURE:
<223> OTHER INFORMATION: Synthetic Sequence

<400> SEQUENCE: 141

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ile Met Met Trp Val Arg Gln Ala Pro Gly Lys Gly Leu Glu Trp Val
35 40 45

Ser Ser Ile Tyr Pro Ser Gly Gly Ile Thr Phe Tyr Ala Asp Thr Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ile Lys Leu Gly Thr Val Thr Thr Val Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 142
<211> LENGTH: 216
<212> TYPE: PRT
<213> ORGANISM: Artificial Sequence
<220> FEATURE:
<223> OTHER INFORMATION: Synthetic Sequence

<400> SEQUENCE: 142

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 143
<211> LENGTH: 123
<212> TYPE: PRT
<213> ORGANISM: Artificial Sequence
<220> FEATURE:
<223> OTHER INFORMATION: Synthetic Sequence

<400> SEQUENCE: 143

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120
```

<210> SEQ ID NO 144
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 144

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

<210> SEQ ID NO 145
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 145

```
Gln Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Asp Tyr
            20                  25                  30

Gly Phe Ser Trp Val Arg Gln Ala Pro Gly Gln Gly Leu Glu Trp Met
        35                  40                  45

Gly Trp Ile Thr Ala Tyr Asn Gly Asn Thr Asn Tyr Ala Gln Lys Leu
    50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys
                85                  90                  95

Ala Arg Asp Tyr Phe Tyr Gly Met Asp Val Trp Gly Gln Gly Thr Thr
            100                 105                 110

Val Thr Val Ser Ser
        115


<210> SEQ ID NO 146
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 146

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Val Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105


<210> SEQ ID NO 147
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val His Trp Val Arg Gln Ala Pro Gly Gln Arg Leu Glu Trp Met
        35                  40                  45

Gly Trp Leu His Ala Asp Thr Gly Ile Thr Lys Phe Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu Arg Ile Gln Leu Trp Phe Asp Tyr Trp Gly Gln Gly Thr
            100                 105                 110

Leu Val Thr Val Ser Ser
        115


<210> SEQ ID NO 148
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105


<210> SEQ ID NO 149
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Val Ser Gly Gly Ile Phe Ser Thr Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Ala Asn His Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Gly Ile Ala Ala Ala Leu Phe Asp Tyr Trp Gly Gln
            100                 105                 110

Gly Thr Leu Val Thr Val Ser Ser
        115                 120


<210> SEQ ID NO 150
<211> LENGTH: 108
<212> TYPE: PRT
<213> ORGANISM: Artificial Sequence
<220> FEATURE:
<223> OTHER INFORMATION: Synthetic Sequence
```

<400> SEQUENCE: 150

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys
100 105

<210> SEQ ID NO 151
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 151

Glu Val Gln Leu Val Glu Ser Gly Gly Gly Leu Val Gln Pro Gly Arg
1 5 10 15

Ser Leu Arg Leu Ser Cys Ala Val Ser Gly Phe Thr Phe Asp Asp Tyr
20 25 30

Val Val His Trp Val Arg Gln Ala Pro Gly Lys Gly Leu Glu Trp Val
35 40 45

Ser Gly Ile Ser Gly Asn Ser Gly Asn Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Val Pro Phe Asp Tyr Trp Gly Gln Gly Thr Leu Val Thr Val Ser
100 105 110

Ser

<210> SEQ ID NO 152
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 152

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Tyr
85 90 95

Thr Phe Gly Gln Gly Thr Lys Leu Glu Ile Lys
100 105

<210> SEQ ID NO 153
<211> LENGTH: 123
<212> TYPE: PRT
<213> ORGANISM: Artificial Sequence
<220> FEATURE:
<223> OTHER INFORMATION: Synthetic Sequence

<400> SEQUENCE: 153

Gln Val Gln Leu Val Gln Ser Gly Ala Glu Val Lys Lys Pro Gly Ser
1 5 10 15

Ser Val Lys Val Ser Cys Lys Thr Ser Gly Asp Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Arg Ala His Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Phe Cys
85 90 95

Ala Arg Lys Phe His Phe Val Ser Gly Ser Pro Phe Gly Met Asp Val
100 105 110

Trp Gly Gln Gly Thr Thr Val Thr Val Ser Ser
115 120

<210> SEQ ID NO 154
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 154

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Thr
85 90 95

Phe Gly Gln Gly Thr Lys Val Glu Ile Lys
100 105

<210> SEQ ID NO 155
<211> LENGTH: 123
<212> TYPE: PRT
<213> ORGANISM: Artificial Sequence
<220> FEATURE:
<223> OTHER INFORMATION: Synthetic Sequence

<400> SEQUENCE: 155

Gln Val Gln Leu Val Gln Ser Gly Ala Glu Val Lys Lys Pro Gly Ser
1 5 10 15

Ser Val Lys Val Ser Cys Lys Thr Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Lys Ala His Tyr Ala Gln Lys Phe
50 55 60

Gln Gly Arg Val Thr Ile Thr Ala Asp Glu Ser Thr Thr Thr Ala Tyr
65 70 75 80

Met Glu Leu Ser Ser Leu Arg Ser Glu Asp Thr Ala Val Tyr Tyr Cys
85 90 95

Ala Arg Lys Tyr Asp Tyr Val Ser Gly Ser Pro Phe Gly Met Asp Val
100 105 110

Trp Gly Gln Gly Thr Thr Val Thr Val Ser Ser
115 120

<210> SEQ ID NO 156
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 156

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Thr
85 90 95

Phe Gly Gln Gly Thr Lys Val Glu Ile Lys
100 105

<210> SEQ ID NO 157
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 157

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Asn Trp Val Arg Gln Ala Pro Gly Gln Gly Leu Glu Trp Met
35 40 45

Gly Gly Ile Ile Pro Ile Phe Gly Ser Ala Asn Tyr Ala Gln Lys Phe
    50                  55                  60

Gln Asp Arg Val Thr Ile Thr Ala Asp Glu Ser Thr Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Ser Arg Tyr Tyr Met Asp Val Trp Gly
            100                 105                 110

Gln Gly Thr Thr Val Thr Val Ser Ser
        115                 120

<210> SEQ ID NO 158
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 158

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Gly Gly Gly Thr Lys Val Glu Ile Lys
            100                 105

<210> SEQ ID NO 159
<211> LENGTH: 123
<212> TYPE: PRT
<213> ORGANISM: Artificial Sequence
<220> FEATURE:
<223> OTHER INFORMATION: Synthetic Sequence

<400> SEQUENCE: 159

Gln Val Gln Leu Val Gln Ser Gly Ala Glu Val Lys Glu Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Ile Ala His Tyr Ala Gln Lys Phe
    50                  55                  60

Gln Gly Arg Val Thr Ile Thr Ala Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Lys Tyr Ser Tyr Val Ser Gly Ser Pro Phe Gly Met Asp Val
            100                 105                 110

Trp Gly Gln Gly Thr Thr Val Thr Val Ser Ser
        115                 120

<210> SEQ ID NO 160
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 160

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Arg Leu Glu Ile Lys
            100                 105
```

<210> SEQ ID NO 161
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 161

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Ile Thr Phe Asp Asp Tyr
            20                  25                  30

Gly Met His Trp Val Arg Gln Ala Pro Gly Lys Gly Leu Glu Trp Val
        35                  40                  45

Ser Gly Ile Ser Trp Asn Arg Gly Arg Ile Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Phe Arg Tyr Phe Asp Trp Phe Leu Asp Tyr Trp Gly
            100                 105                 110

Gln Gly Thr Leu Val Thr Val Ser Ser
        115                 120
```

<210> SEQ ID NO 162
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 162

```
Ala Ile Gln Leu Thr Gln Ser Pro Ser Ser Leu Ser Ala Ser Val Gly
1               5                   10                  15
```

```
Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105


<210> SEQ ID NO 163
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 163

Glu Val Lys Leu Gln Glu Ser Gly Pro Ser Leu Val Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Val
        35                  40                  45

Gly Tyr Ile Ser Tyr Thr Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Ser Glu Asp Thr Ala Thr Tyr Tyr Cys Ala
                85                  90                  95

Arg Tyr Gly Gly Trp Leu Ser Pro Phe Asp Tyr Trp Gly Gln Gly Thr
            100                 105                 110

Thr Leu Thr Val Ser Ser
        115


<210> SEQ ID NO 164
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 164

Asp Ile Val Met Thr Gln Ser His Lys Leu Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Asp Ser Ser Tyr Pro Leu
                85                  90                  95
```

-continued

Thr Phe Gly Ala Gly Thr Lys Val Glu Leu Lys
100 105

<210> SEQ ID NO 165
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 165

Glu Val Gln Leu Gln Glu Ser Gly Pro Gly Leu Val Ala Pro Ser Gln
1 5 10 15

Ser Leu Ser Ile Thr Cys Thr Val Ser Gly Phe Ser Leu Thr Thr Tyr
20 25 30

Ser Ile Asn Trp Ile Arg Gln Pro Pro Gly Lys Gly Leu Glu Trp Leu
35 40 45

Gly Val Met Trp Ala Gly Gly Gly Thr Asn Ser Asn Ser Val Leu Lys
50 55 60

Ser Arg Leu Ile Ile Ser Lys Asp Asn Ser Lys Ser Gln Val Phe Leu
65 70 75 80

Lys Met Asn Ser Leu Gln Thr Asp Asp Thr Ala Arg Tyr Tyr Cys Ala
85 90 95

Arg Tyr Tyr Gly Asn Ser Pro Tyr Tyr Ala Ile Asp Tyr Trp Gly Gln
100 105 110

Gly Thr Ser Val Thr Val Ser Ser
115 120

<210> SEQ ID NO 166
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 166

Asp Ile Val Thr Thr Gln Ser His Lys Leu Met Ser Thr Ser Val Gly
1 5 10 15

Asp Arg Val Ser Ile Thr Cys Lys Ala Ser Gln Asp Val Gly Thr Ala
20 25 30

Val Ala Trp Tyr Gln Gln Lys Pro Gly Gln Ser Pro Lys Leu Leu Ile
35 40 45

Tyr Trp Ala Ser Thr Arg His Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Asp Tyr Phe Cys Gln Gln Asp Ser Ser Tyr Pro Leu
85 90 95

Thr Phe Gly Ala Gly Thr Lys Val Glu Leu Lys
100 105

<210> SEQ ID NO 167
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 167

```
Glu Val Lys Leu Gln Glu Ser Gly Pro Ser Leu Val Lys Pro Ser Gln
1               5                   10                  15

Thr Leu Ser Leu Thr Cys Ser Val Thr Gly Tyr Ser Ile Ile Ser Asp
            20                  25                  30

Tyr Trp Asn Trp Ile Arg Lys Phe Pro Gly Asn Lys Leu Glu Tyr Leu
        35                  40                  45

Gly Tyr Ile Ser Tyr Thr Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Arg Gly Gly Trp Leu Leu Pro Phe Asp Tyr Trp Gly Gln Gly Thr
            100                 105                 110

Thr Leu Thr Val Ser Ser
        115
```

<210> SEQ ID NO 168
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 168

```
Asp Ile Val Met Thr Gln Ser Pro Ser Ser Leu Ala Val Ser Val Gly
1               5                   10                  15

Glu Lys Val Ser Met Gly Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Asp Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Gly Tyr Pro Leu Thr Phe Gly Ala Gly Thr Lys Leu Glu Leu
            100                 105                 110

Lys
```

<210> SEQ ID NO 169
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 169

```
Glu Val Lys Leu Gln Glu Ser Gly Pro Ser Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Phe Pro Arg Asp Asn Asn Thr Lys Tyr Asn Glu Asn Phe
    50                  55                  60
```

```
Lys Gly Lys Ala Thr Leu Thr Val Asp Thr Ser Ser Thr Thr Ala Tyr
65                  70                  75                  80

Met Glu Leu His Ser Leu Thr Ser Glu Asp Ser Ala Val Tyr Phe Cys
                85                  90                  95

Thr Lys Glu Asn Trp Val Gly Asp Phe Asp Tyr Trp Gly Gln Gly Thr
            100                 105                 110

Thr Leu Thr Leu Ser Ser
        115


<210> SEQ ID NO 170
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 170

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Ile Arg Tyr Met
            20                  25                  30

His Trp Tyr Gln Gln Lys Pro Gly Thr Ser Pro Lys Arg Trp Ile Ser
        35                  40                  45

Asp Thr Ser Lys Leu Thr Ser Gly Val Pro Ala Arg Phe Ser Gly Ser
    50                  55                  60

Gly Ser Gly Thr Ser Tyr Ala Leu Thr Ile Ser Ser Met Glu Ala Glu
65                  70                  75                  80

Asp Ala Ala Thr Tyr Tyr Cys His Gln Arg Ser Ser Tyr Pro Trp Thr
                85                  90                  95

Phe Gly Gly Gly Thr Lys Leu Glu Ile Lys
            100                 105


<210> SEQ ID NO 171
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 171

Glu Val Gln Leu Gln Gln Ser Gly Pro Asp Leu Val Thr Pro Gly Ala
1               5                   10                  15

Ser Val Arg Ile Ser Cys Gln Ala Ser Gly Tyr Thr Phe Pro Asp Tyr
            20                  25                  30

Tyr Met Asn Trp Val Lys Gln Ser His Gly Lys Ser Leu Glu Trp Ile
        35                  40                  45

Gly Asp Ile Asp Pro Asn Tyr Gly Gly Thr Thr Tyr Asn Gln Lys Phe
    50                  55                  60

Lys Gly Lys Ala Ile Leu Thr Val Asp Arg Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Ala Leu Thr Asp Trp Gly Gln Gly Thr Ser Leu Thr Val
            100                 105                 110

Ser Ser


<210> SEQ ID NO 172
<211> LENGTH: 106
```

```
<212> TYPE: PRT
<213> ORGANISM: Artificial Sequence
<220> FEATURE:
<223> OTHER INFORMATION: Synthetic Sequence

<400> SEQUENCE: 172

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

Tyr Trp Phe Gln Gln Lys Pro Gly Ser Ser Pro Lys Pro Trp Ile Tyr
        35                  40                  45

Ala Thr Phe Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Thr Glu
65                  70                  75                  80

Asp Ala Ala Thr Tyr Tyr Cys Gln Gln Trp Ser Asn Asn Pro Leu Thr
                85                  90                  95

Phe Gly Ala Gly Thr Lys Leu Glu Leu Lys
            100                 105


<210> SEQ ID NO 173
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 173

Glu Val Gln Leu Val Gln Ser Gly Pro Glu Leu Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115


<210> SEQ ID NO 174
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 174

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Ala Pro Gly Gln Arg Leu Glu Trp Ile
```

```
        35                  40                  45

Gly Tyr Val Asn Pro Phe Asn Asp Gly Thr Lys Tyr Asn Glu Met Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115


<210> SEQ ID NO 175
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 175

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115


<210> SEQ ID NO 176
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 176

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Gln Ala Trp Gly Tyr Pro Trp Gly Gln Gly Thr Leu Val Thr
            100                 105                 110

Val Ser Ser
        115


<210> SEQ ID NO 177
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 177

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115


<210> SEQ ID NO 178
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 178

Asp Ile Val Leu Thr Gln Ser Pro Ala Ser Leu Ala Leu Ser Pro Gly
1               5                   10                  15

Glu Arg Ala Thr Leu Ser Cys Arg Ala Thr Glu Ser Val Glu Tyr Tyr
            20                  25                  30

Gly Thr Ser Leu Val Gln Trp Tyr Gln Gln Lys Pro Gly Gln Pro Pro
        35                  40                  45

Lys Leu Leu Ile Tyr Ala Ala Ser Ser Val Asp Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Glu Glu Asp Ala Ala Met Tyr Phe Cys Gln Gln Ser Arg
                85                  90                  95

Arg Val Pro Tyr Thr Phe Gly Gln Gly Thr Lys Leu Glu Ile Lys
            100                 105                 110


<210> SEQ ID NO 179
<211> LENGTH: 111
<212> TYPE: PRT
<213> ORGANISM: Artificial Sequence
<220> FEATURE:
<223> OTHER INFORMATION: Synthetic Sequence
```

<400> SEQUENCE: 179

Asp Ile Val Leu Thr Gln Ser Pro Ala Thr Leu Ser Leu Ser Pro Gly
1 5 10 15

Glu Arg Ala Thr Leu Ser Cys Arg Ala Thr Glu Ser Val Glu Tyr Tyr
20 25 30

Gly Thr Ser Leu Val Gln Trp Tyr Gln Gln Lys Pro Gly Gln Pro Pro
35 40 45

Lys Leu Leu Ile Tyr Ala Ala Ser Ser Val Asp Ser Gly Val Pro Ser
50 55 60

Arg Phe Ser Gly Ser Gly Ser Gly Thr Asp Phe Thr Leu Thr Ile Asn
65 70 75 80

Ser Leu Glu Ala Glu Asp Ala Ala Met Tyr Phe Cys Gln Gln Ser Arg
85 90 95

Arg Val Pro Tyr Thr Phe Gly Gln Gly Thr Lys Leu Glu Ile Lys
100 105 110

<210> SEQ ID NO 180
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 180

Glu Ile Val Leu Thr Gln Ser Pro Ala Thr Leu Ser Leu Ser Pro Gly
1 5 10 15

Glu Arg Ala Thr Leu Ser Cys Arg Ala Thr Glu Ser Val Glu Tyr Tyr
20 25 30

Gly Thr Ser Leu Val Gln Trp Tyr Gln Gln Lys Pro Gly Gln Pro Pro
35 40 45

Lys Leu Leu Ile Tyr Ala Ala Ser Ser Val Asp Ser Gly Val Pro Ser
50 55 60

Arg Phe Ser Gly Ser Gly Ser Gly Thr Asp Phe Thr Leu Thr Ile Asn
65 70 75 80

Ser Leu Glu Ala Glu Asp Ala Ala Met Tyr Phe Cys Gln Gln Ser Arg
85 90 95

Arg Val Pro Tyr Thr Phe Gly Gln Gly Thr Lys Leu Glu Ile Lys
100 105 110

<210> SEQ ID NO 181
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 181

Asp Ile Val Leu Thr Gln Ser Pro Ala Thr Leu Ser Leu Ser Pro Gly
1 5 10 15

Glu Arg Ala Thr Leu Ser Cys Arg Ala Thr Glu Ser Val Glu Tyr Tyr
20 25 30

Gly Thr Ser Leu Val Gln Trp Tyr Gln Gln Lys Pro Gly Gln Pro Pro
35 40 45

Lys Leu Leu Ile Tyr Ala Ala Ser Ser Val Asp Ser Gly Val Pro Ser
50 55 60

Arg Phe Ser Gly Ser Gly Ser Gly Thr Asp Phe Thr Leu Thr Ile Asn
65 70 75 80

```
Ser Leu Glu Ala Glu Asp Ala Ala Thr Tyr Phe Cys Gln Gln Ser Arg
                85                  90                  95

Arg Val Pro Tyr Thr Phe Gly Gln Gly Thr Lys Leu Glu Ile Lys
            100                 105                 110


<210> SEQ ID NO 182
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 182

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Asp Tyr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Lys Ala Glu Asp Thr Ala Val Tyr Tyr Cys
                85                  90                  95

Ala Arg Asp Leu Val Thr Ser Met Val Ala Phe Asp Tyr Trp Gly Gln
            100                 105                 110

Gly Thr Leu Val Thr Val Ser Ser
        115                 120


<210> SEQ ID NO 183
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 183

Ser Tyr Glu Leu Thr Gln Pro Pro Ser Val Ser Val Ser Pro Gly Gln
1               5                   10                  15

Ala Ala Arg Ile Thr Cys Ser Gly Asp Ala Leu Pro Gln Lys Tyr Val
            20                  25                  30

Phe Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Arg Ser Gly Asn His
                85                  90                  95

Arg Val Phe Gly Gly Gly Thr Arg Leu Thr Val Leu
            100                 105


<210> SEQ ID NO 184
<211> LENGTH: 120
<212> TYPE: PRT
<213> ORGANISM: Artificial Sequence
<220> FEATURE:
<223> OTHER INFORMATION: Synthetic Sequence
```

<400> SEQUENCE: 184

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Gly Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Asn Tyr Gly Tyr Tyr Asp Met Asp Val Trp Gly Gln
            100                 105                 110

Gly Thr Thr Val Thr Val Ser Ser
        115                 120
```

<210> SEQ ID NO 185
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 185

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Phe Gln Gln Lys Pro Gly Gln Ala Pro Arg Leu Leu
        35                  40                  45

Ile Phe Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ile
                85                  90                  95

Phe Thr Phe Gly Pro Gly Thr Lys Val Asp Ile Lys
            100                 105
```

<210> SEQ ID NO 186
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 186

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60
```

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120


<210> SEQ ID NO 187
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 187

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Glu Val Glu Ile Lys
            100                 105


<210> SEQ ID NO 188
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Arg Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu His Tyr Asp Ser Ser Gly Tyr Leu Asp Tyr Trp Gly
            100                 105                 110

Gln Gly Thr Leu Val Thr Val Ser Ser
        115                 120


<210> SEQ ID NO 189
```

<211> LENGTH: 107
<212> TYPE: PRT
<213> ORGANISM: Artificial Sequence
<220> FEATURE:
<223> OTHER INFORMATION: Synthetic Sequence

<400> SEQUENCE: 189

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Gly Lys Ala Pro Lys Leu Leu Ile
        35                  40                  45

Tyr Ala Ile Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105
```

<210> SEQ ID NO 190
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 190

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Gly Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Val Gln Leu Tyr Ser Asp Tyr Phe Asp Tyr Trp Gly Gln Gly
            100                 105                 110

Thr Leu Val Thr Val Ser Ser
        115
```

<210> SEQ ID NO 191
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 191

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30
```

-continued

```
Leu Ala Trp Tyr Gln Gln Lys Ser Gly Lys Ala Pro Lys Leu Leu Ile
        35                  40                  45

Tyr Ala Ala Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser His Ser Leu Pro Pro
                85                  90                  95

Thr Phe Gly Gln Gly Thr Lys Val Glu Ile Lys
            100                 105


<210> SEQ ID NO 192
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 192

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Phe Thr Phe Ser Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Val Glu Asp Ser Ala Val Tyr Ser Cys
                85                  90                  95

Ala Lys Val Leu Val Gly Phe Asn Asn Gly Cys Trp Asp Tyr Trp Gly
            100                 105                 110

Gln Gly Thr Leu Val Thr Val Ser Ser
        115                 120


<210> SEQ ID NO 193
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 193

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asn Asp His
                85                  90                  95

Val Val Phe Gly Gly Gly Thr Lys Leu Thr Val Leu
            100                 105
```

<210> SEQ ID NO 194
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 194

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Ser Gly Asp Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Val Thr Ser Met Val Ala Phe Asp Tyr Trp Gly Gln
            100                 105                 110

Gly Thr Leu Val Thr Val Ser Ser
        115                 120
```

<210> SEQ ID NO 195
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 195

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Gln Lys Tyr Val
            20                  25                  30

Phe Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Arg Ser Gly Asn His
                85                  90                  95

Arg Val Phe Gly Gly Gly Thr Lys Leu Thr Val Leu
            100                 105
```

<210> SEQ ID NO 196
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 196

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120


<210> SEQ ID NO 197
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 197

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105


<210> SEQ ID NO 198
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 198

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95
```

```
Ala Arg Asp Tyr Arg Lys Gly Leu Tyr Ala Met Asp Tyr Trp Gly Gln
            100                 105                 110

Gly Thr Thr Val Thr Val Ser Ser
        115                 120


<210> SEQ ID NO 199
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 199

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120


<210> SEQ ID NO 200
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 200

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Pro Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120


<210> SEQ ID NO 201
<211> LENGTH: 120
<212> TYPE: PRT
```

<213> ORGANISM: Artificial Sequence
<220> FEATURE:
<223> OTHER INFORMATION: Synthetic Sequence

<400> SEQUENCE: 201

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Ile Arg Gln Ser Pro Ser Arg Gly Leu Glu Trp Leu
        35                  40                  45

Gly Arg Ile Asp Pro Asn Ser Gly Ser Thr Lys Tyr Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120
```

<210> SEQ ID NO 202
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 202

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Ile Arg Gln Pro Pro Gly Lys Gly Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120
```

<210> SEQ ID NO 203
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 203

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Trp Met Tyr Trp Ile Arg Gln Ser Pro Ser Arg Gly Leu Glu Trp Leu
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120


<210> SEQ ID NO 204
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 204

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120


<210> SEQ ID NO 205
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 205

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Tyr Thr Phe Thr Ser Tyr
            20                  25                  30

Trp Met Tyr Trp Val Arg Gln Ala Pro Gly Lys Gly Leu Glu Trp Val
        35                  40                  45

Ser Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
```

85 90 95

Ala Arg Asp Tyr Arg Lys Gly Leu Tyr Ala Met Asp Tyr Trp Gly Gln
100 105 110

Gly Thr Thr Val Thr Val Ser Ser
115 120

<210> SEQ ID NO 206
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 206

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Val Arg Gln Ala Arg Gly Gln Arg Leu Glu Trp Ile
35 40 45

Gly Arg Ile Asp Pro Asn Ser Gly Ser Thr Lys Tyr Asn Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser
115 120

<210> SEQ ID NO 207
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 207

Asp Ile Val Met Thr Gln Thr Pro Leu Ser Leu Pro Val Thr Pro Gly
1 5 10 15

Glu Pro Ala Ser Ile Ser Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Ser Tyr Pro Leu
85 90 95

Thr Phe Gly Gln Gly Thr Lys Val Glu Ile Lys
100 105

<210> SEQ ID NO 208
<211> LENGTH: 107
<212> TYPE: PRT
<213> ORGANISM: Artificial Sequence
<220> FEATURE:

<223> OTHER INFORMATION: Synthetic Sequence

<400> SEQUENCE: 208

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu
85 90 95

Thr Phe Gly Gln Gly Thr Lys Val Glu Ile Lys
100 105

<210> SEQ ID NO 209
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 209

Glu Ile Val Leu Thr Gln Ser Pro Asp Phe Gln Ser Val Thr Pro Lys
1 5 10 15

Glu Lys Val Thr Ile Thr Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Val Pro Asp Arg Phe Ser Gly
50 55 60

Ser Gly Ser Gly Thr Asp Phe Thr Leu Lys Ile Ser Arg Val Glu Ala
65 70 75 80

Glu Asp Val Gly Val Tyr Tyr Cys Gln Gln Tyr Asn Ser Tyr Pro Leu
85 90 95

Thr Phe Gly Gln Gly Thr Lys Val Glu Ile Lys
100 105

<210> SEQ ID NO 210
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 210

Glu Ile Val Leu Thr Gln Ser Pro Asp Phe Gln Ser Val Thr Pro Lys
1 5 10 15

Glu Lys Val Thr Ile Thr Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Phe Thr Ile Ser Ser Leu Gln Pro

```
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105


<210> SEQ ID NO 211
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 211

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Asn Ser Tyr Pro Leu
                85                  90                  95

Thr Phe Gly Gln Gly Thr Lys Val Glu Ile Lys
            100                 105


<210> SEQ ID NO 212
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 212

Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105


<210> SEQ ID NO 213
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 213
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105


<210> SEQ ID NO 214
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 214

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105


<210> SEQ ID NO 215
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 215

Glu Ile Val Leu Thr Gln Ser Pro Asp Phe Gln Ser Val Thr Pro Lys
1               5                   10                  15

Glu Lys Val Thr Ile Thr Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
```

```
                85                  90                  95

Thr Phe Gly Gln Gly Thr Lys Val Glu Ile Lys
            100                 105


<210> SEQ ID NO 216
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 216

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ile Phe Arg Ser Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Glu
        115


<210> SEQ ID NO 217
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 217

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Thr Thr Tyr Tyr Pro Asp Ser Val Lys
    50                  55                  60

Gly Arg Phe Ile Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Lys Gly Tyr Asp Ser Gly Phe Ala Tyr Trp Gly Gln Gly Thr Leu Val
            100                 105                 110

Ile Val Ser Ala
        115


<210> SEQ ID NO 218
<211> LENGTH: 116
<212> TYPE: PRT
<213> ORGANISM: Artificial Sequence
<220> FEATURE:
```

<223> OTHER INFORMATION: Synthetic Sequence

<400> SEQUENCE: 218

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Thr Tyr
20 25 30

Gly Val His Trp Val Arg Gln Ser Pro Gly Lys Gly Leu Glu Trp Leu
35 40 45

Gly Val Ile Trp Arg Gly Val Thr Thr Asp Tyr Asn Ala Ala Phe Met
50 55 60

Ser Arg Leu Thr Ile Thr Lys Asp Asn Ser Lys Ser Gln Val Phe Phe
65 70 75 80

Lys Met Asn Ser Leu Gln Ala Asn Asp Thr Ala Ile Tyr Tyr Cys Ala
85 90 95

Arg Leu Gly Phe Tyr Ala Met Asp Tyr Trp Gly Gln Gly Thr Ser Val
100 105 110

Thr Val Ser Ser
115

<210> SEQ ID NO 219
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 219

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Ser Tyr
20 25 30

Gly Val His Trp Val Arg Gln Ser Pro Gly Lys Gly Leu Glu Trp Leu
35 40 45

Gly Val Ile Trp Ser Gly Gly Val Thr Asp Tyr Asn Ala Ala Phe Ile
50 55 60

Ser Arg Leu Ser Ile Ser Lys Asp Asn Ser Lys Ser Gln Val Phe Phe
65 70 75 80

Lys Met Asn Ser Leu Gln Ala Asn Asp Thr Ala Ile Tyr Tyr Cys Ala
85 90 95

Arg Leu Gly Phe Tyr Ala Met Asp Tyr Trp Gly Gln Gly Thr Ser Val
100 105 110

Thr Val Ser Ser
115

<210> SEQ ID NO 220
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 220

Glu Val Lys Leu Phe Glu Ser Gly Gly Gly Leu Val Gln Pro Gly Gly
1 5 10 15

Ser Leu Lys Leu Ser Cys Val Ala Ser Gly Phe Asp Phe Ser Thr Tyr
20 25 30

Trp Met His Trp Val Arg Gln Ala Pro Gly Gln Gly Leu Glu Trp Ile 35 40 45

Gly Gln Ile Asn Pro Asp Ser Thr Thr Ile Asn Tyr Ala Pro Ser Leu
50 55 60

Lys Asp Arg Phe Ile Ile Ser Arg Asp Asn Ala Lys Asn Thr Leu Phe
65 70 75 80

Leu Gln Met Ser Lys Val Arg Ser Glu Asp Thr Ala Leu Tyr Tyr Cys
85 90 95

Ala Lys Pro Gly Asp Tyr Gly Tyr Asp Phe Asp Cys Trp Gly Gln Gly
100 105 110

Thr Thr Leu Thr Val Ser Ser
115

<210> SEQ ID NO 221
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 221

Glu Val Gln Leu Gln Glu Ser Gly Pro Ser Leu Val Lys Pro Ser Gln
1 5 10 15

Thr Leu Ser Leu Thr Cys Ser Val Thr Gly Asp Ser Ile Thr Ser Gly
20 25 30

Tyr Trp Asn Trp Ile Arg Lys Phe Pro Gly Asn Lys Leu Glu Tyr Met
35 40 45

Gly Tyr Ile Ser Tyr Ser Gly Ser Thr Tyr Tyr Asn Pro Ser Leu Lys
50 55 60

Ser Arg Ile Ser Ile Thr Arg Asp Thr Ser Lys Asn Gln Tyr Tyr Leu
65 70 75 80

Gln Leu Asn Ser Val Thr Thr Glu Asp Thr Ala Thr Tyr Tyr Cys Ala
85 90 95

Arg Ser Leu Leu Trp Phe Ser Thr Gly Phe Ala Tyr Trp Gly Gln Gly
100 105 110

Thr Leu Val Thr Val Ser Ala
115

<210> SEQ ID NO 222
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 222

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Ser Tyr
20 25 30

Gly Val His Trp Val Arg Gln Ser Pro Gly Lys Gly Leu Glu Trp Leu
35 40 45

Gly Val Ile Trp Ser Gly Gly Ile Thr Asp Tyr Asn Ala Ala Phe Lys
50 55 60

Ser Arg Leu Ser Ile Ser Lys Asp Asn Ser Lys Ser Gln Val Phe Phe
65 70 75 80

Lys Met Asn Ser Leu Gln Ala Asn Asp Thr Ala Ile Tyr Phe Cys Ala
85 90 95

```
Arg Leu Gly Phe Tyr Ala Met Asp Tyr Trp Gly Gln Gly Thr Ser Val
            100                 105                 110

Thr Val Ser Ser
        115


<210> SEQ ID NO 223
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 223

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Gly Met Ser Trp Ala Arg Gln Ile Pro Glu Lys Arg Leu Glu Trp Val
        35                  40                  45

Ala Ser Ile Ser Ser Gly Gly Thr Thr Tyr Tyr Leu Gly Ser Val Gln
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Tyr Asp Ala Gly Phe Ala Tyr Trp Gly Gln Gly Thr Leu Val
            100                 105                 110

Ser Val Ser Glu
        115


<210> SEQ ID NO 224
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 224

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Thr Trp Ile Arg Lys Phe Pro Gly Asn Lys Leu Glu Tyr Met
        35                  40                  45

Gly Tyr Ile Ser Tyr Thr Gly Ser Thr Tyr Tyr Asn Pro Ser Leu Lys
    50                  55                  60

Ser Arg Ile Ser Ile Ser Arg Asp Thr Ser Lys Ser Gln Tyr Tyr Leu
65                  70                  75                  80

Gln Leu Asn Ser Val Thr Thr Glu Asp Thr Ala Thr Tyr Tyr Cys Ala
                85                  90                  95

Arg Gln Arg Asp Trp Leu Gly Phe Ala Tyr Trp Gly Gln Gly Thr Leu
            100                 105                 110

Val Thr Val Ser Ala
        115


<210> SEQ ID NO 225
<211> LENGTH: 116
<212> TYPE: PRT
<213> ORGANISM: Artificial Sequence
```

<220> FEATURE:
<223> OTHER INFORMATION: Synthetic Sequence

<400> SEQUENCE: 225

Glu Glu Lys Leu Val Glu Ser Gly Gly Gly Leu Val Lys Pro Gly Gly
1 5 10 15

Ser Leu Lys Leu Ser Cys Ala Ala Ser Gly Phe Ser Phe Ser Ser Tyr
20 25 30

Gly Met Ser Trp Val Arg Gln Thr Pro Glu Lys Arg Leu Glu Trp Val
35 40 45

Ala Ser Ile Ser Ser Gly Gly Ser Ile Tyr Tyr Pro Asp Ser Val Lys
50 55 60

Gly Arg Phe Thr Ile Ser Arg Asp Asn Ala Arg Asn Ile Leu Tyr Leu
65 70 75 80

Gln Met Ser Ser Leu Arg Ser Glu Asp Thr Ala Met Tyr Tyr Cys Ala
85 90 95

Arg Gly Tyr Asp Ala Gly Phe Ala Phe Trp Gly Gln Gly Thr Leu Val
100 105 110

Thr Ala Ser Ala
115

<210> SEQ ID NO 226
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 226

Gln Ile Thr Leu Lys Glu Ser Gly Pro Thr Leu Val Lys Pro Thr Gln
1 5 10 15

Thr Leu Thr Leu Thr Cys Thr Val Ser Gly Phe Ser Leu Ser Thr Tyr
20 25 30

Gly Val His Trp Ile Arg Gln Pro Pro Gly Lys Ala Leu Glu Trp Leu
35 40 45

Gly Val Ile Trp Arg Gly Val Thr Thr Asp Tyr Asn Ala Ala Phe Met
50 55 60

Ser Arg Leu Thr Ile Thr Lys Asp Asn Ser Lys Asn Gln Val Val Leu
65 70 75 80

Thr Met Asn Asn Met Asp Pro Val Asp Thr Ala Thr Tyr Tyr Cys Ala
85 90 95

Arg Leu Gly Phe Tyr Ala Met Asp Tyr Trp Gly Gln Gly Thr Leu Val
100 105 110

Thr Val Ser Ser
115

<210> SEQ ID NO 227
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 227

Glu Val Gln Leu Val Glu Ser Gly Gly Gly Leu Val Lys Pro Gly Gly
1 5 10 15

Ser Leu Arg Leu Ser Cys Ala Ala Ser Gly Phe Ile Phe Arg Ser Tyr
20 25 30

-continued

```
Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser
        115
```

```
<210> SEQ ID NO 228
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 228

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110
```

```
<210> SEQ ID NO 229
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 229

Asp Ile Val Leu Thr Gln Ser Pro Pro Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Ser Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110
```

<210> SEQ ID NO 230
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 230

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ala Asn Arg Tyr Thr Gly Val Pro Asp Arg Phe Thr Gly
    50                  55                  60

Ser Gly Tyr Gly Thr Asp Phe Thr Phe Thr Ile Ser Ile Val Gln Ala
65                  70                  75                  80

Glu Asp Leu Ala Val Tyr Phe Cys Gln Gln Asp Tyr Thr Ser Pro Tyr
                85                  90                  95

Thr Phe Gly Gly Gly Thr Lys Leu Glu Ile Lys
            100                 105
```

<210> SEQ ID NO 231
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 231

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Gly Trp Tyr Gln Gln Lys Pro Gly Gln Ser Pro Lys Leu Leu Ile
        35                  40                  45

Tyr Tyr Ala Ser Asn Arg Tyr Ser Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Thr Ser Pro Tyr
                85                  90                  95

Thr Phe Gly Gly Gly Thr Lys Leu Glu Ile Lys
            100                 105
```

<210> SEQ ID NO 232
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 232

```
Asp Val Leu Met Thr Gln Thr Pro Leu Tyr Leu Pro Val Ser Leu Gly
1               5                   10                  15

Asp Gln Ala Ser Ile Ser Cys Arg Ser Ser Gln Ile Ile Val His Ser
            20                  25                  30
```

Asn Ala Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 233
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 233

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Asn Gln Gln Lys Pro Gly Ser Ser Pro Lys Val Trp
        35                  40                  45

Ile Tyr Asn Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Arg Ser Tyr Pro
                85                  90                  95

Pro Thr Leu Gly Ala Gly Thr Lys Leu Glu Leu Lys
            100                 105

<210> SEQ ID NO 234
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 234

Gln Ile Val Leu Thr Gln Ser Pro Ala Ile Met Ser Ala Ser Pro Gly
1               5                   10                  15

Glu Lys Val Thr Met Thr Cys Ser Ala Asn Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Gly Ala Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105

<210> SEQ ID NO 235

<211> LENGTH: 111
<212> TYPE: PRT
<213> ORGANISM: Artificial Sequence
<220> FEATURE:
<223> OTHER INFORMATION: Synthetic Sequence

<400> SEQUENCE: 235

Asp Ile Val Leu Thr Gln Ser Pro Ala Ser Leu Ala Val Ser Leu Gly
1 5 10 15

Gln Arg Ala Thr Ile Ser Cys Arg Ala Ser Gln Ser Val Ser Thr Ser
20 25 30

Ser Tyr Ser Tyr Met His Trp Tyr Gln Gln Lys Pro Gly Gln Pro Pro
35 40 45

Lys Leu Leu Ile Lys Tyr Ala Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Thr Ala Thr Tyr Tyr Cys Gln Asn Ser Trp
85 90 95

Glu Ile Pro Tyr Thr Phe Gly Gly Gly Thr Lys Leu Glu Ile Lys
100 105 110

<210> SEQ ID NO 236
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 236

Asp Ile Val Met Thr Gln Thr Pro Ser Ser Leu Ala Val Ser Leu Gly
1 5 10 15

Glu Lys Val Thr Met Ser Cys Lys Ser Ser Gln Ser Leu Leu Tyr Ser
20 25 30

Ser Asn Gln Lys Asn Ser Leu Ala Trp Tyr Gln Gln Lys Pro Gly Gln
35 40 45

Ser Pro Lys Leu Leu Ile Tyr Trp Ala Ser Asn Arg Glu Ser Gly Val
50 55 60

Pro Asp Arg Phe Thr Gly Ser Ser Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Ser Tyr Pro Leu Thr Phe Gly Ala Gly Thr Lys Leu Glu Leu
100 105 110

Lys

<210> SEQ ID NO 237
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 237

Asp Ile Val Leu Thr Gln Ser Pro Ala Ser Leu Ala Val Ser Leu Gly
1 5 10 15

Gln Arg Ala Thr Ile Ser Cys Arg Ala Ser Gln Ser Val Ser Thr Ser
20 25 30

Ser Tyr Ser Tyr Val His Trp Tyr Gln Gln Lys Pro Gly Gln Pro Pro

```
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110


<210> SEQ ID NO 238
<211> LENGTH: 107
<212> TYPE: PRT
<213> ORGANISM: Artificial Sequence
<220> FEATURE:
<223> OTHER INFORMATION: Synthetic Sequence

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ala Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys
            100                 105


<210> SEQ ID NO 239
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 239

Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Ser Thr Ser
            20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Trp
                85                  90                  95

Glu Ile Pro Tyr Thr Phe Gly Gln Gly Thr Lys Leu Glu Ile Lys
            100                 105                 110


<210> SEQ ID NO 240
<211> LENGTH: 112
```

<212> TYPE: PRT
<213> ORGANISM: Artificial Sequence
<220> FEATURE:
<223> OTHER INFORMATION: Synthetic Sequence

<400> SEQUENCE: 240

Asp Ile Val Leu Thr Gln Ser Pro Ala Ser Leu Ala Val Ser Leu Gly
1 5 10 15

Gln Arg Ala Thr Ile Ser Cys Arg Ala Ser Gln Ser Val Ser Thr Ser
20 25 30

Ser Ser Ser Phe Met His Trp Tyr Gln Gln Lys Pro Gly Gln Pro Pro
35 40 45

Lys Leu Leu Ile Lys Tyr Ala Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Thr Ala Thr Tyr Tyr Cys Gln His Ser Trp
85 90 95

Glu Ile Pro Tyr Thr Phe Gly Gly Gly Thr Lys Leu Glu Ile Lys Arg
100 105 110

<210> SEQ ID NO 241
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 241

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Thr Tyr
20 25 30

Trp Met His Trp Ile Arg Gln Ser Pro Ser Arg Gly Leu Glu Trp Leu
35 40 45

Gly Asn Ile Tyr Pro Gly Thr Gly Gly Ser Asn Phe Asp Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Thr Arg Trp Thr Thr Gly Thr Gly Ala Tyr Trp Gly Gln Gly Thr Thr
100 105 110

Val Thr Val Ser Ser
115

<210> SEQ ID NO 242
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 242

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Thr Tyr
20 25 30

Trp Met His Trp Ile Arg Gln Ser Pro Ser Arg Gly Leu Glu Trp Leu

```
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115


<210> SEQ ID NO 243
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 243

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115


<210> SEQ ID NO 244
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 244

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Glu Phe Thr Leu Thr
65                  70                  75                  80

Ile Ser Ser Leu Gln Pro Asp Asp Phe Ala Thr Tyr Tyr Cys Gln Asn
                85                  90                  95
```

Asp Tyr Ser Tyr Pro Tyr Thr Phe Gly Gln Gly Thr Lys Val Glu Ile
100 105 110

Lys

<210> SEQ ID NO 245
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 245

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Ile
50 55 60

Pro Pro Arg Phe Ser Gly Ser Gly Tyr Gly Thr Asp Phe Thr Leu Thr
65 70 75 80

Ile Asn Asn Ile Glu Ser Glu Asp Ala Ala Tyr Tyr Phe Cys Gln Asn
85 90 95

Asp Tyr Ser Tyr Pro Tyr Thr Phe Gly Gln Gly Thr Lys Val Glu Ile
100 105 110

Lys

<210> SEQ ID NO 246
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 246

Glu Ile Val Leu Thr Gln Ser Pro Ala Thr Leu Ser Leu Ser Pro Gly
1 5 10 15

Glu Arg Ala Thr Leu Ser Cys Lys Ser Ser Gln Ser Leu Leu Asp Ser
20 25 30

Gly Asn Gln Lys Asn Phe Leu Thr Trp Tyr Gln Gln Lys Pro Gly Lys
35 40 45

Ala Pro Lys Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Gln Pro Glu Asp Ile Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 247
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 247

Asp Ile Val Met Thr Gln Thr Pro Leu Ser Leu Pro Val Thr Pro Gly
1 5 10 15

Glu Pro Ala Ser Ile Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 248
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 248

Glu Ile Val Leu Thr Gln Ser Pro Ala Thr Leu Ser Leu Ser Pro Gly
1 5 10 15

Glu Arg Ala Thr Leu Ser Cys Lys Ser Ser Gln Ser Leu Leu Asp Ser
20 25 30

Gly Asn Gln Lys Asn Phe Leu Thr Trp Tyr Gln Gln Lys Pro Gly Lys
35 40 45

Ala Pro Lys Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 249
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 249

Glu Ile Val Leu Thr Gln Ser Pro Asp Phe Gln Ser Val Thr Pro Lys
1 5 10 15

Glu Lys Val Thr Ile Thr Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 250
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 250

Glu Ile Val Leu Thr Gln Ser Pro Ala Thr Leu Ser Leu Ser Pro Gly
1 5 10 15

Glu Arg Ala Thr Leu Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 251
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 251

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Asp Ser
20 25 30

Gly Asn Gln Lys Asn Phe Leu Thr Trp Tyr Leu Gln Lys Pro Gly Gln
35 40 45

Ser Pro Gln Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 252
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 252

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 253
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 253

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115
```

<210> SEQ ID NO 254
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 254

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Leu Tyr His Pro Ala
85 90 95

Thr Phe Gly Gln Gly Thr Lys Val Glu Ile Lys Arg
100 105

<210> SEQ ID NO 255
<211> LENGTH: 126
<212> TYPE: PRT
<213> ORGANISM: Artificial Sequence
<220> FEATURE:
<223> OTHER INFORMATION: Synthetic Sequence

<400> SEQUENCE: 255

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Asp Tyr Tyr
20 25 30

Ala Ile Gly Trp Phe Arg Gln Ala Pro Gly Lys Glu Arg Glu Trp Ala
35 40 45

Ser Ser Ile Ser Ser Ser Asp Gly Ser Thr Tyr Tyr Ala Asp Ser Val
50 55 60

Lys Gly Arg Phe Thr Ile Ser Arg Asp Asn Ala Lys Asn Thr Val Phe
65 70 75 80

Leu Gln Met Asn Ser Leu Lys Pro Glu Asp Thr Ala Val Tyr Ser Cys
85 90 95

Ala Ala Ser Gln Ala Pro Ile Thr Ile Ala Thr Met Met Lys Pro Phe
100 105 110

Tyr Asp Tyr Trp Gly Gln Gly Thr Gln Val Thr Val Ser Ser
115 120 125

<210> SEQ ID NO 256
<211> LENGTH: 123
<212> TYPE: PRT
<213> ORGANISM: Artificial Sequence
<220> FEATURE:
<223> OTHER INFORMATION: Synthetic Sequence

<400> SEQUENCE: 256

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Asp Tyr Tyr
20 25 30

Ala Lys Cys Trp Phe Arg Gln Ala Pro Gly Lys Glu Arg Glu Trp Val
35 40 45

Ser Cys Ile Ser Ser Ser Asp Gly Ser Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Phe Cys
85 90 95

```
Ala Ala Arg His Gly Gly Pro Leu Thr Val Glu Tyr Phe Phe Asp Tyr
            100                 105                 110

Trp Gly Gln Gly Thr Gln Val Thr Val Ser Ser
        115                 120


<210> SEQ ID NO 257
<211> LENGTH: 124
<212> TYPE: PRT
<213> ORGANISM: Artificial Sequence
<220> FEATURE:
<223> OTHER INFORMATION: Synthetic Sequence

<400> SEQUENCE: 257

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Tyr
            20                  25                  30

Ala Ile Gly Trp Phe Arg Gln Ala Pro Gly Lys Ala Arg Glu Gly Val
        35                  40                  45

Ser Cys Ile Ser Gly Gly Asp Asn Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Gly Gly Trp Lys Tyr Cys Ser Gly Tyr Asp Pro Glu Tyr Ile
            100                 105                 110

Tyr Trp Gly Gln Gly Thr Gln Val Thr Val Ser Ser
        115                 120


<210> SEQ ID NO 258
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 258

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ser Gln Tyr
            20                  25                  30

Asp Val Gly Trp Tyr Arg Gln Ala Pro Gly Lys Gln Arg Glu Leu Val
        35                  40                  45

Ala Phe Ser Ser Ser Gly Gly Arg Thr Ile Tyr Pro Asp Ser Val Lys
    50                  55                  60

Gly Arg Phe Thr Phe Ser Arg Asp Asn Thr Lys Asn Thr Val Tyr Leu
65                  70                  75                  80

Gln Met Thr Ser Leu Lys Pro Glu Asp Thr Ala Val Tyr Tyr Cys Lys
                85                  90                  95

Ile Asp Trp Tyr Leu Asn Ser Tyr Trp Gly Gln Gly Thr Gln Val Thr
            100                 105                 110

Val Ser Ser
        115


<210> SEQ ID NO 259
<211> LENGTH: 114
<212> TYPE: PRT
```

<213> ORGANISM: Artificial Sequence
<220> FEATURE:
<223> OTHER INFORMATION: Synthetic Sequence

<400> SEQUENCE: 259

Glu Val Gln Leu Val Glu Ser Gly Gly Gly Leu Val Gln Ala Gly Gly
1 5 10 15

Ser Leu Arg Leu Ser Cys Ala Ala Ser Gly Val Asp Ala Ser Asn Ser
20 25 30

Ala Met Gly Trp Tyr Arg Gln Ala Pro Gly Lys Gln Arg Glu Trp Val
35 40 45

Ala Arg Ile Thr Gly Gly Gly Leu Ile Ala Tyr Thr Asp Ser Val Lys
50 55 60

Gly Arg Phe Thr Ile Ser Arg Asp Asn Ala Lys Ser Thr Val Tyr Leu
65 70 75 80

Gln Met Asn Ser Leu Glu Pro Glu Asp Thr Ala Val Tyr Tyr Cys Asn
85 90 95

Thr Ile Asn Ser Arg Asp Gly Trp Gly Gln Gly Thr Gln Val Thr Val
100 105 110

Ser Ser

<210> SEQ ID NO 260
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 260

Glu Val Gln Leu Val Glu Ser Gly Gly Gly Leu Val Gln Ala Gly Gly
1 5 10 15

Ser Leu Thr Ile Ser Cys Ala Ala Ser Gly Ile Thr Phe Ser Asp Ser
20 25 30

Ile Val Ser Trp Tyr Arg Arg Ala Arg Gly Lys Gln Arg Glu Trp Val
35 40 45

Ala Gly Ile Ser Asn Gly Gly Thr Thr Lys Tyr Ala Glu Ser Val Leu
50 55 60

Gly Arg Phe Thr Ile Ser Arg Asp Asn Ala Lys Asn Asn Val Tyr Leu
65 70 75 80

Gln Met Asn Gly Leu Asn Pro Glu Asp Thr Ala Val Tyr Leu Cys Lys
85 90 95

Val Arg Gln Tyr Trp Gly Gln Gly Thr Gln Val Thr Val Ser Ser
100 105 110

<210> SEQ ID NO 261
<211> LENGTH: 123
<212> TYPE: PRT
<213> ORGANISM: Artificial Sequence
<220> FEATURE:
<223> OTHER INFORMATION: Synthetic Sequence

<400> SEQUENCE: 261

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Asp Tyr Tyr
20 25 30

Ala Lys Cys Trp Phe Arg Gln Ala Pro Gly Lys Glu Arg Glu Trp Val
35 40 45

Ser Cys Ile Ser Ser Ser Asp Gly Ser Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Phe Cys
85 90 95

Ala Ala Arg His Gly Gly Pro Leu Thr Val Glu Tyr Phe Phe Asp Tyr
100 105 110

Trp Gly Gln Gly Thr Gln Val Thr Val Ser Ser
115 120

<210> SEQ ID NO 262
<211> LENGTH: 130
<212> TYPE: PRT
<213> ORGANISM: Artificial Sequence
<220> FEATURE:
<223> OTHER INFORMATION: Synthetic Sequence

<400> SEQUENCE: 262

Glu Val Gln Leu Val Glu Ser Gly Gly Gly Leu Val Gln Ala Gly Gly
1 5 10 15

Ser Leu Arg Leu Ser Cys Ala Ala Ser Glu Ser Thr Val Leu Ile Asn
20 25 30

Ala Met Gly Trp Tyr Arg Gln Ala Pro Gly Lys Gln Arg Glu Leu Val
35 40 45

Ala Ser Ile Ser Ser Gly Gly Ser Thr Asn Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Asn
85 90 95

Ala Asp Val Tyr Pro Gln Asp Tyr Gly Leu Gly Tyr Val Glu Gly Lys
100 105 110

Val Tyr Tyr Gly His Asp Tyr Trp Gly Thr Gly Thr Leu Val Thr Val
115 120 125

Ser Ser
130

<210> SEQ ID NO 263
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 263

Glu Val Gln Leu Val Glu Ser Gly Gly Gly Leu Val Gln Ala Gly Gly
1 5 10 15

Ser Leu Arg Leu Ser Cys Ala Ala Ser Gly Ser Thr Phe Ser Asn Tyr
20 25 30

Val Ser Asn Tyr Ala Met Gly Trp Gly Arg Gln Ala Pro Gly Thr Gln
35 40 45

Arg Glu Leu Val Ala Ser Ile Ser Asn Gly Asp Thr Thr Asn Tyr Ala
50 55 60

Asp Ser Val Lys Gly Arg Phe Thr Ile Ser Arg Asp Asn Ala Lys Asn
65 70 75 80

Thr Val Tyr Leu Gln Met Asn Ser Leu Lys Pro Glu Asp Thr Ala Val
85 90 95

Tyr Tyr Cys Phe Glu His Gln Val Ala Gly Leu Thr Trp Gly Gln Gly
100 105 110

Thr Gln Val Thr Val Ser Ser
115

<210> SEQ ID NO 264
<211> LENGTH: 118
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid

<400> SEQUENCE: 264

Glu Val Gln Leu Val Glu Ser Gly Gly Gly Leu Val Gln Ala Gly Gly
1 5 10 15

Ser Leu Arg Leu Ser Cys Val Ala Ser Gly Xaa Ala Leu Lys Ile Xaa
20 25 30

Val Met Gly Trp Tyr Arg Gln Ala Pro Gly Lys Gln Arg Glu Leu Val
35 40 45

Ala Ala Ile Thr Ser Gly Gly Arg Thr Asn Tyr Ser Asp Ser Val Lys
50 55 60

Gly Arg Phe Thr Ile Ser Gly Asp Asn Ala Xaa Asn Thr Val Tyr Leu
65 70 75 80

Gln Met Asn Ser Leu Lys Ser Glu Asp Thr Ala Val Tyr Tyr Cys Arg
85 90 95

Glu Trp Asn Ser Gly Tyr Pro Pro Val Asp Tyr Trp Gly Gln Gly Thr
100 105 110

Gln Val Thr Val Ser Ser
115

<210> SEQ ID NO 265
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 265

Glu Val Gln Leu Val Glu Ser Gly Gly Gly Leu Val Gln Ala Gly Gly
1 5 10 15

Ser Leu Arg Leu Ser Cys Ala Ala Ser Gly Arg Thr Phe Ser Ser Gly
20 25 30

Thr Met Gly Trp Phe Arg Arg Ala Pro Gly Lys Glu Arg Glu Phe Val
35 40 45

Ala Ser Ile Pro Trp Ser Gly Gly Arg Thr Tyr Tyr Ala Asp Ser Val
50 55 60

Lys Asp Arg Phe Thr Ile Ser Arg Asp Asn Ala Gln Asn Thr Val Phe
65 70 75 80

Leu Gln Met Asn Ser Leu Lys Pro Glu Asp Thr Ala Val Tyr Tyr Cys

```
                85                  90                  95

Ala Phe Lys Glu Arg Ser Thr Gly Trp Asp Phe Ala Ser Trp Gly Gln
            100                 105                 110

Gly Ile Gln Val Thr Val Ser Ser
        115                 120


<210> SEQ ID NO 266
<211> LENGTH: 127
<212> TYPE: PRT
<213> ORGANISM: Artificial Sequence
<220> FEATURE:
<223> OTHER INFORMATION: Synthetic Sequence

<400> SEQUENCE: 266

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Leu Asp Tyr Tyr
            20                  25                  30

Gly Ile Gly Trp Phe Arg Gln Ala Pro Gly Lys Glu Arg Glu Gly Val
        35                  40                  45

Ser Phe Ile Ser Gly Ser Asp Gly Ser Thr Tyr Tyr Ala Glu Ser Val
    50                  55                  60

Lys Gly Arg Phe Thr Ile Ser Arg Asp Lys Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Trp Gly Pro Pro Ser Ile Ala Thr Met Thr Ser Tyr
            100                 105                 110

Glu Tyr Lys His Trp Gly Gln Gly Thr Gln Val Thr Val Ser Ser
        115                 120                 125


<210> SEQ ID NO 267
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ile Trp Leu Arg Arg Ala Pro Gly Lys Gly Phe Glu Trp Val
        35                  40                  45

Ser Thr Ile Asp Lys Asp Gly Asn Thr Asn Tyr Val Asp Ser Val Lys
    50                  55                  60

Gly Arg Phe Ala Val Ser Arg Asp Asn Thr Lys Asn Thr Leu Tyr Leu
65                  70                  75                  80

Gln Met Asn Ser Leu Lys Pro Glu Asp Thr Ala Met Tyr Tyr Cys Thr
                85                  90                  95

Lys His Gly Ser Ser Ala Arg Gly Gln Gly Thr Arg Val Thr Val Ser
            100                 105                 110

Ser


<210> SEQ ID NO 268
<211> LENGTH: 114
<212> TYPE: PRT
```

<213> ORGANISM: Artificial Sequence
<220> FEATURE:
<223> OTHER INFORMATION: Synthetic Sequence

<400> SEQUENCE: 268

Glu Val Gln Leu Val Glu Ser Gly Gly Gly Leu Val Glu Pro Gly Gly
1               5                   10                  15

Ser Leu Arg Leu Ser Cys Val Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Asn Ser Gly Gly Gly Ile Thr Tyr Arg Gly Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Glu
                85                  90                  95

Asn Gly Gly Ser Ser Tyr Arg Arg Gly Gln Gly Thr Gln Val Thr Val
            100                 105                 110

Ser Ser

<210> SEQ ID NO 269
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 269

Gln Val Gln Leu Val Gln Ser Gly Ala Glu Leu Lys Lys Pro Gly Ala
1               5                   10                  15

Ser Val Lys Met Ser Cys Lys Ala Ser Gly Tyr Thr Phe Thr Gly Tyr
            20                  25                  30

Thr Met His Trp Val Lys Gln Ala Pro Gly Gln Gly Leu Glu Trp Ile
        35                  40                  45

Gly Tyr Ile Asn Pro Arg Ser Gly Tyr Thr Glu Tyr Asn Gln Lys Phe
    50                  55                  60

Lys Asp Arg Thr Thr Leu Thr Ala Asp Lys Ser Thr Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Pro Trp Phe Ala Tyr Trp Gly Gln Gly Thr Leu Val Thr Val
            100                 105                 110

Ser Ser

<210> SEQ ID NO 270
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 270

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Gly Tyr
            20                  25                  30

Thr Met His Trp Val Lys Gln Ala Pro Gly Gln Gly Leu Glu Trp Ile

```
        35                  40                  45

Gly Tyr Ile Asn Pro Arg Ser Gly Tyr Thr Glu Tyr Asn Gln Lys Phe
    50                  55                  60

Lys Asp Arg Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Trp Phe Ala Tyr Trp Gly Gln Gly Thr Leu Val Thr Val
            100                 105                 110

Ser Ser


<210> SEQ ID NO 271
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 271

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Gly Tyr
            20                  25                  30

Thr Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Gln Lys Phe
    50                  55                  60

Lys Asp Arg Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Trp Phe Ala Tyr Trp Gly Gln Gly Thr Leu Val Thr Val
            100                 105                 110

Ser Ser


<210> SEQ ID NO 272
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 272

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Gln Lys Phe
    50                  55                  60

Lys Asp Arg Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Trp Phe Ala Tyr Trp Gly Gln Gly Thr Leu Val Thr Val
            100                 105                 110
```

Ser Ser

<210> SEQ ID NO 273
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 273

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Gln Lys Phe
    50                  55                  60

Lys Asp Arg Thr Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Trp Phe Ala Tyr Trp Gly Gln Gly Thr Leu Val Thr Val
            100                 105                 110

Ser Ser

<210> SEQ ID NO 274
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 274

Asp Ile Val Met Thr Gln Ser Pro Ala Ser Leu Thr Val Thr Pro Gly
1               5                   10                  15

Glu Lys Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Leu Glu Ile
            100                 105                 110

Lys

<210> SEQ ID NO 275
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 275

-continued

```
Asp Ile Val Met Thr Gln Ser Pro Ala Ser Leu Ser Val Thr Pro Gly
1               5                   10                  15

Glu Lys Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Leu Glu Ile
            100                 105                 110

Lys


<210> SEQ ID NO 276
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 276

Asp Ile Val Met Thr Gln Ser Pro Ala Phe Leu Ser Val Thr Pro Gly
1               5                   10                  15

Glu Lys Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Leu Glu Ile
            100                 105                 110

Lys


<210> SEQ ID NO 277
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 277

Asp Ile Val Met Thr Gln Ser Pro Ala Phe Leu Ser Val Thr Pro Gly
1               5                   10                  15

Glu Lys Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
```

```
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Leu Glu Ile
            100                 105                 110

Lys


<210> SEQ ID NO 278
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 278

Gly Gly Ser Gly Gly Ser Gly Gly Gly Gly Ser Gly Gly Gly Gly Ser
1               5                   10                  15


<210> SEQ ID NO 279
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 279

Gly Gly Gly Gly Ser
1               5


<210> SEQ ID NO 280
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: REPEAT
<222> LOCATION: (1)..(5)
<223> OTHER INFORMATION: (GGGGS)n (n=1-4)

<400> SEQUENCE: 280

Gly Gly Gly Gly Ser Gly Gly Gly Gly Ser Gly Gly Gly Gly Ser Gly
1               5                   10                  15

Gly Gly Gly Ser
            20


<210> SEQ ID NO 281
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 281

Gly Leu Tyr Gly Leu Tyr Gly Leu Tyr Gly Leu Tyr Gly Leu Tyr Gly
1               5                   10                  15

Leu Tyr Gly Leu Tyr Gly Leu Tyr
            20


<210> SEQ ID NO 282
<211> LENGTH: 18
<212> TYPE: PRT
<213> ORGANISM: Artificial Sequence
<220> FEATURE:
<223> OTHER INFORMATION: Synthetic Sequence
```

<400> SEQUENCE: 282

Gly Leu Tyr Gly Leu Tyr Gly Leu Tyr Gly Leu Tyr Gly Leu Tyr Gly
1 5 10 15

Leu Tyr

<210> SEQ ID NO 283
<211> LENGTH: 15
<212> TYPE: PRT
<213> ORGANISM: Artificial Sequence
<220> FEATURE:
<223> OTHER INFORMATION: Synthetic Sequence
<220> FEATURE:
<221> NAME/KEY: REPEAT
<222> LOCATION: (1)..(5)
<223> OTHER INFORMATION: (EAAAK)n (n=1-3)

<400> SEQUENCE: 283

Glu Ala Ala Ala Lys Glu Ala Ala Ala Lys Glu Ala Ala Ala Lys
1 5 10 15

<210> SEQ ID NO 284
<211> LENGTH: 27
<212> TYPE: PRT
<213> ORGANISM: Artificial Sequence
<220> FEATURE:
<223> OTHER INFORMATION: Synthetic Sequence
<220> FEATURE:
<221> NAME/KEY: REPEAT
<222> LOCATION: (2)..(6)
<223> OTHER INFORMATION: A(EAAAK)nA (n = 2-5)

<400> SEQUENCE: 284

Ala Glu Ala Ala Ala Lys Glu Ala Ala Ala Lys Glu Ala Ala Ala Lys
1 5 10 15

Glu Ala Ala Ala Lys Glu Ala Ala Ala Lys Ala
20 25

<210> SEQ ID NO 285
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 285

Ala Glu Ala Ala Ala Lys Glu Ala Ala Ala Lys Ala
1 5 10

<210> SEQ ID NO 286
<211> LENGTH: 46
<212> TYPE: PRT
<213> ORGANISM: Artificial Sequence
<220> FEATURE:
<223> OTHER INFORMATION: Synthetic Sequence

<400> SEQUENCE: 286

Ala Glu Ala Ala Ala Lys Glu Ala Ala Ala Lys Glu Ala Ala Ala Lys
1 5 10 15

Glu Ala Ala Ala Lys Ala Leu Glu Ala Glu Ala Ala Ala Lys Glu Ala
20 25 30

Ala Ala Lys Glu Ala Ala Ala Lys Glu Ala Ala Ala Lys Ala
35 40 45

<210> SEQ ID NO 287

<211> LENGTH: 5
<212> TYPE: PRT
<213> ORGANISM: Artificial Sequence
<220> FEATURE:
<223> OTHER INFORMATION: Synthetic Sequence

<400> SEQUENCE: 287

Pro Ala Pro Ala Pro
1 5

<210> SEQ ID NO 288
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 288

Lys Glu Ser Gly Ser Val Ser Ser Glu Gln Leu Ala Gln Phe Arg Ser
1 5 10 15

Leu Asp

<210> SEQ ID NO 289
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 289

Glu Gly Lys Ser Ser Gly Ser Gly Ser Glu Ser Lys Ser Thr
1 5 10

<210> SEQ ID NO 290
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 290

Gly Ser Ala Gly Ser Ala Ala Gly Ser Gly Glu Phe
1 5 10

<210> SEQ ID NO 291
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 291
gatgtgcagc tgcaggagtc tggrggagg 29

<210> SEQ ID NO 292
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 292
ggactagtgc ggccgctgga gacggtgacc tgggt 35

<210> SEQ ID NO 293
<211> LENGTH: 22

<212> TYPE: DNA
<213> ORGANISM: Artificial Sequence
<220> FEATURE:
<223> OTHER INFORMATION: Synthetic Sequence

<400> SEQUENCE: 293
tcacacagga aacagctatg ac 22

<210> SEQ ID NO 294
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 294
cgccagggtt ttcccagtca cgac 24

<210> SEQ ID NO 295
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 295

Gln Val Gln Leu Gln Glu Ser Gly Gly Gly
1 5 10

<210> SEQ ID NO 296
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 296

Met Glu Val Gly Trp Tyr Arg Ser Pro Phe Ser Arg Val Val His Leu
1 5 10 15

Tyr Arg Asn Gly Lys
20

<210> SEQ ID NO 297
<211> LENGTH: 399
<212> TYPE: DNA
<213> ORGANISM: Artificial Sequence
<220> FEATURE:
<223> OTHER INFORMATION: Synthetic polymer.

<400> SEQUENCE: 297
gatgtgcagc tggtggagtc tgggggagga ttggtgcagg ctggaggctc tctgagactc 60
tcctgtgcaa cctctggact gaccttgagt agctatcaca tgggctggta ccgccaggct 120
ccagggcggg agcgtgagtt tgtcgcgcaa attagctgga gtgatgatag cacatactat 180
gcggactccg tgaagggccg attcaccatc tccagagaca atgccaggaa cacggtgtat 240
ctgcagatga acaatctgaa acctgaggac acggccatct attactgtga tgcacgtaaa 300
gtaggtggtc cggactactg gggccagggg acccaggtca ccgtctccag cggccgctac 360
ccgtacgacg ttccggacta cggttccggc cgagcatag 399

<210> SEQ ID NO 298
<211> LENGTH: 399
<212> TYPE: DNA
<213> ORGANISM: Artificial Sequence -continued
<220> FEATURE:
<223> OTHER INFORMATION: Synthetic polymer.

<400> SEQUENCE: 298
gatgtgcagc tggtggagtc tgggggagga ttggtgcagg ctggaggctc tctgagactc 60
tcctgtgcaa cctctggact gaccttcagt agctattaca cgggctggta ccgccaggct 120
ccagggcggg agcgtgagtt tgtcgcgcaa attagctgga gtgatgatag cacatactat 180
gcggactccg tgaagggccg attcaccatc tccagagaca atgccaggaa cacggtgtat 240
ctgcagatga acaatctgaa acctggcgac acggccatct attactgtga tgcacgtaaa 300
gtaggtggtc cggactactg gggccagggg acccaggtca ccgtctccag cggccgctac 360
ccgtacgacg ttccggacta cggttccggc cgagcatag 399

<210> SEQ ID NO 299
<211> LENGTH: 399
<212> TYPE: DNA
<213> ORGANISM: Artificial Sequence
<220> FEATURE:
<223> OTHER INFORMATION: Synthetic polymer.

<400> SEQUENCE: 299
gatgtgcagc tggtggagtc tgggggagga ttggtgcagg ctggaggctc tctgagactc 60
tcctgtgcaa tctctggact gaccttcagt aggtatcaca tgggctggta ccgccaggct 120
ccagggcggg agcgtgagtt tgtcgcgcaa attacctgga gtgatggtac gacatactat 180
ccgggctccg tgaagggccg attcaccatc tccagagaca atgccaggaa cacggtgtat 240
ctgcagattg acaatctgaa acctgaggac acggccatct attactgtga tgcacgtaaa 300
gtaggtggtc ccgactactg gggccagggg acccaggtca ccgtctccag cggccgctac 360
ccgtacgacg ttccggacta cggttccggc cgagcatag 399

<210> SEQ ID NO 300
<211> LENGTH: 399
<212> TYPE: DNA
<213> ORGANISM: Artificial Sequence
<220> FEATURE:
<223> OTHER INFORMATION: Synthetic polymer.

<400> SEQUENCE: 300
gatgtgcagc tggtggagtc tgggggaggt tcggtgcagg ctggaggctc tctgagactc 60
tcctgtgcaa tctctggact gaccttcagt aactatcaca tgggctggta ccgccaggct 120
ccagggcggg agcgtgaatt tgtcgcgcaa attacctgga gtgacgctag tatatattat 180
gcgggctccg tgaagggccg attcaccatt tccagagaca atgtcaagaa catcgtgtat 240
ctgcagatcg acaatctgaa acctgaggac acggccatct attactgtga tgcacgtaaa 300
gtaggtggtc cggactactg gggccagggg acccaggtca ccgtctccag cggccgctac 360
ccgtacgacg ttccggacta cggttccggc cgagcatag 399

<210> SEQ ID NO 301
<211> LENGTH: 399
<212> TYPE: DNA
<213> ORGANISM: Artificial Sequence
<220> FEATURE:
<223> OTHER INFORMATION: Synthetic polymer.

<400> SEQUENCE: 301
caggtgcagc tggtggagtc tgggggagga ttggtgcagg ctggaggctc tcttacactc 60
tcctgtgcaa tctctggact gaccttcagt agctatcaca tgggctggta ccgccaggct 120
ccagggcggg agcgtgagtt tgtcgcgcag attacgtgga gtgacactag tatatattat 180
gcgggctccg tgaagggccg attcaccatt tccagagaca atgtcaagaa catcgtgtat 240
ctgcagatcg acaatctgaa acctgaggac acggccatct attactgtga tgcacgtaaa 300
gtaggtggtc cggactactg gggccagggg acccaggtca ccgtctccag cggccgctac 360
ccgtacgacg ttccggacta cggttccggc cgagcatag 399

<210> SEQ ID NO 302
<211> LENGTH: 399
<212> TYPE: DNA
<213> ORGANISM: Artificial Sequence
<220> FEATURE:
<223> OTHER INFORMATION: Synthetic polymer.

<400> SEQUENCE: 302
caggtgcagc tggtggagtc tgggggagga ttggtgcagg ctggaggctc tctgagactc 60
tcctgtgcaa cctctggact gaccttaagt agctattaca tagcctggta ccgccaggct 120
ccagggcggg agcgtgagtt tgtcgcgcaa attaggtgga gtgatgatag cacatactat 180
ccgggctccg tgaagggccg attcaccatc tccagagaca atgccaggaa cacggtgtat 240
ctgcggatgg acaatctgaa gcctgaggac acggccaggt attactgtga tgcacgtaaa 300
gtaggcgggc ccgactactg gggccagggg acccaggtca ccgtctccag cggccgctac 360
ccgtacgacg ttccggacta cggttccggc cgagcatag 399

<210> SEQ ID NO 303
<211> LENGTH: 393
<212> TYPE: DNA
<213> ORGANISM: Artificial Sequence
<220> FEATURE:
<223> OTHER INFORMATION: Synthetic polymer.

<400> SEQUENCE: 303
gatgtgcagc tggtggagtc tgggggagga ttggtgcagg ctgggggctc tctgagactc 60
tcctgtgcag cctctggacg cacctcaagt ccttatgtca cgggctggta ccgccagact 120
ccagggaagg agcgtgaacc tgtcgcgact gttagctggg gtggtgttac atactatgct 180
gactccgtga agggccgatt caccatctcc agagacaacg ccaagaacac ggtatatctg 240
caaatgaacg ccctgaaacc tgaggacacg gccatctatt actgtaatgt caatactttt 300
ggcaatgtct actggggcca ggggacccag gtcaccgtct ccagcggccg ctacccgtac 360
gacgttccgg actacggttc cggccgagca tag 393

<210> SEQ ID NO 304
<211> LENGTH: 399
<212> TYPE: DNA
<213> ORGANISM: Artificial Sequence
<220> FEATURE:
<223> OTHER INFORMATION: Synthetic polymer.

<400> SEQUENCE: 304
caggtgcagc tggtggagtc tgggggagag tcggtgcagg ctgggggctc tctgagactc 60
tcctgtgcag cctccggacg caccatcagt aactatgaca tggcgtggtc ccgccaggct 120
ccagggaagg agcgtgaatt tgtcgcacgt attagcggga gtggtgatag gacagactat 180
gcagactccg tgaagggccg attcaccatc tccagagaca acgccaagaa cacggtatat 240
ctgcaaatga acagcctgaa acctgaggac acggccatct ataactgtca gacccaaatc 300
tttgggtcgc ccaacttctc gggccagggg acccaggtca ccgtctccag cggccgctac 360
ccgtacgacg ttccggacta cggttccggc cgagcatag 399

<210> SEQ ID NO 305
<211> LENGTH: 399
<212> TYPE: DNA
<213> ORGANISM: Artificial Sequence
<220> FEATURE:
<223> OTHER INFORMATION: Synthetic polymer.

<400> SEQUENCE: 305
caggtgcagc tggtggagtc tgggggagga tcggtgcagg ctgggggctc tctgagactc 60
tcctgtgcag cctccggacg caccattagt aactatgaca tggcgtggtc ccgccaggct 120
ccagggaagg agcgtgaatt tgtcgcacgt attagcggga gtggtgatag gacagactat 180
gcagactccg tgaagggccg attcaccatc tccagagaca acgccaagaa cacggtatat 240
ctgcaaatga acagcctgaa acctgaggac acggccatct attactgtca gatccaagac 300
tttgggtcgc ccagcttctc gggccagggg acccaggtca ccgtctccag cggccgctac 360
ccgtacgacg ttccggacta cggttccggc cgagcatag 399

<210> SEQ ID NO 306
<211> LENGTH: 399
<212> TYPE: DNA
<213> ORGANISM: Artificial Sequence
<220> FEATURE:
<223> OTHER INFORMATION: Synthetic polymer.

<400> SEQUENCE: 306
gatgtgcagc tggtggagtc tgggggagga tcggtgcagg ctgggggctc tctgagactc 60
tcctgtgcag cctccgggcg caccatcagt aactatgaca tggcgtggtc ccgccaggct 120
ccagggaagg agcgtgaatt tgtcgcacgt attagcggga gtggtgatag gacagactat 180
gcagactccg tgaagggccg attcaccatc tccagagaca acgccaagaa cacggtatat 240
ctgcaaatga acagcctgaa acctgaggac acggccatct attactgtca gatccaagac 300
tttcggtcgc ccgacttctg gagccagggg acccaggtca ccgtctccag cggccgctac 360
ccgtacgacg ttccggacta cggttccggc cgagcatag 399

<210> SEQ ID NO 307
<211> LENGTH: 396
<212> TYPE: DNA
<213> ORGANISM: Artificial Sequence
<220> FEATURE:
<223> OTHER INFORMATION: Synthetic polymer.

<400> SEQUENCE: 307
caggtgcagc tggtggagtc tgggggagga ttggtgcagg ctggggactc tctgagactc 60
tcctgtgcag cctctggacg cacgttcact acctctctca tgcaatggca ccgccaggct 120
ccagggaagg agcgtgagtt tgtcgcgagt attacttgga gtactggtaa cacacactat 180
gcagactccg tgaagggccg attcaccatc tccagagaca acgccaggaa cacggtgtat 240
ctgcagatga acagcctgaa acctgaggac acggccatct atacttgtcg tgtattggct 300
attcatgggg actactgggg ccaggggacc caggtcaccg tctccagcgg ccgctacccg 360
tacgacgttc cggactacgg ttccggccga gcatag 396

<210> SEQ ID NO 308

<211> LENGTH: 393
<212> TYPE: DNA
<213> ORGANISM: Artificial Sequence
<220> FEATURE:
<223> OTHER INFORMATION: Synthetic polymer.

<400> SEQUENCE: 308
caggtgcagc tggtggagtc tgggggaggc ttggtgcacc ctggggggtc tctgagactc 60
tcctgtgcag cctctggaag tttctccagt atcaatgtca tgggctggta ccgccaggct 120
ccaggaaagg agcgcgagtt ggtcgcacgt attacgaatt tgggcttgcc aaactatgca 180
gactcagtga cgggccgatt caccatctcc agagacaacg ccaagaacac ggtgtatctg 240
caaatgaaca gcctgaaacc tgaggacacg gccgtctatt actgttactt agtagcacta 300
aaggctgaat actggggcca ggggacccag gtcaccgtct ccagcggccg ctacccgtac 360
gacgttccgg actacggttc cggccgagca tag 393

<210> SEQ ID NO 309
<211> LENGTH: 393
<212> TYPE: DNA
<213> ORGANISM: Artificial Sequence
<220> FEATURE:
<223> OTHER INFORMATION: Synthetic polymer.

<400> SEQUENCE: 309
caggtgcagc tggtggagtc tgggggaggc ttggtgcacc ctggggggtc tctgagactc 60
tcctgtgcag cctctggaag tatctccagt atcaatgtca tgggctggta ccgccaggct 120
ccaggaaagg agcgcgagtt ggtcgcacgt attacgaatt tgggtttgcc aaactatgca 180
gactggctga aggaccgatt caccatctcc agagacaacg ccaagaacac ggtgtatctg 240
caaatgaaca gcctgaaacc tgaggacacg gccgtctatt actgttactt agtagcacta 300
tcggctgaat actggggcca ggggacccag gtcaccgtct ccagcggccg ctacccgtac 360
gacgttccgg actacggttc cggccgagca tag 393

<210> SEQ ID NO 310
<211> LENGTH: 393
<212> TYPE: DNA
<213> ORGANISM: Artificial Sequence
<220> FEATURE:
<223> OTHER INFORMATION: Synthetic polymer.

<400> SEQUENCE: 310
caggtgcagc tggtggagtc tgggggaggc ttggtgcacc gtggggggtc tctgagactc 60
tcctgtgcag cctctggaag tatctccagt atcaatatca tgggctggta ccgccaggct 120
ccaggaaagg agcgcgagtt ggtcgcacgt attacgaata ttggtttgcc aaactatgca 180
gactccgtga agggccgatt caccatctcc agagacaacg ccaagagcac ggtgtatctg 240
caaatgaaca gcctgaacgc tgaggacacg gccgtctatt actgctactt agtagcacta 300
aaggctgaat actggggcca ggggacccag gtcaccgtct ccagcggccg ctacccgtac 360
gacgttccgg actacggttc cggccgagca tag 393

<210> SEQ ID NO 311
<211> LENGTH: 393
<212> TYPE: DNA
<213> ORGANISM: Artificial Sequence
<220> FEATURE:
<223> OTHER INFORMATION: Synthetic polymer.

<400> SEQUENCE: 311
caggtgcagc tggtggagtc tgggggaggc ttggtgcaac ctgggggtc tctgagactc 60 tcctgtgcag cctctggaag tatctccagt atcaatgtca tgggctggta ccgccaggct 120
ccaggaaagg agcgcgagct ggtcgcacgt attacgaatt tgggtttgcc aaactatgca 180
gactccgtgg agggccgatt taccatctcc agagataagg acgagaacac ggtgtatcta 240
gaaatgaaca cactgaaacc tgaggacacg gccgtctatt actgttactt agtaggactc 300
aaggctgaat actggggcca ggggacccag gtcaccgtct ccagcggccg ctacccgtac 360
gacgttccgg actacggttc cggccgagca tag 393

<210> SEQ ID NO 312
<211> LENGTH: 411
<212> TYPE: DNA
<213> ORGANISM: Artificial Sequence
<220> FEATURE:
<223> OTHER INFORMATION: Synthetic polymer.

<400> SEQUENCE: 312
caggtgcagc tggtggagtc tgggggaggc ttagtgcagc ctgggggtc tctgagactc 60 tcctgtgcag cctctggaag cagtgatagt atcaatgcca tgggctggta ccgccaggct 120
ccagggaagg agcgcgaatt ggtcgcggct atcactagtg gtggtagagt agtctattca 180
gactccgtga agggccgagg caccatctcc agagacaacg ccaagaacac ggtgtatctg 240
caaatagcca gcctgaaacc tgaggacacg gccgtctatt actgcaatgt aaaaacgaag 300
tcggcagttc tcttcggcgg catggactac tggggcaaag ggacccaggt caccgtctcc 360
agcggccgct acccgtacga cgttccggac tacggttccg gccgagcata g 411

<210> SEQ ID NO 313
<211> LENGTH: 393
<212> TYPE: DNA
<213> ORGANISM: Artificial Sequence
<220> FEATURE:
<223> OTHER INFORMATION: Synthetic polymer.

<400> SEQUENCE: 313
caggtgcagc tggtggagtc tgggggaggc ttggtgcagc ctgggggtc tctgagactc 60 tcctgtgcag cctctgtaag tatcttcagt atcaatgcca tgggctggta ccgccaggct 120
ccagggaagg agcgcgagtt ggtcgcagct atcactagtg gtggtagaac agcctatgca 180
gactccgtga agggccgatt caccatctcc agagacaact ccaagaacac ggtgtatctg 240
caaatggaca gcctgaaacc tgaggacacg gacgtctatt actgtaaagc gtatattcgc 300
ggcgaagact actggggcaa agggacccag gtcaccgtct ccagcggccg ctacccgtac 360
gacgttccgg actacggttc cggccgagca tag 393

<210> SEQ ID NO 314
<211> LENGTH: 393
<212> TYPE: DNA
<213> ORGANISM: Artificial Sequence
<220> FEATURE:
<223> OTHER INFORMATION: Synthetic polymer.

<400> SEQUENCE: 314
gatgtgcagc tggtggagtc tgggggaggc ttggtgcagc ctgggggtc tctgagactc 60 tcctgtgcag cctctggaag catcttcagt ctcaatgcca tgggctggta ccgccaggct 120
ccagggaagg agcgcgagtt ggtcgcacat attacgagtg atggtaggat agtgtatgca 180

```
gaccccgtga agggccgatt caccatctcc agagtcgacg gcaagaacat ggtgactctg    240

caaatgaaca gcctgaaacc tgaggacacg gccgtctatt actgtaatgc caaacattat    300

gcctcgaact actggggcca ggggacccag gtcaccgtct ccagcggccg ctacccgtac    360

gacgttccgg actacggttc cggccgagca tag                                 393
```

<210> SEQ ID NO 315
<211> LENGTH: 396
<212> TYPE: DNA
<213> ORGANISM: Artificial Sequence
<220> FEATURE:
<223> OTHER INFORMATION: Synthetic polymer.

<400> SEQUENCE: 315

```
caggtgcagc tggtggagtc tgggggagga ttggtgcagg ctggggactc tctgagactc     60

tcctgtgcag cctctgaacg caacttgaga atctatgaca tggcctggta tcgccaggct    120

ccagggaagg agcgggagta tgtcgcagtg attagttcga gtggagatag cacgcactat    180

tcagacttcg tgaagggccg gttcaccatc tcccgagaca acgccaagaa cacggtgtct    240

ttgcagatgg acagcctgaa acctgaggac acggccttct attattgtaa tgtaaattca    300

atacgacagt ggccctgggg ccaggggacc caggtcaccg tctccagcgg ccgctacccg    360

tacgacgttc cggactacgg ttccggccga gcatag                              396
```

<210> SEQ ID NO 316
<211> LENGTH: 396
<212> TYPE: DNA
<213> ORGANISM: Artificial Sequence
<220> FEATURE:
<223> OTHER INFORMATION: Synthetic polymer.

<400> SEQUENCE: 316

```
gatgtgcagc tggtggagtc tgggggagga ttggtgcagg ctggggactc tctgagactc     60

tcctgtgcag cctctgaacg caacttgaga atctatgaca tggcctggta tcgccaggct    120

ccagggaagg agcgggagta tgtcgcagtg attagttcga gtggagatag cacgcactat    180

tcagacttcg tgaagggccg gttcaccatc tcccgagaca acgccaagaa cacggtgtct    240

ttgcagatgg acagcctgaa acctgaggac acggccttct attattgtaa tgtaaatcag    300

atacgacagt ggccctgggg ccaggggacc caggtcaccg tctccagcgg ccgctacccg    360

tacgacgttc cggactacgg ttccggccga gcatag                              396
```

<210> SEQ ID NO 317
<211> LENGTH: 396
<212> TYPE: DNA
<213> ORGANISM: Artificial Sequence
<220> FEATURE:
<223> OTHER INFORMATION: Synthetic polymer.

<400> SEQUENCE: 317

```
caggtgcagc tggtggagtc tgggggagga ttggtgcagg ctggggactc tctgagactc     60

tcctgtacag cctctgaacg caacttgaga agctatgaca tggcctggtg gcgccaggct    120

ccagggaagg agcgggagta tgtcgcagtg attacgtcga gtggagatag cacgcactat    180

tcagacttcg tgaagggccg gttcaccatc tcccgagaca acgccaagaa cacggtgtct    240

ttgcagatgg acagcctgaa acctgaggac acggcctctt attattgtaa tgtcaatgcg    300

atacgacagt ggccctgggg ccaggggacc caggtcaccg tctccagcgg ccgctacccg    360

tacgacgttc cggactacgg ttccggccga gcatag                              396
```

<210> SEQ ID NO 318
<211> LENGTH: 384
<212> TYPE: DNA
<213> ORGANISM: Artificial Sequence
<220> FEATURE:
<223> OTHER INFORMATION: Synthetic polymer.

<400> SEQUENCE: 318
caggtgcagc tggtggagtc tgggggaggc ttggtgcagc ctgggggggtc tctgagactc 60 tcctgtgcag cctctggatt caccttcagc ggctatgtta tgagctgggt ccgccaggct 120
ccaggaaagg ggctcgagtg ggtcgcgagt attggtagtg gtggtggtta cccaagctat 180
acagactccg tggagggccg attcaccatc tccagagaca acgccaagaa cacgctttat 240
ctgcaaatga acaacttgaa acctgatgac acggccgtgt attactgcga aatgttgggc 300
aggaggggcc aggggaccca ggtcaccgtc tccagcggcc gctacccgta cgacgttccg 360
gactacggtt ccggccgagc atag 384

<210> SEQ ID NO 319
<211> LENGTH: 384
<212> TYPE: DNA
<213> ORGANISM: Artificial Sequence
<220> FEATURE:
<223> OTHER INFORMATION: Synthetic polymer.

<400> SEQUENCE: 319
caggtgcagc tggtggagtc tgggggaggc ttggtgcagc ctgggggggtc tctgagactc 60 tcctgtgcag cctctggatt caccttcagc ggctatgtta tgagctgggt ccgccaggct 120
ccaggaaagg ggctcgagtg ggtcgcgagt attggtagtg gtggtggtta cccaagctat 180
acaggctccg ttgagggccg attcaccatc tccagagaca acgccaagaa cacgctgtat 240
ctgctgatga acaacttgaa acctgatgac acggccgtgt attactgcga aatgttgggc 300
aggaggggcc aggggaccca ggtcaccgtc tccagcggcc gctacccgta cgacgttccg 360
gactacggtt ccggccgagc atag 384

<210> SEQ ID NO 320
<211> LENGTH: 384
<212> TYPE: DNA
<213> ORGANISM: Artificial Sequence
<220> FEATURE:
<223> OTHER INFORMATION: Synthetic polymer.

<400> SEQUENCE: 320
caggtgcagc tggtggagtc tgggggaggc ttggtgcagc ctgggggggtc tctgagactc 60 tcctgtgcag cctctggatt caccttcagt ggctatgtta tgagctgggt ccgccaggct 120
ccaggaaagg ggctcgagtg ggtcgcgagt attggtagtg gtggtggtta cccgagctat 180
acagactccg tggagggccg attcaccatc tccagagaca acgccaagaa cacgctgtat 240
ctgctaatgg acaacttgaa acctgatgac acggccgtgt attactgcga aatgttgggc 300
aggaggggcc aggggaccca ggtcaccgtc tccagcggcc gctacccgta cgacgttccg 360
gactacggtt ccggccgagc atag 384

<210> SEQ ID NO 321
<211> LENGTH: 384
<212> TYPE: DNA
<213> ORGANISM: Artificial Sequence
<220> FEATURE:

<223> OTHER INFORMATION: Synthetic polymer.

<400> SEQUENCE: 321
caggtgcagc tggtggagtc tgggggaggc ttggtgcagc ctggggggtc tctgagactc 60
tcctgtgcag cctctggatt caccttcagc ggctatgtta tgagctgggt ccgccaggct 120
ccaggaaagg ggctcgagtg ggtcgcgcat attggtagtg gtggtggata cccaagctat 180
acagactccg tgcagggccg attcaccatc tccagagaca acgccaagaa cactctgtat 240
ctgcaaatga acaacttgaa acctgaggac acggccgtgt attactgtga aatgctgggc 300
aggaggggcc aggggaccca ggtcaccgtc tccagcggcc gctacccgta cgacgttccg 360
gactacggtt ccggccgagc atag 384

<210> SEQ ID NO 322
<211> LENGTH: 384
<212> TYPE: DNA
<213> ORGANISM: Artificial Sequence
<220> FEATURE:
<223> OTHER INFORMATION: Synthetic polymer.

<400> SEQUENCE: 322
caggtgcagc tggtggagtc tgggggaggc ttggtgcagc ctggggggtc tctgagactc 60
tcctgtgcag cctctggatt caccttcagc ggctatgtta tgacctgggt ccgccaggct 120
ccaggaaagg ggctcgagtg ggtcgcgcac attggaagtg gtggtgggca cgcaacctat 180
acagactccg tcgagggccg attcaccatc tccagagaca acgccaagaa cacgctgtat 240
ctgcaaatga acaacttgaa agctgaggac acggccgtgt attactgtga attcttgggc 300
aggaggggcc aggggaccca ggtcaccgtc tccagcggcc gctacccgta cgacgttccg 360
gactacggtt ccggccgagc atag 384

<210> SEQ ID NO 323
<211> LENGTH: 384
<212> TYPE: DNA
<213> ORGANISM: Artificial Sequence
<220> FEATURE:
<223> OTHER INFORMATION: Synthetic polymer.

<400> SEQUENCE: 323
caggtgcagc tggtggagtc tgggggaggc ttggtgcagc ccggggggtc tctgagactc 60
tcctgtgcag cctccggatt taccttcagc ggctatctta tgagctgggt ccgccaggct 120
ccaggaaagg ggctcgagtg ggtcgcgact attggtagtg gtggtggtat cacaagctat 180
gcagactccg tgaagggccg attcaccatc tccagagaca acgccaagaa cacgctgtat 240
ctgcaaatga acaacttgaa acatgaagac acggccgtgt attactgtga aacagtgatc 300
aagcggggcc aggggaccca ggtcaccgtc tccagcggcc gctacccgta cgacgttccg 360
gactacggtt ccggccgagc atag 384

<210> SEQ ID NO 324
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 324

Gly Ser Ser Asp Ser Ile Asn Ala Met Gly
1 5 10

CLEC9A BINDING AGENTS

CROSS-REFERENCE TO RELATED APPLICATIONS

This application claims the benefit of U.S. Provisional Patent Application Nos. 62/291,769, filed Feb. 5, 2016; 62/335,880, filed May 13, 2016; 62/411,805, filed Oct. 24, 2016; 62/291,772, filed Feb. 5, 2016; 62/291,774, filed Feb. 5, 2016; 62/335,965, filed May 13, 2016; 62/291,776, filed Feb. 5, 2016; 62/335,968, filed May 13, 2016; 62/335,979, filed May 13, 2016; 62/336,030, filed May 13, 2016, 62/353, 607, filed Jun. 23, 2016; and 62/291,779, filed Feb. 5, 2016, the entire contents of all of which are herein incorporated by reference.

FIELD

The present invention relates, in part, to binding agents which bind Clec9A and their use as therapeutic and diagnostic agents.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ORN-012C1 ST25.txt, date recorded: Nov. 15, 2024; file size: 306, 152 bytes).

BACKGROUND

Dendritic cells (DCs) are antigen-presenting cells (APCs) equipped with the ability to induce primary immune responses and play an important role in various aspects of immunity. Activated dendritic cells are capable of recruiting additional immune cells such as macrophages, eosinophils, natural killer cells, and T cells such as natural killer T cells. Dendritic cells also capture antigens and present the antigens on their surfaces to activate T cells (e.g. cytotoxic T cells (CTLs).

Despite major advances in cancer treatment, cancer remains one of the leading causes of death globally. Hurdles in designing effective therapies include cancer immune evasion, in which cancer cells escape destructive immunity, as well as the toxicity of many conventional cancer treatments such as radiation therapy and chemotherapy, which significantly impacts a patient's ability to tolerate the therapy and/or impacts the efficacy of the treatment.

One mechanism by which cancers evade immune detection and destruction is by crippling dendritic cell functionality through prevention of dendritic cell (DC) recruitment and activation. Accordingly, there remains a need for cancer therapies that can effectively derail tumor evasion and enhance anti-tumor immunity as mediated, for example, by dendritic cells.

Multiple sclerosis (MS) is an autoimmune disease of the central nervous system with both autoimmune and neurodegenerative features. The most frequent form of MS is relapsing-remitting multiple sclerosis (RRMS), which is clinically characterized by recurring episodes of neurological symptoms. More than 2.3 million people worldwide suffer from MS, with 400,000 people in the U.S. alone having the disease.

Current pharmacological treatments for MS, including disease modifying therapies (DMTs), either modify or suppress the body's immune system. Many of the current pharmacological agents for MS are limited by incomplete efficacy, side effects and medical risks. These treatments have been shown to modestly reduce neurological relapses of the disease and, in some instances, incompletely slow the progression of neurological disability. Accordingly, there also remains a pressing need for improved MS treatments.

SUMMARY

In various aspects, the present invention relates to Clec9A binding agents having at least one targeting moiety that specifically binds to Clec9A. In various embodiments, these Clec9A binding agents bind to, but do not functionally modulate (e.g. partially or fully neutralize) Clec9A. Therefore, in various embodiments, the present Clec9A binding agents have use in, for instance, directly or indirectly recruiting a Clec9A-expressing cell to a site of interest while still allowing the Clec9A-expressing cell to signal via Clec9A (i.e. the binding of the Clec9A binding agent does not reduce or eliminate Clec9A signaling at the site of interest). In an embodiment, the targeting moiety is a single domain antibody (VHH, or NANOBODY). In various embodiments, the Clec9A binding agent further comprises a signaling agent, e.g., without limitation, an interferon, an interleukin, and a tumor necrosis factor, that may be modified to attenuate activity. In various embodiments, the Clec9A binding agent comprises additional targeting moieties that bind to other targets (e.g. antigens, receptor) of interest. In an embodiment, the other targets (e.g. antigens, receptor) of interest are present on tumor cells. In another embodiment, the other targets (e.g. antigens, receptor) of interest are present on immune cells. In some embodiments, the present Clec9A binding agent may directly or indirectly recruit an immune cell (e.g. a dendritic cell) to a site of action (such as, by way of non-limiting example, the tumor microenvironment). In some embodiments, the present Clec9A binding agent facilitates the presentation of antigens (e.g., tumor antigens) by dendritic cells.

In various embodiments, the present Clec9A binding agents find use in the treatment of various diseases or disorders such as cancer, infections, immune disorders, and other diseases and disorders, and the present invention encompasses various methods of treatment.

BRIEF DESCRIPTION OF DRAWINGS

FIG. 5 provides a table depicting that the 27 different VHHs belonged to 11 different groups. Members of groups 5 and 7 bind to both mouse and human Clec9A.

FIG. 10, panel B shows mean body weight as described in Example 7 for various treatments (including various fusions) also described in Example 7.

DETAILED DESCRIPTION

Figure 1:
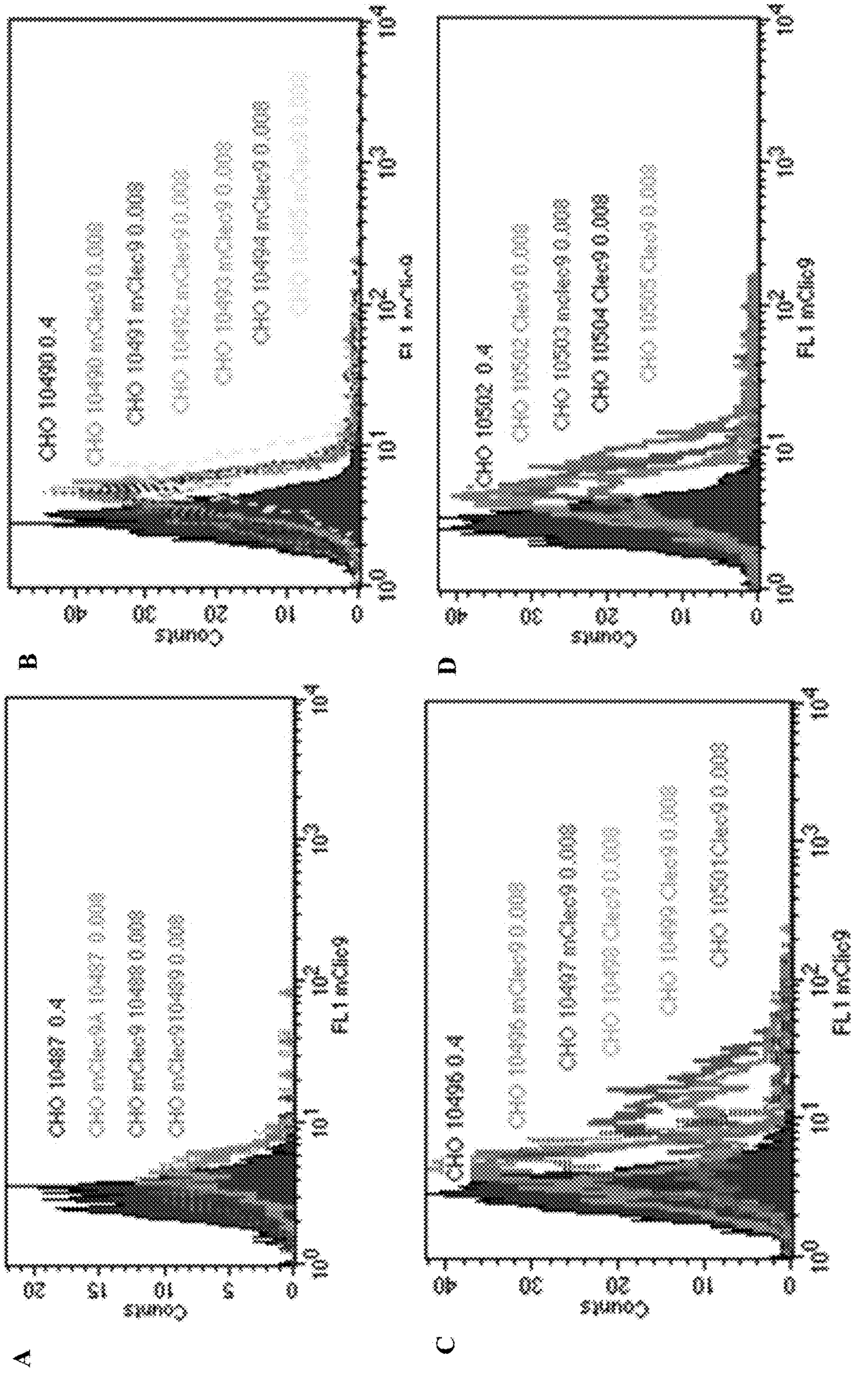
FIG. 1 panels A-F provide histograms showing the binding of six VHHs specific for mouse Clec9A to CHO cells transfected with Clec9A.
Figure 1:
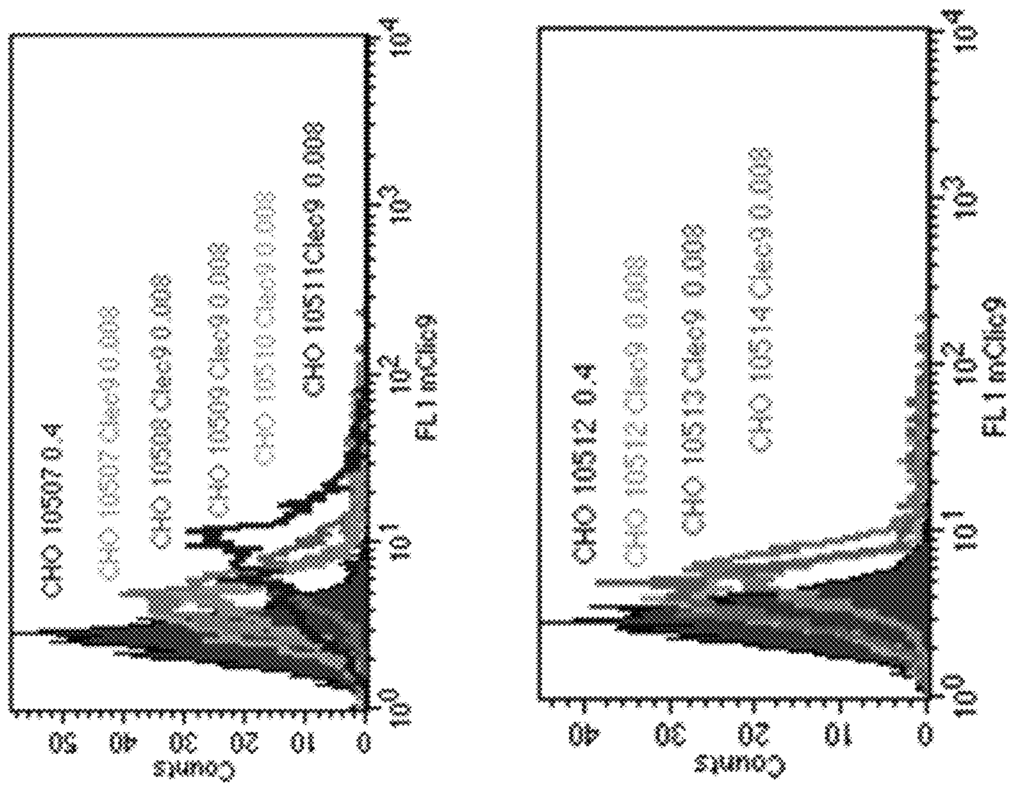

The present invention is based, in part, on the discovery of agents (e.g. antibodies such as, by way of non-limiting example, VHHs) that recognize and bind to Clec9A. In some embodiments, the present Clec9A binding agents are part of a chimeric or fusion protein with one or more targeting moieties and/or one or more signaling agents. In some embodiments, these Clec9A binding agents bind to, but do not functionally modulate Clec9A.

In some embodiments, these Clec9A binding agents may bind and directly or indirectly recruit immune cells to sites in need of therapeutic action (e.g. a tumor or tumor microenvironment). In some embodiments, the Clec9A binding agents enhance tumor antigen presentation for elicitation of effective antitumor immune response.

In some embodiments, the Clec9A binding agents modulate antigen presentation. In some embodiments, the Clec9A binding agents temper the immune response to avoid or reduce autoimmunity. In some embodiments, the Clec9A binding agents provide immunosuppression. In some embodiments, the Clec9A binding agents cause an increase a ratio of Tregs to CD8+ T cells and/or CD4+ T cells in a patient. In some embodiments, the present methods relate to reduction of auto-reactive T cells in a patient.

The present invention provides pharmaceutical compositions comprising the Clec9A binding agents and their use in the treatment of various diseases, including cancer, autoimmune, and/or neurodegenerative diseases.

Clec9A Binding Agents

In various embodiments, the present Clec9A binding agent is a protein-based agent capable of specific binding to Clec9A. In various embodiments, the present Clec9A binding agent is a protein-based agent capable of specific binding to Clec9A without functional modulation (e.g., partial or full neutralization) of Clec9A. Clec9A is a group V C-type lectin-like receptor (CTLR) expressed on the surface of a subset of dendritic cells (i.e., $BDCA_3$+ dendritic cells)

specialized for the uptake and processing of materials from dead cells. Clec9A recognizes a conserved component within nucleated and nonnucleated cells, exposed when cell membranes are damaged. Clec9A is expressed at the cell surface as a glycosylated dimer and can mediate endocytosis, but not phagocytosis. Clec9A possesses a cytoplasmic immunoreceptor tyrosine-based activation-like motif that can recruit Syk kinase and induce proinflammatory cytokine production (see Huysamen et al. (2008), JBC, 283:16693-701).

In various embodiments, the Clec9A binding agent of the invention comprises a targeting moiety having an antigen recognition domain that recognizes an epitope present on Clec9A. In an embodiment, the antigen-recognition domain recognizes one or more linear epitopes present on Clec9A. As used herein, a linear epitope refers to any continuous sequence of amino acids present on Clec9A. In another embodiment, the antigen-recognition domain recognizes one or more conformational epitopes present on Clec9A. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the Clec9A binding agent of the present invention may bind to the full-length and/or mature forms and/or isoforms and/or splice variants and/or fragments and/or any other naturally occurring or synthetic analogs, variants, or mutants of human Clec9A. In various embodiments, the Clec9A binding agent of the invention may bind to any forms of the human Clec9A, including monomeric, dimeric, heterodimeric, multimeric and associated forms. In an embodiment, the Clec9A binding agent binds to the monomeric form of Clec9A. In another embodiment, the Clec9A binding agent binds to a dimeric form of Clec9A. In a further embodiment, the Clec9A binding agent binds to glycosylated form of Clec9A, which may be either monomeric or dimeric.

In an embodiment, the present Clec9A binding agent comprises a targeting moiety with an antigen recognition domain that recognizes one or more epitopes present on human Clec9A. In an embodiment, the human Clec9A comprises the amino acid sequence of:

(SEQ ID NO: 1)

```
MHEEEIYTSLQWDSPAPDTYQKCLSSNKCSGACCLVMVISCVFCMGLLTA

SIFLGVKLLQVSTIAMQQQEKLIQQERALLNFTEWKRSCALQMKYCQAFM

QNSLSSAHNSSPCPNNWIQNRESCYYVSEIWSIWHTSQENCLKEGSTLLQ

IESKEEMDFITGSLRKIKGSYDYWVGLSQDGHSGRWLWQDGSSPSPGLLP

AERSQSANQVCGYVKSNSLLSSNCSTWKYFICEKYALRSSV.
```

In various embodiments, the present Clec9A binding agent comprises a targeting moiety capable of specific binding. In various embodiments, the Clec9A binding agent comprises a targeting moiety having an antigen recognition domain such as an antibody or derivatives thereof. In an embodiment, the Clec9A binding agent comprises a targeting moiety which is an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region (CO. The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the Clec9A binding agent comprises a targeting moiety which is an antibody derivative or format. In some embodiments, the present Clec9A binding agent comprises a targeting moiety which is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; an Affimer, a Transbody; an Anticalin; an AdNectin; an Affilin; a Microbody; a peptide aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a $F(ab')_2$, a peptide mimetic molecule, or a synthetic molecule, as described in U.S. Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the Clec9A binding agent comprises a targeting moiety which is a single-domain antibody, such as a VHH. The VHH may be derived from, for example, an organism that produces VHH antibody such as a camelid, a shark, or the VHH may be a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain ($V_HH$) and two constant domains (CH2 and CH3). VHHs are commercially available under the trademark of NANOBODIES. In an embodiment, the Clec9A binding agent comprises a VHH.

In some embodiments, the Clec9A binding agent comprises a targeting moiety which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In various embodiments, the Clec9A binding agent comprises a VHH having a variable domain comprising at least one CDR1, CDR2, and/or CDR3 sequences. In various embodiments, the Clec9A binding agent comprises a VHH having a variable region comprising at least one FR1, FR2, FR3, and FR4 sequences.

In exemplary embodiments, the CDR1 sequence is selected from:

GSISSINVMG; (SEQ ID NO: 2)

GSFSSINVMG; (SEQ ID NO: 3)

GSISSINIMG; (SEQ ID NO: 4)

GSISSINIMG; (SEQ ID NO: 5)

VSIFSINAMG; (SEQ ID NO: 6)

GSIFSLNAMG; (SEQ ID NO: 7)

GRTISNYDMA; (SEQ ID NO: 8)

GRTFTTSLMQ; (SEQ ID NO: 9)

ERNLRIYDMA; (SEQ ID NO: 10)

ERNLRSYDMA; (SEQ ID NO: 11)

GLTFSNYHMG; (SEQ ID NO: 12)

GLTFSSYHMG; (SEQ ID NO: 13)

GLTFSRYHMG; (SEQ ID NO: 14)

GLTLSSYYIA; (SEQ ID NO: 15)

GLTFSSYYTG; (SEQ ID NO: 16)

GLTLSSYHMG; (SEQ ID NO: 17)

GRTSSPYVTG; (SEQ ID NO: 18)

GFTFSGYVMS; (SEQ ID NO: 19)

GFTFSGYVMT; (SEQ ID NO: 20)
or

GFTFSGYLMS. (SEQ ID NO: 21)

In exemplary embodiments, the CDR2 sequence is selected from:

RITNLGLPNYADWLKD; (SEQ ID NO: 22)

RITNLGLPNYADSVTG; (SEQ ID NO: 23)

RITNIGLPNYADSVKG; (SEQ ID NO: 24)

RITNLGLPNYADSVEG; (SEQ ID NO: 25)

AITSGGRVVYSDSVKG; (SEQ ID NO: 26)

-continued

AITSGGRTAYADSVKG; (SEQ ID NO: 27)

HITSDGRIVYADPVKG; (SEQ ID NO: 28)

RISGSGDRTDYADSVKG; (SEQ ID NO: 29)

SITWSTGNTHYADSVKG; (SEQ ID NO: 30)

VISSSGDSTHYSDFVKG; (SEQ ID NO: 31)

VITSSGDSTHYSDFVKG; (SEQ ID NO: 32)

QITWSDASIYYAGSVKG; (SEQ ID NO: 33)

QITWSDTSIYYAGSVKG; (SEQ ID NO: 34)

QITWSDGTTYYPGSVKG; (SEQ ID NO: 35)

QIRWSDDSTYYPGSVKG; (SEQ ID NO: 36)

QISWSDDSTYYADSVKG; (SEQ ID NO: 37)

TVSWGGVTYYADSVKG; (SEQ ID NO: 38)

SIGSGGGYPSYTDSVEG; (SEQ ID NO: 39)

SIGSGGGYPSYTGSVEG; (SEQ ID NO: 40)

HIGSGGGYPSYTDSVQG; (SEQ ID NO: 41)

HIGSGGGHATYTDSVEG; (SEQ ID NO: 42)
or

TIGSGGGITSYADSVKG. (SEQ ID NO: 43)

In exemplary embodiments, the CDR3 sequence is selected from:

VALSAEY; (SEQ ID NO: 44)

VALKAEY; (SEQ ID NO: 45)

VGLKAEY; (SEQ ID NO: 46)

In an exemplary embodiment, the Clec9A binding agent comprises SEQ ID NO:2, SEQ ID NO:22, and SEQ ID NO:44.

In an exemplary embodiment, the Clec9A binding agent comprises SEQ ID NO:3, SEQ ID NO:23, and SEQ ID NO:45.

In an exemplary embodiment, the Clec9A binding agent comprises SEQ ID NO:4, SEQ ID NO:24, and SEQ ID NO:45.

In an exemplary embodiment, the Clec9A binding agent comprises SEQ ID NO:2, SEQ ID NO:25, and SEQ ID NO:46.

In an exemplary embodiment, the Clec9A binding agent comprises SEQ ID NO:5, SEQ ID NO:26, and SEQ ID NO:47.

In an exemplary embodiment, the Clec9A binding agent comprises SEQ ID NO:6, SEQ ID NO:27, and SEQ ID NO:48.

In an exemplary embodiment, the Clec9A binding agent comprises SEQ ID NO:7, SEQ ID NO:28, and SEQ ID NO:49.

In an exemplary embodiment, the Clec9A binding agent comprises SEQ ID NO:8, SEQ ID NO:29, and SEQ ID NO:50.

In an exemplary embodiment, the Clec9A binding agent comprises SEQ ID NO:8, SEQ ID NO:29, and SEQ ID NO:51.

In an exemplary embodiment, the Clec9A binding agent comprises SEQ ID NO:8, SEQ ID NO:29, and SEQ ID NO:52.

In an exemplary embodiment, the Clec9A binding agent comprises SEQ ID NO:9, SEQ ID NO:30, and SEQ ID NO:53.

In an exemplary embodiment, the Clec9A binding agent comprises SEQ ID NO:10, SEQ ID NO:31, and SEQ ID NO:54.

In an exemplary embodiment, the Clec9A binding agent comprises SEQ ID NO:10, SEQ ID NO:31, and SEQ ID NO:55.

In an exemplary embodiment, the Clec9A binding agent comprises SEQ ID NO:11, SEQ ID NO:32, and SEQ ID NO:56.

In an exemplary embodiment, the Clec9A binding agent comprises SEQ ID NO:12, SEQ ID NO:33, and SEQ ID NO:57.

In an exemplary embodiment, the Clec9A binding agent comprises SEQ ID NO:13, SEQ ID NO:34, and SEQ ID NO:57.

In an exemplary embodiment, the Clec9A binding agent comprises SEQ ID NO:14, SEQ ID NO:35, and SEQ ID NO:57.

In an exemplary embodiment, the Clec9A binding agent comprises SEQ ID NO:15, SEQ ID NO:36, and SEQ ID NO:57.

In an exemplary embodiment, the Clec9A binding agent comprises SEQ ID NO:16, SEQ ID NO:37, and SEQ ID NO:57.

In an exemplary embodiment, the Clec9A binding agent comprises SEQ ID NO:17, SEQ ID NO:37, and SEQ ID NO:57.

In an exemplary embodiment, the Clec9A binding agent comprises SEQ ID NO:18, SEQ ID NO:38, and SEQ ID NO:58.

In an exemplary embodiment, the Clec9A binding agent comprises SEQ ID NO:19, SEQ ID NO:39, and LGR.

In an exemplary embodiment, the Clec9A binding agent comprises SEQ ID NO:19, SEQ ID NO:40, and LGR.

In an exemplary embodiment, the Clec9A binding agent comprises SEQ ID NO:19, SEQ ID NO:41, and LGR.

In an exemplary embodiment, the Clec9A binding agent comprises SEQ ID NO:20, SEQ ID NO:42, and LGR.

In an exemplary embodiment, the Clec9A binding agent comprises SEQ ID NO:21, SEQ ID NO:43, and VIK.

In various exemplary embodiments, the Clec9A binding agent comprises an amino acid sequence selected from the following sequences:

R2CHCL8

(SEQ ID NO: 59)

QVQLVESGGGLVHPGGSLRLSCAASGSISSINVMGWYRQAPGKERELVAR

ITNLGLPNYADWLKDRFTISRDNAKNTVYLQMNSLKPEDTAVYYCYLVALS

AEYWGQGTQVTVSS;

R1CHCL50

(SEQ ID NO: 60)

QVQLVESGGGLVHPGGSLRLSCAASGSFSSINVMGWYRQAPGKERELVA

RITNLGLPNYADSVTGRFTISRDNAKNTVYLQMNSLKPEDTAVYYCYLVAL

KAEYWGQGTQVTVSS;

R1CHCL21

(SEQ ID NO: 61)

QVQLVESGGGLVHRGGSLRLSCAASGSISSINIMGWYRQAPGKERELVAR

ITNIGLPNYADSVKGRFTISRDNAKSTVYLQMNSLNAEDTAVYYCYLVAL

KAEYWGQGTQVTVSS;

R2CHCL87

(SEQ ID NO: 62)

QVQLVESGGGLVQPGGSLRLSCAASGSISSINVMGWYRQAPGKERELVA

RITNLGLPNYADSVEGRFTISRDKDENTVYLEMNTLKPEDTAVYYCYLVG

LKAEYWGQGTQVTVSS;

R2CHCL24

(SEQ ID NO: 63)

QVQLVESGGGLVQPGGSLRLSCAASGSSDSINAMGWYRQAPGKERELVA

AITSGGRVVYSDSVKGRGTISRDNAKNTVYLQIASLKPEDTAVYYCNVKT

KSAVLFGGMDYWGKGTQVTVSS;

R2CHCL38

(SEQ ID NO: 64)

QVQLVESGGGLVQPGGSLRLSCAASVSIFSINAMGWYRQAPGKERELVAA

ITSGGRTAYADSVKGRFTISRDNSKNTVYLQMDSLKPEDTDVYYCKAYIR

GEDYWGKGTQVTVSS;

R1CHCL16

(SEQ ID NO: 65)

DVQLVESGGGLVQPGGSLRLSCAASGSIFSLNAMGWYRQAPGKERELVA

HITSDGRIVYADPVKGRFTISRVDGKNMVTLQMNSLKPEDTAVYYCNAKH

YASNYWGQGTQVTVSS;

R2CHCL10

(SEQ ID NO: 66)

QVQLVESGGGSVQAGGSLRLSCAASGRTISNYDMAWSRQAPGKEREFVA

RISGSGDRTDYADSVKGRFTISRDNAKNTVYLQMNSLKPEDTAIYYCQIQ

DFGSPSFSGQGTQVTVSS;

R1CHCL34

(SEQ ID NO: 67)

DVQLVESGGGSVQAGGSLRLSCAASGRTISNYDMAWSRQAPGKEREFVA

RISGSGDRTDYADSVKGRFTISRDNAKNTVYLQMNSLKPEDTAIYYCQIQ

DFRSPDFWSQGTQVTVSS;

R1CHCL82

(SEQ ID NO: 68)

QVQLVESGGESVQAGGSLRLSCAASGRTISNYDMAWSRQAPGKEREFVA

RISGSGDRTDYADSVKGRFTISRDNAKNTVYLQMNSLKPEDTAIYNCQTQ

IFGSPNFSGQGTQVTVSS;

R2CHCL3

-continued (SEQ ID NO: 69)
QVQLVESGGGLVQAGDSLRLSCAASGRTFTTSLMQWHRQAPGKEREFVA

SITWSTGNTHYADSVKGRFTISRDNARNTVYLQMNSLKPEDTAIYTCRVL

AIHGDYWGQGTQVTVSS;

R2CHCL69

(SEQ ID NO: 70)
DVQLVESGGGLVQAGDSLRLSCAASERNLRIYDMAWYRQAPGKEREYVA

VISSSGDSTHYSDFVKGRFTISRDNAKNTVSLQMDSLKPEDTAFYYCNVN

QIRQWPWGQGTQVTVSS

R1CHCL56

(SEQ ID NO: 71)
QVQLVESGGGLVQAGDSLRLSCAASERNLRIYDMAWYRQAPGKEREYVA

VISSSGDSTHYSDFVKGRFTISRDNAKNTVSLQMDSLKPEDTAFYYCNVN

SIRQWPWGQGTQVTVSS;

R2CHCL32

(SEQ ID NO: 72)
QVQLVESGGGLVQAGDSLRLSCTASERNLRSYDMAWWRQAPGKEREYVA

VITSSGDSTHYSDFVKGRFTISRDNAKNTVSLQMDSLKPEDTASYYCNVN

AIRQWPWGQGTQVTVSS;

R2CHCL49

(SEQ ID NO: 73)
DVQLVESGGGSVQAGGSLRLSCAISGLTFSNYHMGWYRQAPGREREFVA

QITWSDASIYYAGSVKGRFTISRDNVKNIVYLQIDNLKPEDTAIYYCDAR

KVGGPDYWGQGTQVTVSS

R2CHCL53

(SEQ ID NO: 74)
QVQLVESGGGLVQAGGSLTLSCAISGLTFSSYHMGWYRQAPGREREFVA

QITWSDTSIYYAGSVKGRFTISRDNVKNIVYLQIDNLKPEDTAIYYCDAR

KVGGPDYWGQGTQVTVSS;

R2CHCL22

(SEQ ID NO :75)
DVQLVESGGGLVQAGGSLRLSCAISGLTFSRYHMGWYRQAPGREREFVA

QITWSDGTTYYPGSVKGRFTISRDNARNTVYLQIDNLKPEDTAIYYCDAR

KVGGPDYWGQGTQVTVSS;

R2CHCL25

(SEQ ID NO: 76)
QVQLVESGGGLVQAGGSLRLSCATSGLTLSSYYIAWYRQAPGREREFVAQ

IRWSDDSTYYPGSVKGRFTISRDNARNTVYLRMDNLKPEDTARYYCDARK

VGGPDYWGQGTQVTVSS;

R2CHCL18

(SEQ ID NO: 77)
DVQLVESGGGLVQAGGSLRLSCATSGLTFSSYYTGWYRQAPGREREFVA

QISWSDDSTYYADSVKGRFTISRDNARNTVYLQMNNLKPGDTAIYYCDAR

KVGGPDYWGQGTQVTVSS;

R1CHCL23

(SEQ ID NO: 78)
DVQLVESGGGLVQAGGSLRLSCATSGLTLSSYHMGWYRQAPGREREFVA

QISWSDDSTYYADSVKGRFTISRDNARNTVYLQMNNLKPEDTAIYYCDAR

KVGGPDYWGQGTQVTVSS;

R1CHCL27

-continued (SEQ ID NO: 79)
DVQLVESGGGLVQAGGSLRLSCAASGRTSSPYVTGWYRQTPGKEREPVA

TVSWGGVTYYADSVKGRFTISRDNAKNTVYLQMNALKPEDTAIYYCNVNT

FGNVYWGQGTQVTVSS;

R2CHCL13

(SEQ ID NO: 80)
QVQLVESGGGLVQPGGSLRLSCAASGFTFSGYVMSWVRQAPGKGLEWV

ASIGSGGGYPSYTDSVEGRFTISRDNAKNTLYLLMDNLKPDDTAVYYCE

MLGRRGQGTQVTVSS;

R2CHCL14

(SEQ ID NO: 81)
QVQLVESGGGLVQPGGSLRLSCAASGFTFSGYVMSWVRQAPGKGLEWV

ASIGSGGGYPSYTDSVEGRFTISRDNAKNTLYLQMNNLKPDDTAVYYCEM

LGRRGQGTQVTVSS

R2CHCL42

(SEQ ID NO: 82)
QVQLVESGGGLVQPGGSLRLSCAASGFTFSGYVMSWVRQAPGKGLEWV

ASIGSGGGYPSYTGSVEGRFTISRDNAKNTLYLLMNNLKPDDTAVYYCEM

LGRRGQGTQVTVSS;

R2CHCL41

(SEQ ID NO: 83)
QVQLVESGGGLVQPGGSLRLSCAASGFTFSGYVMSWVRQAPGKGLEWV

AHIGSGGGYPSYTDSVQGRFTISRDNAKNTLYLQMNNLKPEDTAVYYCEM

LGRRGQGTQVTVSS;

R2CHCL94

(SEQ ID NO: 84)
QVQLVESGGGLVQPGGSLRLSCAASGFTFSGYVMTWVRQAPGKGLEWV

AHIGSGGGHATYTDSVEGRFTISRDNAKNTLYLQMNNLKAEDTAVYYCEFL

GRRGQGTQVTVSS;
or

R2CHCL27

(SEQ ID NO: 85)
QVQLVESGGGLVQPGGSLRLSCAASGFTFSGYLMSWVRQAPGKGLEWV

ATIGSGGGITSYADSVKGRFTISRDNAKNTLYLQMNNLKHEDTAVYYCET

VIKRGQGTQVTVSS.

In various embodiments, the present invention contemplates the use of any natural or synthetic analogs, mutants, variants, alleles, homologs and orthologs (herein collectively referred to as "analogs") of the Clec9A binding agent of the invention as described herein. In various embodiments, the amino acid sequence of the Clec9A binding agent further includes an amino acid analog, an amino acid derivative, or other non-classical amino acids.

In various embodiments, the Clec9A binding agent comprises a targeting moiety comprising a sequence that is at least 60% identical to any one of the sequences disclosed herein. For example, the Clec9A binding agent may comprise a targeting moiety comprising a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of the sequences disclosed herein).

In various embodiments, the Clec9A binding agent comprises a targeting moiety comprising an amino acid sequence having one or more amino acid mutations with respect to any one of the sequences disclosed herein. In various embodiments, the Clec9A binding agent comprises a targeting moiety comprising an amino acid sequence having one, or two, or three, or four, or five, or six, or seen, or eight, or nine, or ten, or fifteen, or twenty amino acid mutations with respect to any one of the sequences disclosed herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids. Exemplary non-classical amino acids include, but are not limited to, selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general.

In various embodiments, the amino acid mutation may be in the CDRs of the targeting moiety (e.g., the CDR1, CDR2 or CDR3 regions). In another embodiment, amino acid alteration may be in the framework regions (FRs) of the targeting moiety (e.g., the FR1, FR2, FR3, or FR4 regions).

Modification of the amino acid sequences may be achieved using any known technique in the art e.g., site-directed mutagenesis or PCR based mutagenesis. Such techniques are described, for example, in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

In various embodiments, the mutations do not substantially reduce the present Clec9A binding agent's capability to specifically bind to Clec9A. In various embodiments, the mutations do not substantially reduce the present Clec9A binding agent's capability to specifically bind to Clec9A and without functionally modulating (e.g., partially or fully neutralizing) Clec9A.

In various embodiments, the binding affinity of the Clec9A binding agent of the invention for the full-length and/or mature forms and/or isoforms and/or splice variants and/or fragments and/or monomeric and/or dimeric forms and/or any other naturally occurring or synthetic analogs, variants, or mutants (including monomeric and/or dimeric forms) of human Clec9A may be described by the equilibrium dissociation constant ($K_D$). In various embodiments, the Clec9A binding agent comprises a targeting moiety that binds to the full-length and/or mature forms and/or isoforms and/or splice variants and/or fragments and/or any other naturally occurring or synthetic analogs, variants, or mutants (including monomeric and/or dimeric forms) of human Clec9A with a $K_D$ of less than about 1 uM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, or about 5 nM, or about 1 nM.

In various embodiments, the Clec9A binding agent comprises a targeting moiety that binds but does not functionally modulate (e.g., partially or fully neutralize) the antigen of interest, i.e., Clec9A. For instance, in various embodiments, the targeting moiety of the Clec9A binding agent simply targets the antigen but does not substantially functionally modulate (e.g. partially or fully inhibit, reduce or neutralize) a biological effect that the antigen has. In various embodiments, the targeting moiety of the Clec9A binding agent binds an epitope that is physically separate from an antigen site that is important for its biological activity (e.g. an antigen's active site).

Such binding without significant function modulation finds use in various embodiments of the present invention, including methods in which the present Clec9A binding agent is used to directly or indirectly recruit active immune cells to a site of need via an effector antigen. For example, in various embodiments, the present Clec9A binding agent may be used to directly or indirectly recruit dendritic cells via Clec9A to a tumor cell in a method of reducing or eliminating a tumor (e.g. the Clec9A binding agent may comprise a targeting moiety having an anti-Clec9A antigen recognition domain and a targeting moiety having a recognition domain (e.g. antigen recognition domain) directed against a tumor antigen or receptor). In such embodiments, it is desirable to directly or indirectly recruit dendritic cells but not to functionally modulate or neutralize the Clec9A activity. In these embodiments, Clec9A signaling is an important piece of the tumor reducing or eliminating effect.

In some embodiments, the Clec9A binding agent enhances antigen-presentation by dendritic cells. For example, in various embodiments, the present Clec9A binding agent directly or indirectly recruits dendritic cells via Clec9A to a tumor cell, where tumor antigens are subsequently endocytosed and presented on the dendritic cell for induction of potent humoral and cytotoxic T cell responses.

In other embodiments (for example, related to treating autoimmune or neurodegenerative disease), the Clec9A binding agent comprises a targeting moiety that binds and neutralizes the antigen of interest, i.e., Clec9A. For instance, in various embodiments, the present methods may inhibit or reduce Clec9A signaling or expression, e.g. to cause a reduction in an immune response.

Therapeutic Agents Comprising the Present Clec9A Binding Agents

Chimeras and Fusions with Signaling Agents

In various embodiments, the Clec9A binding agent of the invention is part of a chimera or fusion with one or more signaling agents. Accordingly, the present invention provides for chimeric or fusion proteins that include, for example, a targeting moiety against Clec9A and one or more signaling agents.

In various embodiments, the signaling agent is modified to have reduced affinity or activity for one or more of its receptors, which allows for attenuation of activity (inclusive of agonism or antagonism) and/or prevents non-specific signaling or undesirable sequestration of the chimeric or fusion protein. In various embodiments, the signaling agent is antagonistic in its wild type form and bears one or more mutations that attenuate its antagonistic activity. In various embodiments, the signaling agent is antagonistic due to one or more mutations, e.g. an agonistic signaling agent is converted to an antagonistic signaling agent and, such a converted signaling agent, optionally, also bears one or more mutations that attenuate its antagonistic activity (e.g. as described in WO 2015/007520, the entire contents of which are hereby incorporated by reference).

Accordingly, in various embodiments, the signaling agent is a modified (e.g. mutant) form of the signaling agent having one or more mutations. In various embodiments, the modifications (e.g. mutations) allow for the modified signaling agent to have one or more of attenuated activity such as one or more of reduced binding affinity, reduced endogenous activity, and reduced specific bioactivity relative to unmodified or unmutated, i.e. the wild type form of the signaling agent (e.g. comparing the same signaling agent in a wild type form versus a modified or mutant form). In some embodiments, the mutations which attenuate or reduce binding or affinity include those mutations which substantially reduce or ablate binding or activity. In some embodiments, the mutations which attenuate or reduce binding or affinity are different than those mutations which substantially reduce or ablate binding or activity. Consequentially, in various embodiments, the mutations allow for the signaling agent to have improved safety, e.g. reduced systemic toxicity, reduced side effects, and reduced off-target effects relative to unmutated, i.e. wild type, signaling agent (e.g. comparing the same signaling agent in a wild type form versus a modified (e.g. mutant) form).

As described herein, the agent may have improved safety due to one of more modifications, e.g. mutations. In various embodiments, improved safety means that the present chimeric protein provides lower toxicity (e.g. systemic toxicity and/or tissue/organ-associated toxicities); and/or lessened or substantially eliminated side effects; and/or increased tolerability, lessened or substantially eliminated adverse events; and/or reduced or substantially eliminated off-target effects; and/or an increased therapeutic window.

In various embodiments, the signaling agent is modified to have one or more mutations that reduce its binding affinity or activity for one or more of its receptors. In some embodiments, the signaling agent is modified to have one or more mutations that substantially reduce or ablate binding affinity or activity for the receptors. In some embodiments, the activity provided by the wild type signaling agent is agonism at the receptor (e.g. activation of a cellular effect at a site of therapy). For example, the wild type signaling agent may activate its receptor. In such embodiments, the mutations result in the modified signaling agent to have reduced or ablated activating activity at the receptor. For example, the mutations may result in the modified signaling agent to deliver a reduced activating signal to a target cell or the activating signal could be ablated. In some embodiments, the activity provided by the wild type signaling agent is antagonism at the receptor (e.g. blocking or dampening of a cellular effect at a site of therapy). For example, the wild type signaling agent may antagonize or inhibit the receptor. In these embodiments, the mutations result in the modified signaling agent to have a reduced or ablated antagonizing activity at the receptor. For example, the mutations may result in the modified signaling agent to deliver a reduced inhibitory signal to a target cell or the inhibitory signal could be ablated. In various embodiments, the signaling agent is antagonistic due to one or more mutations, e.g. an agonistic signaling agent is converted to an antagonistic signaling agent (e.g. as described in WO 2015/007520, the entire contents of which are hereby incorporated by reference) and, such a converted signaling agent, optionally, also bears one or more mutations that reduce its binding affinity or activity for one or more of its receptors or that substantially reduce or ablate binding affinity or activity for one or more of its receptors.

In some embodiments, the reduced affinity or activity at the receptor is restorable by attachment with one or more of the targeting moieties as described herein (e.g., targeting moiety against Clec9A or any other targeting moiety described herein). In other embodiments, the reduced affinity or activity at the receptor is not substantially restorable by the activity of one or more of the targeting moieties.

In various embodiments, the chimeric proteins of the present invention reduce off-target effects because their signaling agents have mutations that weaken or ablate binding affinity or activity at a receptor. In various embodiments, this reduction in side effects is observed relative with, for example, the wild type signaling agents. In various embodiments, the signaling agent is active on target cells because the targeting moiety(ies) compensates for the missing/insufficient binding (e.g., without limitation and/or avidity) required for substantial activation. In various embodiments, the modified signaling agent is substantially inactive en route to the site of therapeutic activity and has its effect substantially on specifically targeted cell types which greatly reduces undesired side effects.

In some embodiments, the signaling agent may include one or more mutations that attenuate or reduce binding or affinity for one receptor (i.e., a therapeutic receptor) and one or more mutations that substantially reduce or ablate binding or activity at a second receptor. In such embodiments, these mutations may be at the same or at different positions (i.e., the same mutation or multiple mutations). In some embodiments, the mutation(s) that reduce binding and/or activity at one receptor is different than the mutation(s) that substantially reduce or ablate at another receptor. In some embodiments, the mutation(s) that reduce binding and/or activity at one receptor is the same as the mutation(s) that substantially reduce or ablate at another receptor. In some embodiments, the present chimeric proteins have a modified signaling agent that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative to wild type signaling agent).

In some embodiments, the substantial reduction or ablation of binding or activity is not substantially restorable with a targeting moiety (e.g., a targeting moiety against Clec9A or any other targeting moiety described herein). In some embodiments, the substantial reduction or ablation of binding or activity is restorable with a targeting moiety. In various embodiments, substantially reducing or ablating binding or activity at a second receptor also may prevent deleterious effects that are mediated by the other receptor. Alternatively, or in addition, substantially reducing or ablating binding or activity at the other receptor causes the therapeutic effect to improve as there is a reduced or eliminated sequestration of the therapeutic chimeric proteins away from the site of therapeutic action. For instance, in some embodiments, this obviates the need of high doses of the present chimeric proteins that compensate for loss at the other receptor. Such ability to reduce dose further provides a lower likelihood of side effects.

In various embodiments, the modified signaling agent comprises one or more mutations that cause the signaling agent to have reduced, substantially reduced, or ablated affinity, e.g. binding (e.g. $K_D$) and/or activation (for instance, when the modified signaling agent is an agonist of its receptor, measurable as, for example, $K_A$ and/or $EC_{50}$) and/or inhibition (for instance, when the modified signaling agent is an antagonist of its receptor, measurable as, for example, $K_I$ and/or $IC_{50}$), for one or more of its receptors. In various embodiments, the reduced affinity at the immunomodulating agent's receptor allows for attenuation of activity (inclusive of agonism or antagonism). In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent.

In embodiments wherein the chimeric protein has mutations that reduce binding at one receptor and substantially reduce or ablate binding at a second receptor, the attenuation or reduction in binding affinity of a modified signaling agent for one receptor is less than the substantial reduction or ablation in affinity for the other receptor. In some embodiments, the attenuation or reduction in binding affinity of a modified signaling agent for one receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In various embodiments, substantial reduction or ablation refers to a greater reduction in binding affinity and/or activity than attenuation or reduction.

In various embodiments, the modified signaling agent comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent.

In some embodiments, the modified signaling agent comprises one or more mutations that cause the signaling agent to have reduced affinity for its receptor that is lower than the binding affinity of the targeting moiety(ies) for its(their) receptor(s). In some embodiments, this binding affinity differential is between signaling agent/receptor and targeting moiety/receptor on the same cell. In some embodiments, this binding affinity differential allows for the signaling agent, e.g. mutated signaling agent, to have localized, on-target effects and to minimize off-target effects that underlie side effects that are observed with wild type signaling agent. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

In various embodiments, the signaling agent is an immune-modulating agent, e.g. one or more of an interleukin, interferon, and tumor necrosis factor.

In some embodiments, the signaling agent is an interleukin or a modified interleukin, including for example IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; IL-36 or a fragment, variant, analogue, or family-member thereof. Interleukins are a group of multi-functional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. Interleukin activity can be determined using assays known in the art: Matthews et al., in *Lymphokines and Interferons: A Practical Approach*, Clemens et al., eds, IRL Press, Washington, D.C. 1987, pp. 221-225; and Orencole & Dinarello (1989) Cytokine 1, 14-20.

In some embodiments, the signaling agent is an interferon or a modified version of an interferon such as interferon types I, II, and III. Illustrative interferons, including for example, interferon-α-1, 2, 4, 5, 6, 7, 8, 10, 13, 14, 16, 17, and 21, interferon-β and interferon-γ, interferon κ, interferon ε, interferon τ, and interferon $\overline{\omega}$.

In some embodiments, the signaling agent is a tumor necrosis factor (TNF) or a modified version of a tumor necrosis factor (TNF) or a protein in the TNF family, including but not limited to, TNF-α, TNF-β, LT-β, CD40L, CD27L, CD30L, FASL, 4-1BBL, OX40L, and TRAIL.

The amino acid sequences of the wild type signaling agents described herein are well known in the art. Accordingly, in various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the modified signaling agent comprises an amino acid sequence having one or more amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions, as described elsewhere herein.

In various embodiments, the substitutions may also include non-classical amino acids as described elsewhere herein.

As described herein, the modified signaling agents bear mutations that affect affinity and/or activity at one or more receptors. The receptors of any signaling agents, as described herein, are known in the art.

Illustrative mutations which provide reduced affinity and/or activity (e.g. agonistic) at a receptor are found in WO 2013/107791 (e.g. with regard to interferons), WO 2015/007542 (e.g. with regard to interleukins), and WO 2015/007903 (e.g. with regard to TNF), the entire contents of each of which are hereby incorporated by reference. Illustrative mutations which provide reduced affinity and/or activity (e.g. antagonistic) at a receptor are found in WO 2015/007520, the entire contents of which are hereby incorporated by reference.

In an embodiment, the modified signaling agent is interferon α. In such embodiments, the modified IFN-α agent has reduced affinity and/or activity for the IFN-α/β receptor (IFNAR), i.e., IFNAR1 and/or IFNAR2 chains. In some embodiments, the modified IFN-α agent has substantially reduced or ablated affinity and/or activity for the IFN-α/β receptor (IFNAR), i.e., IFNAR1 and/or IFNAR2 chains.

Mutant forms of interferon α are known to the person skilled in the art. In an illustrative embodiment, the modified signaling agent is the allelic form IFN-α2a having the amino acid sequence of:

```
IFN-α2a:
                                              (SEQ ID NO: 86)
CDLPQTHSLGSRRTLMLLAQMRKISLFSCLKDRHDFGFPQEEFGNQFQKA

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE.
```

In an illustrative embodiment, the modified signaling agent is the allelic form IFN-α2b having the amino acid sequence of (which differs from IFN-α2a at amino acid position 23):

```
IFN-α2b:
                                              (SEQ ID NO: 87)
CDLPQTHSLGSRRTLMLLAQMRRISLFSCLKDRHDFGFPQEEFGNQFQKA

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE.
```

In some embodiments, said IFN-α2 mutant (IFN-α2a or IFN-α2b) is mutated at one or more amino acids at positions 144-154, such as amino acid positions 148, 149 and/or 153. In some embodiments, the IFN-α2 mutant comprises one or more mutations selected from L153A, R149A, and M148A. Such mutants are described, for example, in WO2013/107791 and Piehler et al., (2000) J. Biol. Chem, 275:40425-33, the entire contents of all of which are hereby incorporated by reference.

In some embodiments, the IFN-α2 mutants have reduced affinity and/or activity for IFNAR1. In some embodiments, the IFN-α2 mutant comprises one or more mutations selected from F64A, N65A, T69A, L80A, Y85A, and Y89A, as described in WO2010/030671, the entire contents of which is hereby incorporated by reference.

In some embodiments, the IFN-α2 mutant comprises one or more mutations selected from K133A, R144A, R149A, and L153A as described in WO2008/124086, the entire contents of which is hereby incorporated by reference.

In some embodiments, the IFN-α2 mutant comprises one or more mutations selected from R120E and R120E/K121E, as described in WO2015/007520 and WO2010/030671, the entire contents of which are hereby incorporated by reference. In such embodiments, said IFN-α2 mutant antagonizes wildtype IFN-α2 activity. In such embodiments, said mutant IFN-α2 has reduced affinity and/or activity for IFNAR1 while affinity and/or activity of IFNR2 is retained.

In some embodiments, the human IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2. In an embodiment, the human IFN-α2 mutant comprises R120E and L153A.

In some embodiments, the human IFN-α2 mutant comprises one or more mutations selected from, L15A, A19W, R22A, R23A, L26A, F27A, L30A, L30V, K31A, D32A, R33K, R33A, R33Q, H34A, D35A, Q40A, D114R, L117A, R120A, R125A, K134A, R144A, A145G, A145M, M148A, R149A, S152A, L153A, and N156A as disclosed in WO 2013/059885, the entire disclosures of which are hereby incorporated by reference. In some embodiments, the human IFN-α2 mutant comprises the mutations H57Y, E58N, Q61S, and/or L30A as disclosed in WO 2013/059885. In some embodiments, the human IFN-α2 mutant comprises the mutations H57Y, E58N, Q61S, and/or R33A as disclosed in WO 2013/059885. In some embodiments, the human IFN-α2 mutant comprises the mutations H57Y, E58N, Q61S, and/or M148A as disclosed in WO 2013/059885. In some embodiments, the human IFN-α2 mutant comprises the mutations H57Y, E58N, Q61S, and/or L153A as disclosed in WO 2013/059885. In some embodiments, the human IFN-α2 mutant comprises the mutations N65A, L80A, Y85A, and/or Y89A as disclosed in WO 2013/059885. In some embodiments, the human IFN-α2 mutant comprises the mutations N65A, L80A, Y85A, Y89A, and/or D114A as disclosed in WO 2013/059885.

In an embodiment, the modified signaling agent is interferon β. In such embodiments, the modified interferon β agent has reduced affinity and/or activity for the IFN-α/β receptor (IFNAR), i.e., IFNAR1 and/or IFNAR2 chains. In some embodiments, the modified interferon β agent has substantially reduced or ablated affinity and/or activity for the IFN-α/β receptor (IFNAR), i.e., IFNAR1 and/or IFNAR2 chains.

In an embodiment, the modified signaling agent is interferon γ. In such embodiments, the modified interferon γ agent has reduced affinity and/or activity for the interferon-gamma receptor (IFNGR), i.e., IFNGR1 and IFNGR2 chains. In some embodiments, the modified interferon γ agent has substantially reduced or ablated affinity and/or activity for the interferon-gamma receptor (IFNGR), i.e., IFNGR1 and/or IFNGR2 chains.

In an embodiment, the modified signaling agent is TNF-α. TNF is a pleiotropic cytokine with many diverse functions, including regulation of cell growth, differentiation, apoptosis, tumorigenesis, viral replication, autoimmunity, immune cell functions and trafficking, inflammation, and septic shock. It binds to two distinct membrane receptors on target cells: TNFR1 (p55) and TNFR2 (p75). TNFR1 exhibits a very broad expression pattern whereas TNFR2 is expressed preferentially on certain populations of lymphocytes, Tregs, endothelial cells, certain neurons, microglia, cardiac myocytes and mesenchymal stem cells. Very distinct biological pathways are activated in response to receptor activation, although there is also some overlap. As a general rule, without wishing to be bound by theory, TNFR1 signaling is associated with induction of apoptosis (cell death) and TNFR2 signaling is associated with activation of cell survival signals (e.g. activation of NFkB pathway). Administration of TNF is systemically toxic, and this is largely due to TNFR1 engagement. However, it should be noted that activation of TNFR2 is also associated with a broad range of activities and, as with TNFR1, in the context of developing TNF based therapeutics, control over TNF targeting and activity is important.

In some embodiments, the modified signaling agent has reduced affinity and/or activity for TNFR1 and/or TNFR2. In some embodiments, the modified signaling agent has substantially reduced or ablated affinity and/or activity for TNFR1 and/or TNFR2. TNFR1 is expressed in most tissues, and is involved in cell death signaling while, by contrast, TNFR2 is involved in cell survival signaling. Accordingly in embodiments directed to methods of treating cancer, the modified signaling agent has reduced affinity and/or activity for TNFR1 and/or substantially reduced or ablated affinity and/or activity for TNFR2. In these embodiments, the chimeric proteins may be targeted to a cell for which apoptosis is desired, e.g. a tumor cell or a tumor vasculature endothelial cell. In embodiments directed to methods of promoting cell survival, for example, in neurogenesis for the treatment of neurodegenerative disorders, the modified signaling agent has reduced affinity and/or activity for TNFR2 and/or substantially reduced or ablated affinity and/or activity for TNFR1. Stated another way, the present chimeric proteins, in some embodiments, comprise modified TNF-α agent that allows of favoring either death or survival signals.

In some embodiments, the chimeric protein has a modified TNF having reduced affinity and/or activity for TNFR1 and/or substantially reduced or ablated affinity and/or activity for TNFR2. Such a chimera, in some embodiments, is a more potent inducer of apoptosis as compared to a wild type TNF and/or a chimera bearing only mutation(s) causing reduced affinity and/or activity for TNFR1. Such a chimera, in some embodiments, finds use in inducing tumor cell death or a tumor vasculature endothelial cell death (e.g. in the treatment of cancers). Also, in some embodiments, these chimeras avoid or reduce activation of $T_{reg}$ cells via TNFR2, for example, thus further supporting TNFR1-mediated antitumor activity in vivo.

In some embodiments, the chimeric protein has a modified TNF having reduced affinity and/or activity for TNFR2 and/or substantially reduced or ablated affinity and/or activity for TNFR1. Such a chimera, in some embodiments, is a more potent activator of cell survival in some cell types, which may be a specific therapeutic objective in various disease settings, including without limitation, stimulation of neurogenesis. In addition, such a TNFR2-favoring chimeras also are useful in the treatment of autoimmune diseases (e.g. Crohn's, diabetes, MS, colitis etc. and many others described herein). In some embodiments, the chimera is targeted to auto-reactive T cells. In some embodiments, the chimera promotes $T_{reg}$ cell activation and indirect suppression of cytotoxic T cells.

In some embodiments, the chimera causes the death of auto-reactive T cells, e.g. by activation of TNFR2 and/or avoidance TNFR1 (e.g. a modified TNF having reduced affinity and/or activity for TNFR2 and/or substantially reduced or ablated affinity and/or activity for TNFR1). Without wishing to be bound by theory these auto-reactive T cells, have their apoptosis/survival signals altered e.g. by NF-κB pathway activity/signaling alterations.

In some embodiments, a TNFR-2 based chimera has additional therapeutic applications in diseases, including various autoimmune diseases, heart diseases, de-myelinating and neurodegenerative disorders, and infectious disease, among others.

In an embodiment, the wild type TNF-α has the amino acid sequence of:

```
TNF-α
                                        (SEQ ID NO: 88)
VRSSSRTPSDKPVAHVVANPQAEGQLQWLNRRANALLANGVELRDNQLV

VPSEGLYLIYSQVLFKGQGCPSTHVLLTHTISRIAVSYQTKVNLLSAIK

SPCQRETPEGAEAKPWYEPIYLGGVFQLEKGDRLSAEINRPDYLDFAES

GQVYFGIIAL.
```

In such embodiments, the modified TNF-α agent has mutations at one or more amino acid positions 29, 31, 32, 84, 85, 86, 87, 88, 89, 145, 146 and 147 which produces a modified TNF-α with reduced receptor binding affinity. See, for example, U.S. Pat. No. 7,993,636, the entire contents of which are hereby incorporated by reference.

In some embodiments, the modified TNF-α moiety has mutations at one or more amino acid positions R32, N34, Q67, H73, L75, T77, S86, Y87, V91, I97, T105, P106, A109, P113, Y115, E127, N137, D143, and A145, as described, for example, in WO/2015/007903, the entire contents of which is hereby incorporated by reference (numbering according to the human TNF sequence, Genbank accession number BAG70306, version BAG70306.1 GI: 197692685). In some embodiments, the modified TNF-α moiety has substitution mutations selected from R32G, N34G, Q67G, H73G, L75G, L75A, L75S, T77A, S86G, Y87Q, Y87L, Y87A, Y87F, V91G, V91A, I97A, I97Q, I97S, T105G, P106G, A109Y, P113G, Y115G, Y115A, E127G, N137G, D143N, A145G and A145T. In an embodiment, the TNF-α moiety has a mutation selected from Y87Q, Y87L, Y87A, and Y87F. In another embodiment, the TNF-α moiety has a mutation selected from I97A, I97Q, and I97S. In a further embodiment, the TNF-α moiety has a mutation selected from Y115A and Y115G.

In some embodiments, the modified TNF-α agent has one or more mutations selected from N39Y, S147Y, and Y87H, as described in WO2008/124086, the entire contents of which is hereby incorporated by reference.

In some embodiments, the modified human TNF-α moiety has mutations that provide receptor selectivity as described in PCT/IB2016/001668, the entire contents of which are hereby incorporated by reference. In some embodiments, the mutations to TNF are TNF-R1 selective. In some embodiments, the mutations to TNF which are TNF-R1 selective are at one or more of positions R32, S86, and E146. In some embodiments, the mutations to TNF which are TNF-R1 selective are one or more of R32W, S86T, and E146K. In some embodiments, the mutations to TNF which are TNF-R1 selective are one or more of R32W, R32W/S86T, R32W/E146K and E146K. In some embodiments, the mutations to TNF are TNF-R2 selective. In some embodiments, the mutations to TNF which are TNF-R2 selective are at one or more of positions A145, E146, and S147. In some embodiments, the mutations to TNF which are TNF-R2 selective are one or more of A145T, A145R, E146D, and S147D. In some embodiments, the mutations to TNF which are TNF-R2 selective are one or more of A145R, A145T/S147D, and A145T/E146D/S 147D.

In an embodiment, the modified signaling agent is TNF-β. TNF-β can form a homotrimer or a heterotrimer with LT-β (LT-α1β2). In some embodiments, the modified signaling agent has substantially reduced or ablated affinity and/or activity for TNFR1 and/or TNFR2 and/or herpes virus entry mediator (HEVM) and/or LT-βR.

In an embodiment, the wild type TNF-β has the amino acid sequence of:

```
TNF-beta
                                        (SEQ ID NO: 89)
LPGVGLTPSAAQTARQHPKMHLAHSNLKPAAHLIGDPSKQNSLLWRANTD

RAFLQDGFSLSNNSLLVPTSGIYFVYSQWFSGKAYSPKATSSPLYLAHEV

QLFSSQYPFHVPLLSSQKMVYPGLQEPWLHSMYHGAAFQLTQGDQLSTH

TDGIPHLVLSPSTVFFGAFAL.
```

In such embodiments, the modified TNF-β agent may comprise mutations at one or more amino acids at positions 106-113, which produce a modified TNF-β with reduced receptor binding affinity to TNFR2. In an embodiment, the modified signaling agent has one or more substitution mutations at amino acid positions 106-113. In illustrative embodiments, the substitution mutations are selected from Q107E, Q107D, S106E, S106D, Q107R, Q107N, Q107E/S106E, Q107E/S106D, Q107D/S106E, and Q107D/S106D. In another embodiment, the modified signaling agent has an insertion of about 1 to about 3 amino acids at positions 106-113.

In some embodiments, the modified agent is a TNF family member (e.g. TNF-alpha, TNF-beta) which can be a single chain trimeric version as described in WO 2015/007903, the entire contents of which are incorporated by reference.

In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR1. In these embodiments, the modified agent is a TNF family member (e.g. TNF-alpha, TNF-beta) which also, optionally, has substantially reduced or ablated affinity and/or activity for TNFR2. In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR2. In these embodiments, the modified agent is a TNF family member (e.g. TNF-alpha, TNF-beta) which also, optionally, has substantially reduced or ablated affinity and/or activity for TNFR1. The constructs of such embodiments find use in, for example, methods of dampening TNF response in a cell specific manner. In some embodiments, the antagonistic TNF family member (e.g. TNF-alpha, TNF-beta) is a single chain trimeric version as described in WO 2015/007903.

In an embodiment, the modified signaling agent is TRAIL. In some embodiments, the modified TRAIL agent has reduced affinity and/or activity for DR4 (TRAIL-RI) and/or DR5 (TRAIL-RII) and/or DcR1 and/or DcR2. In some embodiments, the modified TRAIL agent has substantially reduced or ablated affinity and/or activity for DR4 (TRAIL-RI) and/or DR5 (TRAIL-RII) and/or DcR1 and/or DcR2.

In an embodiment, the wild type TRAIL has the amino acid sequence of:

```
TRAIL
                                          (SEQ ID NO: 90)
MAMMEVQGGPSLGQTCVLIVIFTVLLQSLCVAVTYVYFTNELKQMQDKYS

KSGIACFLKEDDSYWDPNDEESMNSPCWQVKWQLRQLVRKMILRTSEETI

STVQEKQQNISPLVRERGPQRVAAHITGTRGRSNTLSSPNSKNEKALGRK

INSWESSRSGHSFLSNLHLRNGELVIHEKGFYYIYSQTYFRFQEEIKENT

KNDKQMVQYIYKYTSYPDPILLMKSARNSCWSKDAEYGLYSIYQGGIFEL

KENDRIFVSVTNEHLIDMDHEASFFGAFLVG.
```

In such embodiments, the modified TRAIL agent may comprise a mutation at amino acid positions T127-R132, E144-R149, E155-H161, Y189-Y209, T214-1220, K224-A226, W231, E236-L239, E249-K251, T261-H264 and H270-E271 (Numbering based on the human sequence, Genbank accession number NP_003801, version 10 NP_003801.1, GI: 4507593; see above).

In an embodiment, the modified signaling agent is an interleukin. In an embodiment, the modified signaling agent is IL-1. In an embodiment, the modified signaling agent is IL-1α or IL-β. In some embodiments, the modified signaling agent has reduced affinity and/or activity for IL-1R1 and/or IL-1RAcP. In some embodiments, the modified signaling agent has substantially reduced or ablated affinity and/or activity for IL-1R1 and/or IL-1RAcP. In some embodiments, the modified signaling agent has reduced affinity and/or activity for IL-1R2. In some embodiments, the modified signaling agent has substantially reduced or ablated affinity and/or activity for IL-1R2. For instance, in some embodiments, the present modified IL-1 agents avoid interaction at IL-1R2 and therefore substantially reduce its function as a decoy and/or sink for therapeutic agents.

In an embodiment, the wild type IL-1β has the amino acid sequence of:

```
IL-1 beta (mature form, wild type)
                                          (SEQ ID NO: 91)
APVRSLNCTLRDSQQKSLVMSGPYELKALHLQGQDMEQQVVFSMSFVQG

EESNDKIPVALGLKEKNLYLSCVLKDDKPTLQLESVDPKNYPKKKMEKR

FVFNKIEINNKLEFESAQFPNWYISTSQAENMPVFLGGTKGGQDITDFT

MQFVSS.
```

IL1 is a proinflammatory cytokine and an important immune system regulator. It is a potent activator of CD4 T cell responses, increases proportion of Th17 cells and expansion of IFNγ and IL-4 producing cells. IL-1 is also a potent regulator of $CD8^+$ T cells, enhancing antigen-specific $CD8^+$ T cell expansion, differentiation, migration to periphery and memory. IL-1 receptors comprise IL-1R1 and IL-1R2. Binding to and signaling through the IL-1R1 constitutes the mechanism whereby IL-1 mediates many of its biological (and pathological) activities. IL1-R2 can function as a decoy receptor, thereby reducing IL-1 availability for interaction and signaling through the IL-1R1.

In some embodiments, the modified IL-1 has reduced affinity and/or activity (e.g. agonistic activity) for IL-1R1. In some embodiments, the modified IL-1 has substantially reduced or ablated affinity and/or activity for IL-1R2. In such embodiments, there is restorable IL-1/IL-1R1 signaling and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating cancer, including, for example, stimulating the immune system to mount an anti-cancer response.

In some embodiments, the modified IL-1 has reduced affinity and/or activity (e.g. antagonistic activity, e.g. natural antagonistic activity or antagonistic activity that is the result of one or more mutations, see, e.g., WO 2015/007520, the entire contents of which are hereby incorporated by reference) for IL-1R1. In some embodiments, the modified IL-1 has substantially reduced or ablated affinity and/or activity for IL-1R2. In such embodiments, there is the IL-1/IL-1R1 signaling is not restorable and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating autoimmune diseases, including, for example, suppressing the immune system.

In such embodiments, the modified signaling agent has a deletion of amino acids 52-54 which produces a modified human IL-1β with reduced binding affinity for type I IL-1R and reduced biological activity. See, for example, WO 1994/000491, the entire contents of which are hereby incorporated by reference. In some embodiments, the modified human IL-1β has one or more substitution mutations selected from A117G/P118G, R120X, L122A, T125G/L126G, R127G, Q131X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, 1172A, V174A, K208E, K209X, K209A/K210A, K219X, E221X, E221 S/N224A, N224S/K225S, E244K, N245Q (where X can be any change in amino acid, e.g., a non-conservative change), which exhibit reduced binding to IL-1R, as described, for example, in WO2015/007542 and WO/2015/007536, the entire contents of which is hereby incorporated by reference (numbering base on the human IL-1β sequence, Genbank accession number NP_000567, version NP-000567.1, GI: 10835145). In some embodiments, the modified human IL-1β may have one or more mutations selected from R120A, R120G, Q130A, Q130W, H146A, H146G, H146E, H146N, H146R, Q148E, Q148G, Q148L, K209A, K209D, K219S, K219Q, E221S and E221K. In an embodiment, the modified human IL-1β comprises the mutations Q131G and Q148G. In an embodiment, the modified human IL-1β comprises the mutations Q148G and K208E. In an embodiment, the modified human IL-1β comprises the mutations R120G and Q131G. In an embodiment, the modified human IL-1β comprises the mutations R120G and H146A. In an embodiment, the modified human IL-1β comprises the mutations R120G and H146N. In an embodiment, the modified human IL-1β comprises the mutations R120G and H146R. In an embodiment, the modified human IL-1β comprises the mutations R120G and H146E. In an embodiment, the modified human IL-1β comprises the mutations R120G and H146G. In an embodiment, the modified human IL-1β comprises the mutations R120G and K208E. In an embodiment, the modified human IL-1β comprises the mutations R120G, F162A, and Q164E.

In an embodiment, the modified signaling agent is IL-2. In such an embodiment, the modified signaling agent has reduced affinity and/or activity for IL-2Rα and/or IL-2Rβ and/or IL-2Rγ. In some embodiments, the modified signaling agent has reduced affinity and/or activity for IL-2Rβ and/or IL-2Rγ. In some embodiments, the modified signaling agent has substantially reduced or ablated affinity and/or activity for IL-2Rα. Such embodiments may be relevant for treatment of cancer, for instance when the modified IL-2 is agonistic at IL-2Rβ and/or IL-2Rγ. For instance, the present constructs may favor attenuated activation of $CD8^+$ T cells (which can provide an anti-tumor effect), which have IL2 receptors β and γ and disfavor $T_{regs}$ (which can provide an immune suppressive, pro-tumor effect), which have IL2 receptors α, β, and γ. Further, in some embodiments, the preferences for IL-2Rβ and/or IL-2Rγ over IL-2Rα avoid IL-2 side effects such as pulmonary edema. Also, IL-2-based chimeras are useful for the treatment of diseases (e.g., autoimmune diseases), for instance when the modified IL-2 is antagonistic (e.g. natural antagonistic activity or antagonistic activity that is the result of one or more mutations, see, e.g., WO 2015/007520, the entire contents of which are hereby incorporated by reference) at IL-2Rβ and/or IL-2Rγ. For instance, the present constructs may favor attenuated suppression of $CD8^+$ T cells (and therefore dampen the immune response), which have IL2 receptors β and γ and disfavor $T_{regs}$ which have IL2 receptors α, β, and γ. Alternatively, in some embodiments, the chimeras bearing IL-2 favor the activation of $T_{regs}$, and therefore immune suppression, and activation of disfavor of $CD8^+$ T cells. For instance, these constructs find use in the treatment of diseases or diseases that would benefit from immune suppression, e.g., autoimmune diseases.

In some embodiments, the chimeric protein has targeting moieties as described herein directed to $CD8^+$ T cells as well as a modified IL-2 agent having reduced affinity and/or activity for IL-2Rβ and/or IL-2Rγ and/or substantially reduced or ablated affinity and/or activity for IL-2Rα. In some embodiments, these constructs provide targeted $CD8^+$ T cell activity and are generally inactive (or have substantially reduced activity) towards $T_{reg}$ cells. In some embodiments, such constructs have enhanced immune stimulatory effect compared to wild type IL-2 (e.g., without wishing to be bound by theory, by not stimulating Tregs), whilst eliminating or reducing the systemic toxicity associated with IL-2.

In an embodiment, the wild type IL-2 has the amino acid sequence of:

```
IL-2 (mature form, wild type)
                                        (SEQ ID NO: 92)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT.
```

In such embodiments, the modified IL-2 agent has one or more mutations at amino acids L72 (L72G, L72A, L72S, L72T, L72Q, L72E, L72N, L72D, L72R, or L72K), F42 (F42A, F42G, F42S, F42T, F42Q, F42E, F42N, F42D, F42R, or F42K) and Y45 (Y45A, Y45G, Y45S, Y45T, Y45Q, Y45E, Y45N, Y45D, Y45R or Y45K). Without wishing to be bound by theory, it is believed that these modified IL-2 agents have reduced affinity for the high-affinity IL-2 receptor and preserves affinity to the intermediate-affinity IL-2 receptor, as compared to the wild-type IL-2. See, for example, US Patent Publication No. 2012/0244112, the entire contents of which are hereby incorporated by reference.

In an embodiment, the modified signaling agent is IL-3. In some embodiments, the modified signaling agent has reduced affinity and/or activity for the IL-3 receptor, which is a heterodimer with a unique alpha chain paired with the common beta (beta c or CD131) subunit. In some embodiments, the modified signaling agent has substantially reduced or ablated affinity and/or activity for the IL-3 receptor, which is a heterodimer with a unique alpha chain paired with the common beta (beta c or CD131) subunit.

In an embodiment, the modified signaling agent is IL-4. In such an embodiment, the modified signaling agent has reduced affinity and/or activity for type 1 and/or type 2 IL-4 receptors. In such an embodiment, the modified signaling agent has substantially reduced or ablated affinity and/or activity for type 1 and/or type 2 IL-4 receptors. Type 1 IL-4 receptors are composed of the IL-4Rα subunit with a common γ chain and specifically bind IL-4. Type 2 IL-4 receptors include an IL-4Rα subunit bound to a different subunit known as IL-13Rα1. In some embodiments, the modified signaling agent has substantially reduced or ablated affinity and/or activity the type 2 IL-4 receptors.

In an embodiment, the wild type IL-4 has the amino acid sequence of:

```
IL-4 (mature form, wild type)
                                        (SEQ ID NO: 93)
HKCDITLQEIIKTLNSLTEQKTLCTELTVTDIFAASKNTTEKETFCRAAT

VLRQFYSHHEKDTRCLGATAQQFHRHKQURFLKRLDRNLWGLAGLNSCPV

KEANQSTLENFLERLKTIMREKYSKCSS.
```

In such embodiments, the modified IL-4 agent has one or more mutations at amino acids R121 (R121A, R121D, R121E, R121F, R121H, R121I, R121K, R121N, R121P, R121T, R121W), E122 (E122F), Y124 (Y124A, Y124Q, Y124R, Y124S, Y124T) and S125 (S125A). Without wishing to be bound by theory, it is believed that these modified IL-4 agents maintain the activity mediated by the type I receptor, but significantly reduces the biological activity mediated by the other receptors. See, for example, U.S. Pat. No. 6,433,157, the entire contents of which are hereby incorporated by reference.

In an embodiment, the modified signaling agent is IL-6. IL-6 signals through a cell-surface type I cytokine receptor complex including the ligand-binding IL-6R chain (CD126), and the signal-transducing component gp130. IL-6 may also bind to a soluble form of IL-6R (sIL-6R), which is the extracellular portion of IL-6R. The sIL-6R/IL-6 complex may be involved in neurites outgrowth and survival of neurons and, hence, may be important in nerve regeneration through remyelination. Accordingly, in some embodiments, the modified signaling agent has reduced affinity and/or activity for IL-6R/gp130 and/or sIL-6R. In some embodiments, the modified signaling agent has substantially reduced or ablated affinity and/or activity for IL-6R/gp130 and/or sIL-6R.

In an embodiment, the wild type IL-6 has the amino acid sequence of:

```
IL-6 (mature form, wild type)
                                    (SEQ ID NO: 94)
APVPPGEDSKDVAAPHRQPLTSSERIDKQIRYILDGISALRKETCNKSNM

CESSKEALAENNLNLPKMAEKDGCFQSGFNEETCLVKIITGLLEFEVYLE

YLQNRFESSEEQARAVQMSTKVLIQFLQKKAKNLDAITTPDPTTNASLTT

KLQAQNQWLQDMTTHLILRSFKEFLQSSLRALRQM.
```

In such embodiments, the modified signaling agent has one or more mutations at amino acids 58, 160, 163, 171 or 177. Without wishing to be bound by theory, it is believed that these modified IL-6 agents exhibit reduced binding affinity to IL-6Ralpha and reduced biological activity. See, for example, WO 97/10338, the entire contents of which are hereby incorporated by reference.

In an embodiment, the modified signaling agent is IL-10. In such an embodiment, the modified signaling agent has reduced affinity and/or activity for IL-10 receptor-1 and IL-10 receptor-2. In some embodiments, the modified signaling agent has ablated or substantially reduced affinity and/or activity for IL-10 receptor-1 and IL-10 receptor-2

In an embodiment, the modified signaling agent is IL-11. In such an embodiment, the modified signaling agent has reduced affinity and/or activity for IL-11Rα and/or IL-11Rβ and/or gp130. In such an embodiment, the modified signaling agent has ablated or substantially reduced affinity and/or activity for IL-11Rα and/or IL-11Rβ and/or gp130.

In an embodiment, the modified signaling agent is IL-12. In such an embodiment, the modified signaling agent has reduced affinity and/or activity for IL-12Rβ1 and/or IL-12Rβ2. In such an embodiment, the modified signaling agent has substantially reduced or ablated affinity and/or activity for IL-12Rβ1 and/or IL-12Rβ2.

In an embodiment, the modified signaling agent is IL-13. In such an embodiment, the modified signaling agent has reduced affinity and/or activity for the IL-4 receptor (IL-4Rα) and IL-13Rα1. In some embodiments, the modified signaling agent has substantially reduced or ablated affinity and/or activity for IL-4 receptor (IL-4Rα) or IL-13Rα1.

In an embodiment, the wild type IL-13 has the amino acid sequence of:

```
IL-13 (mature form, wild type)
                                    (SEQ ID NO: 95)
SPGPVPPSTALRELIEELVNITQNQKAPLCNGSMVWSINLTAGMYCAALE

SLINVSGCSAIEKTQRMLSGFCPHKVSAGQFSSLHVRDTKIEVAQFVKDL

LLHLKKLFREGRFN.
```

In such embodiments, the modified IL-13 agent has one or more mutations at amino acids 13, 16, 17, 66, 69, 99, 102, 104, 105, 106, 107, 108, 109, 112, 113 and 114. Without wishing to be bound by theory, it is believed that these modified IL-13 agents exhibit reduced biological activity. See, for example, WO 2002/018422, the entire contents of which are hereby incorporated by reference.

In an embodiment, the modified signaling agent is IL-18. In some embodiments, the modified signaling agent has reduced affinity and/or activity for IL-18Rα and/or IL-18Rβ. In some embodiments, the modified signaling agent has substantially reduced or ablated affinity and/or activity for IL-18Rα and/or IL-18Rβ. In some embodiments, the modified signaling agent has substantially reduced or ablated affinity and/or activity for IL-18Rα type II, which is an isoform of IL-18Rα that lacks the TIR domain required for signaling.

In an embodiment, the wild type IL-18 has the amino acid sequence of:

```
IL-18 (wild type)
                                    (SEQ ID NO: 96)
MAAEPVEDNCINFVAMKFIDNTLYFIAEDDENLESDYFGKLESKLSVIRN

LNDQVLFIDQGNRPLFEDMTDSDCRDNAPRTIFIISMYKDSQPRGMAVTI

SVKCEKISTLSCENKIISFKEMNPPDNIKDTKSDIIFFQRSVPGHDNKMQ

FESSSYEGYFLACEKERDLFKLILKKEDELGDRSIMFTVQNEDL.
```

In such embodiments, the modified IL-18 agent may comprise one or more mutations in amino acids or amino acid regions selected from Y37-K44, R49-Q54, D59-R63, E67-C74, R80, M87-A97, N127-K129, Q139-M149, K165-K171, R183 and Q190-N191, as described in WO/2015/007542, the entire contents of which are hereby incorporated by reference (numbering based on the human IL-18 sequence, Genbank accession number AAV38697, version AAV38697.1, GI: 54696650).

In an embodiment, the modified signaling agent is IL-33. In such an embodiment, the modified signaling agent has reduced affinity and/or activity for the ST-2 receptor and IL-1RAcP. In some embodiments, the modified signaling agent has substantially reduced or ablated affinity and/or activity for the ST-2 receptor and IL-1RAcP.

In an embodiment, the wild type IL-33 has the amino acid sequence of:

```
                                    (SEQ ID NO: 97)
MKPKMKYSTNKISTAKWKNTASKALCFKLGKSQQKAKEVCPMYFMKLRSG

LMIKKEACYFRRETTKRPSLKTGRKHKRHLVLAACQQQSTVECFAFGISG

VQKYTRALHDSSITGISPITEYLASLSTYNDQSITFALEDESYEIYVEDL

KKDEKKDKVLLSYYESQHPSNESGDGVDGKMLMVTLSPTKDFWLHANNKE

HSVELHKCEKPLPDQAFFVLHNMHSNCVSFECKTDPGVFIGVKDNHLALI

KVDSSENLCTENILFKLSET.
```

In such embodiments, the modified IL-33 agent may comprise one or more mutations in amino acids or amino acid regions selected from I113-Y122, S127-E139, E144-D157, Y163-M183, E200, Q215, L220-C227 and T260-E269, as described in WO/2015/007542, the entire contents of which are hereby incorporated by reference (numbering based on the human sequence, Genbank accession number NP_254274, version NP_254274.1, GI:15559209).

In one embodiment, the present chimeric protein has (i) a targeting moiety against Clec9A and (ii) a targeting moiety which is directed against a tumor cell, along with any of the modified or mutant signaling agents described herein. In an embodiment, the present chimeric protein has a targeting moiety directed against Clec9A on dendritic cells and a second targeting moiety directed against PD-L1 or PD-L2 on tumor cells.

In one embodiment, the present chimeric protein has (i) a targeting moiety against Clec9A and (ii) a targeting moiety which is directed against a checkpoint inhibitor marker, along with any of the modified or mutant interferons described herein. In an embodiment, the present chimeric protein has a targeting moiety directed against Clec9A on dendritic cells and a second targeting moiety directed against PD-1.

In various embodiments, the signaling agent is a toxin or toxic enzyme. In some embodiments, the toxin or toxic enzyme is derived from plants and bacteria. Illustrative toxins or toxic enzymes include, but are not limited to, the diphtheria toxin, *Pseudomonas* toxin, anthrax toxin, ribosome-inactivating proteins (RIPs) such as ricin and saporin, modeccin, abrin, gelonin, and poke weed antiviral protein. Additional toxins include those disclosed in Mathew et al., (2009) Cancer Sci 100(8): 1359-65, the entire disclosures are hereby incorporated by reference. In such embodiments, the chimeric proteins of the invention may be utilized to induce cell death in cell-type specific manner. In such embodiments, the toxin may be modified, e.g. mutated, to reduce affinity and/or activity of the toxin for an attenuated effect, as described with other signaling agents herein.

Multi-Specific Chimeras and Fusions with Signaling Agents

In various embodiments, the Clec9A binding agent of the invention is part of a chimera or fusion with one or more signaling agents as described herein and/or one or more additional targeting moieties. Accordingly, the present invention provides for chimeric or fusion proteins that include one or more signaling agents and a targeting moiety against Clec9A and/or one or more additional targeting moieties. Accordingly, in various embodiments, the term "Clec9A binding agent" encompasses such chimeras or fusion proteins with one or more signaling agents and/or one or more additional targeting moieties.

In various embodiments, the chimeric proteins of the present invention have targeting moieties which target two different cells (e.g. to make a synapse) or the same cell (e.g. to get a more concentrated signaling agent effect).

In various embodiments, the Clec9A binding agent of the invention is multispecific, i.e., the Clec9A binding agent comprises two or more targeting moieties having recognition domains (e.g. antigen recognition domains) that recognize and bind two or more targets (e.g. antigens, or receptors, or epitopes). In such embodiments, the Clec9A binding agent of the invention may comprises two more targeting moieties having recognition domains that recognize and bind two or more epitopes on the same antigen or on different antigens or on different receptors. In various embodiments, such multi-specific Clec9A binding agents exhibit advantageous properties such as increased avidity and/or improved selectivity. In an embodiment, the Clec9A binding agent of the invention comprises two targeting moieties and is bispecific, i.e., binds and recognizes two epitopes on the same antigen or on different antigens or different receptors. Accordingly, in various embodiments, the term "Clec9A binding agent" encompasses such multispecific Clec9A binding agents comprising two or more targeting moieties.

In various embodiments, the multispecific Clec9A binding agent of the invention comprises two or more targeting moieties with each targeting moiety being an antibody or an antibody derivative as described herein. In an embodiment, the multispecific Clec9A binding agent of the invention comprises at least one VHH comprising an antigen recognition domain against Clec9A and one antibody or antibody derivative comprising a recognition domain against a tumor antigen and/or an immune cell marker.

In various embodiments, the present multispecific Clec9A binding agents have two or more targeting moieties that target different antigens or receptors, and one targeting moiety may be attenuated for its antigen or receptor, e.g. the targeting moiety binds its antigen or receptor with a low affinity or avidity (including, for example, at an affinity or avidity that is less than the affinity or avidity the other targeting moiety has for its for its antigen or receptor, for instance the difference between the binding affinities may be about 10-fold, or 25-fold, or 50-fold, or 100-fold, or 300-fold, or 500-fold, or 1000-fold, or 5000-fold; for instance the lower affinity or avidity targeting moiety may bind its antigen or receptor at a $K_D$ in the mid- to high-nM or low- to mid-μM range while the higher affinity or avidity targeting moiety may bind its antigen or receptor at a $K_D$ in the mid- to high-pM or low- to mid-nM range). For instance, in some embodiments, the present multispecific Clec9A binding agent comprises an attenuated targeting moiety that is directed against a promiscuous antigen or receptor, which may improve targeting to a cell of interest (e.g. via the other targeting moiety) and prevent effects across multiple types of cells, including those not being targeted for therapy (e.g. by binding promiscuous antigen or receptor at a higher affinity than what is provided in these embodiments).

The multispecific Clec9A binding agent of the invention may be constructed using methods known in the art, see for example, U.S. Pat. No. 9,067,991, U.S. Patent Publication No. 20110262348 and WO 2004/041862, the entire contents of which are hereby incorporated by reference. In an illustrative embodiment, the multispecific Clec9A binding agent of the invention comprising two or more targeting moieties may be constructed by chemical crosslinking, for example, by reacting amino acid residues with an organic derivatizing agent as described by Blattler et al., Biochemistry 24, 1517-1524 and EP294703, the entire contents of which are hereby incorporated by reference. In another illustrative embodiment, the multispecific Clec9A binding agent comprising two or more targeting moieties is constructed by genetic fusion, i.e., constructing a single polypeptide which includes the polypeptides of the individual targeting moieties. For example, a single polypeptide construct may be formed which encodes a first VHH with an antigen recognition domain against Clec9A and a second antibody or antibody derivative with an antigen recognition domain against e.g., a tumor antigen or a checkpoint inhibitor. A method for producing bivalent or multivalent VHH polypeptide constructs is disclosed in PCT patent application WO 96/34103, the entire contents of which is hereby incorporated by reference. In a further illustrative embodiment, the multispecific Clec9A binding agent of the invention may be constructed by using linkers. For example, the carboxy-terminus of a first VHH with an antigen recognition domain against Clec9A may be linked to the amino-terminus of a second antibody or antibody derivative with an antigen recognition domain against e.g., a tumor antigen or a checkpoint inhibitor (or vice versa). Illustrative linkers that may be used are described herein. In some embodiments, the components of the multispecific Clec9A binding agent of the invention are directly linked to each other without the use of linkers.

In various embodiments, the multi-specific Clec9A binding agent of the invention recognizes and binds to Clec9A and one or more antigens found on one or more immune cells, which can include, without limitation, megakaryocytes, thrombocytes, erythrocytes, mast cells, basophils, neutrophils, eosinophils, monocytes, macrophages, natural killer cells, T lymphocytes (e.g., cytotoxic T lymphocytes, T helper cells, natural killer T cells), B lymphocytes, plasma cells, dendritic cells, or subsets thereof. In some embodiments, the CLEC9A binding agent specifically binds to an antigen of interest and effectively directly or indirectly recruits one of more immune cells.

In various embodiments, the multi-specific Clec9A binding agent of the invention recognizes and binds to Clec9A and one or more antigens found on tumor cells. In these embodiments, the present Clec9A binding agents may directly or indirectly recruit an immune cell to a tumor cell or the tumor microenvironment. In some embodiments, the present Clec9A binding agents may directly or indirectly recruit an immune cell, e.g. a dendritic cell, to a site of action (such as, by way of non-limiting example, the tumor microenvironment). In some embodiments, the present Clec9A binding agent enhances antigen presentation (e.g. tumor antigen presentation) by dendritic cells for the induction of a potent humoral and cytotoxic T cell response.

In some embodiments, the present Clec9A binding agents are capable of, or find use in methods involving, shifting the balance of immune cells in favor of immune attack of a tumor. For instance, the present Clec9A binding agents can shift the ratio of immune cells at a site of clinical importance in favor of cells that can kill and/or suppress a tumor (e.g. T cells, cytotoxic T lymphocytes, T helper cells, natural killer (NK) cells, natural killer T (NKT) cells, anti-tumor macrophages (e.g. M1 macrophages), B cells, and dendritic cells and in opposition to cells that protect tumors (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the present Clec9A binding agent is capable of increasing a ratio of effector T cells to regulatory T cells.

In some embodiments, the multi-specific Clec9A binding agent of the invention comprises a targeting moiety having a recognition domain that specifically binds to a target (e.g. antigen or receptor) associated with tumor cells. In some embodiments, the targeting moiety directly or indirectly recruits tumor cells. For instance, in some embodiments, the recruitment of the tumor cell is to one or more effector cell (e.g. an immune cell as described herein) that can kill and/or suppress the tumor cell.

Tumor cells, or cancer cells refer to an uncontrolled growth of cells or tissues and/or an abnormal increased in cell survival and/or inhibition of apoptosis which interferes with the normal functioning of bodily organs and systems. For example, tumor cells include benign and malignant cancers, polyps, hyperplasia, as well as dormant tumors or micrometastases. Illustrative tumor cells include, but are not limited to cells of: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

Tumor cells, or cancer cells also include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative tumor antigens include, but are not limited to, MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pme1117, PRAME, NY-ESO-1, cdc27, adenomatous polyposis *coli* protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD20, CD22, CD30, CD33, CD37, CD56, CD70, CD74, CD138, AGS16, MUC1, GPNMB, Ep-CAM, PD-L1, PD-L2, PMSA, and BCMA (TNFRSF17). In various embodiments, the CLEC9A binding agent comprises a targeting moiety that binds one or more of these tumor antigens.

In some embodiments, the present multi-specific Clec9A binding agent recognizes and binds to Clec9A as well as an antigen on a tumor cell. In some embodiments, the multi-specific Clec9A binding agent directly or indirectly recruits dendritic cells to the tumor cell or tumor microenvironment.

In some embodiments, the multi-specific Clec9A binding agent of the invention comprises a targeting moiety having a recognition domain that specifically binds to a target (e.g. an antigen or receptor) associated with T cells. In some embodiments, the targeting moiety directly or indirectly recruits T cells. In an embodiment, the antigen recognition domains specifically bind to effector T cells. In some embodiments, the antigen recognition domain directly or indirectly recruits effector T cells, e.g., in some embodiments, to a therapeutic site (e.g. a locus with one or more disease cell or cell to be modulated for a therapeutic effect). Illustrative effector T cells include cytotoxic T cells (e.g. αβ TCR, $CD3^+$, $CD8^+$, $CD45RO^+$); $CD4^+$ effector T cells (e.g. αβ TCR, $CD3^+$, $CD4^+$, $CCR7^+$, CD62Lhi, $IL^-7R/CD127^+$); $CD8^+$ effector T cells (e.g. αβ TCR, $CD3^+$, $CD8^+$, $CCR7^+$, CD62Lhi, $IL^-7R/CD127^+$); effector memory T cells (e.g. CD62Llow, $CD44^+$, TCR, $CD3^+$, $IL^-7R/CD127^+$, $IL\text{-}15R^+$, CCR7low); central memory T cells (e.g. $CCR7^+$, $CD62L^+$, $CD27^+$; or CCR7hi, $CD44^+$, CD62Lhi, TCR, $CD3^+$, IL-7R/$CD127^+$, $IL\text{-}15R^+$); $CD62L^+$ effector T cells; $CD8^+$ effector memory T cells (TEM) including early effector memory T cells ($CD27^+$ $CD62L^-$) and late effector memory T cells ($CD27^-$ $CD62L^-$) (TemE and TemL, respectively); CD127($^+$)CD25(low/−) effector T cells; CD127($^-$)CD25($^-$) effector T cells; $CD8^+$ stem cell memory effector cells (TSCM) (e.g. CD44(low)CD62L(high)CD122(high)sca($^+$)); TH1 effector T-cells (e.g. $CXCR3^+$, $CXCR6^+$ and $CCR5^+$; or αβ TCR, $CD3^+$, $CD4^+$, $IL\text{-}12R^+$, $IFN\gamma R^+$, $CXCR3^+$), TH2 effector T cells (e.g. $CCR3^+$, $CCR4^+$ and $CCR8^+$; or αβ TCR, $CD3^+$, $CD4^+$, $IL\text{-}4R^+$, $IL\text{-}33R^+$, $CCR4^+$, $IL\text{-}17RB^+$, $CRTH2^+$); TH9 effector T cells (e.g. αβ TCR, $CD3^+$, $CD4^+$); TH17 effector T cells (e.g. αβ TCR, $CD3^+$, $CD4^+$, $IL\text{-}23R^+$, $CCR6^+$, $IL\text{-}1R^+$); $CD4^+CD45RO^+CCR7^+$ effector T cells, $ICOS^+$ effector T cells; $CD4^+CD45RO^+$CCR7($^-$) effector T cells; and effector T cells secreting IL-2, IL-4 and/or IFN-γ.

Illustrative T cell antigens of interest include, for example (and inclusive of the extracellular domains, where applicable): CD8, CD3, SLAMF4, IL-2Rα, 4-1BB/TNFRSF9, IL-2R β, ALCAM, B7-1, IL-4 R, B7-H3, BLAME/SLAMFS, CEACAM1, IL-6 R, CCR3, IL-7 Rα, CCR4, CXCRI/IL-S RA, CCR5, CCR6, IL-10R α, CCR 7, IL-I 0 R β, CCRS, IL-12 R β1, CCR9, IL-12 R β2, CD2, IL-13 R α1, IL-13, CD3, CD4, ILT2/CDS5j, ILT3/CDS5k, ILT4/CDS5d, ILT5/CDS5α, lutegrin α 4/CD49d, CDS, Integrin αE/CD103, CD6, Integrin αM/CD 11 b, CDS, Integrin α X/CD11c, Integrin β 2/CDIS, KIR/CD15S, CD27/TNFRSF7, KIR2DL1, CD2S, KIR2DL3, CD30/TNFRSFS, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, RANK/TNFRSF11A, CX3CR1, CX3CL1, L-Selectin, CXCR3, SIRP β1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2fTNFRSF10B, ICAM-2/CD102, TRAILR3/TNFRSF10C, IFN-γR1, TRAILR4/TNFRSF10D, IFN-γ R2, TSLP, IL-1 R1 and TSLP R. In various embodiments, the CLEC9A binding agent comprises a targeting moiety that binds one or more of these illustrative T cell antigens.

By way of non-limiting example, in various embodiments, the present chimeric protein has a targeting moiety directed against a checkpoint marker expressed on a T cell, e.g. one or more of PD-1, CD28, CTLA4, ICOS, BTLA, KIR, LAG3, CD137, OX40, CD27, CD40L, TIM3, and A2aR.

In some embodiments, the multi-specific Clec9A binding agent of the invention comprises a targeting moiety having a recognition domain that specifically binds to a target (e.g. an antigen or receptor) associated with B cells. In some embodiments, the targeting moiety directly or indirectly recruits B cells, e.g., in some embodiments, to a therapeutic site (e.g. a locus with one or more disease cell or cell to be modulated for a therapeutic effect). Illustrative B cell antigens of interest include, for example, CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138, CDw150, and B-cell maturation antigen (BCMA). In various embodiments, the Clec9A binding agent comprises a targeting moiety that binds one or more of these illustrative B cell antigens.

In some embodiments, the multi-specific Clec9A binding agent of the invention comprises a targeting moiety having a recognition domain that specifically binds to a target (e.g. an antigen or receptor) associated with Natural Killer cells. In some embodiments, the targeting moiety directly or indirectly recruits Natural Killer cells, e.g., in some embodiments, to a therapeutic site (e.g. a locus with one or more disease cell or cell to be modulated for a therapeutic effect). Illustrative Natural Killer cell antigens of interest include, for example TIGIT, 2B4/SLAMF4, KIR2DS4, CD155/PVR, KIR3DL1, CD94, LMIR1/CD300A, CD69, LMIR2/CD300c, CRACC/SLAMF7, LMIR3/CD300LF, Kir1alpha, DNAM-1, LMIR5/CD300LB, Fc-epsilon RII, LMIR6/CD300LE, Fc-γ RI/CD64, MICA, Fc-γRIIB/CD32b, MICB, Fc-γRIIC/CD32c, MULT-1, Fc-γRIIA/CD32a, Nectin-2/CD112, Fc-γ RIII/CD16, NKG2A, FcRH1/IRTA5, NKG2C, FcRH2/IRTA4, NKG2D, FcRH4/IRTA1, NKp30, FcRH5/IRTA2, NKp44, Fc-Receptor-like 3/CD16-2, NKp46/NCR1, NKp80/KLRF1, NTB-A/SLAMF6, Rae-1, Rae-1α, Rae-1β, Rae-1 delta, H60, Rae-1 epsilon, ILT2/CD85j, Rae-1γ, ILT3/CD85k, TREM-1, ILT4/CD85d, TREM-2, ILT5/CD85a, TREM-3, KIR/CD158, TREML1/TLT-1, KIR2DL1, ULBP-1, KIR2DL3, ULBP-2, KIR2DL4/CD158d and ULBP-3. In various embodiments, the CLEC9A binding agent comprises a targeting moiety that binds one or more of these illustrative NK cell antigens.

In some embodiments, the multi-specific Clec9A binding agent of the invention comprises a targeting moiety having a recognition domain that specifically binds to a target (e.g. an antigen or receptor) associated with macrophages/monocytes. In some embodiments, the targeting moiety directly or indirectly directly or indirectly recruits macrophages/monocytes, e.g., in some embodiments, to a therapeutic site (e.g. a locus with one or more disease cell or cell to be modulated for a therapeutic effect). Illustrative macrophages/monocyte antigens of interest include, for example SIRP1a, B7-1/CD80, ILT4/CD85d, B7-H1, ILT5/CD85a, Common β Chain, Integrin α 4/CD49d, BLAME/SLAMF8, Integrin α X/CD11c, CCL6/C10, Integrin β 2/CD18, CD155/PVR, Integrin β3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/

SLAMF9, MARCO, CRACC/SLAMF7, MD-1, ECF-L, MD-2, EMMPRIN/CD147, MGL2, Endoglin/CD105, Osteoactivin/GPNMB, Fc-γRI/CD64, Osteopontin, Fc-γ RIIB/CD32b, PD-L2, Fc-γRIIC/CD32c, Siglec-3/CD33, Fc-γRIIA/CD32a, SIGNR1/CD209, Fc-γRIII/CD16, SLAM, GM-CSF R α, TCCR/WSX-1, ICAM-2/CD102, TLR3, IFN-γ RI, TLR4, IFN-gannna R2, TREM-I, IL-I RII, TREM-2, ILT2/CD85j, TREM-3, ILT3/CD85k, TREML1/TLT-1,2B4/SLAMF 4, IL-10 R α, ALCAM, IL-10 R β, AminopeptidaseN/ANPEP, ILT2/CD85j, Common β Chain, ILT3/CD85k, C1q R1/CD93, ILT4/CD85d, CCR1, ILT5/CD85a, CCR2, CD206, Integrin α4/CD49d, CCR5, Integrin αM/CDII b, CCR8, Integrin αX/CD11c, CD155/PVR, Integrin β2/CD18, CD14, Integrin β3/CD61, CD36/SR-B3, LAIR1, CD43, LAIR2, CD45, Leukotriene B4-R1, CD68, LIMPIIISR-B2, CD84/SLAMF5, LMIR1/CD300A, CD97, LMIR2/CD300c, CD163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γRI/CD64, PSGL-1, Fc-γRIIICD16, RP105, G-CSF R, L-Selectin, GM-CSF R a, Siglec-3/CD33, HVEM/TNFRSF14, SLAM, ICAM-1/CD54, TCCR/WSX-1, ICAM-2/CD102, TREM-1, IL-6 R, TREM-2, CXCRI/IL-8 RA, TREM-3 and TREMLI/TLT-1. In various embodiments, the CLEC9A binding agent comprises a targeting moiety that binds one or more of these illustrative macrophage/monocyte antigens.

In some embodiments, the multi-specific Clec9A binding agent of the invention comprises a targeting moiety having a recognition domain that specifically binds to a target (e.g. an antigen or receptor) associated with dendritic cells. In some embodiments, the targeting moiety directly or indirectly recruits dendritic cells, e.g., in some embodiments, to a therapeutic site (e.g. a locus with one or more disease cell or cell to be modulated for a therapeutic effect). Illustrative dendritic cell antigens of interest include, for example, CLEC9A, XCR1, RANK, CD36/SRB3, LOX-1/SR-E1, CD68, MARCO, CD163, SR-A1/MSR, CD5L, SREC-1, CL-PI/COLEC12, SREC-II, LIMPIIISRB2, RP105, TLR4, TLR1, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin α4/CD49d, Aag, Integrin β2/CD18, AMICA, Langerin, B7-2/CD86, Leukotriene B4 RI, B7-H3, LMIR1/CD300A, BLAME/SLAMF8, LMIR2/CD300c, C1q R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, CLEC-8, Siglec-2/CD22, CRACC/SLAMF7, Siglec-3/CD33, DC-SIGN, DCE205, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD147, TCCR/WSX-1, Fc-γR1/CD64, TLR3, Fc-γRIIB/CD32b, TREM-1, Fc-γRIIC/CD32c, TREM-2, Fc-γRIIA/CD32α, TREM-3, Fc-γRIII/CD16, TREML1/TLT-1, ICAM-2/CD102 and Vanilloid R1. In various embodiments, the CLEC9A binding agent comprises a targeting moiety that binds one or more of these illustrative DC antigens.

In some embodiments, the multi-specific Clec9A binding agent of the invention comprises a targeting moiety having a recognition domain that specifically binds to a target (e.g. an antigen or receptor) associated with immune cells selected from, but not limited to, megakaryocytes, thrombocytes, erythrocytes, mast cells, basophils, neutrophils, eosinophils, or subsets thereof. In some embodiments, the antigen recognition domains directly or indirectly recruit megakaryocytes, thrombocytes, erythrocytes, mast cells, basophils, neutrophils, eosinophils, or subsets thereof, e.g., in some embodiments, to a therapeutic site (e.g. a locus with one or more disease cell or cell to be modulated for a therapeutic effect).

In some embodiments, the multi-specific CLEC9A binding agent of the invention comprises a targeting moiety having a recognition domain that specifically binds to a target (e.g. an antigen or receptor) associated with megakaryocytes and/or thrombocytes. Illustrative megakaryocyte and/or thrombocyte antigens of interest include, for example, GP IIb/IIIa, GPIb, vWF, PF4, and TSP. In various embodiments, the CLEC9A binding agent comprises a targeting moiety that binds one or more of these illustrative megakaryocyte and/or thrombocyte antigens.

In some embodiments, the multi-specific Clec9A binding agent of the invention comprises a targeting moiety having a recognition domain that specifically binds to a target (e.g. an antigen or receptor) associated with erythrocytes. Illustrative erythrocyte antigens of interest include, for example, CD34, CD36, CD38, CD41a (platelet glycoprotein IIb/IIIa), CD41b (GPIIb), CD71 (transferrin receptor), CD105, glycophorin A, glycophorin C, c-kit, HLA-DR, H2 (MHC-II), and Rhesus antigens. In various embodiments, the CLEC9A binding agent comprises a targeting moiety that binds one or more of these illustrative erythrocyte antigens.

In some embodiments, the multi-specific Clec9A binding agent of the invention comprises a targeting moiety having a recognition domain that specifically binds to a target (e.g. an antigen or receptor) associated with mast cells. Illustrative mast cells antigens of interest include, for example, SCFR/CD117, $Fc_{\varepsilon}RI$, CD2, CD25, CD35, CD88, CD203c, C5R1, CMAI, FCERIA, FCER2, TPSABI. In various embodiments, the CLEC9A binding agent comprises a targeting moiety that binds one or more of these mast cell antigens.

In some embodiments, the multi-specific Clec9A binding agent of the invention comprises a targeting moiety having a recognition domain that specifically binds to a target (e.g. an antigen or receptor) associated with basophils. Illustrative basophils antigens of interest include, for example, $Fc_{\varepsilon}RI$, CD203c, CD123, CD13, CD107a, CD107b, and CD164. In various embodiments, the CLEC9A binding agent comprises a targeting moiety that binds one or more of these basophil antigens.

In some embodiments, the multi-specific Clec9A binding agent of the invention comprises a targeting moiety having a recognition domain that specifically binds to a target (e.g. an antigen or receptor) associated with neutrophils. Illustrative neutrophils antigens of interest include, for example, 7D5, CD10/CALLA, CD13, CD16 (FcRIII), CD18 proteins (LFA-1, CR3, and p150, 95), CD45, CD67, and CD177. In various embodiments, the CLEC9A binding agent comprises a targeting moiety that binds one or more of these neutrophil antigens.

In some embodiments, the multi-specific Clec9A binding agent of the invention comprises a targeting moiety having a recognition domain that specifically binds to a target (e.g. an antigen or receptor) associated with eosinophils. Illustrative eosinophils antigens of interest include, for example, CD35, CD44 and CD69. In various embodiments, the CLEC9A binding agent comprises a targeting moiety that binds one or more of these eosinophil antigens.

In various embodiments, the multi-specific Clec9A binding agent of the invention comprises a targeting moiety having a recognition domain that specifically binds to an appropriate antigen or cell surface marker known by the skilled artisan. In some embodiments, the antigen or cell surface marker is a tissue-specific marker. Illustrative tissue-specific markers include, but are not limited to, endothelial cell surface markers such as ACE, CD14, CD34, CDH5, ENG, ICAM2, MCAM, NOS3, PECAMI, PROCR, SELE, SELP, TEK, THBD, VCAMI, VWF; smooth muscle cell surface markers such as ACTA2, MYHIO, MYHI 1, MYH9, MYOCD; fibroblast (stromal) cell surface markers such as ALCAM, CD34, COLIAI, COL1A2, COL3A1, FAP, PH-4; epithelial cell surface markers such as CDID, K61RS2, KRTIO, KRT13, KRT17, KRT18, KRT19, KRT4, KRT5, KRT8, MUCI, TACSTDI; neovasculature markers such as CD13, TFNA, Alpha-v beta-3 ($\alpha V\beta 3$), E-selectin; and adipocyte surface markers such as ADIPOQ, FABP4, and RETN. In various embodiments, the CLEC9A binding agent comprises a targeting moiety that binds one or more of these antigens. In various embodiments, a targeting moiety of the chimeric protein binds one or more of cells having these antigens.

In various embodiments, the multi-specific Clec9A binding agent of the invention has one or more targeting moieties directed against a checkpoint marker, e.g. one or more of PD-1/PD-L1 or PD-L2, CD28/CD80 or CD86, CTLA4/CD80 or CD86, ICOS/ICOSL or B7RP1, BTLA/HVEM, KIR, LAG3, CD137/CD137L, OX40/OX40L, CD27, CD40L, TIM3/Gal9, and A2aR. In some embodiments, the multispecific Clec9A binding agent of the invention may comprise an antibody or antibody format, e.g. VHH, against a checkpoint inhibitor marker selected from one of CTLA-4, PD-L1, PD-L2, and PD-1.

By way of non-limiting example, in various embodiments, the present multispecific Clec9A binding agent has a targeting moiety directed against (i) a checkpoint marker expressed on a T cell, e.g. one or more of PD-1, CD28, CTLA4, ICOS, BTLA, KIR, LAG3, CD137, OX40, Cd27, CD40L, TIM3, and A2aR and (ii) a targeting moiety is directed against a tumor cell, along with any of the modified (e.g. mutant) signaling agents described herein.

In various embodiments, the present multi-specific Clec9A binding agent has one or more targeting moieties directed against PD-1. In some embodiments, the Clec9A binding agent has one or more targeting moieties which selectively bind a PD-1 polypeptide. In some embodiments, the Clec9A binding agent comprises one or more antibodies, antibody derivatives or formats, peptides or polypeptides, or fusion proteins that selectively bind a PD-1 polypeptide.

In an embodiment, the targeting moiety comprises the anti-PD-1 antibody pembrolizumab (aka MK-3475, KEYTRUDA), or fragments thereof. Pembrolizumab and other humanized anti-PD-1 antibodies are disclosed in Hamid, et al. (2013) New England Journal of Medicine 369 (2): 134-44, U.S. Pat. No. 8,354,509, and WO 2009/114335, the entire disclosures of which are hereby incorporated by reference. In illustrative embodiments, pembrolizumab or an antigen-binding fragment thereof for use in the methods provided herein comprises a heavy chain comprising the amino acid sequence of:

(SEQ ID NO: 98)
QVQLVQSGVEVKKPGASVKVSCKASGYTFTNYYMYWVRQAPGQGLEWMGG
INPSNGGTNFNEKFKNRVTLTTDSSTTTAYMELKSLQFDDTAVYYCARRD
YRFDMGFDYWGQGTTVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK;

and/or a light chain comprising the amino acid sequence of:

(SEQ ID NO: 99)
EIVLTQSPATLSLSPGERATLSCRASKGVSTSGYSYLHWYQQKPGQAPRL
LIYLASYLESGVPARFSGSGSGTDFTLTISSLEPEDFAVYYCQHSRDLPL
TFGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC.

In an embodiment, the targeting moiety comprises the anti-PD-1 antibody, nivolumab (aka BMS-936558, MDX-1106, ONO-4538, OPDIVO), or fragments thereof. Nivolumab (clone 5C4) and other human monoclonal antibodies that specifically bind to PD-1 are disclosed in U.S. Pat. No. 8,008,449 and WO 2006/121168, the entire disclosures of which are hereby incorporated by reference. In illustrative embodiments, nivolumab or an antigen-binding fragment thereof comprises a heavy chain comprising the amino acid sequence of:

(SEQ ID NO: 100)
QVQLVESGGG VVQPGRSLRL DCKASGITFS NSGMHWVRQA
PGKGLEWVAV IWYDGSKRYY ADSVKGRFTI SRDNSKNTLF
LQMNSLRAED TAVYYCATND DYWGQGTLVT VSSASTKGPS
VFPLAPCSRS TSESTAALGC LVKDYFPEPV TVSWNSGALT
SGVHTFPAVL QSSGLYSLSS VVTVPSSSLG TKTYTCNVDH
KPSNTKVDKR VESKYGPPCP PCPAPEFLGG PSVFLFPPKP
KDTLMISRTP EVTCVVVDVS QEDPEVQFNW YVDGVEVHNA
KTKPREEQFN STYRVVSVLT VLHQDWLNGK EYKCKVSNKG
LPSSIEKTIS KAKGQPREPQ VYTLPPSQEE MTKNQVSLTC
LVKGFYPSDI AVEWESNGQP ENNYKTTPPV LDSDGSFFLY
SRLTVDKSRW QEGNVFSCSV MHEALHNHYT QKSLSLSLGK;

and/or a light chain comprising the amino acid sequence of:

(SEQ ID NO: 101)
EIVLTQSPAT LSLSPGERAT LSCRASQSVS SYLAWYQQKP GQAPRLLIYD ASNRATGIPA RFSGSGSGTD FTLTISSLEP EDFAVYYCQQ SSNWPRTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC.

In an embodiment, the targeting moiety comprises the anti-PD-1 antibody pidilizumab (aka CT-011, hBAT or hBAT-1), or fragments thereof. Pidilizumab and other humanized anti-PD-I monoclonal antibodies are disclosed in US 2008/0025980 and WO 2009/101611, the entire disclosures of which are hereby incorporated by reference. In illustrative embodiments, the anti-PD-1 antibody or an antigen-binding fragment thereof for use in the methods provided herein comprises a light chain variable regions comprising an amino acid sequence selected from SEQ ID NOS: 15-18 of US 2008/0025980:

SEQ ID No: 15 of US 2008/0025980 (SEQ ID NO: 102):
EIVLTQSPSSLSASVGDRVTITCSARSSVSYMHWYQQKPGKAPKLLIYRT SNLASGVPSRFSGSGSGTDFTLTINSLQPEDFATYYCQQRSSFPLTFGGG TKLEIK;

SEQ ID No: 16 of US 2008/0025980 (SEQ ID NO: 103):
EIVLTQSPSSLSASVGDRVTITCSARSSVSYMHWFQQKPGKAPKLWIYRT SNLASGVPSRFSGSGSGTDYTLTINSLQPEDFATYYCQQRSSFPLTFGGG TKLEIK;

SEQ ID No: 17 of US 2008/0025980 (SEQ ID NO: 104):
EIVLTQSPSSLSASVGDRVTITCSARSSVSYMHWFQQKPGKAPKLWIYRT SNLASGVPSRFSGSGSGTDYCLTINSLQPEDFATYYCQQRSSFPLTFGGG TKLEIK;

SEQ ID No: 18 of US 2008/0025980 (SEQ ID NO: 105):
EIVLTQSPSSLSASVGDRVTITCSARSSVSYMHWFQQKPGKAPKLWIYRT SNLASGVPSRFSGSGSGTSYCLTINSLQPEDFATYYCQQRSSFPLTFGGG TKLEIK;

and/or a heavy chain comprising an amino acid sequence selected from SEQ ID NOS: 20-24 of US 2008/0025980:

SEQ ID No: 20 of US 2008/0025980
(SEQ ID NO: 106)::
QVQLVQSGSELKKPGASVKISCKASGYSFSNYGMNWVRQAPGQGLQWMGW INTDSGESTYAEEFKGRFVFSLDTSVSTAYLQITSLTAEDTGMYFCAKVG YDALDYWGQGTLVTVSS;

SEQ ID No: 21 of US 2008/0025980 (SEQ ID NO: 107):
QVQLVQSGSELKKPGASVKISCKASGYTFTNYGMNWVRQAPGQGLQWMGW INTDSGESTYAEEFKGRFVFSLDTSVSTAYLQITSLTAEDTGMYFCAKVG YDALDYWGQGTLVTVSS;

-continued

SEQ ID No: 22 of US 2008/0025980 (SEQ ID NO: 108):
QVQLVQSGSELKKPGASVKISCKASGYTFTNYGMNWVRQAPGQGLQWMGW INTDSGESTYAEEFKGRFVFSLDTSVNTAYLQITSLTAEDTGMYFCVRVG YDALDYWGQGTLVTVSS;

SEQ ID No: 23 of US 2008/0025980 (SEQ ID NO: 109):
QIQLVQSGSELKKPGASVKISCKASGYTFTNYGMNWVRQAPGQGLQWMGW INTDSGESTYAEEFKGRFVFSLDTSVNTAYLQITSLTAEDTGMYFCVRVG YDALDYWGQGTLVTVSS;

SEQ ID No: 24 of US 2008/0025980 (SEQ ID NO: 110):
QIQLVQSGSELKKPGASVKISCKASGYTFTNYGMNWVKQAPGQGLKWMGW INTDSGESTYAEEFKGRFAFSLDTSVNTAYLQITSLNAEDTGMYFCVRVG YDALDYWGQGTLVTVSS.

In an embodiment, the targeting moiety comprises a light chain comprising SEQ ID NO:18 of US 2008/0025980 and a heavy chain comprising SEQ ID NO:22 of US 2008/0025980.

In an embodiment, the targeting moiety comprises AMP-514 (aka MEDI-0680).

In an embodiment, the targeting moiety comprises the PD-L2-Fc fusion protein AMP-224, which is disclosed in WO2010/027827 and WO 2011/066342, the entire disclosures of which are hereby incorporated by reference. In such an embodiment, the targeting moiety may include a targeting domain which comprises SEQ ID NO:4 of WO2010/027827 (SEQ ID NO:111):

LFTVTVPKELYIIEHGSNVTLECNFDTGSHVNLGAITASLQKVENDTSPH RERATLLEEQLPLGKASFHIPQVQVRDEGQYQCIIIYGVAWDYKYLTLKV KASYRKINTHILKVPETDEVELTCQATGYPLAEVSWPNVSVPANTSHSRT PEGLYQVTSVLRLKPPPGRNFSCVFWNTHVRELTLASIDLQSQMEPRTHP TWLLHIFIPFCIIAFIFIATVIALRKQLCQKLYSSKDTTKRPVTTTKREV NSAI and/or the B7-DC fusion protein which comprises SEQ ID NO:83 of WO2010/027827 (SEQ ID NO:112):

MIFLLLMLSLELQLHQIAALFTVTVPKELYIIEHGSNVTLECNFDTGSHV NLGAITASLQKVENDTSPHRERATLLEEQLPLGKASFHIPQVQVRDEGQY QCIIIYGVAWDYKYLTLKVKASYRKINTHILKVPETDEVELTCQATGYPL AEVSWPNVSVPANTSHSRTPEGLYQVTSVLRLKPPPGRNFSCVFWNTHVR ELTLASIDLQSQMEPRTHPTWEPKSCDKTHTCPPCPAPELLGGPSVFLFP PKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTT PPVLDSDGSFFLYSKLTVDKSRWQQGNVFSCSVMHEALHNHYTQKSLSLS PGK

In an embodiment, the targeting moiety comprises the peptide AUNP 12 or any of the other peptides disclosed in US 2011/0318373 or U.S. Pat. No. 8,907,053. For example, the targeting moiety may comprise AUNP 12 (i.e., Compound 8 or SEQ ID NO:49 of US 2011/0318373) which has the sequence of SEQ ID NO:113:

SNTSESFK(SNTSESF)FRVTQLAPKAQIKE-NH2

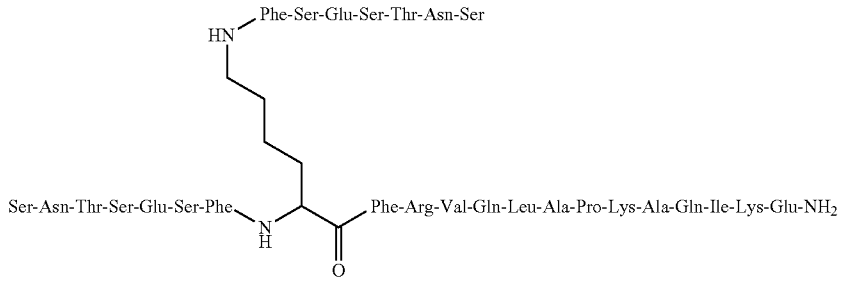

or:

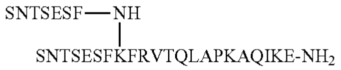

In an embodiment, the targeting moiety comprises the anti-PD-1 antibody 1E3, or fragments thereof, as disclosed in US 2014/0044738, the entire disclosures of which are hereby incorporated by reference. In illustrative embodiments, 1E3 or an antigen-binding fragment thereof for use in the methods provided herein comprises a heavy chain variable region comprising the amino acid sequence of:

(SEQ ID NO: 114)
EVQLQQSGPV LVKPGASVKM SCKASGYTFT DYYMNWVKQS
HGKSLEWIGN INPYNGGTTY NQKFKGKATL TVDKSSRTAY
MEINSLTSED SAVYYCARGR IYDGSLDYWG QGTALTVSS;

and/or a light chain variable region comprising the amino acid sequence of:

(SEQ ID NO: 115)
DIQMTQFPSS LCASQGGKVT VTCKASQDIN NYMAWYQHKP
GKGPRLLIHY TSTLLSGIPS RFSGSGSGRD YSFSISNLEP
EDIATYYCLQ YDNLWTFGGG TKLEIK.

In an embodiment, the targeting moiety comprises the anti-PD-1 antibody 1E8, or fragments thereof, as disclosed in US 2014/0044738, the entire disclosures of which are hereby incorporated by reference. In illustrative embodiments, 1E8 or an antigen-binding fragment thereof for use in the methods provided herein comprises a heavy chain variable region comprising the amino acid sequence of:

(SEQ ID NO: 116)
QVQLQQSGAE LAKPGASVRL SCKASGYTFT NYWMHWVKQR
PGQGLEWIGH INPSSGFTTY NQNFKDKATL TADKSSNTAY
MQLSSLTYED SAVYFCARED YDVDYWGQGT TLTVSS;

and/or a light chain variable region comprising the amino acid sequence of:

(SEQ ID NO: 117)
DIVMTQSQKF MSTSVGDRVS VTCKASQSVD TNVAWYQQKP
GQSPKALIFS ASYRYSGVPD RFTGSGSGTD FTLTINSVQS
EDLAEYFCQQ YNSYPYTFGS GTKLEIK.

In an embodiment, the targeting moiety comprises the anti-PD-1 antibody 1H3, or fragments thereof, as disclosed in US 2014/0044738, the entire disclosures of which are hereby incorporated by reference. In illustrative embodiments, 1H3 or an antigen-binding fragment thereof for use in the methods provided herein comprises a heavy chain variable region comprising the amino acid sequence of:

(SEQ ID NO: 118)
EVQLVESGGG LVKPGGSLKL SCAASGFTFS DYGMHWVRQA
PEKGLEWVAY ISSGSYTIYY TDTVKGRFTI SRDNAKNTLF
LQMTSLRSED TAMYYCARRG YGSFYEYYFD YWGQGTTLTV SS;

and/or light chain variable region comprising the amino acid sequence of:

(SEQ ID NO: 119)
QIVLTQSPAL MSASPGEKVT MTCSASSSVS YMYWYQQKPR
SSPKPWIYLT SNLASGVPAR FSGSGSGTSY SLTISSMEAE
DAATYYCQQW SSNPFTFGSG TKLEIK.

In an embodiment, the targeting moiety comprises a VHH directed against PD-1 as disclosed, for example, in U.S. Pat. No. 8,907,065 and WO 2008/071447, the entire disclosures of which are hereby incorporated by reference. In illustrative embodiments, the VHHs against PD-1 comprise SEQ ID NOS: 347-351 of U.S. Pat. No. 8,907,065:

SEQ ID No: 347 of US 8,907,065 (SEQ ID NO: 120):
EVQLVESGGGLVQAGKSLRLSCAASGSIFSIHAMGWFRQAPGKEREFVAA
ITWSGGITYYEDSVKGRFTISRDNAKNTVYLQMNSLKPEDTAIYYCAADR
AESSWYDYWGQGTQVTVSS;

SEQ ID No: 348 of US 8,907,065 (SEQ ID NO: 121):
EVQLVESGGGLVQAGGSLRLSCAASGSIASIHAMGWFRQAPGKEREFVAV
ITWSGGITYYADSVKGRFTISRDNAKNTVYLQMNSLKPEDTAIYYCAGDK
HQSSWYDYWGQGTQVTVSS;

-continued

SEQ ID No: 349 of US 8,907,065 (SEQ ID NO: 122):
EVQLVESGGGLVQAGGSLRLSCAASGSISSIHAMGWFRQAPGKEREFVAA

ITWSGGITYYADSLKGRFTISRDNAKNTGYLQMNSLKPEDTAIYYCAADR

AQSSWYDYWGQGTQVTVSS;

SEQ ID No: 350 of US 8,907,065 (SEQ ID NO: 123):
EVQLVESGGGLVQAGGSLGLSCAASGSIFSINAMAWFRQAPGKEREFVAL

ISWSGGSTYYEDSVKGRFTISRDNAKNTVYLQMNSLKPEDTAIYYCAADR

VDSNWYDYWGQGTQVTVSS;

SEQ ID No: 351 of US 8,907,065 (SEQ ID NO: 124):
EVQLVESGGGLVQAGGSLRLSCAASGRAFSSGTMGWFRRAPGKEREFVA

SIPWSGGRIYYADSVKGRFTISRDNAQNTVYLQMNSLKPEDTAVYYCAVK

ERSTGWDFASWGQCTQVTVSS.

In an embodiment, the targeting moiety comprises any one of the anti-PD-1 antibodies, or fragments thereof, as disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID NOS: 25-29 of US2011/0271358:

SEQ ID No: 25 of US2011/0271358 (SEQ ID NO: 125):
QVQLVQSGAELKQPGASVKMSCKASGYSFTSSWIHWVKQAPGQGLEWIGY

IYPSTGFTEYNQKFKDRATLTADKSTSTAYMELSSLRSEDSAVYYCARWR

DSSGYHAMDYWGQGTSVTVSS;

SEQ ID No: 26 of US2011/0271358 (SEQ ID NO: 126):
QVQLVQSGAEVKQPGASVKMSCKASGYSFTSSWIHWVKQAPGQGLEWIGY

IYPSTGFTEYNQKFKDRATLTADKSTSTAYMELSSLRSEDTAVYY3/d10

CARWRDSSGYHAMDYWGQGTSVTVSS;

SEQ ID No: 27 of US2011/0271358 (SEQ ID NO: 127):
QVQLVQSGHEVKQPGASVKMSCKASGYSFTSSWIHWVKQAPGQGLEWIGY

IYPSTGFTEYNQKFKDRATLTADKSTSTAYMELSSLRSEDTAVYYCARWR

DSSGYHAMDYWGQGTLVTVSS;

SEQ ID No: 28 of US2011/0271358 (SEQ ID NO: 128):
QVQLVQSGHEVKQPGASVKMSCKASGYSFTSSWIHWVRQAPGQGLEWIGY

IYPSTGFTEYNQKFKDRATLTADKSTSTAYMELSSLRSEDTAVYYCARWR

DSSGYHAMDYWGQGTLVTVSS;

SEQ ID No: 29 of US2011/0271358 (SEQ ID NO: 129):
QVQLVQSGHEVKQPGASVKVSCKASGYSFTSSWIHWVRQAPGQGLEWIGY

IYPSTGFTEYNQKFKDRATITADKSTSTAYMELSSLRSEDTAVYYCARWR

DSSGYHAMDYWGQGTLVTVSS;

and/or a light chain comprising an amino acid sequence selected from SEQ ID NOS: 30-33 of US2011/0271358:

SEQ ID No: 30 of US2011/0271358 (SEQ ID NO: 130):
DIVLTQSPASLTLSPGQRLTISCRASQSVSTSGYSYMHWYQQKPDQSPKL

LIKFGSNLESGIPARFSGSGSGTDFTLTISSLEEEDFATYYCQHSWEIPY

TFGQGTKLEIK;

-continued

SEQ ID No: 31 of US2011/0271358 (SEQ ID NO: 131):
DIVLTQSPATLSLSPGQRLTISCRASQSVSTSGYSYMHWYQQKPDQSPKL

LIKFGSNLESGIPARFSGSGSGTDFTLTISSLEPEDFATYYCQHSWEIPY

TFGQGTKLEIK;

SEQ ID No: 32 of US2011/0271358 (SEQ ID NO: 132):
EIVLTQSPATLSLSPGQRLTISCRASQSVSTSGYSYMHWYQQKPDQSPKL

LIKFGSNLESGIPARFSGSGSGTDFTLTISSLEPEDFATYYCQHSWEIPY

TFGQGTKLEIK;

SEQ ID No: 33 of US2011/0271358 (SEQ ID NO: 133):
DIVLTQSPATLSLSPGQRLTISCRASQSVSTSGYSYMHWYQQKPDQSPKL

LIKFGSNLESGIPARFSGSGSGTDFTLTISSLEPEDFAVYYCQHSWEIPY

TFGQGTKLEIK.

In various embodiments, the present multi-specific Clec9A binding agent comprises one or more antibodies directed against PD-1, or antibody fragments thereof, selected from TSR-042 (Tesaro, Inc.), REGN2810 (Regeneron Pharmaceuticals, Inc.), PDR001 (Novartis Pharmaceuticals), and BGB-A317 (BeiGene Ltd.)

In an exemplary embodiment, the present multi-specific Clec9A binding agent comprises a targeting moiety directed against PD-1, such as SEQ ID NO:134:

EVQLVESGGGLVQAGKSLRLSCAASGSIFSIHAMGWFRQAPGKEREFVAA

ITWSGGITYYEDSVKGRFTISRDNAKNTVYLQMNSLKPEDTAIYYCAADR

AESSWYDYWGQGTQVTVSS.

In various embodiments, the present multi-specific Clec9A binding agent has one or more targeting moieties directed against PD-L1. In some embodiments, the Clec9A binding agent has one or more targeting moieties which selectively bind a PD-L1 polypeptide. In some embodiments, the Clec9A binding agent comprises one or more antibodies, antibody derivatives or formats, peptides or polypeptides, or fusion proteins that selectively bind a PD-L1 polypeptide.

In an embodiment, the targeting moiety comprises the anti-PD-L1 antibody MEDI4736 (aka durvalumab), or fragments thereof. MEDI4736 is selective for PD-L1 and blocks the binding of PD-L1 to the PD-1 and CD80 receptors. MEDI4736 and antigen-binding fragments thereof for use in the methods provided herein comprises a heavy chain and a light chain or a heavy chain variable region and a light chain variable region. The sequence of MEDI4736 is disclosed in WO/2016/06272, the entire contents of which are hereby incorporated by reference. In illustrative embodiments, MEDI4736 or an antigen-binding fragment thereof for use in the methods provided herein comprises a heavy chain comprising the amino acid sequence of:

(SEQ ID NO: 135)
EVQLVESGGG LVQPGGSLRL SCAASGFTFS RYWMSWVRQA

PGKGLEWVAN IKQDGSEKYY VDSVKGRFTI SRDNAKNSLY

LQMNSLRAED TAVYYCAREG GWFGELAFDY WGQGTLVTVS

SASTKGPSVF PLAPSSKSTS GGTAALGCLV KDYFPEPVTV

-continued

```
SWNSGALTSG VHTFPAVLQS SGLYSLSSVV TVPSSSLGTQ
TYICNVNHKP SNTKVDKRVE PKSCDKTHTC PPCPAPEFEG
GPSVFLFPPK PKDTLMISRT PEVTCVVVDV SHEDPEVKFN
WYVDGVEVHN AKTKPREEQY NSTYRVVSVL TVLHQDWLNG
KEYKCKVSNK ALPASIEKTI SKAKGQPREP QVYTLPPSRE
EMTKNQVSLT CLVKGFYPSD IAVEWESNGQ PENNYKTTPP
VLDSDGSFFL YSKLTVDKSR WQQGNVFSCS VMHEALHNHY
TQKSLSLSPG K;
```

and/or a light chain comprising the amino acid sequence of:

```
                                      (SEQ ID NO: 136)
EIVLTQSPGT LSLSPGERAT LSCRASQRVS SSYLAWYQQK
PGQAPRLLIY DASSRATGIP DRFSGSGSGT DFTLTISRLE
PEDFAVYYCQ QYGSLPWTFG QGTKVEIKRT VAAPSVFIFP
PSDEQLKSGT ASVVCLLNNF YPREAKVQWK VDNALQSGNS
QESVTEQDSK DSTYSLSSTL TLSKADYEKH KVYACEVTHQ
GLSSPVTKSF NRGEC.
```

In illustrative embodiments, the MEDI4736 or an antigen-binding fragment thereof for use in the methods provided herein comprises a heavy chain variable region comprising the amino acid sequence of SEQ ID NO:4 of WO/2016/06272 (SEQ ID NO:137):

```
EVQLVESGGGLVQPGGSLRLSCAASGFTFSRYWMSWVRQAPGKGLEWVAN
IKQDGSEKYYVDSVKGRFTISRDNAKNSLYLQMNSLRAEDTAVYYCAREG
GWFGELAFDYWGQGTLVTVSS;
```

and/or a light chain variable region comprising the amino acid sequence of SEQ ID NO:3 of WO/2016/06272 (SEQ ID NO:138):

```
EIVLTQSPGTLSLSPGERATLSCRASQRVSSSYLAWYQQKPGQAPRLLIY
DASSRATGIPDRFSGSGSGTDFTLTISRLEPEDFAVYYCQQYGSLPWTFG
QGTKVEIK
```

In an embodiment, the targeting moiety comprises the anti-PD-L1 antibody atezolizumab (aka MPDL3280A, RG7446), or fragments thereof. In illustrative embodiments, atezolizumab or an antigen-binding fragment thereof for use in the methods provided herein comprises a heavy chain comprising the amino acid sequence of:

```
                                      (SEQ ID NO: 139)
EVQLVESGGGLVQPGGSLRLSCAASGFTFSDSWIHWVRQAPGKGLEWVAW
ISPYGGSTYYADSVKGRFTISADTSKNTAYLQMNSLRAEDTAVYYCARRH
WPGGFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYAST
```

-continued

```
YRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK;
```

and/or a light chain comprising the amino acid sequence of:

```
                                      (SEQ ID NO: 140)
DIQMTQSPSSLSASVGDRVTITCRASQDVSTAVAWYQQKPGKAPKLLIYS
ASFLYSGVPSRFSGSGSGTDFTLTISSLQPEDFATYYCQQYLYHPATFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.
```

In an embodiment, the targeting moiety comprises the anti-PD-L1 antibody avelumab (aka MSB0010718C), or fragments thereof. In illustrative embodiments, avelumab or an antigen-binding fragment thereof for use in the methods provided herein comprises a heavy chain comprising the amino acid sequence of:

```
                                      (SEQ ID NO: 141)
EVQLLESGGG LVQPGGSLRL SCAASGFTFS SYIMMWVRQA
PGKGLEWVSS IYPSGGITFY ADTVKGRFTI SRDNSKNTLY
LQMNSLRAED TAVYYCARIK LGTVTTVDYW GQGTLVTVSS
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKKVEP KSCDKTHTCP PCPAPELLGG
PSVFLFPPKP KDTLMISRTP EVTCVVVDVS HEDPEVKFNW
YVDGVEVHNA KTKPREEQYN STYRVVSVLT VLHQDWLNGK
EYKCKVSNKA LPAPIEKTIS KAKGQPREPQ VYTLPPSRDE
LTKNQVSLTC LVKGFYPSDI AVEWESNGQP ENNYKTTPPV
LDSDGSFFLY SKLTVDKSRW QQGNVFSCSV MHEALHNHYT
QKSLSLSPGK;
```

and/or a light chain comprising the amino acid sequence of:

```
                                      (SEQ ID NO: 142)
QSALTQPASV SGSPGQSITI SCTGTSSDVG GYNYVSWYQQ
HPGKAPKLMI YDVSNRPSGV SNRFSGSKSG NTASLTISGL
QAEDEADYYC SSYTSSSTRV FGTGTKVTVL GQPKANPTVT
LFPPSSEELQ ANKATLVCLI SDFYPGAVTV AWKADGSPVK
AGVETTKPSK QSNNKYAASS YLSLTPEQWK SHRSYSCQVT
HEGSTVEKTV APTECS.
```

In an embodiment, the targeting moiety comprises the anti-PD-L1 antibody BMS-936559 (aka 12A4, MDX-1105), or fragments thereof, as disclosed in US 2013/0309250 and WO2007/005874, the entire disclosures of which are hereby incorporated by reference. In illustrative embodiments, BMS-936559 or an antigen-binding fragment thereof for use in the methods provided herein comprises a heavy chain variable region comprising the amino acid sequence of:

(SEQ ID NO: 143)
QVQLVQSGAEVKKPGSSVKVSCKTSGDTFSTYAISWVRQAPGQGLEWMGG

IIPIFGKAHYAQKFQGRVTITADESTSTAYMELSSLRSEDTAVYFCARKF

HFVSGSPFGMDVWGQGTTVTVSS;

and/or a light chain variable region comprising the amino acid sequence of:

(SEQ ID NO: 144)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPTFGQG

TKVEIK.

In an embodiment, the targeting moiety comprises the anti-PD-L1 antibody 3G10, or fragments thereof, as disclosed in US 2013/0309250 and WO2007/005874, the entire disclosures of which are hereby incorporated by reference. In illustrative embodiments, 3G10 or an antigen-binding fragment thereof for use in the methods provided herein comprises a heavy chain variable region comprising the amino acid sequence of:

(SEQ ID NO: 145)
QVQLVQSGAEVKKPGASVKVSCKASGYTFTDYGFSWVRQAPGQGLEWMGW

ITAYNGNTNYAQKLQGRVTMTTDTSTSTVYMELRSLRSDDTAVYYCARDY

FYGMDVWGQGTTVTVSS;

and/or a light chain variable region comprising the amino acid sequence of:

(SEQ ID NO: 146)
EIVLTQSPATLSLSPGERATLSCRASQSVSSYLVWYQQKPGQAPRLLIYD

ASNRATGIPARFSGSGSGTDFTLTISSLEPEDFAVYYCQQRSNWPRTFGQ

GTKVEIK.

In an embodiment, the targeting moiety comprises the anti-PD-L1 antibody 10A5, or fragments thereof, as disclosed in US 2013/0309250 and WO2007/005874, the entire disclosures of which are hereby incorporated by reference. In illustrative embodiments, 10A5 or an antigen-binding fragment thereof for use in the methods provided herein comprises a heavy chain variable region comprising the amino acid sequence of:

(SEQ ID NO: 147)
QVQLVQSGAEVKKPGASVKVSCKASGYTFTSYDVHWVRQAPGQRLEWMGW

LHADTGITKFSQKFQGRVTITRDTSASTAYMELSSLRSEDTAVYYCARER

IQLWFDYWGQGTLVTVSS;

and/or a light chain variable region comprising the amino acid sequence of:

(SEQ ID NO: 148)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPYTFGQ

GTKLEIK.

In an embodiment, the targeting moiety comprises the anti-PD-L1 antibody 5F8, or fragments thereof, as disclosed in US 2013/0309250 and WO2007/005874, the entire disclosures of which are hereby incorporated by reference. In illustrative embodiments, 5F8 or an antigen-binding fragment thereof for use in the methods provided herein comprises a heavy chain variable region comprising the amino acid sequence of:

(SEQ ID NO: 149)
QVQLVQSGAEVKKPGSSVKVSCKVSGGIFSTYAINWVRQAPGQGLEWMGG

IIPIFGTANHAQKFQGRVTITADESTSTAYMELSSLRSEDTAVYYCARDQ

GIAAALFDYWGQGTLVTVSS;

and/or a light chain variable region comprising the amino acid sequence of:

(SEQ ID NO: 150)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPWTFG

QGTKVEIK.

In an embodiment, the targeting moiety comprises the anti-PD-L1 antibody 10H10, or fragments thereof, as disclosed in US 2013/0309250 and WO2007/005874, the entire disclosures of which are hereby incorporated by reference. In illustrative embodiments, 10H10 or an antigen-binding fragment thereof for use in the methods provided herein comprises a heavy chain variable region comprising the amino acid sequence of:

(SEQ ID NO: 151)
EVQLVESGGGLVQPGRSLRLSCAVSGFTFDDYVVHWVRQAPGKGLEWVSG

ISGNSGNIGYADSVKGRFTISRDNAKNSLYLQMNSLRAEDTALYYCAVPF

DYWGQGTLVTVSS;

and/or a light chain variable region comprising the amino acid sequence of:

(SEQ ID NO: 152)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPYTFGQ

GTKLEIK.

In an embodiment, the targeting moiety comprises the anti-PD-L1 antibody 1B12, or fragments thereof, as disclosed in US 2013/0309250 and WO2007/005874, the entire disclosures of which are hereby incorporated by reference. In illustrative embodiments, 1B12 or an antigen-binding fragment thereof for use in the methods provided herein comprises a heavy chain variable region comprising the amino acid sequence of:

(SEQ ID NO: 153)
QVQLVQSGAEVKKPGSSVKVSCKTSGDTFSSYAISWVRQAPGQGLEWMGG

IIPIFGRAHYAQKFQGRVTITADESTSTAYMELSSLRSEDTAVYFCARKF

HFVSGSPFGMDVWGQGTTVTVSS;

and/or a light chain variable region comprising the amino acid sequence of:

```
                                         (SEQ ID NO: 154)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPTFGQG

TKVEIK.
```

In an embodiment, the targeting moiety comprises the anti-PD-L1 antibody 7H1, or fragments thereof, as disclosed in US 2013/0309250 and WO2007/005874, the entire disclosures of which are hereby incorporated by reference. In illustrative embodiments, 7H1 or an antigen-binding fragment thereof for use in the methods provided herein comprises a heavy chain variable region comprising the amino acid sequence of:

```
                                         (SEQ ID NO: 155)
QVQLVQSGAEVKKPGSSVKVSCKTSGGTFSSYAISWVRQAPGQGLEWMGG

IIPIFGKAHYAQKFQGRVTITADESTTTAYMELSSLRSEDTAVYYCARKY

DYVSGSPFGMDVWGQGTTVTVSS;
```

and/or a light chain variable region comprising the amino acid sequence of:

```
                                         (SEQ ID NO: 156)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPTFGQG

TKVEIK.
```

In an embodiment, the targeting moiety comprises the anti-PD-L1 antibody 11E6, or fragments thereof, as disclosed in US 2013/0309250 and WO2007/005874, the entire disclosures of which are hereby incorporated by reference. In illustrative embodiments, 11E6 or an antigen-binding fragment thereof for use in the methods provided herein comprises a heavy chain variable region comprising the amino acid sequence of:

```
                                         (SEQ ID NO: 157)
QVQLVQSGAEVKKPGSSVKVSCKASGGTFSSYAINWVRQAPGQGLEWMGG

IIPIFGSANYAQKFQDRVTITADESTSAAYMELSSLRSEDTAVYYCARDS

SGWSRYYMDVWGQGTTVTVSS;
```

and/or a light chain variable region comprising the amino acid sequence of:

```
                                         (SEQ ID NO: 158)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPFGGG

TKVEIK.
```

In an embodiment, the targeting moiety comprises the anti-PD-L1 antibody 12B7, or fragments thereof, as disclosed in US 2013/0309250 and WO2007/005874, the entire disclosures of which are hereby incorporated by reference. In illustrative embodiments, 12B7 or an antigen-binding fragment thereof for use in the methods provided herein comprises a heavy chain variable region comprising the amino acid sequence of:

```
                                         (SEQ ID NO: 159)
QVQLVQSGAEVKEPGSSVKVSCKASGGTFNSYAISWVRQAPGQGLEWMGG

IIPLFGIAHYAQKFQGRVTITADESTNTAYMDLSSLRSEDTAVYYCARKY

SYVSGSPFGMDVWGQGTTVTVSS;
```

and/or a light chain variable region comprising the amino acid sequence of:

```
                                         (SEQ ID NO: 160)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPTFGQG

TRLEIK.
```

In an embodiment, the targeting moiety comprises the anti-PD-L1 antibody 13G4, or fragments thereof, as disclosed in US 2013/0309250 and WO2007/005874, the entire disclosures of which are hereby incorporated by reference. In illustrative embodiments, 13G4 or an antigen-binding fragment thereof for use in the methods provided herein comprises a heavy chain variable region comprising the amino acid sequence of:

```
                                         (SEQ ID NO: 161)
EVQLVESGGGLVQPGRSLRLSCAASGITFDDYGMHWVRQAPGKGLEWVSG

ISWNRGRIEYADSVKGRFTISRDNAKNSLYLQMNSLRAEDTALYYCAKGR

FRYFDWFLDYWGQGTLVTVSS;
```

and/or a light chain variable region comprising the amino acid sequence of:

```
                                         (SEQ ID NO: 162)
AIQLTQSPSSLSASVGDRVTITCRASQGISSALAWYQQKPGKAPKLLIYD

ASSLESGVPSRFSGSGSGTDFTLTISSLQPEDFATYYCQQFNSYPFTFGP

GTKVDIK.
```

In an embodiment, the targeting moiety comprises the anti-PD-L1 antibody 1E12, or fragments thereof, as disclosed in US 2014/0044738, the entire disclosures of which are hereby incorporated by reference. In illustrative embodiments, 1E12 or an antigen-binding fragment thereof for use in the methods provided herein comprises a heavy chain variable region comprising the amino acid sequence of:

```
                                         (SEQ ID NO: 163)
   EVKLQESGPS LVKPSQTLSL TCSVTGYSIT SDYWNWIRKF

   PGNKLEYVGY ISYTGSTYYN PSLKSRISIT RDTSKNQYYL

   QLNSVTSEDT ATYYCARYGG WLSPFDYWGQ GTTLTVSS;
```

and/or a light chain variable region comprising the amino acid sequence of:

```
                                         (SEQ ID NO: 164)
   DIVMTQSHKL MSTSVGDRVS ITCKASQDVG TAVAWYQQKP

   GQSPKLLIYW ASTRHTGVPD RFTGSGSGTD FTLTISNVQS

   EDLADYFCQQ DSSYPLTFGA GTKVELK.
```

In an embodiment, the targeting moiety comprises the anti-PD-L1 antibody 1F4, or fragments thereof, as disclosed in US 2014/0044738, the entire disclosures of which are hereby incorporated by reference. In illustrative embodiments, 1F4 or an antigen-binding fragment thereof for use in the methods provided herein comprises a heavy chain variable region comprising the amino acid sequence of:

(SEQ ID NO: 165)
EVQLQESGPG LVAPSQSLSI TCTVSGFSLT TYSINWIRQP

PGKGLEWLGV MWAGGGTNSN SVLKSRLIIS KDNSKSQVFL

KMNSLQTDDT ARYYCARYYG NSPYYAIDYW GQGTSVTVSS;

and/or a light chain variable region comprising the amino acid sequence of:

(SEQ ID NO: 166)
DIVTTQSHKL MSTSVGDRVS ITCKASQDVG TAVAWYQQKP

GQSPKLLIYW ASTRHTGVPD RFTGSGSGTD FTLTISNVQS

EDLADYFCQQ DSSYPLTFGA GTKVELK.

In an embodiment, the targeting moiety comprises the anti-PD-L1 antibody 2G11, or fragments thereof, as disclosed in US 2014/0044738, the entire disclosures of which are hereby incorporated by reference. In illustrative embodiments, 2G11 or an antigen-binding fragment thereof for use in the methods provided herein comprises a heavy chain variable region comprising the amino acid sequence of:

(SEQ ID NO: 167)
EVKLQESGPS LVKPSQTLSL TCSVTGYSII SDYWNWIRKF

PGNKLEYLGY ISYTGSTYYN PSLKSRISIT RDTSKNQYYL

QLNSVTTEDT ATYYCARRGG WLLPFDYWGQ GTTLTVSS;

and/or a light chain variable region comprising the amino acid sequence of:

(SEQ ID NO: 168)
DIVMTQSPSS LAVSVGEKVS MGCKSSQSLL YSSNQKNSLA

WYQQKPGQSP KLLIDWASTR ESGVPDRFTG SGSGTDFTLT

ISSVKAEDLA VYYCQQYYGY PLTFGAGTKL ELK.

In an embodiment, the targeting moiety comprises the anti-PD-L1 antibody 3B6, or fragments thereof, as disclosed in US 2014/0044738, the entire disclosures of which are hereby incorporated by reference. In illustrative embodiments, 3B6 or an antigen-binding fragment thereof for use in the methods provided herein comprises a heavy chain variable region comprising the amino acid sequence of:

(SEQ ID NO: 169)
EVKLQESGPS LVKPGASVKL SCKASGYTFT SYDINWVKQR

PGQGLEWIGW IFPRDNNTKY NENFKGKATL TVDTSSTTAY

MELHSLTSED SAVYFCTKEN WVGDFDYWGQ GTTLTLSS;

and/or a light chain variable region comprising the amino acid sequence of:

(SEQ ID NO: 170)
DIVMTQSPAI MSASPGEKVT MTCSASSSIR YMHWYQQKPG

TSPKRWISDT SKLTSGVPAR FSGSGSGTSY ALTISSMEAE

DAATYYCHQR SSYPWTFGGG TKLEIK.

In an embodiment, the targeting moiety comprises the anti-PD-L1 antibody 3D10, or fragments thereof, as disclosed in US 2014/0044738 and WO2012/145493, the entire disclosures of which are hereby incorporated by reference. In illustrative embodiments, 3D10 or an antigen-binding fragment thereof for use in the methods provided herein comprises a heavy chain variable region comprising the amino acid sequence of:

(SEQ ID NO: 171)
EVQLQQSGPD LVTPGASVRI SCQASGYTFP DYYMNWVKQS

HGKSLEWIGD IDPNYGGTTY NQKFKGKAIL TVDRSSSTAY

MELRSLTSED SAVYYCARGA LTDWGQGTSL TVSS;

and/or a light chain variable region comprising the amino acid sequence of:

(SEQ ID NO: 172)
QIVLSQSPAI LSASPGEKVT MTCRASSSVS YIYWFQQKPG

SSPKPWIYAT FNLASGVPAR FSGSGSGTSY SLTISRVETE

DAATYYCQQW SNNPLTFGAG TKLELK.

In an embodiment, the targeting moiety comprises any one of the anti-PD-L1 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 34-38 of US2011/0271358:

SEQ ID No: 34 of US2011/0271358 (SEQ ID NO: 173):
EVQLVQSGPELKKPGASVKMSCKASGYTFTSYVMHWVKQAPGQRLEWIGY

VNPFNDGTKYNEMFKGRATLTSDKSTSTAYMELSSLRSEDSAVYYCARQA

WGYPWGQGTLVTVSS;

SEQ ID No: 35 of US2011/0271358 (SEQ ID NO: 174):
EVQLVQSGAEVKKPGASVKMSCKASGYTFTSYVMHWVKQAPGQRLEWIGY

VNPFNDGTKYNEMFKGRATLTSDKSTSTAYMELSSLRSEDTAVYYCARQA

WGYPWGQGTLVTVSS;

SEQ ID No: 36 of US2011/0271358 (SEQ ID NO: 175):
EVQLVQSGAEVKKPGASVKMSCKASGYTFTSYVMHWVRQAPGQRLEWIGY

VNPFNDGTKY NEMFKGRATLTSDKSTSTAYMELSSLRSEDTAVYYCA

RQAWGYPWGQGTLVTVSS;

SEQ ID No: 37 of US2011/0271358 (SEQ ID NO: 176):
EVQLVQSGAEVKKPGASVKVSCKASGYTFTSYVMHWVRQAPGQRLEWIGY

VNPFNDGTKYNEMFKGRATLTSDKSTSTAYMELSSLRSEDTAVYYCARQA

WGYPWGQGTLVTVSS;

-continued

SEQ ID No: 38 of US2011/0271358 (SEQ ID NO: 177):
EVQLVQSGAEVKKPGASVKVSCKASGYTFTSYVMHWVRQAPGQRLEWIGY
VNPFNDGTKYNEMFKGRATITSDKSTSTAYMELSSLRSEDTAVYYCARQA
WGYPWGQGTLVTVSS;

and/or a light chain comprising an amino acid sequence selected from SEQ ID Nos: 39-42 of US2011/0271358:

SEQ ID No: 39 of US2011/0271358 (SEQ ID NO: 178):
DIVLTQSPASLALSPGERATLSCRATESVEYYGTSLVQWYQQKPGQPPKL
LIYAASSVDSGVPSRFSGSGSGTDFTLTINSLEEEDAAMYFCQQSRRVPY
TFGQGTKLEIK;

SEQ ID No: 40 of US2011/0271358 (SEQ ID NO: 179):
DIVLTQSPATLSLSPGERATLSCRATESVEYYGTSLVQWYQQKPGQPPKL
LIYAASSVDSGVPSRFSGSGSGTDFTLTINSLEAEDAAMYFCQQSRRVPY
TFGQGTKLEIK;

SEQ ID No: 41 of US2011/0271358 (SEQ ID NO: 180):
EIVLTQSPATLSLSPGERATLSCRATESVEYYGTSLVQWYQQKPGQPPKL
LIYAASSVDSGVPSRFSGSGSGTDFTLTINSLEAEDAAMYFCQQSRRVPY
TFGQGTKLEIK;

SEQ ID No: 42 of US2011/0271358 (SEQ ID NO: 181):
DIVLTQSPATLSLSPGERATLSCRATESVEYYGTSLVQWYQQKPGQPPKL
LIYAASSVDSGVPSRFSGSGSGTDFTLTINSLEAEDAATYFCQQSRRVPY
TFGQGTKLEIK.

In an embodiment, the targeting moiety comprises the anti-PD-L1 antibody 2.7A4, or fragments thereof, as disclosed in WO 2011/066389, U.S. Pat. No. 8,779,108, and US2014/0356353, the entire disclosures of which are hereby incorporated by reference. In illustrative embodiments, 2.7A4 or an antigen-binding fragment thereof for use in the methods provided herein comprises a heavy chain variable region comprising the amino acid sequence of:

SEQ ID No: 2 of WO 2011/066389 (SEQ ID NO: 182):
EVQLVESGGGLVKPGGSLRLSCAASGFTFSTYSMNWVRQAPGKGLEWVSS
ISSSGDYIYYADSVKGRFTISRDNAKNSLFLQMNSLKAEDTAVYYCARDL
VTSMVAFDYWGQGTLVTVSS;

and/or a light chain variable region comprising the amino acid sequence of:

SEQ ID No: 7 of WO 2011/066389 (SEQ ID NO: 183):
SYELTQPPSVSVSPGQAARITCSGDALPQKYVFWYQQKSGQAPVLVIYED
SKRPSGIPERFSGSSSGTMATLTISGAQVEDEADYYCYSTDRSGNHRVFG
GGTRLTVL.

In an embodiment, the targeting moiety comprises the anti-PD-L1 antibody 2.9D10, or fragments thereof, as disclosed in WO 2011/066389, U.S. Pat. No. 8,779,108, and US2014/0356353, the entire disclosures of which are hereby incorporated by reference. In illustrative embodiments, 2.9D10 or an antigen-binding fragment thereof for use in the methods provided herein comprises a heavy chain variable region comprising the amino acid sequence of:

SEQ ID No: 12 of WO 2011/066389 (SEQ ID NO: 184):
EVQLVESGGGLVQPGGSLRLSCAASGFTFSSYWMSWVRQAPGKGLEWVAN
IKQDGGEQYYVDSVKGRFTISRDNAKNSLYLQMNSLRAEDTAVYYCARDW
NYGYYDMDVWGQGTTVTVSS;

and/or a light chain variable region comprising the amino acid sequence of:

SEQ ID No: 17 of WO 2011/066389 (SEQ ID NO: 185):
EIVLTQSPGTLSLSPGERATLSCRASQSVSSNYLAWFQQKPGQAPRLLIF
GTSSRATGIPDRFSGSGSGTDFTLTISRLEPEDFAVYYCQQYGSSIFTFG
PGTKVDIK.

In an embodiment, the targeting moiety comprises the anti-PD-L1 antibody 2.14H9, or fragments thereof, as disclosed in WO 2011/066389, U.S. Pat. No. 8,779,108, and US2014/0356353, the entire disclosures of which are hereby incorporated by reference. In illustrative embodiments, 2.14H9 or an antigen-binding fragment thereof for use in the methods provided herein comprises a heavy chain variable region comprising the amino acid sequence of:

SEQ ID No: 22 of WO 2011/066389 (SEQ ID NO: 186):
EVQLVESGGGLVQPGGSLRLSCAASGFTFSRYWMSWVRQAPGKGLEWVAN
IKQDGSEKYYVDSVKGRFTISRDNAKNSLYLQMNSLRAEDTAVYYCAREG
GWFGELAFDYWGQGTLVTVSS;

and/or a light chain variable region comprising the amino acid sequence of:

SEQ ID No: 27 of WO 2011/066389 (SEQ ID NO: 187):
EIVLTQSPGTLSLSPGERATLSCRASQRVSSSYLAWYQQKPGQAPRLLIY
DASSRATGIPDRFSGSGSGTDFTLTISRLEPEDFAVYYCQQYGSLPWTFG
QGTEVEIK.

In an embodiment, the targeting moiety comprises the anti-PD-L1 antibody 2.20A8, or fragments thereof, as disclosed in WO 2011/066389, U.S. Pat. No. 8,779,108, and US2014/0356353, the entire disclosures of which are hereby incorporated by reference. In illustrative embodiments, 2.20A8 or an antigen-binding fragment thereof for use in the methods provided herein comprises a heavy chain variable region comprising the amino acid sequence of:

SEQ ID No: 32 of WO 2011/066389 (SEQ ID NO: 188):
EVQLLESGGGLVQPGGSLRLSCAASGFTFSNYAMSWVRQAPGKGLEWVSA
IRGSGGSTYYADSVKGRFTISRDNSKNTLYLQMNSLRAEDTAVYYCAKDL
HYDSSGYLDYWGQGTLVTVSS;

and/or a light chain variable region comprising the amino acid sequence of:

SEQ ID No: 37 of WO 2011/066389 (SEQ ID NO: 189):
DIQMTQSPSSVSASVGDRVTITCRASQGIRSWLAWYQQKPGKAPKLLIYA
ISRLQSGVPSRFSGSGSGTDFTLTISSLQPEDFATYYCQQANSFPLTFGG
GTKVEIK.

In an embodiment, the targeting moiety comprises the anti-PD-L1 antibody 3.15G8, or fragments thereof, as disclosed in WO 2011/066389, U.S. Pat. No. 8,779,108, and US2014/0356353, the entire disclosures of which are hereby incorporated by reference. In illustrative embodiments, 3.15G8 or an antigen-binding fragment thereof for use in the methods provided herein comprises a heavy chain variable region comprising the amino acid sequence of:

SEQ ID No: 42 of WO 2011/066389 (SEQ ID NO: 190):
EVQLVESGGGLVQPGGSLRLSCAASGFTFSSYWMSWVRQAPGKGLEWVAN

IKQDGGEKYYVDSVKGRFTISRDNAKNSLFLQMNSLRAEDTAVYYCARVQ

LYSDYFDYWGQGTLVTVSS;

and/or a light chain variable region comprising the amino acid sequence of:

SEQ ID No: 47 of WO 2011/066389 (SEQ ID NO: 191):
DIQMTQSPSSVSASVGDRVTITCRASQGISSWLAWYQQKSGKAPKLLIYA

ASGLQSGVPSRFSGSGSGTDFTLTISSLQPEDLATYYCQQSHSLPPTFGQ

GTKVEIK.

In an embodiment, the targeting moiety comprises the anti-PD-L1 antibody 3.18G1, or fragments thereof, as disclosed in WO 2011/066389, U.S. Pat. No. 8,779,108, and US2014/0356353, the entire disclosures of which are hereby incorporated by reference. In illustrative embodiments, 3.18G1 or an antigen-binding fragment thereof for use in the methods provided herein comprises a heavy chain variable region comprising the amino acid sequence of:

SEQ ID No: 52 of WO 2011/066389 (SEQ ID NO: 192):
EVQLLESGGDLVQPGGSLRLSCAASGFTFNSYAMSWVRQAPGKGLEWVST

ISGSGGFTFSADSVKGRFTISRDNSKNTLFLQMNSLRVEDSAVYSCAKVL

VGFNNGCWDYWGQGTLVTVSS;

and/or a light chain variable region comprising the amino acid sequence of:

SEQ ID No: 57 of WO 2011/066389 (SEQ ID NO: 193):
SYVLTQPPSVSVAPGQTARITCGGNNIGSKSVHWYQQKPGQAPVLVVYDD

SDRPSGIPERFSGSNSGNTATLTISRVEAGDEADYYCQVWDSSNDHVVFG

GGTKLTVL.

In an embodiment, the targeting moiety comprises the anti-PD-L1 antibody 2.7A4OPT, or fragments thereof, as disclosed in WO 2011/066389, U.S. Pat. No. 8,779,108, and US2014/0356353, and US2014/0356353, the entire disclosures of which are hereby incorporated by reference. In illustrative embodiments, 2.7A4OPT or an antigen-binding fragment thereof for use in the methods provided herein comprises a heavy chain variable region comprising the amino acid sequence of:

SEQ ID No: 62 of WO 2011/066389 (SEQ ID NO: 194):
EVQLVESGGGLVKPGGSLRLSCAASGFTFSTYSMNWVRQAPGKGLEWVSS

ISSSGDYIYYADSVKGRFTISRDNAKNSLYLQMNSLRAEDTAVYYCARDL

VTSMVAFDYWGQGTLVTVSS;

and/or a light chain variable region comprising the amino acid sequence of:

SEQ ID No: 67 of WO 2011/066389 (SEQ ID NO: 195):
SYELTQPPSVSVSPGQTARITCSGDALPQKYVFWYQQKSGQAPVLVIYED

SKRPSGIPERFSGSSSGTMATLTISGAQVEDEADYYCYSTDRSGNHRVFG

GGTKLTVL.

In an embodiment, the targeting moiety comprises the anti-PD-L1 antibody 2.14H9OPT, or fragments thereof, as disclosed in WO 2011/066389, U.S. Pat. No. 8,779,108, and US2014/0356353, the entire disclosures of which are hereby incorporated by reference. In illustrative embodiments, 2.14H9OPT or an antigen-binding fragment thereof for use in the methods provided herein comprises a heavy chain variable region comprising the amino acid sequence of:

SEQ ID No: 72 of WO 2011/066389 (SEQ ID NO: 196):
EVQLVESGGGLVQPGGSLRLSCAASGFTFSRYWMSWVRQAPGKGLEWVAN

IKQDGSEKYYVDSVKGRFTISRDNAKNSLYLQMNSLRAEDTAVYYCAREG

GWFGELAFDYWGQGTLVTVSS;

and/or a light chain variable region comprising the amino acid sequence of:

SEQ ID No: 77 of WO 2011/066389 (SEQ ID NO: 197):
EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTFG

QGTKVEIK.

In an embodiment, the targeting moiety comprises any one of the anti-PD-L1 antibodies disclosed in WO2016/061142, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 18, 30, 38, 46, 50, 54, 62, 70, and 78 of WO2016/061142:

SEQ ID No: 18 of WO2016/061142 (SEQ ID NO: 198):
QVQLVQSGAEVKKPGASVKVSCKASGYTFTSYWMYWVRQATGQGLEWMGR

IDPNSGSTKYNEKFKNRFTISRDDSKNTAYLQMNSLKTEDTAVYYCARDY

RKGLYAMDYWGQGTTVTVSS;

SEQ ID No: 30 of WO2016/061142 (SEQ ID NO: 199):
EVQLVQSGAEVKKPGATVKISCKVSGYTFTSYWMYWVRQATGQGLEWMGR

IDPNSGSTKYNEKFKNRVTITADKSTSTAYMELSSLRSEDTAVYYCARDY

RKGLYAMDYWGQGTTVTVSS;

SEQ ID No: 38 of WO2016/061142 (SEQ ID NO: 200):
EVQLVQSGAEVKKPGESLRISCKGSGYTFTSYWMYWVRQAPGQGLEWMGR

IDPNSGSTKYNEKFKNRVTISVDTSKNQFSLKLSSVTAADTAVYYCARDY

RKGLYAMDYWGQGTTVTVSS;

SEQ ID No: 46 of WO2016/061142 (SEQ ID NO: 201):
EVQLVQSGAEVKKPGATVKISCKVSGYTFTSYWMYWIRQSPSRGLEWLGR

IDPNSGSTKYNEKFKNRLTISKDTSKNQVVLTMTNMDPVDTATYYCARDY

RKGLYAMDYWGQGTTVTVSS;

-continued

SEQ ID No: 50 of WO2016/061142 (SEQ ID NO: 202):
EVQLVQSGAEVKKPGESLRISCKGSGYTFTSYWMYWIRQPPGKGLEWIGR

IDPNSGSTKYNEKFKNRVTITADKSTSTAYMELSSLRSEDTAVYYCARDY

RKGLYAMDYWGQGTTVTVSS;

SEQ ID No: 54 of WO2016/061142 (SEQ ID NO: 203):
QVQLVQSGAEVKKPGASVKVSCKASGYTFTSYWMYWIRQSPSRGLEWLGR

IDPNSGSTKYNEKFKNRFTISRDDSKNTAYLQMNSLKTEDTAVYYCARDY

RKGLYAMDYWGQGTTVTVSS;

SEQ ID No: 62 of WO2016/061142 (SEQ ID NO: 204):
EVQLVQSGAEVKKPGESLRISCKGSGYTFTSYWMYWVRQARGQRLEWIGR

IDPNSGSTKYNEKFKNRLTISKDTSKNQVVLTMTNMDPVDTATYYCARDY

RKGLYAMDYWGQGTTVTVSS;

SEQ ID No: 70 of WO2016/061142 (SEQ ID NO: 205):
QITLKESGPTLVKPTQTLTLTCTFSGYTFTSYWMYWVRQAPGKGLEWVSR

IDPNSGSTKYNEKFKNRVTITADKSTSTAYMELSSLRSEDTAVYYCARDY

RKGLYAMDYWGQGTTVTVSS;

SEQ ID No: 78 of WO2016/061142 (SEQ ID NO: 206):
EVQLVQSGAEVKKPGATVKISCKVSGYTFTSYWMYWVRQARGQRLEWIGR

IDPNSGSTKYNEKFKNRFTISRDNSKNTLYLQMNSLRAEDTAVYYCARDY

RKGLYAMDYWGQGTTVTVSS;

and/or a light chain comprising an amino acid sequence selected from SEQ ID Nos: 22, 26, 34, 42, 58, 66, 74, 82, and 86 of WO2016/061142:

SEQ ID No: 22 of WO2016/061142 (SEQ ID NO: 207):
DIVMTQTPLSLPVTPGEPASISCKASQDVGTAVAWYLQKPGQSPQLLIYW

ASTRHTGIPARFSGSGSGTEFTLTISSLQSEDFAVYYCQQYNSYPLTFGQ

GTKVEIK;

SEQ ID No: 26 of WO2016/061142 (SEQ ID NO: 208):
DIQMTQSPSSLSASVGDRVTITCKASQDVGTAVAWYLQKPGQSPQLLIYW

ASTRHTGVPSRFSGSGSGTDFTLTISSLQPEDFATYYCQQYNSYPLTFGQ

GTKVEIK;

SEQ ID No: 34 of WO2016/061142 (SEQ ID NO: 209):
EIVLTQSPDFQSVTPKEKVTITCKASQDVGTAVAWYLQKPGQSPQLLIYW

ASTRHTGVPDRFSGSGSGTDFTLKISRVEAEDVGVYYCQQYNSYPLTFGQ

GTKVEIK;

SEQ ID No: 42 of WO2016/061142 (SEQ ID NO: 210):
EIVLTQSPDFQSVTPKEKVTITCKASQDVGTAVAWYLQKPGQSPQLLIYW

ASTRHTGVPSRFSGSGSGTDFTFTISSLQPEDIATYYCQQYNSYPLTFGQ

GTKVEIK.

SEQ ID No: 58 of WO2016/061142 (SEQ ID NO: 211):
EIVLTQSPATLSLSPGERATLSCKASQDVGTAVAWYLQKPGQSPQLLIYW

ASTRHTGIPPRFSGSGYGTDFTLTINNIESEDAAYYFCQQYNSYPLTFGQ

GTKVEIK;

-continued

SEQ ID No: 66 of WO2016/061142 (SEQ ID NO: 212):
DVVMTQSPLSLPVTLGQPASISCKASQDVGTAVAWYQQKPGQAPRLLIYW

ASTRHTGVPSRFSGSGSGTEFTLTISSLQPDDFATYYCQQYNSYPLTFGQ

GTKVEIK;

SEQ ID No: 74 of WO2016/061142 (SEQ ID NO: 213):
DIQMTQSPSSLSASVGDRVTITCKASQDVGTAVAWYQQKPGQAPRLLIYW

ASTRHTGVPSRFSGSGSGTDFTFTISSLQPEDIATYYCQQYNSYPLTFGQ

GTKVEIK;

SEQ ID No: 82 of WO2016/061142 (SEQ ID NO: 214):
AIQLTQSPSSLSASVGDRVTITCKASQDVGTAVAWYLQKPGQSPQLLIYW

ASTRHTGVPSRFSGSGSGTDFTFTISSLEAEDAATYYCQQYNSYPLTFGQ

GTKVEIK;

SEQ ID No: 86 of WO2016/061142 (SEQ ID NO: 215):
EIVLTQSPDFQSVTPKEKVTITCKASQDVGTAVAWYQQKPGQAPRLLIYW

ASTRHTGVPSRFSGSGSGTEFTLTISSLQPDDFATYYCQQYNSYPLTFGQ

GTKVEIK.

In an embodiment, the targeting moiety comprises any one of the anti-PD-L1 antibodies disclosed in WO2016/022630, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 2, 6, 10, 14, 18, 22, 26, 30, 34, 38, 42, and 46 of WO2016/022630:

SEQ ID No: 2 of WO2016/022630 (SEQ ID NO: 216):
EVKLVESGGGLVKPGGSLKLSCAASGFIFRSYGMSWVRQTPEKRLEWVAS

ISSGGSTYYPDSVKGRFTISRDNARNILYLQMSSLRSEDTAMYDCARGYD

SGFAYWGQGTLVTVSE;

SEQ ID No: 6 of WO2016/022630 (SEQ ID NO: 217):
EVKLVESGGGLVKPGGSLKLSCAASGFTFRSYGMSWVRQTPEKRLEWVAS

ISSGGTTYYPDSVKGRFIISRDNARNILYLQMSSLRSEDTAMYYCAKGYD

SGFAYWGQGTLVIVSA;

SEQ ID No: 10 of WO2016/022630 (SEQ ID NO: 218):
QVQLKQSGPGLVQPSQSLSITCTVSGFSLTTYGVHWVRQSPGKGLEWLGV

IWRGVTTDYNAAFMSRLTITKDNSKSQVFFKMNSLQANDTAIYYCARLGF

YAMDYWGQGTSVTVSS;

SEQ ID No: 14 of WO2016/022630 (SEQ ID NO: 219):
QVQLKQSGPGLVQPSQSLSITCTVSGFSLTSYGVHWVRQSPGKGLEWLGV

IWSGGVTDYNAAFISRLSISKDNSKSQVFFKMNSLQANDTAIYYCARLGF

YAMDYWGQGTSVTVSS;

SEQ ID No: 18 of WO2016/022630 (SEQ ID NO: 220):
EVKLFESGGGLVQPGGSLKLSCVASGFDFSTYWMHWVRQAPGQGLEWIGQ

INPDSTTINYAPSLKDRFIISRDNAKNTLFLQMSKVRSEDTALYYCAKPG

DYGYDFDCWGQGTTLTVSS;

-continued

SEQ ID No: 22 of WO2016/022630 (SEQ ID NO: 221):
EVQLQESGPSLVKPSQTLSLTCSVTGDSITSGYWNWIRKFPGNKLEYMGY
ISYSGSTYYNPSLKSRISITRDTSKNQYYLQLNSVTTEDTATYYCARSLL
WFSTGFAYWGQGTLVTVSA;

SEQ ID No: 26 of WO2016/022630 (SEQ ID NO: 222):
QVQLKQSGPGLVQPSQSLSITCTVSGFSLTSYGVHWVRQSPGKGLEWLGV
IWSGGITDYNAAFKSRLSISKDNS KSQVFFKMNSLQANDTAIYFCARLG
FYAMDYWGQGTSVTVSS;

SEQ ID No: 30 of WO2016/022630 (SEQ ID NO: 223):
EVKLVESGGGLVKPGGSLKLSCAASGFTFRSYGMSWARQIPEKRLEWVAS
ISSGGTTYYLGSVQGRFTISRDNARNILYLQMSSLRSEDTAMYYCARGYD
AGFAYWGQGTLVSVSE;

SEQ ID No: 34 of WO2016/022630 (SEQ ID NO: 224):
EVQLQESGPSLVKPSQTLSLTCSVTGDSITSGYWTWIRKFPGNKLEYMGY
ISYTGSTYYNPSLKSRISISRDTSKSQYYLQLNSVTTEDTATYYCARQRD
WLGFAYWGQGTLVTVSA;

SEQ ID No: 38 of WO2016/022630 (SEQ ID NO: 225):
EEKLVESGGGLVKPGGSLKLSCAASGFSFSSYGMSWVRQTPEKRLEWVAS
ISSGGSIYYPDSVKGRFTISRDNARNILYLQMSSLRSEDTAMYYCARGYD
AGFAFWGQGTLVTASA;

SEQ ID No: 42 of WO2016/022630 (SEQ ID NO: 226):
QITLKESGPTLVKPTQTLTLTCTVSGFSLSTYGVHWIRQPPGKALEWLGV
IWRGVTTDYNAAFMSRLTITKDNSKNQVVLTMNNMDPVDTATYYCARLGF
YAMDYWGQGTLVTVSS;

SEQ ID No: 46 of WO2016/022630 (SEQ ID NO: 227):
EVQLVESGGGLVKPGGSLRLSCAASGFIFRSYGMSWVRQAPGKGLEWVAS
ISSGGSTYYPDSVKGRFTISRDNAKNSLYLQMNSLRAEDTAVYDCARGYD
SGFAYWGQGTLVTVSS;

and/or a light chain comprising an amino acid sequence selected from SEQ ID Nos: 4, 8, 12, 16, 20, 24, 28, 32, 36, 40, 44, and 48 of WO2016/022630:

SEQ ID No: 4 of WO2016/022630 (SEQ ID NO: 228):
DIVLTQSPASLAVSLGQRATISCRASQSVSTSSSSFMHWYQQKPGQPPKL
LIKYASNLESGVPARFSGSGSGTDFTLNIHPVEEEDTATYYCQHSWEIPY
TFGGGTKLEIKR;

SEQ ID No: 8 of WO2016/022630 (SEQ ID NO: 229):
DIVLTQSPPSLAVSLGQRATISCRASQSVSTSSSSYMHWYQQKPGQPPKL
LIKYASNLESGVPARFSGSGSGTDFTLNIHPVEEEDTATYYCQHSWEIPY
TFGGGTKLEIK;

SEQ ID No: 12 of WO2016/022630 (SEQ ID NO: 230):
SIVMTQTPKFLLVSAGDRVTITCKASQSVSNDVAWYQQKPGQSPKLLIYY
AANRYTGVPDRFTGSGYGTDFTFTISIVQAEDLAVYFCQQDYTSPYTFGG
GTKLEIK;

-continued

SEQ ID No: 16 of WO2016/022630 (SEQ ID NO: 231):
SIVMTQTPKFLLVSAGDRVTITCKASQSVSNDVGWYQQKPGQSPKLLIYY
ASNRYSGVPDRFTGSGYGTDFTFTISTVQAEDLAVYFCQQDYTSPYTFGG
GTKLEIK;

SEQ ID No: 20 of WO2016/022630 (SEQ ID NO: 232):
DVLMTQTPLYLPVSLGDQASISCRSSQIIVHSNANTYLEWFLQKPGQSPK
LLIYKVSNRFSGVPDRFSGSGSGTDFTLKISRVEAEDLGVYYCFQGSHVP
YTFGGGTKLEIK;

SEQ ID No: 24 of WO2016/022630 (SEQ ID NO: 233):
QIVLTQSPAIMSASPGEKVTLTCSASSSVSSSYLYWNQQKPGSSPKVWIY
NTSNLASGVPARFSGSGSGTSYSLTISSMEAEDAASYFCHQWRSYPPTLG
AGTKLELK;

SEQ ID No: 28 of WO2016/022630 (SEQ ID NO: 234):
QIVLTQSPAIMSASPGEKVTMTCSANSSVSYMHWYQQKSGTSPKRWIYDT
SKLASGVPARFSGSGSGTSYSLTISSMGAEDAATYYCQQWSSNPWTFGGG
TKLEIK;

SEQ ID No: 32 of WO2016/022630 (SEQ ID NO: 235):
DIVLTQSPASLAVSLGQRATISCRASQSVSTSSYSYMHWYQQKPGQPPKL
LIKYASNLESGVPARFSGSGSGTDFTLNIHPVEEEDTATYYCQNSWEIPY
TFGGGTKLEIK;

SEQ ID No: 36 of WO2016/022630 (SEQ ID NO: 236):
DIVMTQTPSSLAVSLGEKVTMSCKSSQSLLYSSNQKNSLAWYQQKPGQSP
KLLIYWASNRESGVPDRFTGSSSGTDFTLTISSVKAEDLAVYYCQQYYSY
PLTFGAGTKLELK;

SEQ ID No: 40 of WO2016/022630 (SEQ ID NO: 237):
DIVLTQSPASLAVSLGQRATISCRASQSVSTSSYSYVHWYQQKPGQPPKL
LIKYASNLESGVPARFSGSGSGTDFTLNIHPVEEEDTATYYCQHSWEIPY
TFGGGTKLEIK;

SEQ ID No: 44 of WO2016/022630 (SEQ ID NO: 238):
DIQMTQSPSSLSASVGDRVTITCKASQSVSNDVAWYQQKPGKAPKLLIYY
AANRYTGVPDRFSGSGYGTDFTFTISSLQPEDIATYFCQQDYTSPYTFGQ
GTKLEIK;

SEQ ID No: 48 of WO2016/022630 (SEQ ID NO: 239):
DIVLTQSPASLAVSPGQRATITCRASQSVSTSSSSFMHWYQQKPGQPPKL
LIKYASNLESGVPARFSGSGSGTDFTLTINPVEANDTANYYCQHSWEIPY
TFGQGTKLEIK.

In an embodiment, the targeting moiety comprises any one of the anti-PD-L1 antibodies disclosed in WO2015/112900, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 38, 50, 82, and 86 of WO 2015/112900:

SEQ ID No: 38 of WO2015/112900 (SEQ ID NO: 240):
EVQLVQSGAEVKKPGESLRISCKGSGYTFTTYWMHWVRQATGQGLEWMGN
IYPGTGGSNFDEKFKNRVTITADKSTSTAYMELSSLRSEDTAVYYCTRWT
TGTGAYWGQGTTVTVSS;

-continued

SEQ ID No: 50 of WO 2015/112900 (SEQ ID NO: 241):
EVQLVQSGAEVKKPGESLRISCKGSGYTFTTYWMHWIRQSPSRGLEWLGN

IYPGTGGSNFDEKFKNRFTISRDNSKNTLYLQMNSLRAEDTAVYYCTRWT

TGTGAYWGQGTTVTVSS;

SEQ ID No: 82 of WO 2015/112900 (SEQ ID NO: 242):
QVQLVQSGAEVKKPGASVKVSCKASGYTFTTYWMHWIRQSPSRGLEWLGN

IYPGTGGSNFDEKFKNRFTISRDNSKNTLYLQMNSLRAEDTAVYYCTRWT

TGTGAYWGQGTTVTVSS;

SEQ ID No: 86 of WO 2015/112900 (SEQ ID NO: 243):
EVQLVQSGAEVKKPGESLRISCKGSGYTFTTYWMHWVRQAPGQGLEWMGN

IYPGTGGSNFDEKFKNRFTISRDNSKNTLYLQMNSLRAEDTAVYYCTRWT

TGTGAYWGQGTTVTVSS;

and/or a light chain comprising an amino acid sequence selected from SEQ ID Nos: 42, 46, 54, 58, 62, 66, 70, 74, and 78 of WO 2015/112900:

SEQ ID No: 42 of WO2015/112900 (SEQ ID NO: 244):
EIVLTQSPATLSLSPGERATLSCKSSQSLLDSGNQKNFLTWYQQKPGQAP

RLLIYWASTRESGVPSRFSGSGSGTEFTLTISSLQPDDFATYYCQNDYSY

PYTFGQGTKVEIK;

SEQ ID No: 46 of WO 2015/112900 (SEQ ID NO: 245):
DIQMTQSPSSLSASVGDRVTITCKSSQSLLDSGNQKNFLTWYQQKPGQAP

RLLIYWASTRESGIPPRFSGSGYGTDFTLTINNIESEDAAYYFCQNDYSY

PYTFGQGTKVEIK;

SEQ ID No: 54 of WO 2015/112900 (SEQ ID NO: 246):
EIVLTQSPATLSLSPGERATLSCKSSQSLLDSGNQKNFLTWYQQKPGKAP

KLLIYWASTRESGVPSRFSGSGSGTDFTFTISSLQPEDIATYYCQNDYSY

PYTFGQGTKVEIK;

SEQ ID No: 58 of WO 2015/112900 (SEQ ID NO: 247):
DIVMTQTPLSLPVTPGEPASISCKSSQSLLDSGNQKNFLTWYQQKPGQAP

RLLIYWASTRESGVPSRFSGSGSGTDFTFTISSLEAEDAATYYCQNDYSY

PYTFGQGTKVEIK;

SEQ ID No: 62 of WO 2015/112900 (SEQ ID NO: 248):
EIVLTQSPATLSLSPGERATLSCKSSQSLLDSGNQKNFLTWYQQKPGKAP

KLLIYWASTRESGVPSRFSGSGSGTDFTFTISSLEAEDAATYYCQNDYSY

PYTFGQGTKVEIK;

SEQ ID No: 66 of WO 2015/112900 (SEQ ID NO: 249):
EIVLTQSPDFQSVTPKEKVTITCKSSQSLLDSGNQKNFLTWYQQKPGQAP

RLLIYWASTRESGVPSRFSGSGSGTDFTFTISSLEAEDAATYYCQNDYSY

PYTFGQGTKVEIK;

SEQ ID No: 70 of WO 2015/112900 (SEQ ID NO: 250):
EIVLTQSPATLSLSPGERATLSCKSSQSLLDSGNQKNFLTWYQQKPGQAP

RLLIYWASTRESGVPSRFSGSGSGTDFTFTISSLEAEDAATYYCQNDYSY

PYTFGQGTKVEIK;

-continued

SEQ ID No: 74 of WO 2015/112900 (SEQ ID NO: 251):
DIQMTQSPSSLSASVGDRVTITCKSSQSLLDSGNQKNFLTWYLQKPGQSP

QLLIYWASTRESGVPSRFSGSGSGTDFTFTISSLEAEDAATYYCQNDYSY

PYTFGQGTKVEIK;

SEQ ID No: 78 of WO 2015/112900 (SEQ ID NO: 252):
DVVMTQSPLSLPVTLGQPASISCKSSQSLLDSGNQKNFLTWYQQKPGKAP

KLLIYWASTRESGVPSRFSGSGSGTDFTFTISSLEAEDAATYYCQNDYSY

PYTFGQGTKVEIK.

In an embodiment, the targeting moiety comprises any one of the anti-PD-L1 antibodies disclosed in WO 2010/077634 and U.S. Pat. No. 8,217,149, the entire disclosures of which are hereby incorporated by reference. In illustrative embodiments, the anti-PD-L1 antibody or an antigen-binding fragment thereof for use in the methods provided herein comprises a heavy chain region comprising the amino acid sequence of:

SEQ ID No: 20 of WO 2010/077634 (SEQ ID NO: 253):
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA;
and/or a light chain variable region comprising
the amino acid sequence of:

SEQ ID No: 21 of WO 2010/077634 (SEQ ID NO: 254):
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In an embodiment, the targeting moiety comprises any one of the anti-PD-L1 antibodies obtainable from the hybridoma accessible under CNCM deposit numbers CNCM I-4122, CNCM I-4080 and CNCM I-4081 as disclosed in US 20120039906, the entire disclosures of which are hereby incorporated by reference.

In an embodiment, the targeting moiety comprises a VHH directed against PD-L1 as disclosed, for example, in U.S. Pat. No. 8,907,065 and WO 2008/071447, the entire disclosures of which are hereby incorporated by reference. In illustrative embodiments, the VHHs against PD-L1 comprise SEQ ID NOS: 394-399 of U.S. Pat. No. 8,907,065:

SEQ ID No: 394 of US 8,907,065 (SEQ ID NO: 255):
EVQLVESGGGLVQPGGSLRLSCAASGFTLDYYAIGWFRQAPGKEREWASS

ISSSDGSTYYADSVKGRFTISRDNAKNTVFLQMNSLKPEDTAVYSCAASQ

APITIATMMKPFYDYWGQGTQVTVSS;

SEQ ID No: 395 of US 8,907,065 (SEQ ID NO: 256):
EVQLVESGGGLVQPGGSLRLSCAASGFTLDYYAKCWFRQAPGKEREWVSC

ISSSDGSTYYADSVKGRFTISRDNAKNTVYLQMNSLKPEDTAVYFCAARH

GGPLTVEYFFDYWGQGTQVTVSS;

SEQ ID No: 396 of US 8,907,065 (SEQ ID NO: 257):
EVQLVESGGGLVQPGGSLRLSCAASGFTFDYYAIGWFRQAPGKAREGVSC

ISGGDNSTYYADSVKGRFTISRDNAKNTVYLQMNSLKPEDTAVYYCATGG

WKYCSGYDPEYIYWGQGTQVTVSS;

-continued

SEQ ID No: 397 of US 8,907,065 (SEQ ID NO: 258):
EVQLVESGGGLVQAGGSLRLSCAASGSTFSQYDVGWYRQAPGKQRELVA
FSSSGGRTIYPDSVKGRFTFSRDNTKNTVYLQMTSLKPEDTAVYYCKIDW
YLNSYWGQGTQVTVSS;

SEQ ID No: 398 of US 8,907,065 (SEQ ID NO: 259):
EVQLVESGGGLVQAGGSLRLSCAASGVDASNSAMGWYRQAPGKQREWVAR
ITGGGLIAYTDSVKGRFTISRDNAKSTVYLQMNSLEPEDTAVYYCNTINS
RDGWGQGTQVTVSS;

SEQ ID No: 399 of US 8,907,065 (SEQ ID NO: 260):
EVQLVESGGGLVQAGGSLTISCAASGITFSDSIVSWYRRARGKQREWVAG
ISNGGTTKYAESVLGRFTISRDNAKNNVYLQMNGLNPEDTAVYLCKVRQY
WGQGTQVTVSS.

In an exemplary embodiment, the present multi-specific Clec9A binding agent comprises a targeting moiety directed against PDL-1, such as SEQ ID NO:261:

EVQLVESGGGLVQPGGSLRLSCAASGFTLDYYAKCWFRQAPGKEREWVSC
ISSSDGSTYYADSVKGRFTISRDNAKNTVYLQMNSLKPEDTAVYFCAARH
GGPLTVEYFFDYWGQGTQVTVSS

In various embodiments, the present multi-specific Clec9A binding agent has one or more targeting moieties directed against PD-L2. In some embodiments, the Clec9A binding agent has one or more targeting moieties which selectively bind a PD-L2 polypeptide. In some embodiments, the Clec9A binding agent comprises one or more antibodies, antibody derivatives or formats, peptides or polypeptides, or fusion proteins that selectively bind a PD-L2 polypeptide.

In an embodiment, the targeting moiety comprises a VHH directed against PD-L2 as disclosed, for example, in U.S. Pat. No. 8,907,065 and WO 2008/071447, the entire disclosures of which are hereby incorporated by reference. In illustrative embodiments, the VHHs against PD-1 comprise SEQ ID Nos: 449-455 of U.S. Pat. No. 8,907,065:

SEQ ID No: 449 of US 8,907,065 (SEQ ID NO: 262):
EVQLVESGGGLVQAGGSLRLSCAASESTVLINAMGWYRQAPGKQRELVAS
ISSGGSTNYADSVKGRFTISRDNAKNTVYLQMNSLKPEDTAVYYCNADVY
PQDYGLGYVEGKVYYGHDYWGTGTLVTVSS;

SEQ ID No: 450 of US 8,907,065 (SEQ ID NO: 263):
EVQLVESGGGLVQAGGSLRLSCAASGSTFSNYVSNYAMGWGRQAPGTQ
RELVASISNGDTTNYADSVKGRFTISRDNAKNTVYLQMNSLKPEDTAVYY
CFEHQVAGLTWGQGTQVTVSS;

SEQ ID No: 451 of US 8,907,065 (SEQ ID NO: 264):
EVQLVESGGGLVQAGGSLRLSCVASGXALKIXVMGWYRQAPGKQRELV
AAITSGGRTNYSDSVKGRFTISGDNAXNTVYLQMNSLKSEDTAVYYCRE
WNSGYPPVDYWGQGTQVTVSS;

SEQ ID No: 452 of US 8,907,065 (SEQ ID NO: 265):
EVQLVESGGGLVQAGGSLRLSCAASGRTFSSGTMGWFRRAPGKEREFV
ASIPWSGGRTYYADSVKDRFTISRDNAQNTVFLQMNSLKPEDTAVYYCAF
KERSTGWDFASWGQGIQVTVSS;

-continued

SEQ ID No: 453 of US 8,907,065 (SEQ ID NO: 266):
EVQLVESGGGLVQTGGSLRLSCAASGFTLDYYGIGWFRQAPGKEREGVS
FISGSDGSTYYAESVKGRFTISRDKAKNTVYLQMNSLKPEDTAVYYCAAD
PWGPPSIATMTSYEYKHWGQGTQVTVSS;

SEQ ID No: 454 of US 8,907,065 (SEQ ID NO: 267):
EVQLVESGGGLVQPGGSLRLSCAASGFTFSTYTMIWLRRAPGKGFEWV
STIDKDGNTNYVDSVKGRFAVSRDNTKNTLYLQMNSLKPEDTAMYYCTK
HGSSARGQGTRVTVSS;

SEQ ID No: 455 of US 8,907,065 (SEQ ID NO: 268):
EVQLVESGGGLVEPGGSLRLSCVASGFTFSSYDMSWVRQAPGKGLE
WVSTINSGGGITYRGSVKGRFTISRDNAKNTLYLQMNSLKPEDTAVYY
CENGGSSYRRGQGTQVTVSS.

In an embodiment, the targeting moiety comprises any one of the anti-PD-L2 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 43-47 of US2011/0271358:

SEQ ID No: 43 of US2011/0271358 (SEQ ID NO: 269):
QVQLVQSGAELKKPGASVKMSCKASGYTFTGYTMHWVKQAPGQGLEWIGY
INPRSGYTEYNQKFKDRTTLTADKSTSTAYMELSSLRSEDSAVYYCARPW
FAYWGQGTLVTVSS;

SEQ ID No: 44 of US2011/0271358 (SEQ ID NO: 270):
QVQLVQSGAEVKKPGASVKMSCKASGYTFTGYTMHWVKQAPGQGLEWIGY
INPRSGYTEYNQKFKDRTTLTADKSTSTAYMELSSLRSEDTAVYYCARPW
FAYWGQGTLVTVSS;

SEQ ID No: 45 of US2011/0271358 (SEQ ID NO: 271):
QVQLVQSGAEVKKPGASVKMSCKASGYTFTGYTMHWVRQAPGQGLEWIGY
INPRSGYTEYNQKFKDRTTLTADKSTSTAYMELSSLRSEDTAVYYCARPW
FAYWGQGTLVTVSS;

SEQ ID No: 46 of US2011/0271358 (SEQ ID NO: 272):
QVQLVQSGAEVKKPGASVKVSCKASGYTFTGYTMHWVRQAPGQGLEWIGY
INPRSGYTEYNQKFKDRTTLTADKSTSTAYMELSSLRSEDTAVYYCARPW
FAYWGQGTLVTVSS;

SEQ ID No: 47 of US2011/0271358 (SEQ ID NO: 273):
QVQLVQSGAEVKKPGASVKVSCKASGYTFTGYTMHWVRQAPGQGLEWIGY
INPRSGYTEYNQKFKDRTTITADKSTSTAYMELSSLRSEDTAVYYCARPW
FAYWGQGTLVTVSS;

and/or a light chain comprising an amino acid sequence selected from SEQ ID Nos: 48-51 of US2011/0271358:

SEQ ID No: 48 of US2011/0271358 (SEQ ID NO: 274):
DIVMTQSPASLTVTPGEKVTITCKSSQSLLNSGNQKNYLTWYQQKPGQPP
KLLIYWASTRESGVPDRFTGSGSGTDFTLTISSLQAEDVAVYYCQNDYSY
PLTFGQGTKLEIK;

-continued

SEQ ID No: 49 of US2011/0271358 (SEQ ID NO: 275):
DIVMTQSPASLSVTPGEKVTITCKSSQSLLNSGNQKNYLTWYQQKPGQPP

KLLIYWASTRESGVPDRFTGSGSGTDFTLTISSLQAEDVAVYYCQNDYSY

PLTFGQGTKLEIK;

SEQ ID No: 50 of US2011/0271358 (SEQ ID NO: 276):
DIVMTQSPAFLSVTPGEKVTITCKSSQSLLNSGNQKNYLTWYQQKPGQPP

KLLIYWASTRESGVPDRFTGSGSGTDFTLTISSLQAEDVAVYYCQNDYSY

PLTFGQGTKLEIK;

SEQ ID No: 51 of US2011/0271358 (SEQ ID NO: 277):
DIVMTQSPAFLSVTPGEKVTITCKSSQSLLNSGNQKNYLTWYQQKPGQPP

KLLIYWASTRESGVPDRFSGSGSGTDFTLTISSLQAEDVAVYYCQNDYSY

PLTFGQGTKLEIK.

In various embodiments, the targeting moieties of the invention may comprise a sequence that targets PD-1, PD-L1, and/or PD-L2, or any other targets described herein, which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity with any of the sequences disclosed herein).

In various embodiments, the targeting moieties of the invention may comprise any combination of heavy chain, light chain, heavy chain variable region, light chain variable region, complementarity determining region (CDR), and framework region sequences that target PD-1, PD-L1, and/or PD-L2 as disclosed herein.

Additional antibodies, antibody derivatives or formats, peptides or polypeptides, or fusion proteins that selectively bind or target PD-1, PD-L1 and/or PD-L2 are disclosed in WO 2011/066389, US 2008/0025980, US 2013/0034559, U.S. Pat. No. 8,779,108, US 2014/0356353, U.S. Pat. No. 8,609,089, US 2010/028330, US 2012/0114649, WO 2010/027827, WO 2011/066342, U.S. Pat. No. 8,907,065, WO 2016/062722, WO 2009/101611, WO2010/027827, WO 2011/066342, WO 2007/005874, WO 2001/014556, US2011/0271358, WO 2010/036959, WO 2010/077634, U.S. Pat. No. 8,217,149, US 2012/0039906, WO 2012/145493, US 2011/0318373, U.S. Pat. No. 8,779,108, US 20140044738, WO 2009/089149, WO 2007/00587, WO 2016061142, WO 2016,02263, WO 2010/077634, and WO 2015/112900, the entire disclosures of which are hereby incorporated by reference.

In various embodiments, the multi-specific Clec9A binding agent of the invention has one or more targeting moieties directed against XCR1 e.g. on dendritic cells. For instance, the targeting moiety, in some embodiments comprises all or part of XCL1 or an anti-XCR1 agent that does not functionally modulate (e.g. a non-neutralizing) XCR1.

In various embodiments, the multi-specific Clec9A binding agents have targeting moieties having recognition domains which specifically bind to a target (e.g. antigen, receptor) which is part of a non-cellular structure. In some embodiments, the antigen or receptor is not an integral component of an intact cell or cellular structure. In some embodiments, the antigen or receptor is an extracellular antigen or receptor. In some embodiments, the target is a non-proteinaceous, non-cellular marker, including, without limitation, nucleic acids, inclusive of DNA or RNA, such as, for example, DNA released from necrotic tumor cells or extracellular deposits such as cholesterol.

In some embodiments, the target (e.g. antigen, receptor) of interest is part of the non-cellular component of the stroma or the extracellular matrix (ECM) or the markers associated therewith. As used herein, stroma refers to the connective and supportive framework of a tissue or organ. Stroma may include a compilation of cells such as fibroblasts/myofibroblasts, glial, epithelia, fat, immune, vascular, smooth muscle, and immune cells along with the extracellular matrix (ECM) and extracellular molecules. In various embodiments, the target (e.g. antigen, receptor) of interest is part of the non-cellular component of the stroma such as the extracellular matrix and extracellular molecules. As used herein, the ECM refers to the non-cellular components present within all tissues and organs. The ECM is composed of a large collection of biochemically distinct components including, without limitation, proteins, glycoproteins, proteoglycans, and polysaccharides. These components of the ECM are usually produced by adjacent cells and secreted into the ECM via exocytosis. Once secreted, the ECM components often aggregate to form a complex network of macromolecules. In various embodiments, the chimeric protein of the invention comprises a targeting moiety that recognizes a target (e.g., an antigen or receptor or non-proteinaceous molecule) located on any component of the ECM. Illustrative components of the ECM include, without limitation, the proteoglycans, the non-proteoglycan polysaccharides, fibers, and other ECM proteins or ECM non-proteins, e.g. polysaccharides and/or lipids, or ECM associated molecules (e.g. proteins or non-proteins, e.g. polysaccharides, nucleic acids and/or lipids).

In some embodiments, the targeting moiety recognizes a target (e.g. antigen, receptor) on ECM proteoglycans. Proteoglycans are glycosylated proteins. The basic proteoglycan unit includes a core protein with one or more covalently attached glycosaminoglycan (GAG) chains. Proteoglycans have a net negative charge that attracts positively charged sodium ions (Na+), which attracts water molecules via osmosis, keeping the ECM and resident cells hydrated. Proteoglycans may also help to trap and store growth factors within the ECM. Illustrative proteoglycans that may be targeted by the chimeric proteins of the invention include, but are not limited to, heparan sulfate, chondroitin sulfate, and keratan sulfate. In an embodiment, the targeting moiety recognizes a target (e.g. antigen, receptor) on non-proteoglycan polysaccharides such as hyaluronic acid.

In some embodiments, the targeting moiety recognizes a target (e.g. antigen, receptor) on ECM fibers. ECM fibers include collagen fibers and elastin fibers. In some embodiments, the targeting moiety recognizes one or more epitopes on collagens or collagen fibers. Collagens are the most abundant proteins in the ECM. Collagens are present in the ECM as fibrillar proteins and provide structural support to resident cells. In one or more embodiments, the targeting moiety recognizes and binds to various types of collagens present within the ECM including, without limitation, fibrillar collagens (types I, II, III, V, XI), facit collagens (types IX, XII, XIV), short chain collagens (types VIII, X), basement membrane collagens (type IV), and/or collagen types VI, VII, or XIII. Elastin fibers provide elasticity to tissues, allowing them to stretch when needed and then return to their original state. In some embodiments, the target moiety recognizes one or more epitopes on elastins or elastin fibers.

In some embodiments, the targeting moiety recognizes one or more ECM proteins including, but not limited to, a tenascin, a fibronectin, a fibrin, a laminin, or a nidogen/entactin.

In an embodiment, the targeting moiety recognizes and binds to tenascin. The tenascin (TN) family of glycoproteins includes at least four members, tenascin-C, tenascin-R, tenascin-X, and tenascin W. The primary structures of tenascin proteins include several common motifs ordered in the same consecutive sequence: amino-terminal heptad repeats, epidermal growth factor (EGF)-like repeats, fibronectin type III domain repeats, and a carboxyl-terminal fibrinogen-like globular domain. Each protein member is associated with typical variations in the number and nature of EGF-like and fibronectin type III repeats. Isoform variants also exist particularly with respect to tenascin-C. Over 27 splice variants and/or isoforms of tenascin-C are known. In a particular embodiment, the targeting moiety recognizes and binds to tenascin-CA1. Similarly, tenascin-R also has various splice variants and isoforms. Tenascin-R usually exists as dimers or trimers. Tenascin-X is the largest member of the tenascin family and is known to exist as trimers. Tenascin-W exists as trimers. In some embodiments, the targeting moiety recognizes one or more epitopes on a tenascin protein. In some embodiments, the targeting moiety recognizes the monomeric and/or the dimeric and/or the trimeric and/or the hexameric forms of a tenascin protein.

In an embodiment, the targeting moieties recognize and bind to fibronectin. Fibronectins are glycoproteins that connect cells with collagen fibers in the ECM, allowing cells to move through the ECM. Upon binding to integrins, fibronectins unfolds to form functional dimers. In some embodiments, the targeting moiety recognizes the monomeric and/or the dimeric forms of fibronectin. In some embodiments, the targeting moiety recognizes one or more epitopes on fibronectin. In illustrative embodiments, the targeting moiety recognizes fibronectin extracellular domain A (EDA) or fibronectin extracellular domain B (EDB). Elevated levels of EDA are associated with various diseases and disorders including psoriasis, rheumatoid arthritis, diabetes, and cancer. In some embodiments, the targeting moiety recognizes fibronectin that contains the EDA isoform and may be utilized to target the chimeric protein to diseased cells including cancer cells. In some embodiments, the targeting moiety recognizes fibronectin that contains the EDB isoform. In various embodiments, such targeting moieties may be utilized to target the chimeric protein to tumor cells including the tumor neovasculature.

In an embodiment, the targeting moiety recognizes and binds to fibrin. Fibrin is another protein substance often found in the matrix network of the ECM. Fibrin is formed by the action of the protease thrombin on fibrinogen which causes the fibrin to polymerize. In some embodiments, the targeting moiety recognizes one or more epitopes on fibrin. In some embodiments, the targeting moiety recognizes the monomeric as well as the polymerized forms of fibrin.

In an embodiment, the targeting moiety recognizes and binds to laminin. Laminin is a major component of the basal lamina, which is a protein network foundation for cells and organs. Laminins are heterotrimeric proteins that contain an α-chain, a β-chain, and a γ-chain. In some embodiments, the targeting moiety recognizes one or more epitopes on laminin. In some embodiments, the targeting moiety recognizes the monomeric, the dimeric as well as the trimeric forms of laminin.

In an embodiment, the targeting moiety recognizes and binds to a nidogen or entactin. Nidogens/entactins are a family of highly conserved, sulfated glycoproteins. They make up the major structural component of the basement membranes and function to link laminin and collagen IV networks in basement membranes. Members of this family include nidogen-1 and nidogen-2. In various embodiments, the targeting moiety recognizes an epitope on nidogen-1 and/or nidogen-2.

In various embodiments, the targeting moiety comprises an antigen recognition domain that recognizes an epitope present on any of the targets (e.g., ECM proteins) described herein. In an embodiment, the antigen-recognition domain recognizes one or more linear epitopes present on the protein. As used herein, a linear epitope refers to any continuous sequence of amino acids present on the protein. In another embodiment, the antigen-recognition domain recognizes one or more conformational epitopes present on the protein. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the targeting moiety may bind to the full-length and/or mature forms and/or isoforms and/or splice variants and/or fragments and/or any other naturally occurring or synthetic analogs, variants, or mutants of any of the targets (e.g., ECM proteins) described herein. In various embodiments, the targeting moiety may bind to any forms of the proteins described herein, including monomeric, dimeric, trimeric, tetrameric, heterodimeric, multimeric and associated forms. In various embodiments, the targeting moiety may bind to any post-translationally modified forms of the proteins described herein, such as glycosylated and/or phosphorylated forms.

In various embodiments, the targeting moiety comprises an antigen recognition domain that recognizes extracellular molecules such as DNA. In some embodiments, the targeting moiety comprises an antigen recognition domain that recognizes DNA. In an embodiment, the DNA is shed into the extracellular space from necrotic or apoptotic tumor cells or other diseased cells.

In various embodiments, the targeting moiety comprises an antigen recognition domain that recognizes one or more non-cellular structures associated with atherosclerotic plaques. Two types of atherosclerotic plaques are known. The fibro-lipid (fibro-fatty) plaque is characterized by an accumulation of lipid-laden cells underneath the intima of the arteries. Beneath the endothelium there is a fibrous cap covering the atheromatous core of the plaque. The core includes lipid-laden cells (macrophages and smooth muscle cells) with elevated tissue cholesterol and cholesterol ester content, fibrin, proteoglycans, collagen, elastin, and cellular debris. In advanced plaques, the central core of the plaque usually contains extracellular cholesterol deposits (released from dead cells), which form areas of cholesterol crystals with empty, needle-like clefts. At the periphery of the plaque are younger foamy cells and capillaries. A fibrous plaque is also localized under the intima, within the wall of the artery resulting in thickening and expansion of the wall and, sometimes, spotty localized narrowing of the lumen with some atrophy of the muscular layer. The fibrous plaque contains collagen fibers (eosinophilic), precipitates of calcium (hematoxylinophilic) and lipid-laden cells. In some embodiments, the targeting moiety recognizes and binds to one or more of the non-cellular components of these plaques such as the fibrin, proteoglycans, collagen, elastin, cellular debris, and calcium or other mineral deposits or precipitates. In some embodiments, the cellular debris is a nucleic acid, e.g. DNA or RNA, released from dead cells.

In various embodiments, the targeting moiety comprises an antigen recognition domain that recognizes one or more non-cellular structures found in the brain plaques associated with neurodegenerative diseases. In some embodiments, the targeting moiety recognizes and binds to one or more non-cellular structures located in the amyloid plaques found in the brains of patients with Alzheimer's disease. For example, the targeting moiety may recognize and bind to the peptide amyloid beta, which is a major component of the amyloid plaques. In some embodiments, the targeting moiety recognizes and binds to one or more non-cellular structures located in the brains plaques found in patients with Huntington's disease. In various embodiments, the targeting moiety recognizes and binds to one or more non-cellular structures found in plaques associated with other neurodegenerative or musculoskeletal diseases such as Lewy body dementia and inclusion body myositis.

Linkers and Functional Groups

In various embodiments, the Clec9A binding agent may include one or more functional groups, residues, or moieties. In various embodiments, the one or more functional groups, residues, or moieties are attached or genetically fused to any of the signaling agents or targeting moieties described herein. In some embodiments, such functional groups, residues or moieties confer one or more desired properties or functionalities to the Clec9A binding agent of the invention. Examples of such functional groups and of techniques for introducing them into the Clec9A binding agent are known in the art, for example, see Remington's Pharmaceutical Sciences, 16th ed., Mack Publishing Co., Easton, Pa. (1980).

In various embodiments, the Clec9A binding agent may by conjugated and/or fused with another agent to extend half-life or otherwise improve pharmacodynamic and pharmacokinetic properties. In some embodiments, the CD8 binding agent may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In some embodiments, the CD8 binding agent may be fused or conjugated with an antibody or an antibody fragment such as an Fc fragment. For example, the chimeric protein may be fused to either the N-terminus or the C-terminus of the Fc domain of human immunoglobulin (Ig) G. In various embodiments, each of the individual chimeric proteins is fused to one or more of the agents described in BioDrugs (2015) 29:215-239, the entire contents of which are hereby incorporated by reference.

In some embodiments, the functional groups, residues, or moieties comprise a suitable pharmacologically acceptable polymer, such as poly(ethyleneglycol) (PEG) or derivatives thereof (such as methoxypoly(ethyleneglycol) or mPEG). In some embodiments, attachment of the PEG moiety increases the half-life and/or reduces the immunogenicity of the Clec9A binding protein. Generally, any suitable form of pegylation can be used, such as the pegylation used in the art for antibodies and antibody fragments (including but not limited to single domain antibodies such as VHHs); see, for example, Chapman, *Nat. Biotechnol.*, 54, 531-545 (2002); by Veronese and Harris, *Adv. Drug Deliv. Rev.* 54, 453-456 (2003), by Harris and Chess, *Nat. Rev. Drug. Discov.*, 2, (2003) and in WO04060965, the entire contents of which are hereby incorporated by reference. Various reagents for pegylation of proteins are also commercially available, for example, from Nektar Therapeutics, USA. In some embodiments, site-directed pegylation is used, in particular via a cysteine-residue (see, for example, Yang et al., Protein Engineering, 16, 10, 761-770 (2003), the entire contents of which is hereby incorporated by reference). For example, for this purpose, PEG may be attached to a cysteine residue that naturally occurs in the Clec9A binding agent of the invention. In some embodiments, the Clec9A binding agent of the invention is modified so as to suitably introduce one or more cysteine residues for attachment of PEG, or an amino acid sequence comprising one or more cysteine residues for attachment of PEG may be fused to the amino- and/or carboxy-terminus of the Clec9A binding agent, using techniques known in the art.

In some embodiments, the functional groups, residues, or moieties comprise N-linked or O-linked glycosylation. In some embodiments, the N-linked or O-linked glycosylation is introduced as part of a co-translational and/or post-translational modification.

In some embodiments, the functional groups, residues, or moieties comprise one or more detectable labels or other signal-generating groups or moieties. Suitable labels and techniques for attaching, using and detecting them are known in the art and, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled VHHs and polypeptides of the invention may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label.

In some embodiments, the functional groups, residues, or moieties comprise a tag that is attached or genetically fused to the Clec9A binding agent. In some embodiments, the Clec9A binding agent may include a single tag or multiple tags. The tag for example is a peptide, sugar, or DNA molecule that does not inhibit or prevent binding of the Clec9A binding agent to Clec9A or any other antigen of interest such as tumor antigens. In various embodiments, the tag is at least about: three to five amino acids long, five to eight amino acids long, eight to twelve amino acids long, twelve to fifteen amino acids long, or fifteen to twenty amino acids long. Illustrative tags are described for example, in U.S. Patent Publication No. US2013/0058962. In some embodiment, the tag is an affinity tag such as glutathione-S-transferase (GST) and histidine (His) tag. In an embodiment, the Clec9A binding agent comprises a His tag.

In some embodiments, the functional groups, residues, or moieties comprise a chelating group, for example, to chelate one of the metals or metallic cations. Suitable chelating groups, for example, include, without limitation, diethylenetriaminepentaacetic acid (DTPA) or ethylenediaminetetraacetic acid (EDTA).

In some embodiments, the functional groups, residues, or moieties comprise a functional group that is one part of a specific binding pair, such as the biotin-(strept)avidin binding pair. Such a functional group may be used to link the Clec9A binding agent of the invention to another protein, polypeptide or chemical compound that is bound to the other half of the binding pair, i.e., through formation of the binding pair. For example, a Clec9A binding agent of the invention may be conjugated to biotin, and linked to another protein, polypeptide, compound or carrier conjugated to avidin or streptavidin. For example, such a conjugated Clec9A binding agent may be used as a reporter, for example, in a diagnostic system where a detectable signal-producing agent is conjugated to avidin or streptavidin. Such binding pairs may, for example, also be used to bind the Clec9A binding agent to a carrier, including carriers suitable for pharmaceutical purposes. One non-limiting example are the liposomal formulations described by Cao and Suresh, *Journal of Drug Targeting,* 8, 4, 257 (2000). Such binding pairs may also be used to link a therapeutically active agent to the Clec9A binding agent of the invention.

In some embodiments, the present Clec9A binding agent optionally comprises one or more linkers. In some embodiments, the Clec9A binding agent includes a linker that connects each binding region and/or targeting moieties. In some embodiments, the Clec9A binding agent includes a linker that connects each signaling agent and targeting moiety (or, if more than one targeting moiety, a signaling agent to one of the targeting moieties). In some embodiments, the linker may be utilized to link various functional groups, residues, or moieties as described herein to the Clec9A binding agent. In some embodiments, the linker is a single amino acid or a plurality of amino acids that does not affect or reduce the stability, orientation, binding, neutralization, and/or clearance characteristics of the binding regions and the binding protein. In various embodiments, the linker is selected from a peptide, a protein, a sugar, or a nucleic acid.

In some embodiments, the present Clec9A binding agent comprises a linker connecting the targeting moiety and the signaling agent. In some embodiments, the present chimeric protein comprises a linker within the signaling agent (e.g. in the case of single chain TNF, which can comprise two linkers to yield a trimer).

The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present Clec9A binding agent.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In some embodiments, the linker length allows for efficient binding of a targeting moiety and the signaling agent to their receptors. For instance, in some embodiments, the linker length allows for efficient binding of one of the targeting moieties and the signaling agent to receptors on the same cell as well as the efficient binding of the other targeting moiety to another cell. Illustrative pairs of cells are provided elsewhere herein.

In some embodiments the linker length is at least equal to the minimum distance between the binding sites of one of the targeting moieties and the signaling agent to receptors on the same cell. In some embodiments the linker length is at least twice, or three times, or four times, or five times, or ten times, or twenty times, or 25 times, or 50 times, or one hundred times, or more the minimum distance between the binding sites of one of the targeting moieties and the signaling agent to receptors on the same cell.

In some embodiments, a linker connects the two targeting moieties to each other and this linker has a short length and a linker connects a targeting moiety and a signaling agent this linker is longer than the linker connecting the two targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g. 1, 2, 3, 4, 5, 6, 7, or 8. In an embodiment, the linker sequence is GGSGGSGGGGSGGGGS (SEQ ID NO:278). Additional illustrative linkers include, but are not limited to, linkers having the sequence LE, GGGGS (SEQ ID NO:279), $(GGGGS)_n$ (n=1-4) (SEQ ID NO:280), $(Gly)_8$ (SEQ ID NO:281), $(Gly)_6$ (SEQ ID NO:282), $(EAAAK)_n$ (n=1-3) (SEQ ID NO:283), $A(EAAAK)_nA$ (n=2-5) (SEQ ID NO:284), AEAAAKEAAAKA (SEQ ID NO:285), $A(EAAAK)_4ALEA(EAAAK)_4A$ (SEQ ID NO:286), PAPAP (SEQ ID NO:287), KESGSVSSEQLAQFRSLD (SEQ ID NO:288), EGKSSGSGSESKST (SEQ ID NO:289), GSAGSAAGSGEF (SEQ ID NO:290), and $(XP)_n$, with X designating any amino acid, e.g., Ala, Lys, or Glu. In various embodiments, the linker is GGS.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites. In various embodiments, the linker is a hinge-CH2-CH3 domain of a human IgG4 antibody.

If desired, the present Clec9A binding agent can be linked to an antibody Fc region, comprising one or both of $C_H2$ and $C_H3$ domains, and optionally a hinge region. For example, vectors encoding the present Clec9A binding agents linked as a single nucleotide sequence to an Fc region can be used to prepare such polypeptides.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present Clec9A binding agent. In another example, the linker may function to target the Clec9A binding agent to a particular cell type or location.

Modifications and Production of Clec9A Binding Agents

In various embodiments, the Clec9A binding agent comprises a targeting moiety that is a VHH. In various embodiments, the VHH is not limited to a specific biological source or to a specific method of preparation. For example, the VHH can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring $V_HH$ domain from any animal species, such as from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known in the art; (7) by preparing a nucleic acid encoding a VHH using techniques for nucleic acid synthesis known in the art, followed by expression of the nucleic acid thus obtained; and/or (8) by any combination of one or more of the foregoing.

In an embodiment, the Clec9A binding agent comprises a VHH that corresponds to the $V_HH$ domains of naturally occurring heavy chain antibodies directed against human Clec9A. In some embodiments, such $V_HH$ sequences can generally be generated or obtained by suitably immunizing a species of Camelid with a Clec9A molecule, (i.e., so as to raise an immune response and/or heavy chain antibodies directed against Clec9A), by obtaining a suitable biological sample from the Camelid (such as a blood sample, or any sample of B-cells), and by generating $V_HH$ sequences directed against Clec9A, starting from the sample, using any suitable known techniques. In some embodiments, naturally occurring $V_HH$ domains against Clec9A can be obtained from naive libraries of Camelid $V_HH$ sequences, for example, by screening such a library using Clec9A or at least one part, fragment, antigenic determinant or epitope thereof using one or more screening techniques known in the art. Such libraries and techniques are, for example, described in WO9937681, WO0190190, WO03025020 and WO03035694, the entire contents of which are hereby incorporated by reference. In some embodiments, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as for example, described in WO0043507, the entire contents of which are hereby incorporated by reference. In some embodiments, another technique for obtaining $V_HH$ sequences directed against a Clec9A involves suitably immunizing a transgenic mammal that is capable of expressing heavy chain antibodies (i.e., so as to raise an immune response and/or heavy chain antibodies directed against Clec9A), obtaining a suitable biological sample from the transgenic mammal (such as a blood sample, or any sample of B-cells), and then generating $V_HH$ sequences directed against Clec9A starting from the sample, using any suitable known techniques. For example, for this purpose, the heavy chain antibody-expressing mice and the further methods and techniques described in WO02085945 and in WO04049794 (the entire contents of which are hereby incorporated by reference) can be used.

In an embodiment, the Clec9A binding agent comprises a VHH that has been "humanized" i.e., by replacing one or more amino acid residues in the amino acid sequence of the naturally occurring $V_HH$ sequence (and in particular in the framework sequences) by one or more of the amino acid residues that occur at the corresponding position(s) in a VH domain from a conventional 4-chain antibody from a human being. This can be performed using humanization techniques known in the art. In some embodiments, possible humanizing substitutions or combinations of humanizing substitutions may be determined by methods known in the art, for example, by a comparison between the sequence of a VHH and the sequence of a naturally occurring human VH domain. In some embodiments, the humanizing substitutions are chosen such that the resulting humanized VHHs still retain advantageous functional properties. Generally, as a result of humanization, the VHHs of the invention may become more "human-like," while still retaining favorable properties such as a reduced immunogenicity, compared to the corresponding naturally occurring $V_HH$ domains. In various embodiments, the humanized VHHs of the invention can be obtained in any suitable manner known in the art and thus are not strictly limited to polypeptides that have been obtained using a polypeptide that comprises a naturally occurring $V_HH$ domain as a starting material.

In an embodiment, the Clec9A binding agent comprises a VHH that has been "camelized," i.e., by replacing one or more amino acid residues in the amino acid sequence of a naturally occurring VH domain from a conventional 4-chain antibody by one or more of the amino acid residues that occur at the corresponding position(s) in a $V_HH$ domain of a heavy chain antibody of a camelid. In some embodiments, such "camelizing" substitutions are inserted at amino acid positions that form and/or are present at the VH-VL interface, and/or at the so-called Camelidae hallmark residues (see, for example, WO9404678, the entire contents of which are hereby incorporated by reference). In some embodiments, the VH sequence that is used as a starting material or starting point for generating or designing the camelized VHH is a VH sequence from a mammal, for example, the VH sequence of a human being, such as a VH3 sequence. In various embodiments, the camelized VHHs can be obtained in any suitable manner known in the art (i.e., as indicated under points (1)-(8) above) and thus are not strictly limited to polypeptides that have been obtained using a polypeptide that comprises a naturally occurring VH domain as a starting material.

In various embodiments, both "humanization" and "camelization" can be performed by providing a nucleotide sequence that encodes a naturally occurring $V_HH$ domain or VH domain, respectively, and then changing, in a manner known in the art, one or more codons in the nucleotide sequence in such a way that the new nucleotide sequence encodes a "humanized" or "camelized" VHH, respectively. This nucleic acid can then be expressed in a manner known in the art, so as to provide the desired VHH of the invention. Alternatively, based on the amino acid sequence of a naturally occurring $V_HH$ domain or VH domain, respectively, the amino acid sequence of the desired humanized or camelized VHH of the invention, respectively, can be designed and then synthesized de novo using techniques for peptide synthesis known in the art. Also, based on the amino acid sequence or nucleotide sequence of a naturally occurring $V_HH$ domain or VH domain, respectively, a nucleotide sequence encoding the desired humanized or camelized VHH, respectively, can be designed and then synthesized de novo using techniques for nucleic acid synthesis known in the art, after which the nucleic acid thus obtained can be expressed in a manner known in the art, so as to provide the desired VHH of the invention. Other suitable methods and techniques for obtaining the VHHs of the invention and/or nucleic acids encoding the same, starting from naturally occurring VH sequences or $V_HH$ sequences, are known in the art, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a VHH of the invention or a nucleotide sequence or nucleic acid encoding the same.

Methods for producing the Clec9A binding agents of the invention are described herein. For example, DNA sequences encoding the Clec9A binding agents of the invention can be chemically synthesized using methods known in the art. Synthetic DNA sequences can be ligated to other appropriate nucleotide sequences, including, e.g., expression control sequences, to produce gene expression constructs encoding the desired Clec9A binding agents. Accordingly, in various embodiments, the present invention provides for isolated nucleic acids comprising a nucleotide sequence encoding the Clec9A binding agent of the invention.

Nucleic acids encoding the Clec9A binding agent of the invention can be incorporated (ligated) into expression vectors, which can be introduced into host cells through transfection, transformation, or transduction techniques. For example, nucleic acids encoding the Clec9A binding agent of the invention can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the Clec9A binding agent of the invention. Accordingly, in various embodiments, the present invention provides expression vectors comprising nucleic acids that encode the Clec9A binding agent of the invention. In various embodiments, the present invention additional provides host cells comprising such expression vectors.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The Clec9A binding agent of the invention can be produced by growing a host cell transfected with an expression vector encoding the Clec9A binding agent under conditions that permit expression of the protein. Following expression, the protein can be harvested and purified using techniques well known in the art, e.g., affinity tags such as glutathione-S-transferase (GST) and histidine (His) tags or by chromatography. In an embodiment, the Clec9A binding agent comprises a His tag. In an embodiment, the Clec9A binding agent comprises a His tag and a proteolytic site to allow cleavage of the His tag.

Accordingly, in various embodiments, the present invention provides for a nucleic acid encoding a Clec9A binding agent of the present invention. In various embodiments, the present invention provides for a host cell comprising a nucleic acid encoding a Clec9A binding agent of the present invention.

In various embodiments, the methods of modifying and producing the Clec9A binding agents as described herein can be easily adapted for the modification and production of any multi-specific binding agents or chimeras comprising two or more targeting moieties and/or signaling agents. For example, the methods may be adapted for production of a multi-specific Clec9A binding agent comprising a targeting moiety against a checkpoint inhibitor antigen.

Pharmaceutically Acceptable Salts and Excipients

The Clec9A binding agents (and/or any other therapeutic agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-0H-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present invention pertains to pharmaceutical compositions comprising the Clec9A binding agents (and/or any other therapeutic agents) described herein and a pharmaceutically acceptable carrier or excipient. In some embodiments, the present invention pertains to pharmaceutical compositions comprising the present Clec9A binding agents. In another embodiment, the present invention pertains to pharmaceutical compositions comprising any other therapeutic agents described herein. In a further embodiment, the present invention pertains to pharmaceutical compositions comprising a combination of the present Clec9A binding agents and any other therapeutic agents described herein. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

The present invention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In one embodiment, the Clec9A binding agent described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any Clec9A binding agents described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the Clec9A binding agent and/or any therapeutic agents described herein to be administered according to the present invention will vary according to the particular dosage form, and the mode of administration. Many factors that may modify the action of the Clec9A binding agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the Clec9A binding agent and/or any therapeutic agents described herein is in a range of about 0.01 mg/kg to about 10 g/kg of body weight of the subject, about 0.01 mg/kg to about 1 g/kg of body weight of the subject, about 0.01 mg/kg to about 100 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 100 mg/kg body weight, about 1 g/kg of body weight, about 10 g/kg of body weight, inclusive of all values and ranges therebetween.

Individual doses of the Clec9A binding agent and/or any therapeutic agents described herein can be administered in unit dosage forms containing, for example, from about 0.01 mg to about 100 g, from about 0.01 mg to about 75 g, from about 0.01 mg to about 50 g, from about 0.01 mg to about 25 g, about 0.01 mg to about 10 g, about 0.01 mg to about 7.5 g, about 0.01 mg to about 5 g, about 0.01 mg to about 2.5 g, about 0.01 mg to about 1 g, about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 10 g, about 25 g, about 50 g, about 75 g, about 100 g, inclusive of all values and ranges therebetween.

In one embodiment, the Clec9A binding agent and/or any therapeutic agents described herein are administered at an amount of from about 0.01 mg to about 100 g daily, from about 0.01 mg to about 75 g daily, from about 0.01 mg to about 50 g daily, from about 0.01 mg to about 25 g daily, from about 0.01 mg to about 10 g daily, from about 0.01 mg to about 7.5 g daily, from about 0.01 mg to about 5 g daily, from about 0.01 mg to about 2.5 g daily, from about 0.01 mg to about 1 g daily, from about 0.01 mg to about 100 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the Clec9A binding agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 7.5 g, about 10 g, about 25 g, about 50 g, about 75 g, about 100 g, inclusive of all values and ranges therebetween.

In accordance with certain embodiments of the invention, the pharmaceutical composition comprising the Clec9A binding agent and/or any therapeutic agents described herein may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year.

Combination Therapy and Additional Therapeutic Agents

In various embodiments, the pharmaceutical composition of the present invention is co-administered in conjunction with additional therapeutic agent(s). Co-administration can be simultaneous or sequential.

In one embodiment, the additional therapeutic agent and the Clec9A binding agent of the present invention are administered to a subject simultaneously. The term "simultaneously" as used herein, means that the additional therapeutic agent and the Clec9A binding agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the Clec9A binding agent can be by simultaneous administration of a single formulation (e.g., a formulation comprising the additional therapeutic agent and the Clec9A binding agent) or of separate formulations (e.g., a first formulation including the additional therapeutic agent and a second formulation including the Clec9A binding agent).

Co-administration does not require the therapeutic agents to be administered simultaneously, if the timing of their administration is such that the pharmacological activities of the additional therapeutic agent and the Clec9A binding agent overlap in time, thereby exerting a combined therapeutic effect. For example, the additional therapeutic agent and the Clec9A binding agent can be administered sequentially. The term "sequentially" as used herein means that the additional therapeutic agent and the Clec9A binding agent are administered with a time separation of more than about 60 minutes. For example, the time between the sequential administration of the additional therapeutic agent and the Clec9A binding agent can be more than about 60 minutes, more than about 2 hours, more than about 5 hours, more than about 10 hours, more than about 1 day, more than about 2 days, more than about 3 days, more than about 1 week, or more than about 2 weeks, or more than about one month apart. The optimal administration times will depend on the rates of metabolism, excretion, and/or the pharmacodynamic activity of the additional therapeutic agent and the Clec9A binding agent being administered. Either the additional therapeutic agent or the Clec9A binding agent cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the Clec9A binding agent described herein acts synergistically when co-administered with another therapeutic agent. In such embodiments, the Clec9A binding agent and the additional therapeutic agent may be administered at doses that are lower than the doses employed when the agents are used in the context of monotherapy.

In some embodiments, the present invention pertains to chemotherapeutic agents as additional therapeutic agents. For example, without limitation, such combination of the present Clec9A binding agents and chemotherapeutic agent find use in the treatment of cancers, as described elsewhere herein. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU);

folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

Accordingly, in some embodiments, the present invention relates to combination therapies using the Clec9A binding agent and a chemotherapeutic agent. In some embodiments, the present invention relates to administration of the Clec9A binding agent to a patient undergoing treatment with a chemotherapeutic agent. In some embodiments, the chemotherapeutic agent is a DNA-intercalating agent such as, without limitation, doxorubicin, cisplatin, daunorubicin, and epirubicin. In an embodiment, the DNA-intercalating agent is doxorubicin.

In illustrative embodiments, the Clec9A binding agent acts synergistically when co-administered with doxorubicin. In an illustrative embodiment, the Clec9A binding agent acts synergistically when co-administered with doxorubicin for use in treating tumor or cancer. For example, co-administration of the Clec9A binding agent and doxorubicin may act synergistically to reduce or eliminate the tumor or cancer, or slow the growth and/or progression and/or metastasis of the tumor or cancer. In illustrative embodiments, the combination of the Clec9A binding agent and doxorubicin may exhibit improved safety profiles when compared to the agents used alone in the context of monotherapy. In illustrative embodiments, the Clec9A binding agent and doxorubicin may be administered at doses that are lower than the doses employed when the agents are used in the context of monotherapy. In some embodiments, the Clec9A binding agent comprises a mutated interferon such as a mutated IFNα. In illustrative embodiments, the mutated IFNα comprises one or more mutations at positions 148, 149, and 153 with reference to SEQ ID NO: 86 or SEQ ID NO: 87, such as the substitutions M148A, R149A, and L153A.

In some embodiments, the present invention relates to combination therapy with one or more immune-modulating agents, for example, without limitation, agents that modulate immune checkpoint. In various embodiments, the immune-modulating agent targets one or more of PD-1, PD-L1, and PD-L2. In various embodiments, the immune-modulating agent is PD-1 inhibitor. In various embodiments, the immune-modulating agent is an antibody specific for one or more of PD-1, PD-L1, and PD-L2. For instance, in some embodiments, the immune-modulating agent is an antibody such as, by way of non-limitation, nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL328OA (ROCHE). In some embodiments, the immune-modulating agent targets one or more of CD137 or CD137L. In various embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the present chimeric protein is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an agent that targets one or more of CTLA-4, AP2M1, CD80, CD86, SHP-2, and PPP2R5A. In various embodiments, the immune-modulating agent is an antibody specific for one or more of CTLA-4, AP2M1, CD80, CD86, SHP-2, and PPP2R5A. For instance, in some embodiments, the immune-modulating agent is an antibody such as, by way of non-limitation, ipilimumab (MDX-010, MDX-101, Yervoy, BMS) and/or tremelimumab (Pfizer). In some embodiments, the present chimeric protein is combined with ipilimumab (optionally with bavituximab) for the treatment of one or more of melanoma, prostate cancer, and lung cancer. In various embodiments, the immune-modulating agent targets CD20. In various embodiments, the immune-modulating agent is an antibody specific CD20. For instance, in some embodiments, the immune-modulating agent is an antibody such as, by way of non-limitation, Ofatumumab (GENMAB), obinutuzumab (GAZYVA), AME-133v (APPLIED MOLECULAR EVOLUTION), Ocrelizumab (GENENTECH), TRU-015 (TRUBION/EMERGENT), veltuzumab (IMMU-106).

In some embodiments, the present invention relates to combination therapy using the Clec9A binding agent and a checkpoint inhibitor. In some embodiments, the present invention relates to administration of the Clec9A binding agent to a patient undergoing treatment with a checkpoint inhibitor. In some embodiments, the checkpoint inhibitor is an agent that targets one or more of PD-1, PD-L1, PD-L2, and CTLA-4 (including any of the anti-PD-1, anti-PD-L1, anti-PD-L2, and anti-CTLA-4 agents described herein). In some embodiment, the checkpoint inhibitor is one or more of nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE), ipilimumab (MDX-010, MDX-101, Yervoy, BMS) and tremelimumab (Pfizer). In an embodiment, the checkpoint inhibitor is an antibody against PD-L1.

In illustrative embodiments, the Clec9A binding agent acts synergistically when co-administered with the anti-PD-L1 antibody. In an illustrative embodiment, the Clec9A binding agent acts synergistically when co-administered with the anti-PD-L1 antibody for use in treating tumor or cancer. For example, co-administration of the Clec9A binding agent and the anti-PD-L1 antibody may act synergistically to reduce or eliminate the tumor or cancer, or slow the growth and/or progression and/or metastasis of the tumor or cancer. In some embodiments, the combination of the Clec9A binding agent and the anti-PD-L1 antibody may exhibit improved safety profiles when compared to the agents used alone in the context of monotherapy. In some embodiments, the Clec9A binding agent and the anti-PD-L1 antibody may be administered at doses that are lower than the doses employed when the agents are used in the context of monotherapy. In some embodiments, the Clec9A binding agent comprises a mutated interferon such as a mutated IFNα. In illustrative embodiments, the mutated IFNα comprises one or more mutations at positions 148, 149, and 153 with reference to SEQ ID NO: 86 or SEQ ID NO: 87, such as the substitutions M148A, R149A, and L153A.

In some embodiments, the present invention relates to combination therapies using the Clec9A binding agent and an immunosuppressive agent. In some embodiments, the present invention relates to administration of the Clec9A binding agent to a patient undergoing treatment with an immunosuppressive agent. In an embodiment, the immunosuppressive agent is TNF.

In illustrative embodiments, the Clec9A binding agent acts synergistically when co-administered with TNF. In an illustrative embodiment, the Clec9A binding agent acts synergistically when co-administered with TNF for use in treating tumor or cancer. For example, co-administration of the Clec9A binding agent and TNF may act synergistically to reduce or eliminate the tumor or cancer, or slow the growth and/or progression and/or metastasis of the tumor or cancer. In some embodiments, the combination of the Clec9A binding agent and TNF may exhibit improved safety profiles when compared to the agents used alone in the context of monotherapy. In some embodiments, the Clec9A binding agent and TNF may be administered at doses that are lower than the doses employed when the agents are used in the context of monotherapy. In some embodiments, the Clec9A binding agent comprises a mutated interferon such as a mutated IFNα. In illustrative embodiments, the mutated IFNα comprises one or more mutations at positions 148, 149, and 153 with reference to SEQ ID NO: 86 or SEQ ID NO: 87, such as the substitutions M148A, R149A, and L153A.

In some embodiments, the Clec9A binding agent acts synergistically when used in combination with Chimeric Antigen Receptor (CAR) T-cell therapy. In an illustrative embodiment, the Clec9A binding agent acts synergistically when used in combination with CAR T-cell therapy in treating tumor or cancer. In an embodiment, the Clec9A binding agent acts synergistically when used in combination with CAR T-cell therapy in treating blood-based tumors. In an embodiment, the Clec9A binding agent acts synergistically when used in combination with CAR T-cell therapy in treating solid tumors. For example, use of the Clec9A binding agent and CAR T-cells may act synergistically to reduce or eliminate the tumor or cancer, or slow the growth and/or progression and/or metastasis of the tumor or cancer. In various embodiments, the Clec9A binding agent of the invention induces CAR T-cell division. In various embodiments, the Clec9A binding agent of the invention induces CAR T-cell proliferation. In various embodiments, the Clec9A binding agent of the invention prevents anergy of the CAR T cells.

In various embodiments, the CAR T-cell therapy comprises CAR T cells that target antigens (e.g., tumor antigens) such as, but not limited to, carbonic anhydrase IX (CAIX), 5T4, CD19, CD20, CD22, CD30, CD33, CD38, CD47, CS1, CD138, Lewis-Y, L1-CAM, MUC16, ROR-1, IL13Rα2, gp100, prostate stem cell antigen (PSCA), prostate-specific membrane antigen (PSMA), B-cell maturation antigen (BCMA), human papillomavirus type 16 E6 (HPV-16 E6), CD171, folate receptor alpha (FR-α), GD2, human epidermal growth factor receptor 2 (HER2), mesothelin, EGFRvIII, fibroblast activation protein (FAP), carcinoembryonic antigen (CEA), and vascular endothelial growth factor receptor 2 (VEGF-R2), as well as other tumor antigens well known in the art. Additional illustrative tumor antigens include, but are not limited to MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pme1117, PRAME, NY-ESO-1, cdc27, adenomatous polyposis *coli* protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD37, CD56, CD70, CD74, CD138, AGS16, MUC1, GPNMB, Ep-CAM, PD-L1, and PD-L2.

Exemplary CAR T-cell therapy include, but are not limited to, JCAR014 (Juno Therapeutics), JCAR015 (Juno Therapeutics), JCAR017 (Juno Therapeutics), JCAR018 (Juno Therapeutics), JCAR020 (Juno Therapeutics), JCAR023 (Juno Therapeutics), JCAR024 (Juno Therapeutics), CTL019 (Novartis), KTE-C19 (Kite Pharma), BPX-401 (Bellicum Pharmaceuticals), BPX-501 (Bellicum Pharmaceuticals), BPX-601 (Bellicum Pharmaceuticals), bb2121 (Bluebird Bio), CD-19 Sleeping Beauty cells (Ziopharm Oncology), UCART19 (Cellectis), UCART123 (Cellectis), UCART38 (Cellectis), UCARTCS1 (Cellectis), OXB-302 (Oxford BioMedica, MB-101 (Mustang Bio) and CAR T-cells developed by Innovative Cellular Therapeutics.

In some embodiments, the Clec9A binding agent is used in a method of treating multiple sclerosis (MS) in combination with one or more MS therapeutics including, but not limited to, 3-interferons, glatiramer acetate, T-interferon, IFN-R-2 (U.S. Patent Publication No. 2002/0025304), spirogermaniums (e.g., N-(3-dimethylaminopropyl)-2-aza-8,8-dimethyl-8-germanspiro [4:5] decane, N-(3-dimethylaminopropyl)-2-aza-8,8-diethyl-8-germaspiro [4:5] decane, N-(3-dimethylaminopropyl)-2-aza-8,8-dipropyl-8-germaspiro [4:5] decane, and N-(3-dimethylaminopropyl)-2-aza-8,8-dibutyl-8-germaspiro [4:5] decane), vitamin D analogs (e.g., 1,25 (OH) 2D3, (see, e.g., U.S. Pat. No. 5,716, 946)), prostaglandins (e.g., latanoprost, brimonidine, PGE1, PGE2 and PGE3, see, e.g., U.S. Patent Publication No. 2002/0004525), tetracycline and derivatives (e.g., minocycline and doxycycline, see, e.g., U.S. Patent Publication No. 20020022608), a VLA-4 binding antibody (see, e.g., U.S. Patent Publication No. 2009/0202527), adrenocorticotrophic hormone, corticosteroid, prednisone, methylprednisone, 2-chlorodeoxyadenosine, mitoxantrone, sulphasalazine, methotrexate, azathioprine, cyclophosphamide, cyclosporin, fumarate, anti-CD20 antibody (e.g., rituximab), and tizanidine hydrochloride.

In some embodiments, the Clec9A binding agent is used in combination with one or more therapeutic agents that treat one or more symptoms or side effects of MS. Such agents include, but are not limited to, amantadine, baclofen, papaverine, meclizine, hydroxyzine, sulfamethoxazole, ciprofloxacin, docusate, pemoline, dantrolene, desmopressin, dexamethasone, tolterodine, phenyloin, oxybutynin, bisacodyl, venlafaxine, amitriptyline, methenamine, clonazepam, isoniazid, vardenafil, nitrofurantoin, psyllium hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline.

In some embodiments, the Clec9A binding agent is used in a method of treating multiple sclerosis in combination with one or more of the disease modifying therapies (DMTs) described herein (e.g. the agents of Table A). In some embodiments, the present invention provides an improved therapeutic effect as compared to use of one or more of the DMTs described herein (e.g. the agents listed in the Table below) without the one or more disclosed binding agent. In an embodiment, the combination of the Clec9A binding agent and the one or more DMTs produces synergistic therapeutic effects.

Illustrative Disease Modifying Therapies

| Generic Name | Branded Name/Company | Frequency/Route of Delivery/Usual Dose |
|---|---|---|
| teriflunomide | AUBAGIO (GENZYME) | Every day; pill taken orally; 7 mg or 14 mg. |
| interferon beta-1a | AVONEX (BIOGEN IDEC) | Once a week; intramuscular (into the muscle) injection; 30 mcg |
| interferon beta-1b | BETASERON (BAYER HEALTHCARE PHARMACEUTICALS, INC.) | Every other day; subcutaneous (under the skin) injection; 250 mcg. |
| glatiramer acetate | COPAXONE (TEVA NEUROSCIENCE) | Every day; subcutaneous (under the skin) injection; 20 mg (20,000 mcg) OR Three times a week; subcutaneous (under the skin) injection; 40 mg (40,000 mcg) |
| interferon beta-1b | EXTAVIA (NOVARTIS PHARMACEUTICALS CORP.) | Every other day; subcutaneous (under the skin) injection; 250 mcg. |
| fingolimod | GILENYA (NOVARTIS PHARMACEUTICALS CORP.) | Every day; capsule taken orally; 0.5 mg. |
| Alemtuzumab (anti-CD52 monoclonal antibody) | LEMTRADA (GENZYME) | Intravenous infusion on five consecutive days, followed by intravenous infusion on three consecutive days one year later (12 mg) |
| mitoxantrone | NOVANTRONE (EMD SERONO) | Four times a year by IV infusion in a medical facility. Lifetime cumulative dose limit of approximately 8-12 doses over 2-3 years (140 mg/m2). |
| pegylated interferon beta-1a | PLEGRIDY (BIOGEN IDEC) | Every 14 days; subcutaneous (under the skin) injection; 125 mcg |
| interferon beta-1a | REBIF (EMD SERONO, INC.) | Three times a week; subcutaneous (under the skin) injection; 44 mcg |
| dimethyl fumarate (BG-12) | TECFIDERA (BIOGEN IDEC) | Twice a day; capsule taken orally; 120 mg for one week and 240 mg therafter |
| Natalizumab (humanized monoclonal antibody VLA-4 antagonist) | TYSABRI (BIOGEN IDEC) | Every four weeks by IV infusion in a registered infusion facility; 300 mg |
| DMTs in Development | | |
| Amiloride (targets Acid-sensing ion channel-1 Epithelial sodium channel Na+/H+ exchanger) | PAR PHARMACEUTICAL, PERRIGO COMPANY, SIGMAPHARM LABORATORIES | Oral |
| ATX-MS-1467 (targets Major histocompatibility complex class II T cell responses to myelin basic protein) | APITOPE/MERCK SERONO | Intradermal Subcutaneous |

-continued

| Generic Name | Branded Name/Company | Frequency/Route of Delivery/Usual Dose |
|---|---|---|
| BAF312 (targets Sphingosine 1-phosphate (S1P) receptor subtypes S1P1 and S1P5 B cell distrubution T cell distribution) | NOVARTIS PHARMA | Oral |
| BGC20-0134 (targets Proinflammatory and anti-inflammatory cytokines) | BTG PLC | Oral |
| BIIB033 (targets LINGO-1 (“leucine-rich repeat and immunoglobulin-like domain-containing, Nogo receptor-interacting protein”)) | BIOGEN | Intravenous infusion used in Phase I and Phase II trials Subcutaneous injection used in Phase I trial |
| Cladribine (targets CD4+ T cells DNA synthesis and repair E-selectin Intracellular adhesion molecule-1 Pro-inflammatory cytokines interleukin 2 and interleukin 2R Pro-inflammatory cytokines interleukin 8 and RANTES Cytokine secretion Monocyte and lymphocyte migration) | MERCK SERONO | Oral |
| Cyclophosphamide (targets T cells, particularly CD4+ helper T cells B cells) | BAXTER HEALTHCARE CORPORATION | Oral, monthly intravenous pulses |
| Daclizumab (humanized monoclonal antibody targeting CD25 Immune modulator of T cells) | BIOGEN IDEC/ABBVIE BIOTHERAPEUTICS | Projected to be IM injection once monthly |
| Dalfampridine (targets Voltage-gated potassium channels Degenerin/epithelial sodium channels L-type calcium channels that contain subunit Cavbeta3) | ACORDA THERAPEUTICS/ BIOGEN IDEC | One tablet every 12 hours (extended release), 10 mg twice a day |
| Dronabinol (targets Cannabinoid receptor CB1 Cannabinoid receptor CB2) | ABBVIE INC. | Oral |
| Firategrast (targets Alpha4beta1 integrin) | GLAXOSMITHKLINE | Oral |
| GNbAC1MSRV-Env (targets envelope protein of the MS-associated retrovirus) | GENEURO SA/SERVIER | Intravenous infusion |
| Idebenone (targets Reactive oxygen species) | SANTHERA PHARMACEUTICALS | Oral Dose in clinical trial for PPMS is 2250 mg per day (750 mg dose, 3 times per day) |
| Imilecleucel-T (targets Myelin-specific, autoreactive T cells) | OPEXA THERAPEUTICS/ MERCK SERONO | Subcutaneous Given 5 times per year, according to information from the manufacturer |
| Laquinimod | TEVA | Projected to be 0.6 mg or 1.2 mg oral tablet taken daily |
| Masitinib (targets KIT (a stem cell factor, also called c-KIT) receptor as well as select other tyrosine kinases Mast cells) | AB SCIENCE | Oral |
| MEDI-551 (targets CD19, a B cell-specific antigen that is part of the B cell receptor complex and that functions in determining the threshold for B cell activation B cells Plasmablasts, B cells that express CD19 (but not CD20) and that secrete large quantities of antibodies; depletion of plasmablasts may be useful in autoimmune diseases involving pathogenic autoantibodies) | MEDIMMUNE | Intravenous Subcutaneous |

-continued

| Generic Name | Branded Name/Company | Frequency/Route of Delivery/Usual Dose |
|---|---|---|
| Minocycline (targets T cells Microglia Leukocyte migration Matrix metalloproteinases) | VARIOUS | Oral Available as pellet-filled capsules and an oral suspension |
| MIS416 (targets Innate immune system Pathogen-associated molecular pattern recognition receptors of the innate immune system Myeloid cells of the innate immune system, which might be able to remodel the deregulated immune system activity that occurs in SPMS) | INNATE IMMUNOTHERAPEUTICS | Intravenous |
| Mycophenolate mofetil (targets Purine synthesis) | MANUFACTURED BY GENENTECH | Oral |
| Naltrexone (targets Opioid receptors Toll-like receptor 4) | VARIOUS | Given at low doses (3 to 4.5 mg per day) in oral form as"Low-dose naltrexone" (or "LDN") |
| Ocrelizumab and Ofatumumab (humanized monoclonal antibodies targeting CD20 B cell suppression | ROCHE/GSK | Projected to be IV infusion |
| ONO-4641 (targets Sphingosine 1-phosphate receptor) | ONO PHARMACEUTICAL CO. | Oral |
| Phenytoin (targets Sodium channels) | PFIZER | Intravenous Intramuscular (less favored option) Oral |
| Ponesimod | ACTELION | To be determined |
| Raltegravir (targets Retroviral integrase Herpesvirus DNA packaging terminase) | MERCK | Oral 400 mg tablet twice daily, according to information from the manufacturer |
| RHB-104 | REDHILL BIOPHARMA LIMITED | 95 mg clarithromycin, 45 mg rifabutin, and 10 mg clofazimine |
| Riluzole (targets Glutamatergic neurotransmission Glutamate uptake and release Voltage-gated sodium channels Protein kinase C) | COVIS PHARMA/SANOFI | Oral |

MS disease progression may be most intensive, and most damaging, at the earliest stages of disease progression. Accordingly, counter to many reimbursement policies and physician practice in light of, for example, costs and side effect mitigation, it may be most beneficial for a patient's long term disease status to begin treatment with the most intensive DMTs, for instance so-called second-line therapies. In some embodiments, a patient is treated with a regimen of the Clec9A binding agent in combination with a second-line therapy. Such a combination is used to reduce the side effect profile of one or more second-line therapies. In some embodiments, the combination is used to reduce dose of frequency of administration of one or more second-line therapies. For example, the doses of agents listed in the Table provided above may be reduced by about 50%, or about 40%, or about 30%, or about 25% in the context of the combination and the/or the frequency of dosing may be decreased to be half as often, or a third as often or may be reduced from, for example, daily to every other day or weekly, every other day to weekly or bi-weekly, weekly to bi-weekly or monthly, etc. Accordingly, in some embodiments, the Clec9A binding agent increase patient adherence by allowing for more convenient treatment regimens. Further, some DMTs have a suggested lifetime dose limitation e.g. for mitoxantrone, the lifetime cumulative dose should be strictly limited to 140 mg/m$^2$, or 2 to 3 years of therapy. In some embodiments, supplementation with the Clec9A binding agent preserves patient's access to mitoxantrone by allowing for lower or less frequent dosing with this DMT.

In some embodiments, the patient is a naive patient, who has not received treatment with one or more DMTs, and the Clec9A binding agent is used to buffer the side effects of a second-line therapy. Accordingly, the naive patient is able to benefit from the long-term benefits of a second-line therapy at disease outset. In some embodiments, the Clec9A binding agent is used as an entry therapy that precedes the use of a second-line therapy. For example, the Clec9A binding agent may be administered for an initial treatment period of about 3 months to stabilize disease and then the patient may be transitioned to a maintenance therapy of a second line agent.

It is generally believed that naive patients are more likely to respond to therapy as compared to patients that have received, and perhaps failed one or more DMT. In some embodiments, the Clec9a binding agent finds use in patients that have received, and perhaps failed one or more DMT. For example, in some embodiments, the Clec9A binding agent increases the therapeutic effect in patients that have received, and perhaps failed one or more DMT and may allow these patients to respond like naive patients.

In some embodiments, the patient has received or is receiving treatment with one or more DMTs and is not responding well. For example, the patient may be refractory or poorly responsive to one or more DMTs. In some embodiments, the patient is refractory, or poorly responsive to one or more of teriflunomide (AUBAGIO (GENZYME)); interferon beta-1a (AVONEX (BIOGEN IDEC); interferon beta-1b (BETASERON (BAYER HEALTHCARE PHARMACEUTICALS, INC.); glatiramer acetate (COPAXONE (TEVA NEUROSCIENCE); interferon beta-1b (EXTAVIA (NOVARTIS PHARMACEUTICALS CORP.); fingolimod (GILENYA (NOVARTIS PHARMACEUTICALS CORP.); alemtuzumab (LEMTRADA (GENZYME); mitoxantrone (NOVANTRONE (EMD SERONO); pegylated interferon beta-1a (PLEGRIDY (BIOGEN IDEC); interferon beta-1a (REBIF (EMD SERONO, INC.); dimethyl fumarate (BG-12) (TECFIDERA (BIOGEN IDEC); and natalizumab (TYSABRI (BIOGEN IDEC). In some embodiments, the one or more disclosed binding agent results in a therapeutic benefit of one or more DMTs in the patient and therefore reduces or eliminates the non-responsiveness to the DMT. For instance, this may spare the patient therapy with one or more DMTs at a higher dosing or frequency.

In patients with more aggressive disease, one approach is an induction treatment model, where a therapy with strong efficacy but strong safety concerns would be given first, followed by a maintenance therapy. An example of such a model might include initial treatment with alemtuzumab, followed by IFN-3, GA, or BG-12. In some embodiments, the one or more disclosed binding agent is used to prevent the need to switch therapies for maintenance. In some embodiments, the one or more disclosed binding agent is used to as maintenance therapy to one or more DMTs, including second line therapies. In some embodiments, the one or more disclosed binding agent is used to as first therapy in an induction, followed by another DMT as a maintenance therapy—such as, for example, a first line therapy.

In some embodiments, the one or more disclosed binding agent may be administered for an initial treatment period of about 3 months to stabilize disease and then the patient may be transitioned to a maintenance therapy of a first line agent.

In various embodiments, the one or more disclosed binding agent is used to reduce one or more side effects of a DMT, including without limitation any agent disclosed herein. For example, the one or more disclosed binding agent may be used in a regimen that allows dose sparing for one or more DMTs and therefore results in fewer side effects. For example, in some embodiments, the one or more disclosed binding agent may reduce one or more side effects of AUBAGIO or related agents, which may include hair thinning, diarrhea, flu, nausea, abnormal liver tests and unusual numbness or tingling in the hands or feet (paresthesias), levels of white blood cells, which can increase the risk of infections; increase in blood pressure; and severe liver damage. In some embodiments, the one or more disclosed binding agent may reduce one or more side effects of AVONEX or related agents which include flu-like symptoms following injection, depression, mild anemia, liver abnormalities, allergic reactions, and heart problems. In some embodiments, the one or more disclosed binding agent may reduce one or more side effects of BETASERON or related agents which include flu-like symptoms following injection, injection site reactions, allergic reactions, depression, liver abnormalities, and low white blood cell counts. In some embodiments, the one or more disclosed binding agent may reduce one or more side effects of COPAXONE or related agents which include injection site reactions, vasodilation (dilation of blood vessels); chest pain; a reaction immediately after injection, which includes anxiety, chest pain, palpitations, shortness of breath, and flushing. In some embodiments, the one or more disclosed binding agent may reduce one or more side effects of EXTAVIA or related agents which include flu-like symptoms following injection, injection site reactions, allergic reactions, depression, liver abnormalities, and low white blood cell counts. In some embodiments, the one or more disclosed binding agent may reduce one or more side effects of GILENYA or related agents which include headache, flu, diarrhea, back pain, liver enzyme elevations, cough, slowed heart rate following first dose, infections, and swelling in the eye. In some embodiments, the one or more disclosed binding agent may reduce one or more side effects of LEMTRADA or related agents which include rash, headache, fever, nasal congestion, nausea, urinary tract infection, fatigue, insomnia, upper respiratory tract infection, hives, itching, thyroid gland disorders, fungal Infection, pain in joints, extremities and back, diarrhea, vomiting, flushing, and infusion reactions (including nausea, hives, itching, insomnia, chills, flushing, fatigue, shortness of breath, changes in the sense of taste, indigestion, dizziness, pain). In some embodiments, the one or more disclosed binding agent may reduce one or more side effects of NOVANTRONE or related agents which include blue-green urine 24 hours after administration; infections, bone marrow suppression (fatigue, bruising, low blood cell counts), nausea, hair thinning, bladder infections, mouth sores, and serious liver and heart damage. In some embodiments, the one or more disclosed binding agent may reduce one or more side effects of PLEGRIDY or related agents which include flu-like symptoms following injection, injection site reactions, depression, mild anemia, liver abnormalities, allergic reactions, and heart problems. In some embodiments, the one or more disclosed binding agent may reduce one or more side effects of REBIF or related agents which include flu-like symptoms following injection, injection site reactions, liver abnormalities, depression, allergic reactions, and low red or white blood cell counts. In some embodiments, one or more disclosed binding agent may reduce one or more side effects of TECFIDERA or related agents which include flushing (sensation of heat or itching and a blush on the skin), gastrointestinal issues (nausea, diarrhea, abdominal pain), rash, protein in the urine, elevated liver enzymes; and reduction in blood lymphocyte (white blood cell) counts. In some embodiments, the one or more disclosed binding agent may reduce one or more side effects of TYSABRI or related agents which include headache, fatigue, urinary tract infections, depression, respiratory tract infections, joint pain, upset stomach, abdominal discomfort, diarrhea, vaginitis, pain in the arms or legs, rash, allergic or hypersensitivity reactions within two hours of infusion (dizziness, fever, rash, itching, nausea, flushing, low blood pressure, difficulty breathing, chest pain).

In some embodiments, the present invention relates to combination therapy with one or more chimeric agents described in WO 2013/10779, WO 2015/007536, WO 2015/007520, WO 2015/007542, and WO 2015/007903, the entire contents of which are hereby incorporated by reference in their entireties.

In some embodiments, inclusive of, without limitation, infectious disease applications, the present invention pertains to anti-infectives as additional therapeutic agents. In some embodiments, the anti-infective is an antiviral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmmune applications, the additional therapeutic agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin). Additional anti-inflammatory agents are described, for example, in U.S. Pat. No. 4,537,776, the entire contents of which is incorporated by reference herein.

In some embodiments, the Clec9A binding agent described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the Clec9A binding agent described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The Clec9A binding agent described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, *Pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the Clec9A binding agent, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

Methods of Treatment

Methods and compositions described herein have application to treating various diseases and disorders, including, but not limited to cancer, infections, immune disorders, and inflammatory diseases or conditions.

Further, any of the present agents may be for use in the treating, or the manufacture of a medicament for treating, various diseases and disorders, including, but not limited to cancer, infections, immune disorders, inflammatory diseases or conditions, and autoimmune diseases.

In some embodiments, the present invention relates to the treatment of, or a patient having cancer. As used herein, cancer refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); acute myeloid leukemia (AML); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In various embodiments, the present invention provides Clec9A binding agents which are part of a chimera that further comprises modified signaling agents for the treatment of cancer. In some embodiments, the Clec9A binding agents of the invention significantly reduce and/or eliminate tumors. In some embodiments, the present Clec9A binding agents significant reduce and/or eliminate tumors when administered to a subject in combination with other anti-cancer agents such as chemotherapeutic agents, checkpoint inhibitors, and immunosuppressive agents. In various embodiments, the combination of Clec9A binding agents and other anti-cancer agents synergistically reduced tumor size and/or eliminated tumor cells.

In various embodiments, the present invention relates to cancer combination therapies with a Clec9A binding agent that is part of a chimera comprising one or more targeting moieties and one or more modified signaling agents. Accordingly, the present invention provides for chimeric or fusion proteins that include, for example, a targeting moiety against Clec9A and one or more signaling agents and uses thereof in combination with anti-cancer agents.

For instance, in various embodiments, the present invention pertains to combination therapies for cancer involving chimeras of a Clec9A binding agent described herein and a modified signaling agent, including, without limitation a mutated human interferon, such as IFN alpha, including human interferon alpha 2.

In other embodiments, the present Clec9A binding agent is part of a chimera that comprises multiple targeting moieties and therefore be present in bispecific or trispecific formats. For instance, in various embodiments, the present invention pertains to combination therapies for cancer involving chimeras of a Clec9A binding agent and a checkpoint inhibitor binding agent (e.g. anti-PD-L1, anti-PD-1, anti-PD-L2, or anti-CTLA) described herein and a modified signaling agent, including, without limitation a mutated human interferon, such as IFN alpha, including human interferon alpha 2.

In various embodiments, the signaling agent is modified to have reduced affinity or activity for one or more of its receptors, which allows for attenuation of activity (inclusive of agonism or antagonism) and/or prevents non-specific signaling or undesirable sequestration of the chimeric protein. In some embodiments, the reduced affinity or activity at the receptor is restorable by attachment with one or more of the targeting moieties described herein.

In some embodiments, the present invention relates to the treatment of, or a patient having a microbial infection and/or chronic infection. Illustrative infections include, but are not limited to, HIV/AIDS, tuberculosis, osteomyelitis, hepatitis B, hepatitis C, Epstein-Barr virus or parvovirus, T cell leukemia virus, bacterial overgrowth syndrome, fungal or parasitic infections.

In various embodiments, the present compositions are used to treat or prevent one or more inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses.

In various embodiments, the present invention has application to treating autoimmune and/or neurodegenerative diseases.

In various embodiments, the present compositions are used to treat or prevent one or more conditions characterized by undesirable CTL activity, and/or a conditions characterized by high levels of cell death. For instance, in various embodiments, the present compositions are used to treat or prevent one or more conditions associated with uncontrolled or overactive immune response.

In various embodiments, the present compositions are used to treat or prevent one or more autoimmune and/or neurodegenerative diseases or conditions, such as MS, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, myasthenia gravis, Reiter's syndrome, Grave's disease, and other autoimmune diseases.

In various embodiments, the present invention is used to treat or prevent various autoimmune and/or neurodegenerative diseases. In some embodiments, the autoimmune and/or neurodegenerative diseases selected from MS (including without limitation the subtypes described herein), Alzheimer's disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease).

In various embodiments, the present invention is used to treat or prevent MS. In various embodiments, the Clec9a binding agents as described herein are used to eliminate and reduce multiple MS symptoms. Illustrative symptoms associated with multiple sclerosis, which can be prevented or treated with the compositions and methods described herein, include: optic neuritis, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, l'hermitte's sign, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, frigidity, constipation, fecal urgency, fecal incontinence, depression, cognitive dysfunction, dementia, mood swings, emotional lability, euphoria, bipolar syndrome, anxiety, aphasia, dysphasia, fatigue, Uhthoff's symptom, gastroesophageal reflux, and sleeping disorders. Mitigation or amelioration or one more of these symptoms in a subject can be achieved by the one or more agent as described herein.

In various embodiments, the Clec9A binding agents as described herein is used to treat or prevent clinically isolated syndrome (CIS). A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with CIS and MRI lesions go on to develop MS, while approximately 20 percent have a self-limited process. Patients who experience a single clinical attack consistent with MS may have at least one lesion consistent with multiple sclerosis prior to the development of clinically definite multiple sclerosis. In various embodiments, the presently described Clec9a binding agents is used to treat CIS so it does not develop into MS, including, for example RRMS.

In various embodiments, the Clec9A binding agents as described herein are used to treat or prevent radiologically isolated syndrome (RIS). In RIS, incidental imaging findings suggest inflammatory demyelination in the absence of clinical signs or symptoms. In various embodiments, the Clec9A binding agent is used to treat RIS so it does not develop into MS, including, for example RRMS.

In various embodiments, the Clec9A binding agents as described herein are used to treat one or more of benign multiple sclerosis; relapsing-remitting multiple sclerosis (RRMS); secondary progressive multiple sclerosis (SPMS); progressive relapsing multiple sclerosis (PRMS); and primary progressive multiple sclerosis (PPMS).

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis. In various embodiments, the Clec9a binding agent is used to treat benign multiple sclerosis so it does not develop into MS.

Patients suffering from RRMS experience sporadic exacerbations or relapses, as well as periods of remission. Lesions and evidence of axonal loss may or may not be visible on MRI for patients with RRMS. In various embodiments, the Clec9a binding agents as described herein are used to treat RRMS. In some embodiments, RRMS includes patients with RRMS; patients with SPMS and superimposed relapses; and patients with CIS who show lesion dissemination on subsequent MRI scans according to McDonald's criteria. A clinical relapse, which may also be used herein as "relapse," "confirmed relapse," or "clinically defined relapse," is the appearance of one or more new neurological abnormalities or the reappearance of one or more previously observed neurological abnormalities. This change in clinical state must last at least 48 hours and be immediately preceded by a relatively stable or improving neurological state of at least 30 days. In some embodiments, an event is counted as a relapse when the subject's symptoms are accompanied by observed objective neurological changes, consistent with an increase of at least 1.00 in the Expanded Disability Status Scale (EDSS) score or one grade in the score of two or more of the seven FS or two grades in the score of one of FS as compared to the previous evaluation.

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS. In various embodiments, the Clec9a binding agents as described herein is used to treat RRMS so it does not develop into SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS. In various embodiments, the Clec9A binding agent as described herein is used to treat RRMS and/or SPMS so it does not develop into PPMS.

In some embodiments, the Clec9A binding agents as described herein are used in a method of treatment of relapsing forms of MS. In some embodiments, the Clec9A binding agent is used in a method of treatment of relapsing forms of MS to slow the accumulation of physical disability and/or reduce the frequency of clinical exacerbations, and, optionally, for patients who have experienced a first clinical episode and have MRI features consistent with MS. In some embodiments, the Clec9a binding agents as described herein are used in a method of treatment of worsening relapsing-remitting MS, progressive-relapsing MS or secondary-progressive MS to reduce neurologic disability and/or the frequency of clinical exacerbations. In some embodiments, the Clec9A binding agents reduce the frequency and/or severity of relapses.

In some embodiments, the Clec9A binding agents are used in a method of treatment of relapsing forms of MS in patients who have had an inadequate response to (or are refractory to) one, or two, or three, or four, or five, or six, or seven, or eight, or nine, or ten or more disease modifying therapies (DMTs).

In various embodiments, the subject's symptoms may be assessed quantitatively, such as by EDSS, or decrease in the frequency of relapses, or increase in the time to sustained progression, or improvement in the magnetic resonance imaging (MRI) behavior in frequent, serial MRI studies and compare the patient's status measurement before and after treatment. In a successful treatment, the patient status will have improved (e.g., the EDSS measurement number or frequency of relapses will have decreased, or the time to sustained progression will have increased, or the MRI scans will show less pathology).

In some embodiments, the patient can be evaluated, e.g., before, during or after receiving the Clec9a binding agents e.g., for indicia of responsiveness. Various clinical or other indicia of effectiveness of treatment, e.g., EDSS score; MRI scan; relapse number, rate, or severity; multiple sclerosis functional composite (MSFC); multiple sclerosis quality of life inventory (MSQLI); Paced Serial Addition Test (PASAT); symbol digit modalities test (SDMT); 25-foot walk test; 9-hole peg test; low contrast visual acuity; Modified Fatigue Impact Scale; expanded disability status score (EDSS); multiple sclerosis functional composite (MSFC); Beck Depression Inventory; and 7/24 Spatial Recall Test can be used. In various embodiments, the Clec9A binding agents cause an improvement in one or more of these measures. Further, the patient can be monitored at various times during a regimen. In some embodiments, the Clec9a binding agents cause a disease improvement as assessed by MacDonald dissemination in space and time. For example, for dissemination in space, lesion imaging, such as, by way of illustration, Barkhof-Tintore MR imaging criteria, may be used, including at least one gadolinium-enhancing lesion or 9 T2 hyperintense lesions; at least one infratentorial lesion; at least one juxtacortical lesion; at least about three periventricular lesions; and a spinal cord lesion. For dissemination in time, MRI can also be used; for example, if an MRI scan of the brain performed at months after an initial clinical event demonstrates a new gadolinium-enhancing lesion, this may indicate a new CNS inflammatory event, because the duration of gadolinium enhancement in MS is usually less than 6 weeks. If there are no gadolinium-enhancing lesions but a new T2 lesion (presuming an MRI at the time of the initial event), a repeat MR imaging scan after another 3 months may be needed with demonstration of a new T2 lesion or gadolinium-enhancing lesion.

In some embodiments, disease effects are assessed using any of the measures described in Lavery, et al. Multiple Sclerosis International, Vol 2014 (2014), Article ID 262350, the entire contents of which are hereby incorporated by reference.

In some embodiments, the Clec9A binding agent results in one or more of: (a) prevention of worsening in disability defined as deterioration by 1.0 point on EDSS, (b) increase in time to relapse, (c) reduction or stabilization of number and/or volume of gadolinium enhancing lesions, (d) decreased annualized relapse rate, (e) increased relapse duration and severity by NRS score, (f) decrease in disease activity as measured by MRI (annual rate of new or enlarging lesions), (g) lower average number of relapses at 1 year, or 2 years, (h) sustained disease progression as measured by the EDSS at 3 months, (i) prevention of conversion to CDMS, (j) no or few new or enhancing T2 lesions, (k) minimal change in hyperintense T2 lesion volume, (I) increased time to McDonald defined MS, (m) prevention of progression of disability as measured by sustained worsening of EDSS at 12 weeks, (n) reduction in time to relapse at 96 weeks, and (o) reduction or stabilization of brain atrophy (e.g. percentage change from baseline).

In one embodiment, the Clec9A binding agents are administered and is effective to result in a decreased rate of relapse (e.g., at least 10%, 20%, 30%, 40%, 50%, 60%, 70%, 80% or greater reduction in rate of relapse) compared to the rate of relapse before administration (e.g., compared to the rate of relapse following administration for 12 months or for less than 12 months, e.g., about 10, or about 8, or about 4, or about 2 or less months) of treatment, or before commencement of treatment, when measured between 3-24 months (e.g., between 6-18 months, e.g., 12 months) after a previous relapse.

In one embodiment, the Clec9A binding agents are administered and are effective to result in a prevention of an increase in EDSS score from a pre-treatment state. The Kurtzke Expanded Disability Status Scale (EDSS) is a method of quantifying disability in multiple sclerosis. The EDSS replaced the previous Disability Status Scales which used to bunch people with MS in the lower brackets. The EDSS quantifies disability in eight Functional Systems (FS) and allows neurologists to assign a Functional System Score (FSS) in each of these. The Functional Systems are: pyramidal, cerebellar, brainstem, sensory, bowel and bladder, visual and cerebral.

In one embodiment, the Clec9A binding agents are administered and is effective to result in a decreased EDSS score (e.g., a decrease of 1, 1.5, 2, 2.5, 3 points or more, e.g., over at least three months, six months, one year, or longer) compared to the EDSS score following administration of the Clec9a binding agents (e.g. for 12 months or for less than 12 months, e.g., less than 10, 8, 4 or less months, or before the commencement of treatment).

In one embodiment, the Clec9A binding agents are administered and is effective to result in a decreased number of new lesions overall or of any one type (e.g., at least 10%, 20%, 30%, 40% decrease), compared to the number of new lesions following administration of the Clec9A binding agents for 12 months or for less than 12 months, e.g., less than 10, 8, 4 or less months, or before commencement of treatment;

In one embodiment, the Clec9A binding agents are administered and is effective to result in a decreased number of lesions overall or of any one type (e.g., at least 10%, 20%, 30%, 40% decrease), compared to the number of lesions following administration of the Clec9a binding agents for 12 months or for less than 12 months, e.g., less than 10, 8, 4 or less months, or before commencement of treatment;

In one embodiment, the Clec9A binding agents are administered and is effective to result in a reduced rate of appearance of new lesions overall or of any one type (e.g., at least 10%, 20%, 30%, 40% reduced rate), compared to the rate of appearance of new lesions following administration for 12 months or for less than 12 months, e.g., less than 10, 8, 4 or less months, or before commencement of treatment;

In one embodiment, the Clec9A binding agents are administered and is effective to result in a reduced increase in lesion area overall or of any one type (e.g., at least 10%, 20%, 30%, 40% decreased increase), compared to an increase in lesion area following administration for 12 months or less than 12 months, e.g., less than 10, 8, 4 or less months, or before commencement of treatment.

In one embodiment, the Clec9A binding agents are administered and is effective to result in a reduced incidence or symptom of optic neuritis (e.g., improved vision), compared to the incidence or symptom of optic neuritis following administration for 12 months or for less than 12 months, e.g., less than 10, 8, 4 or less months, or before commencement of treatment.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old. In various embodiments, the human has an age of more than 30 years old.

Immune Modulation

In various embodiments, the present compositions are capable of, or find use in methods of, immune modulation. For instance, in various embodiments, the present methods of treatment may involve the immune modulation described herein. In some embodiments, the immune modulation involves IFN signaling, including modified IFN signaling, in the context of a dendritic cell (DC).

In various embodiments, a multi-specific Clec9a binding agent is provided. In some embodiments, such multi-specific Clec9a binding agent of the invention recognizes and binds to Clec9A and one or more antigens found on one or more immune cells, which can include, without limitation, megakaryocytes, thrombocytes, erythrocytes, mast cells, basophils, neutrophils, eosinophils, monocytes, macrophages, natural killer cells, T lymphocytes (e.g., cytotoxic T lymphocytes, T helper cells, natural killer T cells), B lymphocytes, plasma cells, dendritic cells, or subsets thereof. In some embodiments, the Clec9A binding agent specifically binds to an antigen of interest and effectively directly or indirectly recruits one of more immune cells.

In some embodiments, the Clec9a binding agent specifically binds to an antigen of interest and effectively directly or indirectly recruits one of more immune cells to cause an immunosuppressive effect, e.g. the Clec9a binding agent directly or indirectly recruits an immunosuppressive immune cell. In some embodiments, the immunosuppressive immune cell is a regulatory T cell (or "Tregs" which, as used herein, refers to a subpopulation of T cells which modulate the immune system, abrogate autoimmune disease, maintain tolerance to self-antigens and thwart anti-tumor immune responses). Other immunosuppressive immune cells include myeloid suppressor cells (or "MSC," which, as used herein, refers to a heterogeneous population of cells, defined by their myeloid origin, immature state, and ability to potently suppress T cell responses); tumor associated neutrophils (or "TANs" which, as used herein, refers to a subset of neutrophils that are capable of suppressing immune responses); tumor associated macrophages (or "TAMs" which, as used herein, refers to a subset of macrophages that may reduce an immune response), M2 macrophages, and/or tumor-inducing mast cells (which as used herein, refers to a subset of bone marrow-derived, long-lived, heterogeneous cellular population). Also, immunosuppressive immune cells include Th2 cells and Th17 cells. Additionally, immunosuppressive immune cells include immune cells, e.g., CD4+ and/or CD8+ T cells, expressing one or more checkpoint inhibitory receptors (e.g. receptors, including CTLA-4, B7-H3, B7-H4, TIM-3, expressed on immune cells that prevent or inhibit uncontrolled immune responses). See Stagg, J. et. al., Immunotherapeutic approach in triple-negative breast cancer. Ther Adv Med Oncol. (2013) 5(3):169-181).

In some embodiments, the Clec9a binding agent stimulates regulatory T cell (Treg) proliferation. Treg cells are characterized by the expression of the Foxp3 (Forkhead box p3) transcription factor. Most Treg cells are CD4+ and CD25+, and can be regarded as a subset of helper T cells, although a small population may be CD8+. Thus the immune response which is to be modulated by a method of the invention may comprise inducing proliferation of Treg cells, optionally in response to an antigen. Thus the method may comprise administering to the subject a composition comprising the antigen, wherein the antigen is associated with a binding agent having affinity for Clec9A. The antigen may be administered with an adjuvant which promotes proliferation of Treg cells.

Insofar as this method involves stimulating proliferation and differentiation of Treg cells in response to a specific antigen, it can be considered to be a method of stimulating an immune response. However, given that Treg cells may be capable of modulating the response of other cells of the immune system against an antigen in other ways, e.g. inhibiting or suppressing their activity, the effect on the immune system as a whole may be to modulate (e.g. suppress or inhibit) the response against that antigen. Thus the methods of this aspect of the invention can equally be referred to as methods of modulating (e.g. inhibiting or suppressing) an immune response against an antigen.

In some embodiments, the methods therapeutically or prophylactically inhibit or suppress an undesirable immune response against a particular antigen, even in a subject with pre-existing immunity or an on-going immune response to that antigen. This may be particularly useful, for example, in the treatment of autoimmune disease.

Under certain conditions, it may also be possible to tolerize a subject against a particular antigen by targeting the antigen to an antigen presenting cell expressing Clec9A. The invention thus provides a method for inducing tolerance in a subject towards an antigen, comprising administering to the subject a composition comprising the antigen, wherein the antigen is associated with a binding agent having affinity for Clec9A and wherein the antigen is administered in the absence of an adjuvant. Tolerance in this context typically involves depletion of immune cells which would otherwise be capable of responding to that antigen, or inducing a lasting reduction in responsiveness to an antigen in such immune cells.

It may be particularly desirable to raise a Treg response against an antigen to which the subject exhibits, or is at risk of developing, an undesirable immune response. For example, it may be a self-antigen against which an immune response occurs in an autoimmune disease. Examples of autoimmune diseases in which specific antigens have been identified as potentially pathogenically significant include multiple sclerosis (myelin basic protein), insulin-dependent diabetes mellitus (glutamic acid decarboxylase), insulin-resistant diabetes mellitus (insulin receptor), celiac disease (gliadin), bullous pemphigoid (collagen type XVII), auto-immune haemolytic anaemia (Rh protein), auto-immune thrombocytopenia (GpIIb/IIIa), myaesthenia gravis (acetylcholine receptor), Graves' disease (thyroid-stimulating hormone receptor), glomerulonephritis, such as Goodpasture's disease (alpha3(IV)NC1 collagen), and pernicious anaemia (intrinsic factor). Alternatively the target antigen may be an exogenous antigen which stimulates a response which also causes damage to host tissues. For example, acute rheumatic fever is caused by an antibody response to a Streptococcal antigen which cross-reacts with a cardiac muscle cell antigen. Thus these antigens, or particular fragments or epitopes thereof, may be suitable antigens for use in the present invention.

In some embodiments, the present agents, or methods using these agents, disrupt Clec9A signaling (e.g. via neutralization of Clec9A), e.g. by reducing or inhibiting Clec9A binding to its ligand. Some autoimmune diseases are characterized by unusually high levels of cell death and it is believed that immune responses against self antigens associated with these cells may contribute to the pathogenesis of these conditions. Clec9A antagonists may therefore be used to prevent Clec9A from binding to the ligand exposed in dead and dying cells (e.g. those undergoing immunogenic cell death) and may thus inhibit or prevent stimulation of immune responses against these antigens.

In various embodiments, the present agents, or methods using these agents, reduce or suppress autoreactive T cells. In some embodiments, the multi-specific Clec9a binding agent, optionally through an interferon signaling in the context of a chimera, causes this immunosuppression. In some embodiments, the multi-specific Clec9a binding agent stimulates PD-L1 or PD-L2 signaling and/or expression which may suppress autoreactive T cells. In some embodiments, the Clec9A binding agent, optionally through an interferon signaling in the context of a chimera, causes this immunosuppression. In some embodiments, the Clec9A binding agent stimulates PD-L1 or PD-L2 signaling and/or expression which may suppress autoreactive T cells.

In various embodiments, the present methods comprise modulating the ratio of regulatory T cells to effector T cells in favor of immunosuppression, for instance, to treat autoimmune diseases. For instance, the present methods, in some embodiments, reduce and/or suppress one or more of cytotoxic T cells; effector memory T cells; central memory T cells; $CD8^+$ stem cell memory effector cells; TH1 effector T-cells; TH2 effector T cells; TH9 effector T cells; TH17 effector T cells. For instance, the present methods, in some embodiments, increase and/or stimulate one or more of $CD4^+CD25^+FOXP3^+$ regulatory T cells, $CD4^+CD25^+$ regulatory T cells, $CD4^+CD25^-$ regulatory T cells, $CD4^+$ CD25high regulatory T cells, TIM-$3^+$PD-$1^+$ regulatory T cells, lymphocyte activation gene-3 (LAG-3)' regulatory T cells, CTLA-4/$CD152^+$ regulatory T cells, neuropilin-1 (Nrp-1)±regulatory T cells, $CCR4^+CCR8^+$ regulatory T cells, CD62L (L-selectin)$^+$ regulatory T cells, CD45RBlow regulatory T cells, CD127low regulatory T cells, LRRC32/GARP$^+$ regulatory T cells, $CD39^+$ regulatory T cells, $GITR^+$ regulatory T cells, $LAP^+$ regulatory T cells, $1B11^+$ regulatory T cells, $BTLA^+$ regulatory T cells, type 1 regulatory T cells (Tr1 cells), T helper type 3 (Th3) cells, regulatory cell of natural killer T cell phenotype (NKTregs), $CD8^+$ regulatory T cells, $CD8^+CD28^-$ regulatory T cells and/or regulatory T-cells secreting IL-10, IL-35, TGF-$\beta$, TNF-$\alpha$, Galectin-1, IFN-$\gamma$ and/or MCP1.

In some embodiments, the present methods favor immune inhibitory signals over immune stimulatory signals. In some embodiments, the present methods allow for reversing or suppressing immune activating or co-stimulatory signals. In some embodiments, the present methods allow for providing immune inhibitory signals. For instance, in some embodiments, the present agents and methods reduce the effects of an immune stimulatory signal, which, without limitation, is one or more of 4-1BB, OX-40, HVEM, GITR, CD27, CD28, CD30, CD40, ICOS ligand; OX-40 ligand, LIGHT (CD258), GITR ligand, CD70, B7-1, B7-2, CD30 ligand, CD40 ligand, ICOS, ICOS ligand, CD137 ligand and TL1A. Further, in some embodiments, the present agents and methods increase the effects of an immune inhibitory signal, which, without limitation, is one or more of CTLA-4, PD-L1, PD-L2, PD-1, BTLA, HVEM, TIM3, GAL9, LAG3, VISTA, KIR, 2B4, CD160 (also referred to as BY55), CGEN-15049, CHK 1 and CHK2 kinases, A2aR, CEACAM (e.g., CEACAM-1, CEACAM-3 and/or CEACAM-5), and various B-7 family ligands (including, but are not limited to, B7-1, B7-2, B7-DC, B7-H1, B7-H2, B7-H3, B7-H4, B7-H5, B7-H6 and B7-H7. Kits The present invention also provides kits for the administration of any Clec9A binding agent described herein (e.g. with or without additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to effect a desired therapeutic outcome, such as to treat cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the 1050 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EXAMPLES

The term "AcTaferon" is occasionally used herein to reference an interferon-based chimera.

In the following examples, unless noted, mutations to IFN are relative to human IFN-$\alpha$2: SEQ ID NO: 86.

The Q124R mutant is representative of an attenuated human IFN alpha 2 mutant that can be assayed in vivo in a murine model. Specifically, Q124R is a human IFN mutation that is suitable for use in the mouse (i.e. it is a human mutant IFN that functions in mouse). See Nat. Comm. 2014; 5:3016. doi: 10.1038/ncomms4016, the entire contents of which are hereby incorporated by reference.

The R33A/E120R mutant is representative of human IFN alpha 2 mutant that is non-functional (and is used as a control)

Anti-human PD-L1 VHH used in these Examples is SEQ ID NO: 256.

Anti-BcII10 VHH is used in these Examples as a control (targeting an irrelevant antigen, i.e. "untargeted").

Example 1. Construction and Evaluation of VHHs Specific for Mouse Clec9A

Isolation of Antigen-Specific VHHs

A VHH library was subject to 3 consecutive rounds of panning (in solution), performed on stably transfected CHO-K1 cells expressing mouse Clec9A. The enrichment for antigen-specific phages was assessed after each round of panning by comparing the number of phagemid particles eluted from transfected cells after panning (output) with the number of phagemid particles used for panning (input). The phage output increased about 50- and 30-fold in 2nd and $3^{rd}$ rounds, respectively, as compared to the output from $1^{st}$ round. The input phage was always about $10^{11}$ and the output from first round was about $10^9$ phage particles suggesting that there was already enrichment for target-specific phages in the first round. A total of 285 colonies (95 and 190 from $1^{st}$& $2^{nd}$ rounds, respectively) were randomly selected and their crude periplasmic extracts (including soluble VHHs) were analyzed by cell ELISA for specific binding to transfected CHO-K1, as compared to parental CHO-K1 cells. None of these colonies scored positive in cell ELISA suggesting that either the ELISA is not sensitive enough in this case or the antigen is affected by cell fixation in ELISA. We therefore switched to FACS for the identification of antigen specific VHHs. Here, we sequenced 190 randomly selected colonies from 1st and 2nd panning rounds (95 from each round) and then grouped VHHs based on CDR3 sequences. These experiments resulted in the identification of 28 different VHHs belonging to 7 different groups. Table 1 below provides a description of 28 clones representing the 28 different anti-mouse Clec9A VHH genes. *E. coli* TG1 harboring recombinant phagemid pHEN4 containing anti-mouse Clec9A VHH sequences was generated and stored at −80° C. The vector pHEN4 codes for ampicillin resistance.

TABLE 1

| *E. coli* strain + Vector | VHH (Nb) | NSF Reference No. (Glycerol stock) |
|---|---|---|
| TG1, pHEN4 | R1MCL 3 | 1727 |
| TG1, pHEN4 | R1MCL 7 | 1728 |
| TG1, pHEN4 | R1MCL 9 | 1729 |
| TG1, pHEN4 | R1MCL 12 | 1730 |
| TG1, pHEN4 | R1MCL 13 | 1731 |
| TG1, pHEN4 | R1MCL 33 | 1732 |
| TG1, pHEN4 | R1MCL 41 | 1733 |
| TG1, pHEN4 | R1MCL 71 | 1734 |
| TG1, pHEN4 | R1MCL 85 | 1735 |
| TG1, pHEN4 | R1MCL 95 | 1736 |
| TG1, pHEN4 | R2MCL 5 | 1737 |
| TG1, pHEN4 | R2MCL 15 | 1738 |
| TG1, pHEN4 | R2MCL 17 | 1739 |
| TG1, pHEN4 | R2MCL 18 | 1740 |
| TG1, pHEN4 | R2MCL 20 | 1741 |
| TG1, pHEN4 | R2MCL 28 | 1742 |
| TG1, pHEN4 | R2MCL 36 | 1743 |
| TG1, pHEN4 | R2MCL 41 | 1744 |
| TG1, pHEN4 | R2MCL 43 | 1745 |
| TG1, pHEN4 | R2MCL 47 | 1746 |
| TG1, pHEN4 | R2MCL 49 | 1747 |
| TG1, pHEN4 | R2MCL 57 | 1748 |
| TG1, pHEN4 | R2MCL 65 | 1749 |
| TG1, pHEN4 | R2MCL 66 | 1750 |
| TG1, pHEN4 | R2MCL 74 | 1751 |
| TG1, pHEN4 | R2MCL 85 | 1752 |
| TG1, pHEN4 | R2MCL 86 | 1753 |
| TG1, pHEN4 | R2MCL 93 | 1754 |

Using crude periplasmic extracts including VHHs, representative(s) of each group was (were) analyzed by FACS for specificity to mouse Clec9A using CHO-K1 cells transfected with mouse Clec9A. The parental non-transfected CHO-K1 cells served as negative control cell. The representative VHHs tested for their specificity towards mouse Clec9A were as follows: R1MCL3, R1MCL7, R1MCL9, R1MCL12, R1MCL13, R1MCL33, R1MCL71, R1MCL95, R2MCL15, R2MCL18, R2MCL20, R2MCL28, R2MCL36, R2MCL41, R2MCL43, R2MCL47, R2MCL57, R2MCL74, R2MCL86, R2MCL93. All representatives tested were positive for CHO-K1 cells transfected with mouse Clec9A showing that all 28 VHHs bound mouse Clec9A specifically. Next, a representative of each group was analyzed by FACS for specificity to mouse and human Clec9A using CHO-K1 cells transfected with either mouse Clec9A or human Clec9A. Here also, the parental non-transfected CHO-K1 cells served as negative control cell. The representative VH Hs tested for cross-species reactivity were as follows: R1MCL3, R1MCL7, R1MCL9, R1MCL12, R1MCL33, R2MCL18, R2MCL43. None of these VHHs showed any specific binding to human Clec9A suggesting that these VHHs recognize epitopes unique to mouse Clec9A.

Expression and Purification of VHHs

The VHH genes were recloned from pHEN4 to pHEN6c vectors. Specifically, the VHH gene was amplified by PCR using recombinant pHEN4 harboring the VHH gene as template and primers A6E and 38. Primers A6E and 38 were framework 1 and framework 4 primers, respectively. The primer sequences were as follows:

Primer A6E
(SEQ ID NO: 291)
(5' GAT GTG CAG CTG CAG GAG TCT GGR* GGA GG 3').

Primer 38
(SEQ ID NO: 292)
(5' GGA CTA GTG CGG CCG CTG GAG ACG GTG ACC TGG GT 3').

Universal reverse primer
(SEQ ID NO: 293)
(5' TCA CAC AGG AAA CAG CTA TGA C 3').

Universal forward primer
(SEQ ID NO: 294)
(5' CGC CAG GGT TTT CCC AGT CAC GAC 3').
*R stands for A or G.

The amplification protocol included about 30 cycles of PCR, each cycle included 30 seconds at 94° C., 30 seconds at 55° C. and 45 seconds at 72° C., followed by 10 minutes extension at 72° C. at the end of PCR. A fragment of about 400 bp was amplified. All resulting VHHs produced using the protocol described herein start with the following sequence: QVQLQESGGG (SEQ ID NO:295).

The PCR product was purified (e.g. by Qiaquick PCR purification kit from Qiagen) and digested overnight with PstI. The purified PCR product was digested with BstEII overnight (or with Eco91I from Fermentas). The temperature used for digestion varied. For example, digestion with BstEII was done at 50° C. or 60° C. depending on the supplier of the enzyme.

For ligation, the PCR product was purified. The pHEN6c vector was digested with PstI for 3 hours, purified as described above, and then digested with BstEII for 2 to 3 hours. Alternatively, digestion was carried out using Eco91I from Fermentas. The digested vector was ran on 1% agarose gel, with the vector band excised out of the gel and purified (e.g. by Qiaquick gel extraction kit from Qiagen). The PCR fragment was subsequently ligated to the vector.

Electrocompetent WK6 cells were transformed with the ligation reaction, and transformants were selected using LB/agar/ampicillin (100 μg/ml)/glucose (1%) plates. Positive clones were screened by PCR using universal reverse and universal forward primers. A fragment of about 550 bp was amplified, if the insert was present. To verify the identity of the clones, at least 2 clones per each VHH were sequenced using universal reverse primers. Antigen binding capacity was retested by ELISA or any other appropriate assay.

Following the above protocol, the VHH gene cloned in pHEN6c vector was generated which contained PelB signal sequence at the N-terminus and $His_6$-tail at the C-terminus. The PelB leader sequence directed the VHH to the periplasmic space of the *E. coli*, and the His-tag was used for the purification and detection of VHH (e.g. in ELISA, Western Blot, etc.).

Expression and purification of the VHHs were carried out. Specifically, on day 1, 10-20 ml of LB+ampicillin (100 μg/ml)+glucose (1%) were innoculated with a freshly transformed WK6 colony. This pre-culture was incubated at 37° C. overnight with shaking at 200-250 rpm. On day 2, a TB medium was used for expressing the VHHs. The TB medium included, per liter: 2.3 g $KH_2PO_4$, 16.4 g $K_2HPO_4.3H_2O$, 12 g Tryptone (Duchefa Biochemie), 24 g Yeast (Duchefa Biochemie), and 4 ml 100% glycerol (Duchefa Biochemie).

A baffled shaker flask of 1 liter was filled with 330 ml TB and autoclaved. $KH_2PO_4$ and $K_2HPO_4.3H_2O$ were not autoclaved. Instead, $KH_2PO_4$ and $K_2HPO_4.3H_2O$ were prepared, filter sterilized, and then added to the rest of the medium that was already autoclaved. About 1 ml of the pre-culture was added to 330 ml of TB supplemented with 100 μg/ml Ampicillin, 2 mM $MgCl_2$ and 0.1% glucose and subsequently grew at 37° C. with shaking (200-250 rpm) until an $OD_{600}$ of 0.6-0.9 was reached. IPTG (final concentration of 1 mM) was added to induce VHH expression. The culture was incubated at 28° C. with shaking overnight (about 16-18 hours). The $OD_{600}$ after overnight induction was usually between 25 and 30. At least 1 liter of culture (3 bottles) per clone was prepared with an average yield of between 1 and 15 mg/I.

Extraction of the VHHs from the periplasm of *E. coli* was carried out on day 3. The solutions used included: TES: 0.2 M Tris pH 8.0, 0.5 mM EDTA, 0.5 M sucrose, and TES/4: TES diluted 4 times in water.

The overnight induced cultures were centrifuged for 8 minutes at 8000 rpm. The cell pellets from 1 liter culture were resuspended in 12 ml TES by pipetting up and down and shaken for 1 hour on ice. Per each 12 ml TES used, about 18 ml TES/4 were added and incubated on ice for an additional hour with shaking followed by centrifugation for 30 minutes at 8000 rpm at 4° C. The supernatant which contained proteins extracted from the periplasmic space was transferred to fresh falcon tubes.

The VHHs were subsequently purified by IMAC which utilized the following solution: HIS-select (SIGMA), PBS, and 50 mM NaAcetate pH 4.6.

His-select was equilibrated with PBS. Specifically, per periplasmic extract derived from 1 liter culture, 1 ml of Resin (about 2 ml His-select solution) was added to a 50 ml falcon tube. PBS was also added to final volume of 50 ml and mixed. Centrifugation was carried out at 2000 rpm for 2 minutes, and the supernatant was discarded. The resin was washed with PBS twice as described above. The periplasmic extract was added to the resin, incubated for 30 minutes to 1 hour at room temperature with gentle shaking. The samples were loaded on PD-10 columns with a filter at the bottom (GE healthcare, cat. No. 17-0435-01) and washed with 50 to 100 ml PBS (50-100 ml PBS per 1 ml resin used). Elution was carried out for 3 times, each time with 1 ml PBS/0.5 M imidazole per 1 ml resin used (for efficient elution, resuspend the beads and leave overnight at 4° C. with the bottom of the column closed). Dialysis was performed overnight at 4° C. against PBS (cutoff 3500 Daltons) to remove imidazole. For efficient dialysis, the dialysis buffer (PBS) was changed 2-3 times. Alternatively, instead of elution with imidazole, the bound VHHs could be eluted with 10 ml 50 mM Na-acetate pH 4.6. If 50 mM Na-acetate pH 4.6 was used to elute VHHs, the eluted VHHs was immediately neutralized with 1 M Tris pH 8.0, and no dialysis was required.

The amount of protein was estimated by $OD_{280}$ measurement of eluted sample. Extinction coefficient of each clone was determined by protParam tool under primary structure analysis at the Expasy proteomics server. Further purification of VHHs could be achieved by different methods. For example, the samples could be concentrated (Vivaspin 5000 MW cutoff, Vivascience) by centrifuging at 2000 rpm at 4° C. until an appropriate volume for loading on a Superdex 75 16/60 was obtained (max. 4 ml). The concentrated sample was loaded on a Superdex 75 16/60 column equilibrated with PBS. Peak fractions were pooled, and $OD_{280}$ measurements were performed for quantification. In general, VHHs eluted after 85-95 minutes when run at 1 ml/min. Aliquots of concentrated VHH samples were stored at −20° C. at a concentration of about 1 mg/ml.

Functional Analysis of VHHs

The VHHs were tested for binding to Clec9A. FIG. 1 shows binding of the various VHHs to CHO cells stably expressing Clec9A. In all experiments, the VHHs were labeled as follows:

| mClec9A VHHs MBU-I-number | single cells/single cells \| Geometric Mean (FL1-H) | group |
|---|---|---|
| 20140226 CHO mClec9A.control | 3.74 | |
| 20140226 CHO mClec9A.10487 | 6.44 | 1 |
| 20140226 CHO mClec9A.10488 | 5.97 | 3 |
| 20140226 CHO mClec9A.10489 | 7.36 | 2 |
| 20140226 CHO mClec9A.10490 | 6.01 | 7 |
| 20140226 CHO mClec9A.10491 | 5.8 | 3 |
| 20140226 CHO mClec9A.10492 | 6.09 | 4 |
| 20140226 CHO mClec9A.10493 | 5.45 | 1 |
| 20140226 CHO mClec9A.10494 | 6.26 | 4 |
| 20140226 CHO mClec9A.10495 | 8.49 | 6 |
| 20140226 CHO mClec9A.10496 | 6.04 | 4 |
| 20140226 CHO mClec9A.10497 | 12.7 | 1 |
| 20140226 CHO mClec9A.10498 | 6.07 | 1 |
| 20140226 CHO mClec9A.10499 | 7.74 | 1 |
| 20140226 CHO mClec9A.10501 | 7.31 | 6 |
| 20140226 CHO mClec9A.10502 | 6.03 | 3 |
| 20140226 CHO mClec9A.10503 | 7.14 | 6 |
| 20140226 CHO mClec9A.10504 | 8.36 | 1 |
| 20140226 CHO mClec9A.10505 | 6.46 | 5 |
| 20140226 CHO mClec9A.10507 | 5.32 | 1 |
| 20140226 CHO mClec9A.10508 | 8.99 | 2 |
| 20140226 CHO mClec9A.10509 | 6.08 | 1 |
| 20140226 CHO mClec9A.10510 | 5.9 | 3 |
| 20140226 CHO mClec9A.10511 | 10.5 | 1 |
| 20140226 CHO mClec9A.10512 | 5.61 | 3 |
| 20140226 CHO mClec9A.10513 | 6.01 | 3 |
| 20140226 CHO mClec9A.10514 | 7.59 | 6 |

Figure 2:
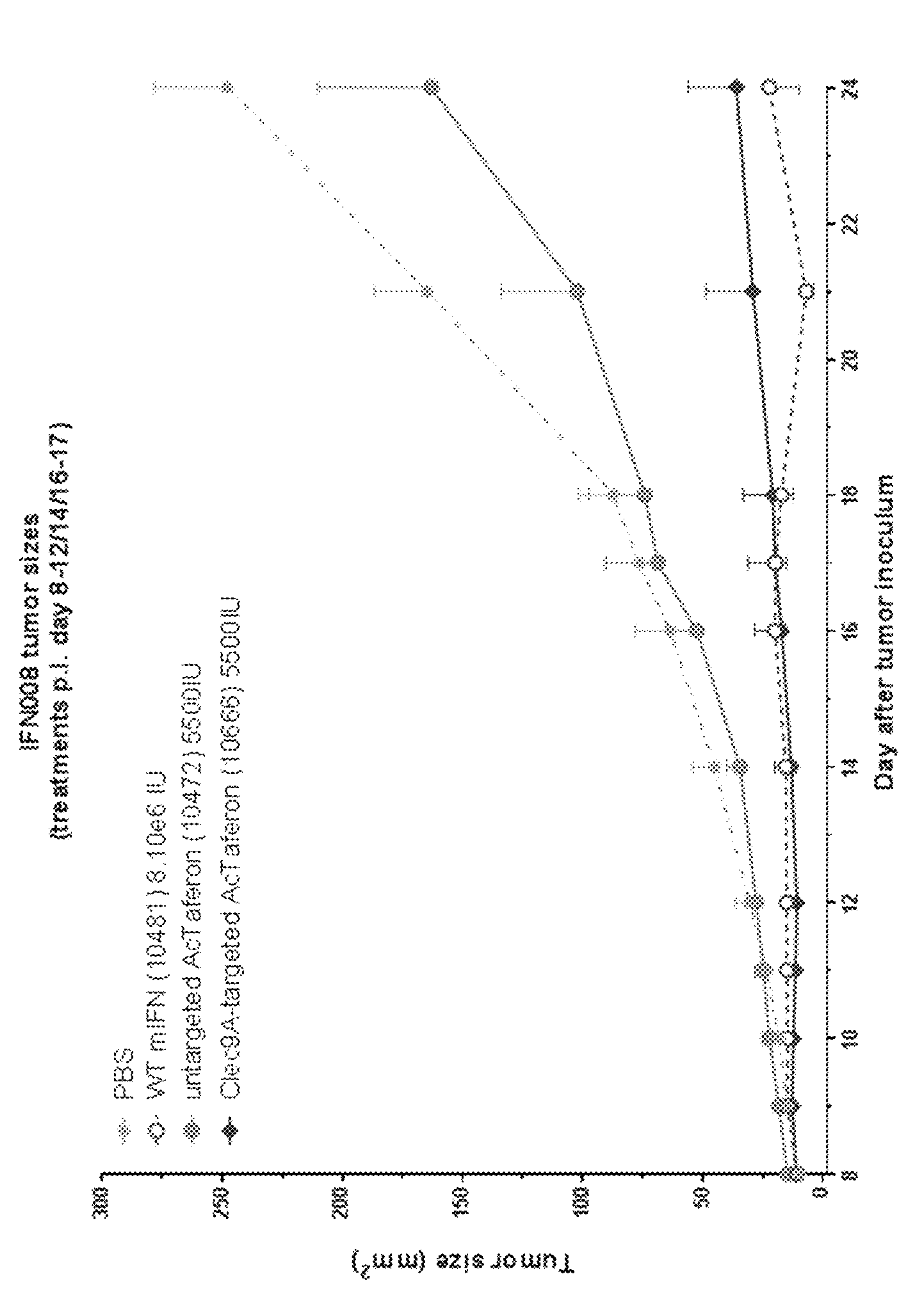
FIG. 2 panel A shows that the administration of a fusion of a VHH specific for mouse Clec9A with a modified human interferon (Q124R mutant, "Clec9A-targeted AcTaferon") led to reductions in tumor size (lines from top to bottom at last time point: PBS, "untargeted AcTaferon" (i.e. modified human interferon (Q124R mutant) fused to a targeting moiety for an irrelevant target—hCD20, "Clec9A-targeted AcTaferon"—fusion of a VHH specific for mouse Clec9A with a modified human interferon (Q124R mutant), and "WT mIFN" (i.e. unmodified murine interferon). Panels B and C show that the administration of the fusion of a VHH specific for mouse Clec9A with a modified human interferon (Q124R mutant) did not result in weight loss or hematological toxicity, respectively (in panel B, lines from top to bottom at last time point: untargeted AcTaferon, PBS, Clec9A-targeted AcTaferon, and WT mIFN, in panel C all graphs, the histograms left to right are: naive mice, PBS, mIFN WT, untargeted AcTaferon, and Clec9A-targeted AcTaferon.
Figure 2:
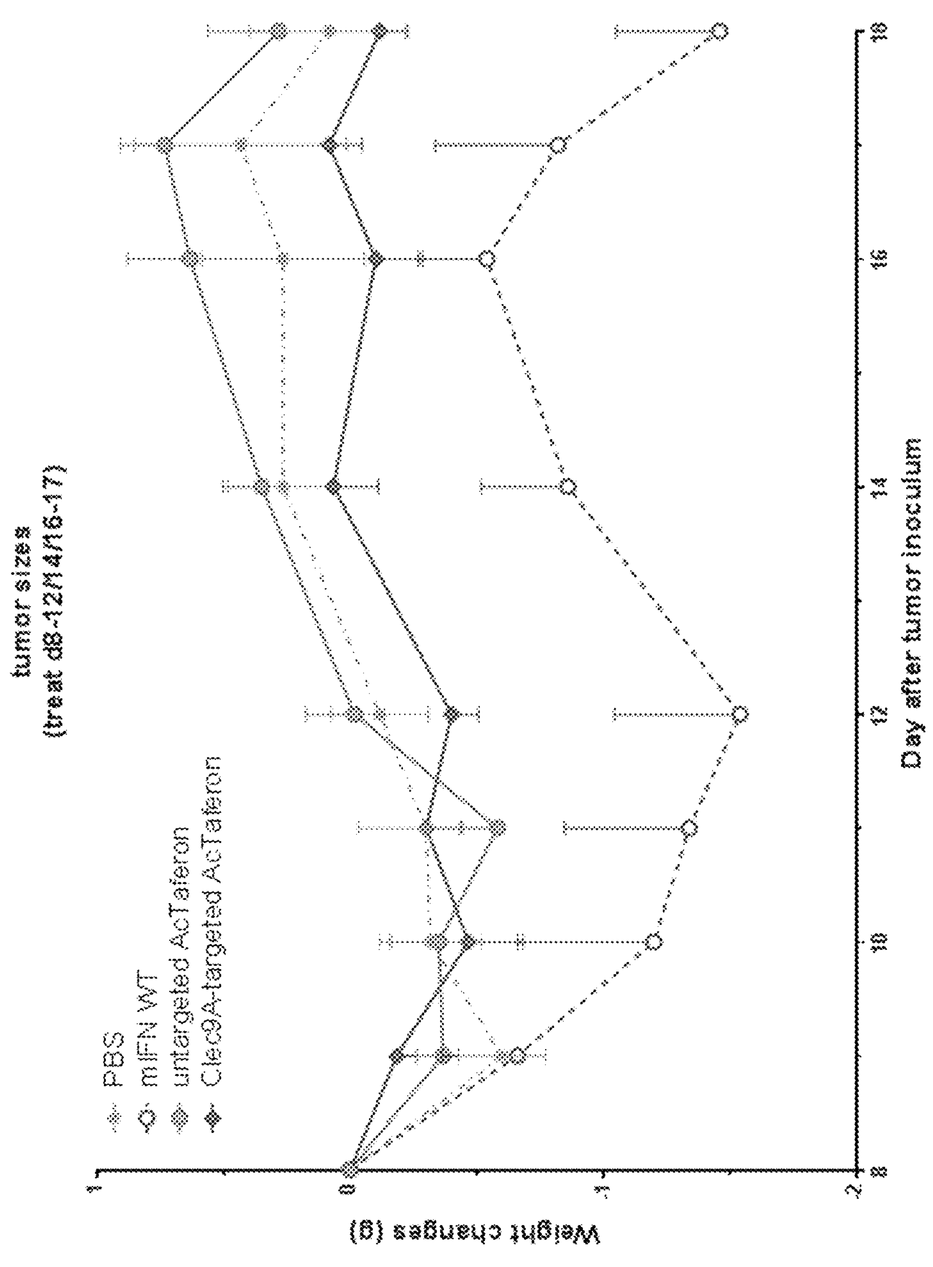
Figure 2:
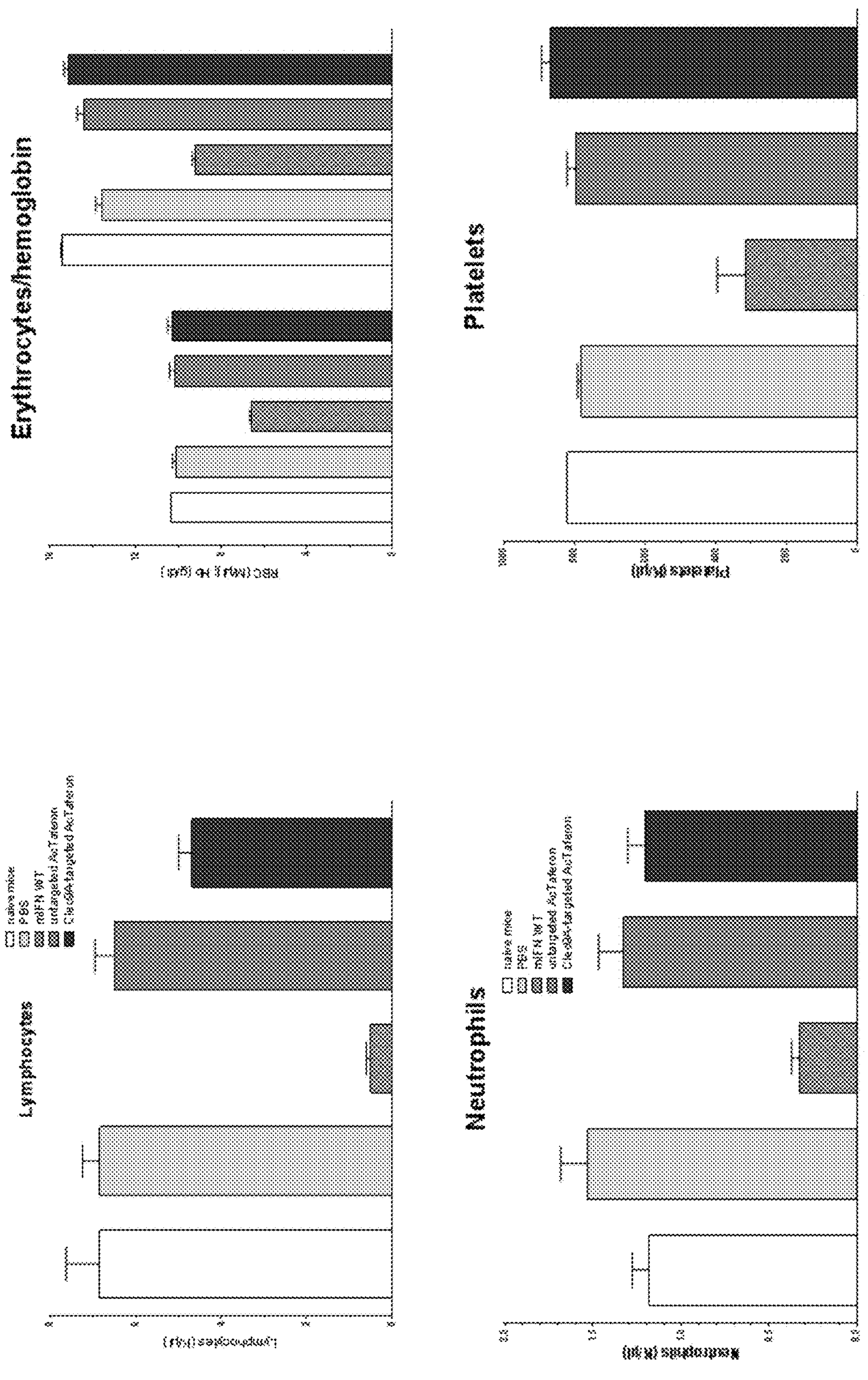

Experiments were carried out to characterize the activity of the VHHs in treating tumors. In the experiments of FIG. 2, female C57BL/6J mice were injected s.c. with $6\times10^5$ B16B16-mCD20 cells in 50 μl PBS. Seven days later, perilesional (=s.c. at the edge of the tumor) treatments were started. WT mIFN was injected in a dose of $8\times10^6$ IU, while 5500 IU of the chimeric protein were injected. Treatments were given at days 8, 9, 10, 11, 12, 14, 16 and 17 after tumor cell inoculation. Control mice were injected with 100 μl PBS. Tumor growth was monitored using a digital caliper. Plotted are means±SEM (n=5) of tumor sizes (FIG. 2 panel A) and body weight changes (FIG. 2 panel B). One day after the last treatment (day 18), EDTA-blood was collected from the tail vein for analysis of hematological parameters (FIG. 2 panel C) using a Hemavet 950FS Analyzer (Drew Scientific).

As shown in FIG. 2, panel A, administration of VHHs against Clec9A effectively reduced tumor size. FIG. 2, panels B and C, demonstrate that treatment with the VHHs did not result in weight loss or hematological toxicity, respectively. Importantly, panels B and C show improved safety parameters (body weight, blood count parameters) of the chimeras relative to wild type interferon.

Example 2. Construction and Evaluation of VHHs Specific for Human Clec9A

Isolation of Antigen-Specific VHHs

Figure 3:
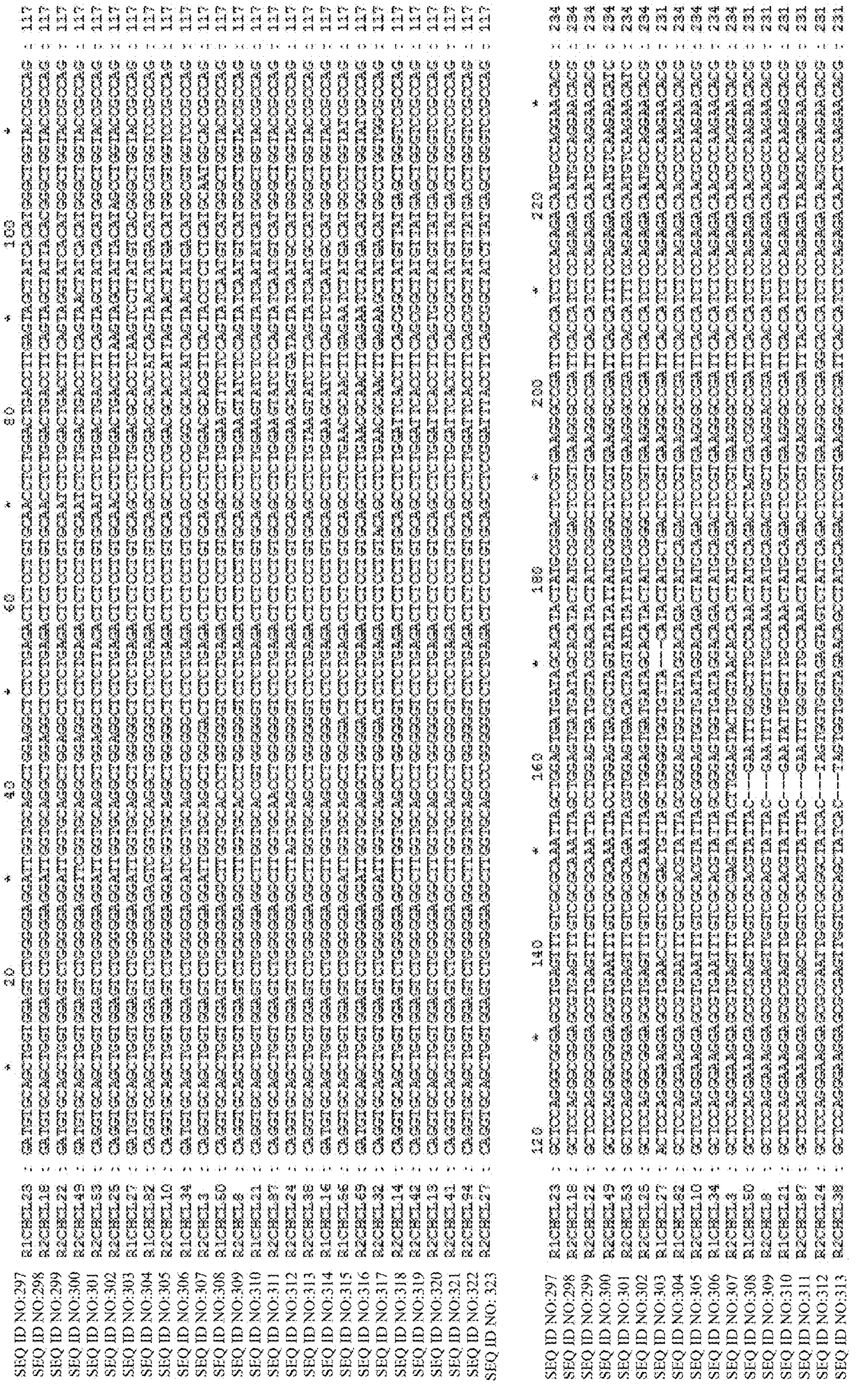
FIG. 3 depicts the nucleotide sequence of 27 different VHHs specific for human Clec9A. Gaps were introduced in order to align sequences. The sequences of FIG. 3 are assigned sequence identifiers as shown in Example 2 below.
Figure 3:
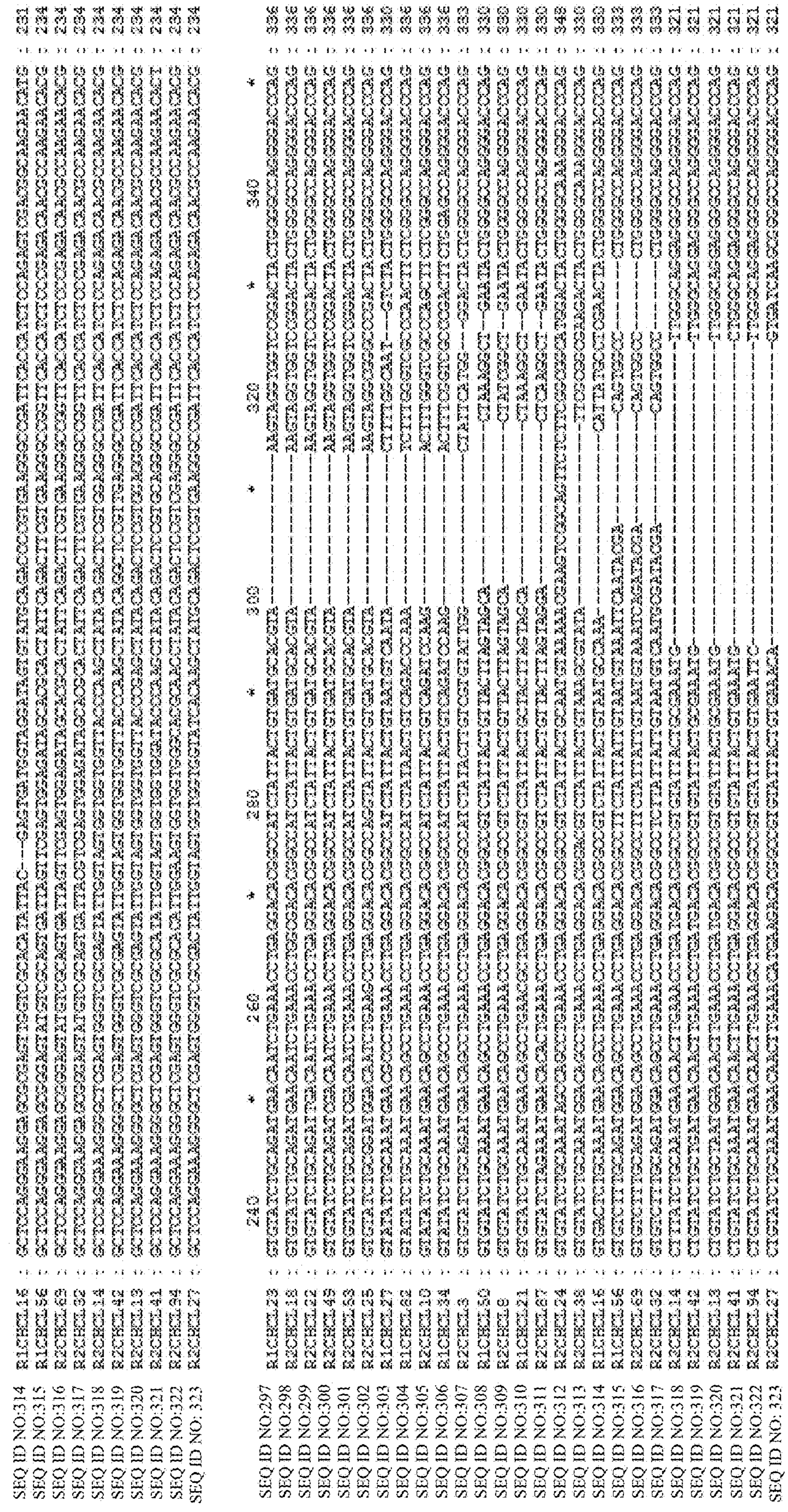
Figure 4:
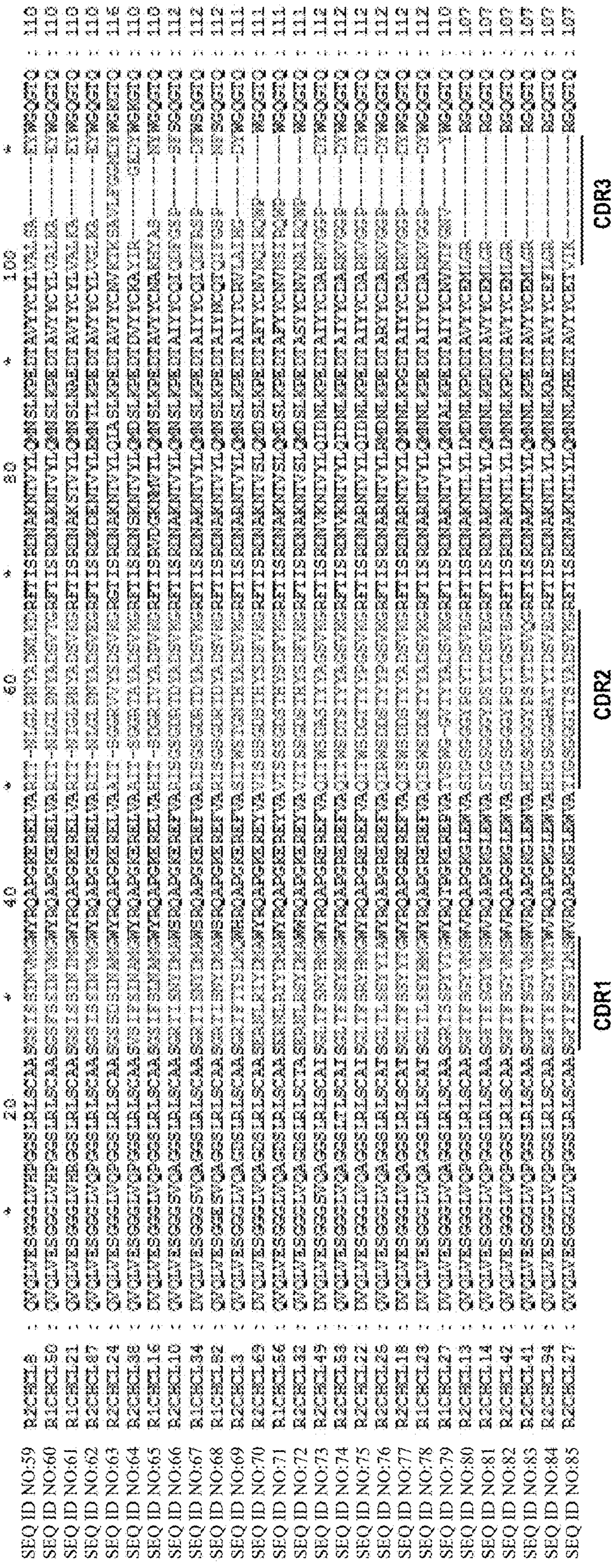
FIG. 4 shows the amino acid sequences of 27 different VHHs specific for human Clec9A. Complementarity determining regions (CDR1, CDR2 and CDR3) as indicated are defined according to Kabat. Gaps were introduced in order to align sequences. The above 27 different VHHs belong to 11 different groups (see FIG. 5). VHHs belonging to the same group are very similar and their amino acid sequences suggest that they are from clonally-related B-cells resulting from somatic hypermutation or from the same B-cell but diversified due to RT and/or PCR error during library construction. VHHs belonging to the same group recognize the same epitope but their other characteristics (e.g. affinity, potency, stability, expression yield, etc.) can be different. The sequences of FIG. 4 are assigned sequence identifiers as shown in Example 2 below.

A VHH library was subject to 2 consecutive rounds of panning (in solution), performed on stably transfected CHO-K1 cells expressing human Clec9A. The enrichment for antigen-specific phages was assessed after each round of panning by comparing the number of phagemid particles eluted from transfected cells after panning (output) with the number of phagemid particles used for panning (input). The phage output increased about $10^2$-fold in the 2nd round, as compared to the output from 1st round. The input phage was about $10^{11}$ and the output from first round was about $2\times10^8$ phage particles. 95 colonies from round were randomly selected and their crude periplasmic extracts (including soluble VHHs) were analyzed by cell ELISA for specific binding to transfected CHO-K1, as compared to parental CHO-K1 cells. None of these colonies scored positive in cell ELISA suggesting that either the ELISA was not sensitive enough in this case or the antigen was affected by cell fixation in ELISA. FACS analysis was therefore used for the identification of antigen-specific VHHs. Here, 190 randomly selected colonies from 1st and 2nd panning rounds (95 from each round) were sequenced and then the VHHs were grouped based on CDR3 sequences. These experiments resulted in the identification of 27 different VHHs belonging to 11 different groups (FIG. 5). The nucleotide and amino acid sequences of the 27 anti-human Clec9A VHHs are shown in FIGS. 3 and 4, respectively. Table 2 below provides a description of 27 clones representing the 27 different anti-human Clec9A VHH genes. *E. coli* TG1 harboring recombinant phagemid pHEN4 containing anti-human Clec9A VHH sequences was generated and stored at −80° C. The vector pHEN4 codes for ampicillin resistance.

TABLE 2

| *E. coli* strain + Vector | VHH (Nb) | NSF Reference No. (Glycerol stock) |
|---|---|---|
| TG1, pHEN4 | R1CHCL 16 | 1755 |
| TG1, pHEN4 | R1CHCL 21 | 1756 |
| TG1, pHEN4 | R1CHCL 23 | 1757 |
| TG1, pHEN4 | R1CHCL 27 | 1758 |
| TG1, pHEN4 | R1CHCL 34 | 1759 |
| TG1, pHEN4 | R1CHCL 50 | 1760 |
| TG1, pHEN4 | R1CHCL 56 | 1761 |
| TG1, pHEN4 | R1CHCL 82 | 1762 |
| TG1, pHEN4 | R2CHCL 3 | 1763 |
| TG1, pHEN4 | R2CHCL 8 | 1764 |
| TG1, pHEN4 | R2CHCL 10 | 1765 |
| TG1, pHEN4 | R2CHCL 13 | 1766 |
| TG1, pHEN4 | R2CHCL 14 | 1767 |
| TG1, pHEN4 | R2CHCL 18 | 1768 |
| TG1, pHEN4 | R2CHCL 22 | 1769 |
| TG1, pHEN4 | R2CHCL 24 | 1770 |
| TG1, pHEN4 | R2CHCL 25 | 1771 |
| TG1, pHEN4 | R2CHCL 27 | 1772 |
| TG1, pHEN4 | R2CHCL 32 | 1773 |
| TG1, pHEN4 | R2CHCL 38 | 1774 |
| TG1, pHEN4 | R2CHCL 41 | 1775 |
| TG1, pHEN4 | R2CHCL 42 | 1776 |
| TG1, pHEN4 | R2CHCL 49 | 1777 |
| TG1, pHEN4 | R2CHCL 53 | 1778 |
| TG1, pHEN4 | R2CHCL 69 | 1779 |
| TG1, pHEN4 | R2CHCL 87 | 1780 |
| TG1, pHEN4 | R2CHCL 94 | 1781 |

Using crude periplasmic extracts including VHHs, representative(s) of each group was (were) analyzed by FACS for specificity to human and mouse Clec9A using CHO-K1 cells transfected with either mouse Clec9A or human Clec9A. The parental non-transfected CHO-K1 cells served as negative control cell. The representative VHHs tested were as follows: R1CHCL16, R1CHCL27, R1CHCL34, R1CHCL50, R2CHCL3, R2CHCL10, R2CHCL13, R2CHCL24, R2CHCL25, R2CHCL27, R2CHCL32, R2CHCL38, R2CHCL49, R2CHCL69 and R2CHCL87. All representatives tested were positive for CHO-K1 cells transfected with human Clec9A showing that all 27 VHHs bound human Clec9A specifically. Moreover, VHH R2CHCL10 from group 5 also reacted strongly with mouse Clec9A in FACS. VHH R1CHCL34, also from group 5, reacted with mouse Clec9A but very weakly. VHH R1CHCL82 from group 5 was not tested in FACS. Additionally, VHH R2CHCL32 from group 7 weakly reacted with mouse Clec9A in FACS. The other 2 members of the group 7 (VHHs R1CHCL56 and R2CHCL69) were not tested in FACS.

Expression and Purification of VHHs

The VHH genes were recloned from pHEN4 to pHEN6c vectors. Specifically, the VHH gene was amplified by PCR using recombinant pHEN4 harboring the VHH gene as template and primers A6E and 38. Primers A6E and 38 were framework) and framework4 primers, respectively. The primer sequences were as follows:

```
Primer A6E
                                        (SEQ ID NO: 291)
(5' GAT GTG CAG CTG CAG GAG TCT GGR* GGA GG 3').

Primer 38
                                        (SEQ ID NO: 292)
(5' GGA CTA GTG CGG CCG CTG GAG ACG GTG ACC TGG

GT 3').

Universal reverse primer
                                        (SEQ ID NO: 293)
(5' TCA CAC AGG AAA CAG CTA TGA C 3').

Universal forward primer
                                        (SEQ ID NO: 294)
(5' CGC CAG GGT TTT CCC AGT CAC GAC 3').
*R stands for A or G.
```

The amplification protocol included about 30 cycles of PCR, each cycle included 30 seconds at 94° C., 30 seconds at 55° C. and 45 seconds at 72° C., followed by 10 minutes extension at 72° C. at the end of PCR. A fragment of about 400 bp was amplified.

The PCR product was purified (e.g. by Qiaquick PCR purification kit from Qiagen) and digested overnight with PstI. The purified PCR product was digested with BstEII overnight (or with Eco91I from Fermentas). The temperature used for digestion varied. For example, digestion with BstEII was done at 50° C. or 60° C. depending on the supplier of the enzyme.

For ligation, the PCR product was purified. The pHEN6c vector was digested with PstI for 3 hours, purified as described above, and then digested with BstEII for 2 to 3 hours. Alternatively, digestion was carried out using Eco91I from Fermentas. The digested vector was ran on 1% agarose gel, with the vector band excised out of the gel and purified (e.g. by Qiaquick gel extraction kit from Qiagen). The PCR fragment was subsequently ligated to the vector.

Electrocompetent WK6 cells were transformed with the ligation reaction, and transformants were selected using LB/agar/ampicillin (100 μg/ml)/glucose (1%) plates. Positive clones were screened by PCR using universal reverse and universal forward primers. A fragment of about 550 bp was amplified, if the insert was present. To verify the identity of the clones, at least 2 clones per each VHH were sequenced using universal reverse primers. Antigen binding capacity was retested by ELISA or any other appropriate assay.

Following the above protocol, the VHH gene cloned in pHEN6c vector was generated which contained PelB signal sequence at the N-terminus and Hiss-tail at the C-terminus. The PelB leader sequence directed the VHH to the periplasmic space of the *E. coli*, and the His-tag was used for the purification and detection of VHH (e.g. in ELISA, Western Blot, etc.).

Expression and purification of the VHHs were carried out. Specifically, on day 1, 10-20 ml of LB+ampicillin (100 μg/ml)+glucose (1%) were innoculated with a freshly transformed WK6 colony. This pre-culture was incubated at 37° C. overnight with shaking at 200-250 rpm. On day 2, a TB medium was used for expressing the VHHs. The TB medium included, per liter: 2.3 g $KH_2PO_4$, 16.4 g $K_2HPO_4.3H_2O$, 12 g Tryptone (Duchefa Biochemie), 24 g Yeast (Duchefa Biochemie), and 4 ml 100% glycerol (Duchefa Biochemie)

A baffled shaker flask of 1 liter was filled with 330 ml TB and autoclaved. $KH_2PO_4$ and $K_2HPO_4.3H_2O$ were not autoclaved. Instead, $KH_2PO_4$ and $K_2HPO_4.3H_2O$ were prepared, filter sterilized, and then added to the rest of the medium that was already autoclaved. About 1 ml of the pre-culture was added to 330 ml of TB supplemented with 100 μg/ml Ampicillin, 2 mM $MgCl_2$ and 0.1% glucose and subsequently grew at 37° C. with shaking (200-250 rpm) until an $OD_{600}$ of 0.6-0.9 was reached. IPTG (final concentration of 1 mM) was added to induce VHH expression. The culture was incubated at 28° C. with shaking overnight (about 16-18 hours). The $OD_{600}$ after overnight induction was usually between 25 and 30. At least 1 liter of culture (3 bottles) per clone was prepared with an average yield of between 1 and 15 mg/l.

Extraction of the VHHs from the periplasm of *E. coli* was carried out on day 3. The solutions used included: TES: 0.2 M Tris pH 8.0, 0.5 mM EDTA, 0.5 M sucrose, and TES/4: TES diluted 4 times in water.

The overnight induced cultures were centrifuged for 8 minutes at 8000 rpm. The cell pellets from 1 liter culture were resuspended in 12 ml TES by pipetting up and down and shaken for 1 hour on ice. Per each 12 ml TES used, about 18 ml TES/4 were added and incubated on ice for an additional hour with shaking followed by centrifugation for 30 minutes at 8000 rpm at 4° C. The supernatant which contained proteins extracted from the periplasmic space was transferred to fresh falcon tubes.

The VHHs were subsequently purified by IMAC which utilized the following solution: HIS-select (SIGMA), PBS, and 50 mM NaAcetate pH 4.6.

His-select was equilibrated with PBS. Specifically, per periplasmic extract derived from 1 liter culture, 1 ml of Resin (about 2 ml His-select solution) was added to a 50 ml falcon tube. PBS was also added to final volume of 50 ml and mixed. Centrifugation was carried out at 2000 rpm for 2 minutes, and the supernatant was discarded. The resin was washed with PBS twice as described above. The periplasmic extract was added to the resin, incubated for 30 minutes to 1 hour at room temperature with gentle shaking. The samples were loaded on PD-10 columns with a filter at the bottom (GE healthcare, cat. No. 17-0435-01) and washed with 50 to 100 ml PBS (50-100 ml PBS per 1 ml resin used). Elution was carried out for 3 times, each time with 1 ml PBS/0.5 M imidazole per 1 ml resin used (for efficient elution, resuspend the beads and leave overnight at 4° C. with the bottom of the column closed). Dialysis was performed overnight at 4° C. against PBS (cutoff 3500 daltons) to remove imidazole. For efficient dialysis, the dialysis buffer (PBS) was changed 2-3 times. Alternatively, instead of elution with imidazole, the bound VH Hs could be eluted with 10 ml of 50 mM Na-acetate pH 4.6. If 50 mM Na-acetate pH 4.6 was used to elute VHHs, the eluted VHHs was immediately neutralized with 1 M Tris pH 8.0, and no dialysis was required.

The amount of protein was estimated by $OD_{280}$ measurement of eluted samples. Extinction coefficient of each clone was determined by protParam tool under primary structure analysis at the Expasy proteomics server. Further purification of VHHs could be achieved by different methods. For example, the samples could be concentrated (Vivaspin 5000 MW cutoff, Vivascience) by centrifuging at 2000 rpm at 4° C. until an appropriate volume for loading on a Superdex 75 16/60 was obtained (max. 4 ml). The concentrated sample was loaded on a Superdex 75 16/60 column equilibrated with PBS. Peak fractions were pooled, and $OD_{280}$ measurements were performed for quantification. In general, VHHs eluted after 85-95 minutes when run at 1 ml/min. Aliquots of concentrated VHH samples were stored at −20° C. at a concentration of about 1 mg/ml.

The sequences of FIG. 3 and FIG. 4 are assigned sequence identifiers as shown in the table below. Further, binding characteristics of the anti-human Clec9A VHHs, after purification, was assayed by binding to HEK-293T cells transfected with Clec9A is shown in the table below. Briefly, Hek293T cells were transfected a human Clec9A expression-plasmid using a standard calcium phosphate procedure. Two days after transfection, cells were resuspended in FACS buffer (PBS supplemented with 2% FBS and 0.5 mM EDTA) and incubated with a serial dilution VHH (1000 ng/ml; 1 over 3) for two hours at 4° C. Unbound VHHs were washed away with FACS buffer. Samples were further stained with a FITC-coupled anti-His Ab for 45 minutes at 4° C. and analysed with a FACSCalibur (BD Biosciences) and the CellQuest Pro Version 4.0.2 software (BD Biosciences).

| Clone | Sequence Identifier | Binding |
|---|---|---|
| R1CHCL23 | SEQ ID NO: 78 | ND |
| R2CHCL18 | SEQ ID NO: 77 | ND |
| R2CHCL22 | SEQ ID NO: 75 | ++ |
| R2CHCL49 | SEQ ID NO: 73 | ND |
| R2CHCL53 | SEQ ID NO: 74 | ND |
| R2CHCL25 | SEQ ID NO: 76 | + |
| R1CHCL27 | SEQ ID NO: 79 | − |
| R1CHCL82 | SEQ ID NO: 68 | ++ |
| R2CHCL10 | SEQ ID NO: 66 | +++ |
| R1CHCL34 | SEQ ID NO: 67 | + |
| R2CHCL3 | SEQ ID NO: 69 | + |
| R1CHCL50 | SEQ ID NO: 60 | +++ |
| R2CHCL8 | SEQ ID NO: 59 | +++ |
| R1CHCL21 | SEQ ID NO: 61 | − |
| R2CHCL87 | SEQ ID NO: 62 | +++ |
| R2CHCL24 | SEQ ID NO: 63 | +++ |
| R2CHCL38 | SEQ ID NO: 64 | − |
| R1CHCL16 | SEQ ID NO: 65 | ++ |
| R1CHCL56 | SEQ ID NO: 71 | ND |
| R2CHCL69 | SEQ ID NO: 70 | − |
| R2CHCL32 | SEQ ID NO: 72 | − |
| R2CHCL14 | SEQ ID NO: 81 | ND |
| R2CHCL42 | SEQ ID NO: 82 | ND |
| R2CHCL13 | SEQ ID NO: 80 | ND |
| R2CHCL41 | SEQ ID NO: 83 | − |
| R2CHCL94 | SEQ ID NO: 84 | ++ |
| R2CHCL27 | SEQ ID NO: 85 | ND |

Example 3. Combination Therapy Using Clec9A Chimeras and Tumor Necrosis Factor

The anti-tumor effects of a combination therapy using VHHs specific for mouse Clec9A and Tumor Necrosis Factor (TNF) were tested. Mice were inoculated subcutaneously with B16 (a mouse melanoma cell line) to induce tumors. The mice were subsequently given perilesional (=s.c. at the edge of the tumor) treatments with a chimeric Clec9A VHH specific for mouse Clec9A fused with a modified human interferon alpha 2 (Q124R mutant, "AcTa Clec9A") with or without TNF. Control mice were treated with PBS or either the chimeric Clec9A VHH alone or TNF alone. Tumor growth was monitored using a digital caliper. EDTA-blood was also collected from the tail vein for analysis of hematological parameters using a Hemavet 950FS Analyzer (Drew Scientific).

Figure 6:
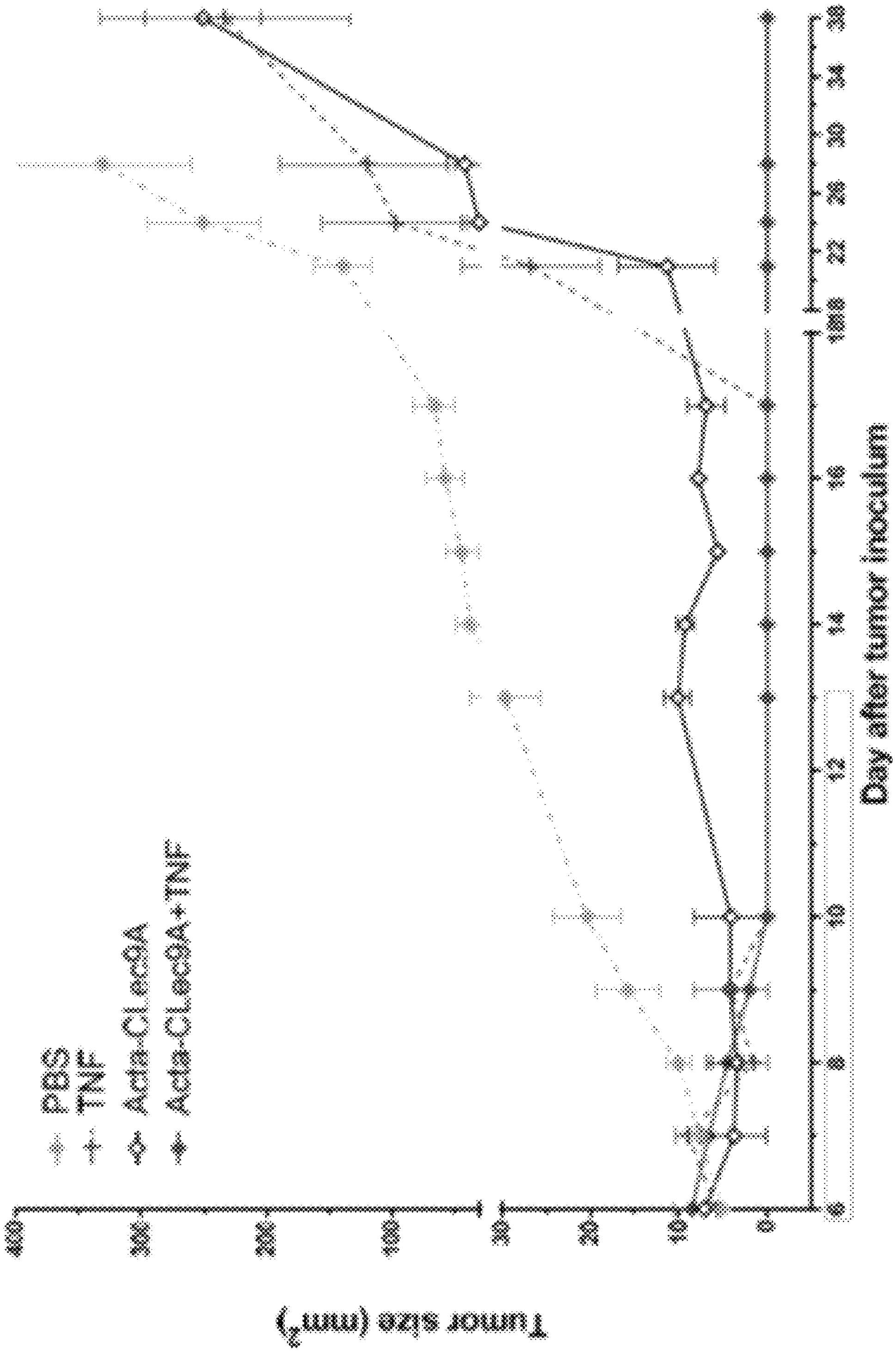
FIG. 6 shows the anti-tumor potential of a chimeric protein comprising a VHH specific for mouse Clec9A fused to a modified human interferon alpha 2 (Q124R mutant, "Acta-Clec9A") in combination with tumor necrosis factor (TNF). Panel A demonstrates that combination treatment using the chimeric protein and TNF exhibited potent anti-tumor activity with no tumor recurrence by day 38 (or 23 days post-dosing). Panel B shows that the combination treatment was well tolerated with no significant hematological toxicity such as thrombocytopenia compared to treatment with wild type IFN or wild type IFN combined with TNF.
Figure 6:
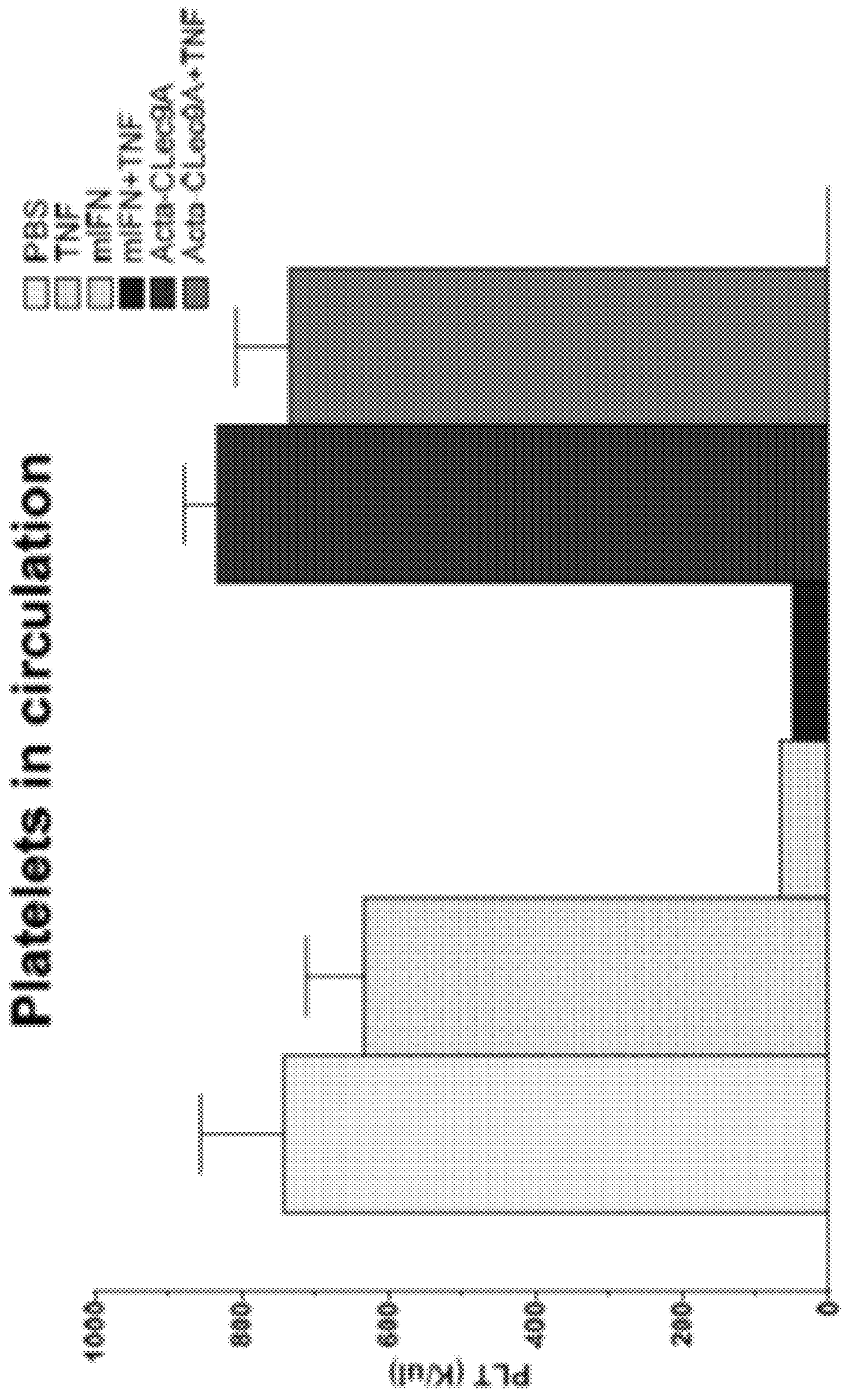

As shown in FIG. 6, panel A, combined treatment using the chimeric Clec9A VHH and TNF elicited potent anti-tumor effects with no tumor recurrence by day 38 compared to treatment with either agent alone. FIG. 6, panel B, shows that the combination treatment was well tolerated and induced no hematological toxicity compared to treatment with wildtype IFN alone or wildtype IFN with TNF. Altogether these data suggests a synergistic effect for combination therapy using chimeric Clec9A VHHs and TNF.

The Q124R mutant is representative of an attenuated human IFN alpha 2 mutant that can be assayed in vivo in a murine model. Specifically, Q124R is a human IFN mutation that is suitable for use in the mouse (i.e. it is a human mutant IFN that functions in mouse). See Nat. Comm. 2014; 5:3016. doi: 10.1038/ncomms4016, the entire contents of which are hereby incorporated by reference.

Example 4. Combination Therapy Using Clec9A Chimeras and anti-PD-L1 Antibodies

Figure 7:
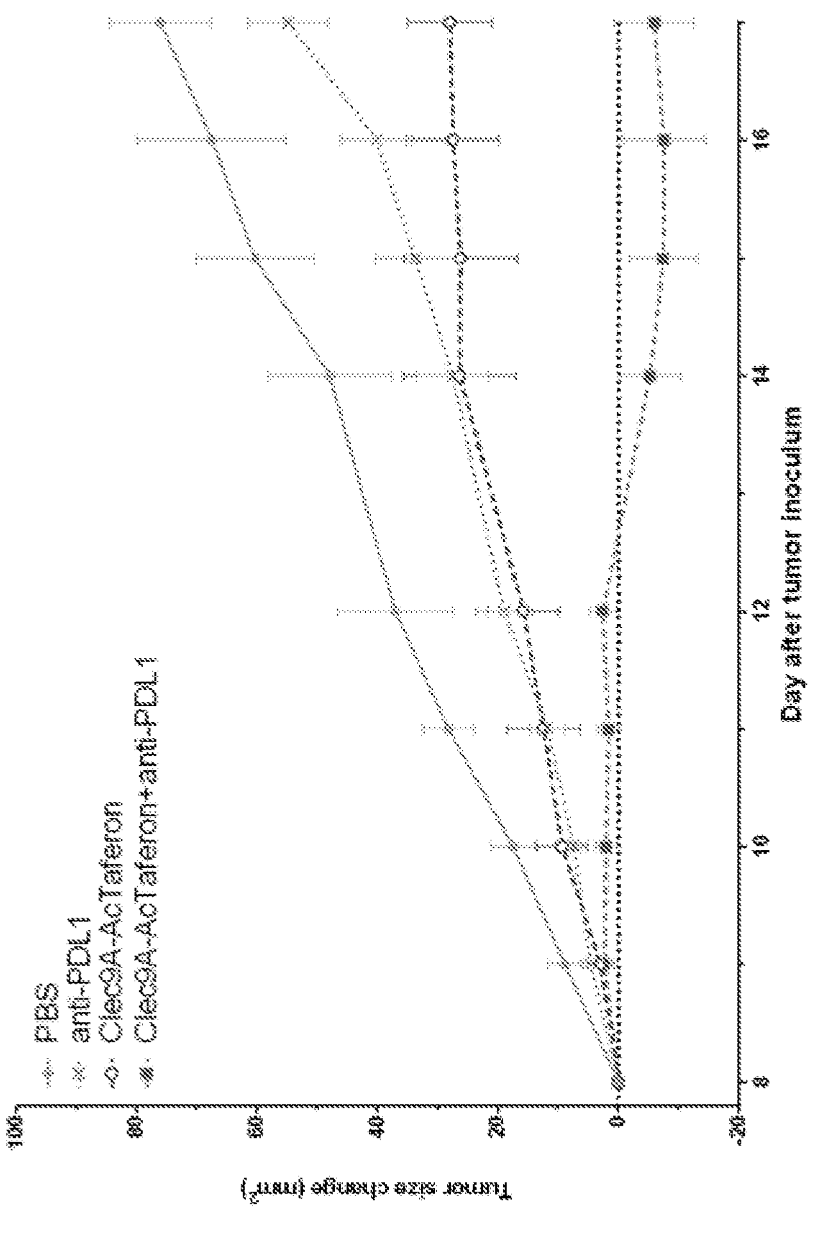
FIG. 7 shows the combined effect of chimera of a VHH specific for mouse Clec9A fused to a modified human interferon alpha 2 (Q124R mutant) and an anti-PD-L1 antibody ("Clec9A-AcTaferon+anti-PD-L1") in comparison to PBS (negative control), chimera of a VHH specific for mouse Clec9A fused to a modified human interferon alpha 2 alone (Q124R mutant, "Clec9A-AcTaferon"), and anti-PD-L1 antibody alone ("anti-PD-L1").

FIG. 7 shows the combined effect of a chimera of a VHH specific for mouse Clec9A fused to a modified human IFN alpha 2 (Q124R mutant) and an anti-PD-L1 antibody ("Clec9A-AcTaferon+anti-PD-L1") in comparison to PBS (negative control), chimera of a VHH specific for mouse Clec9A fused to a modified human IFN (Q124R mutant, "Clec9A-AcTaferon") alone, and anti-PD-L1 antibody ("anti-PD-L1") alone.

As demonstrated by the in vivo experiment of FIG. 7, the combination of a chimera of Clec9A fused to a modified human IFN and an anti-PD-L1 antibody provides synergy with regard to tumor progression. Specifically, the combined treatment provided not only stasis but also tumor shrinkage. This is particularly notable in comparison to, for example, anti-PD-L1 antibody alone, as the mice treated with such were displaying growing tumors at the end of the experiment.

The Q124R mutant is representative of an attenuated human IFN alpha 2 mutant that can be assayed in vivo in a murine model. Specifically, Q124R is a human IFN mutation that is suitable for use in the mouse (i.e. it is a human mutant IFN that functions in mouse). See Nat. Comm. 2014; 5:3016. doi: 10.1038/ncomms4016, the entire contents of which are hereby incorporated by reference.

Example 5. Combination Therapy Using Clec9A Chimeras and Chemotherapy

Figure 8:
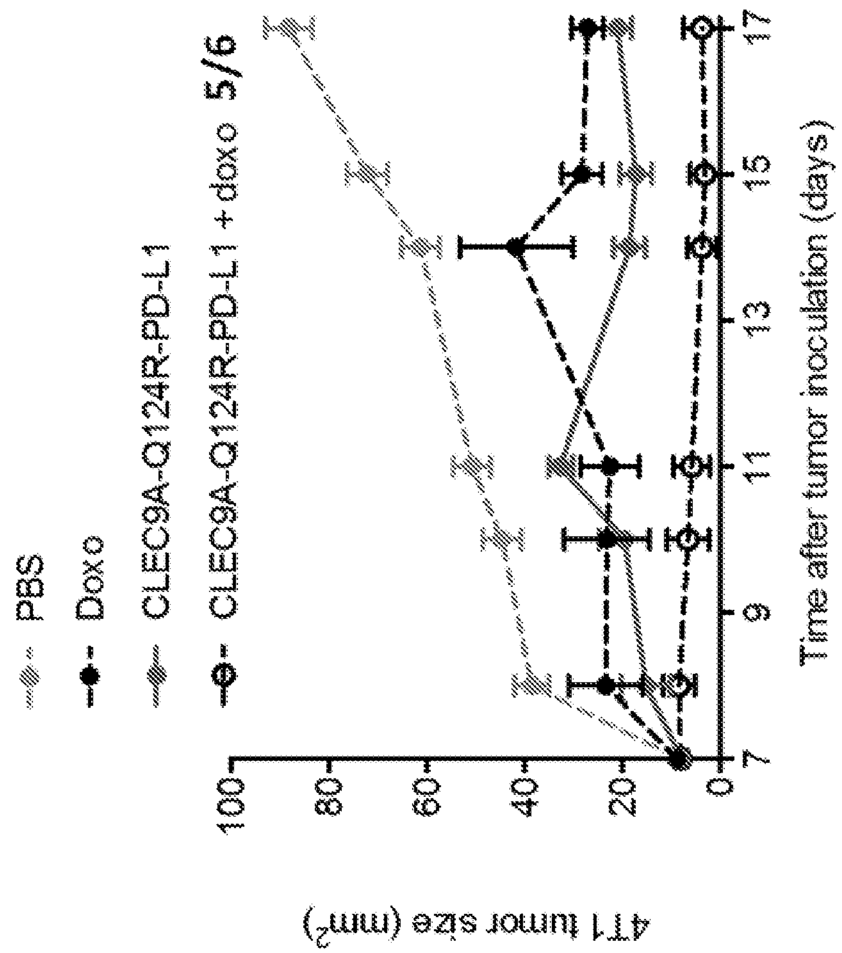
FIG. 8 shows the combined effect of a chimera of a VHH specific for mouse Clec9A fused to a modified human interferon alpha 2 (Q124R) and also fused to an anti-PD-L1 VHH and doxorubicin ("Clec9A-Q124R-PD-L1+doxo"), compared to a chimera of a VHH specific for mouse Clec9A fused to a modified human interferon alpha 2 ("Q124R") and fused to an anti-PD-L1 VHH ("Clec9A-Q124R-PD-L1"), doxorubicin ("doxo"), and PBS (negative control).

FIG. 8 shows the combined effect of a chimera of a VHH specific for mouse Clec9A fused to a modified human IFN (Q124R) and fused to an anti-PD-L1 VHH, and doxorubicin ("Clec9A-Q124R-PD-L1+doxo"), compared to a chimera of a VHH specific for mouse Clec9A fused to a modified human IFN ("Q124R") and fused to an anti-PD-L1 VHH ("Clec9A-Q124R-PD-L1"), doxorubicin ("doxo"), and PBS (negative control).

As demonstrated by the in vivo experiment of FIG. 8, the combination of a chimera of a VHH specific for mouse Clec9A fused to a modified human interferon (Q124R) and fused to an anti-PD-L1 VHH and doxorubicin provides synergy with regard to tumor progression. Importantly, 5 out of 6 mice in the combination therapy group showed a complete tumor regression.

The Q124R mutant is representative of an attenuated human IFN alpha 2 mutant that can be assayed in vivo in a murine model. Specifically, Q124R is a human IFN mutation that is suitable for use in the mouse (i.e. it is a human mutant IFN that functions in mouse). See Nat. Comm. 2014; 5:3016. doi: 10.1038/ncomms4016, the entire contents of which are hereby incorporated by reference.

Example 6. Stimulation of T Cell Proliferation by Mouse Clec9A Chimeras

Chimeric Antigen Receptor (CAR) T-cell therapy is often compromised by the extremely inhospitable solid tumor microenvironment which imposes an immunosuppressive effect on the CAR T cells. For examples, various immunosuppressive cytokines, regulatory modulators, and co-inhibitory receptors are present in the tumor microenvironment which can induce anergy of the CAR T cells. One mechanism for enhancing the efficacy of CAR T-cell therapy entails an induction of the T cells to divide and proliferate within the tumor microenvironment.

Experiments were conducted to evaluate whether a VHH specific for mouse Clec9A fused to a modified human IFN (Q124R) could induce proliferation of CAR T cells in vivo. Specifically, carboxyfluorescein succinimidyl ester (CFSE)-labeled T cell receptor transgenic CD8+ T cells (pmel-1) which recognize the melanocyte differentiation antigen gp100 present on tumor cells were adoptively transferred to mice bearing B16 melanoma tumors. The mice were subsequently treated with either PBS (control) or a VHH specific for mouse Clec9A fused to a modified human IFN (Q124R). T cell proliferation was assessed by evaluating the extent of CFSE-labeled T cells present in the tumor draining lymph nodes using FACS analysis.

Figure 9:
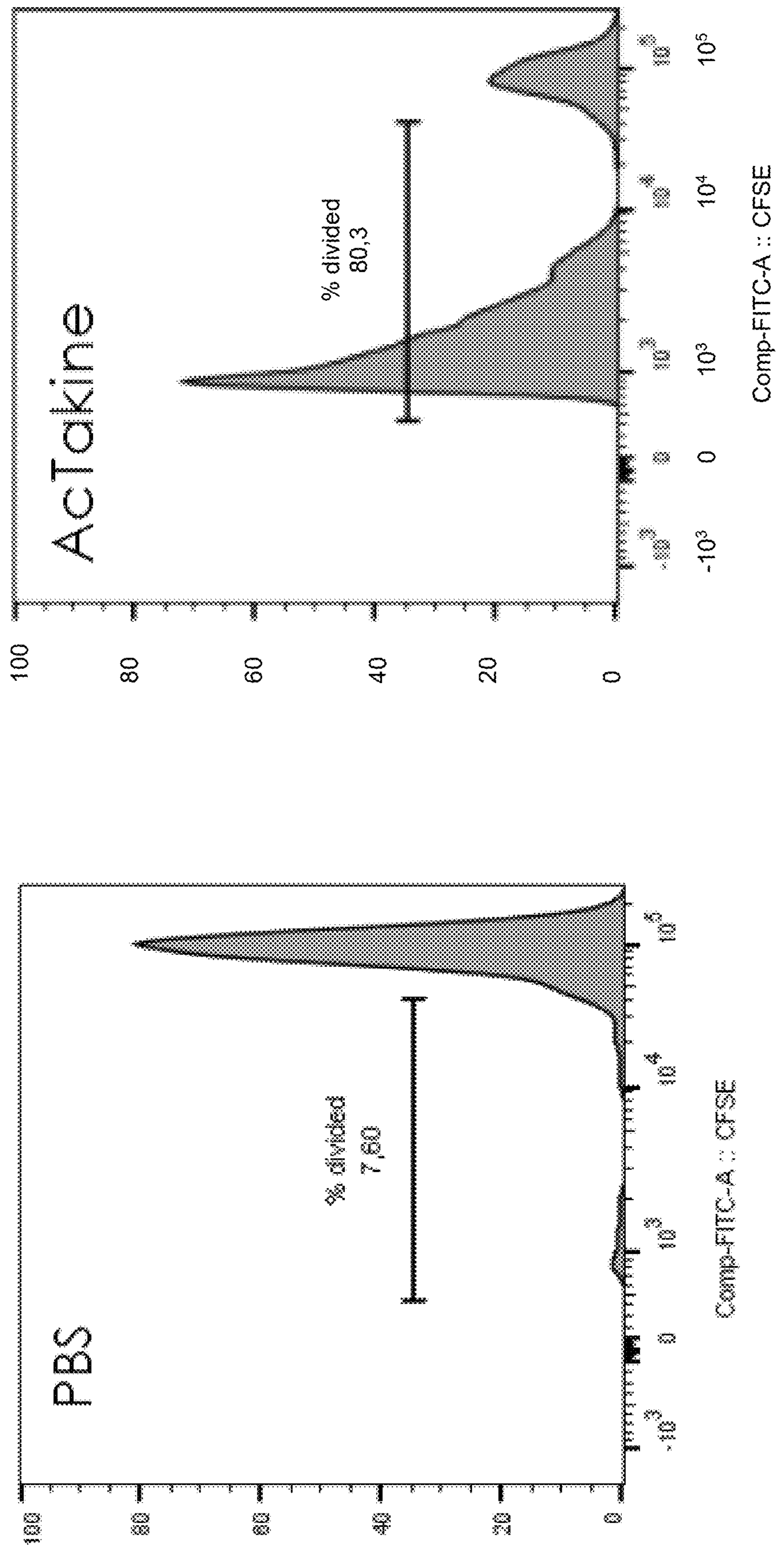
FIG. 9 shows a substantial induction of T cell proliferation in mice in response to administration of a VHH specific for mouse Clec9A fused to a modified human interferon alpha 2 (Q124R mutant, "Actakine").

As shown in FIG. 9, treating the mice with the VHH substantially induced T cell division and proliferation as compared to treatment with PBS. Without wishing to be bound by theory, it is believed that T cell division and proliferation was mediated via dendritic cell activation. Altogether these results suggest that the use of VHHs specific for Clec9A fused to IFN synergistically enhances CAR T-cell therapy.

Example 7. VHHs Specific for Human Clec9A are Effective in an Experimental Autoimmune Encephalomyelitis (EAE) Model This Example shows the therapeutic effects of VHHs specific for mouse Clec9A in an EAE mouse model which mimics human multiple sclerosis (MS). In short, 4 in 5 mice treated with a fusion of Clec9A-IFNQ124R never developed MS symptoms. A single treated mouse got sick, but recovered quickly. Three out of 5 animals treated with a high dose of wild type IFN, that suppressed disease development, died. Mice treated with low-dose wt IFN showed loss of weight. This is in stark contrast with Clec9A-IFNQ124R AcTaferon (i.e. fusion protein) treated animals which actually gained weight.

Figure 10:
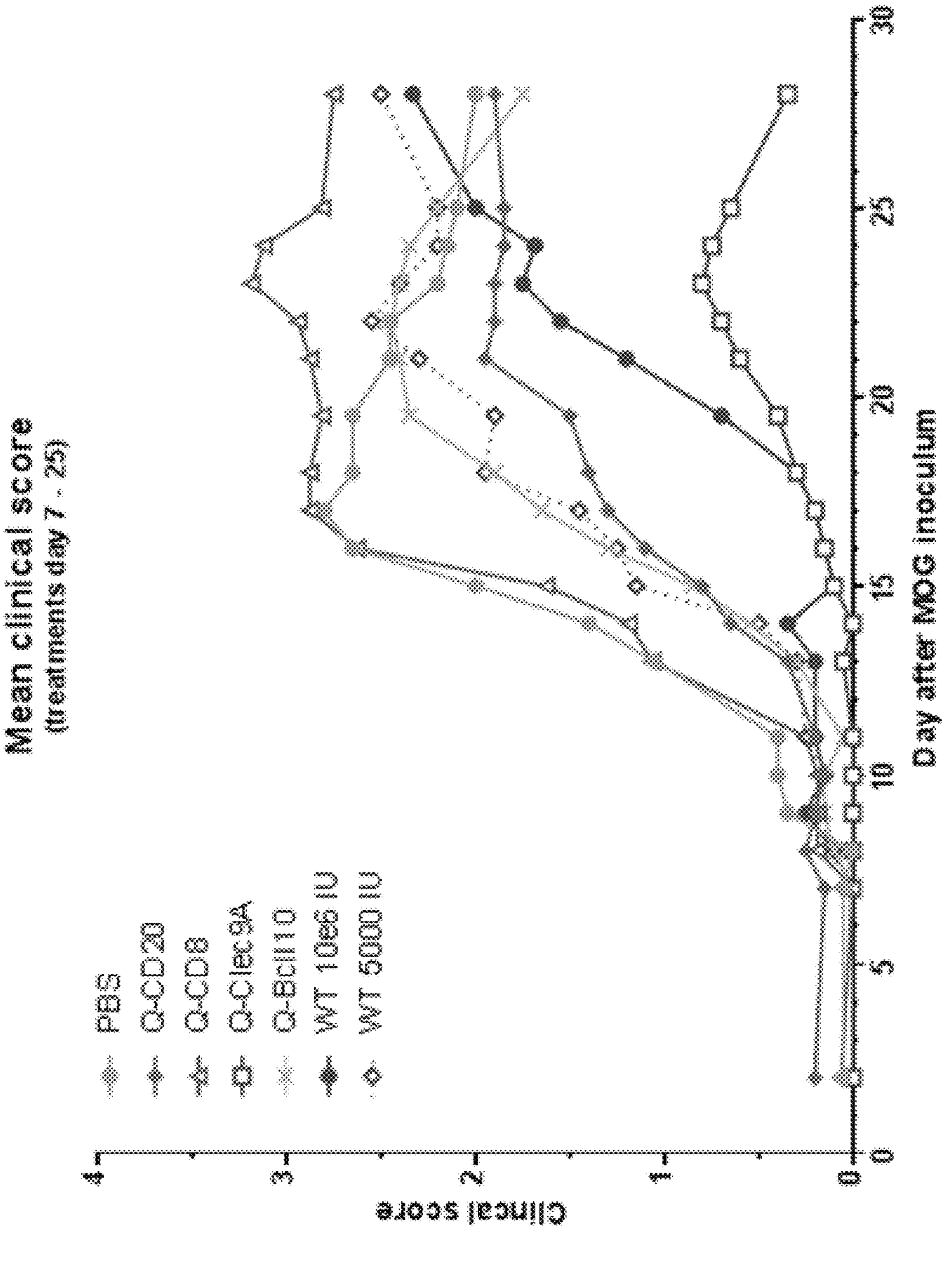
FIG. 10, panel A shows mean clinical scores as described in Example 7 for various treatments (including various fusions) also described in Example 7.
Figure 10:
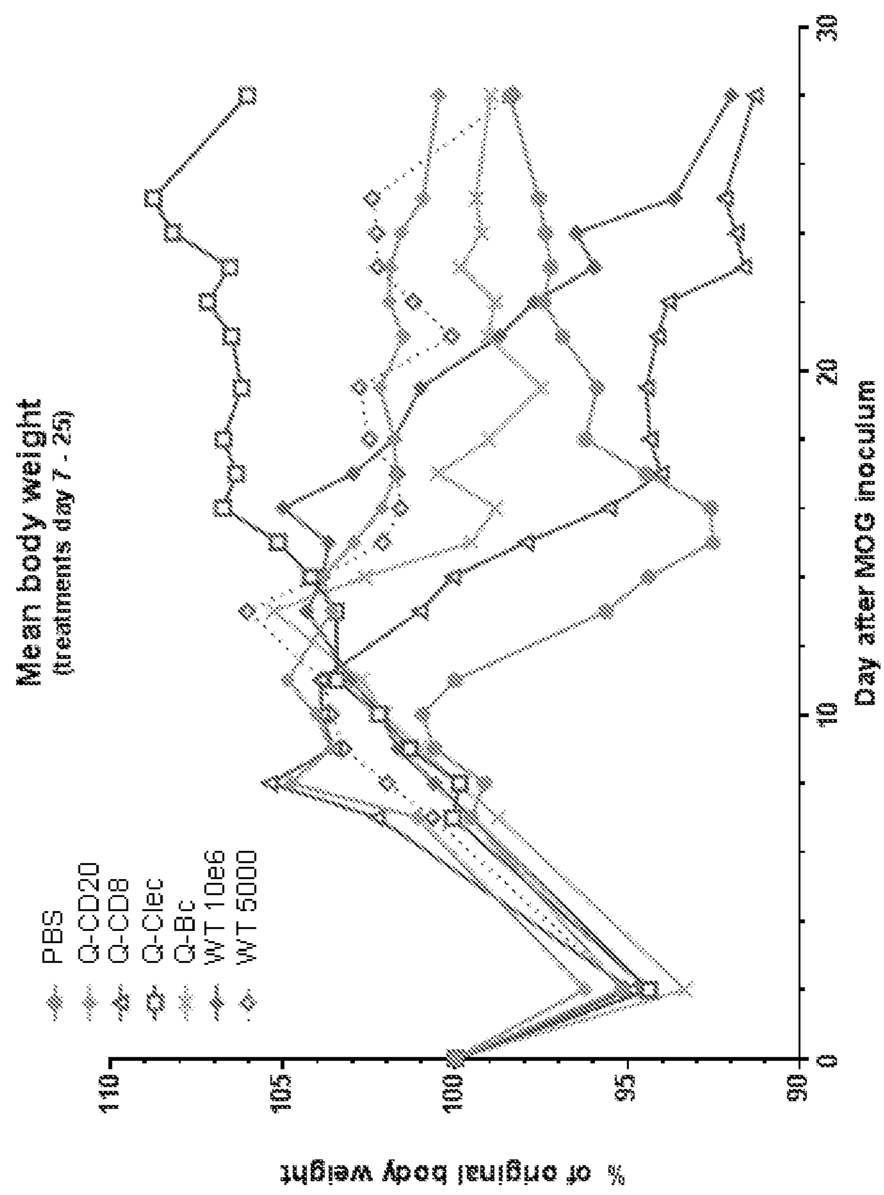
Figure 11:
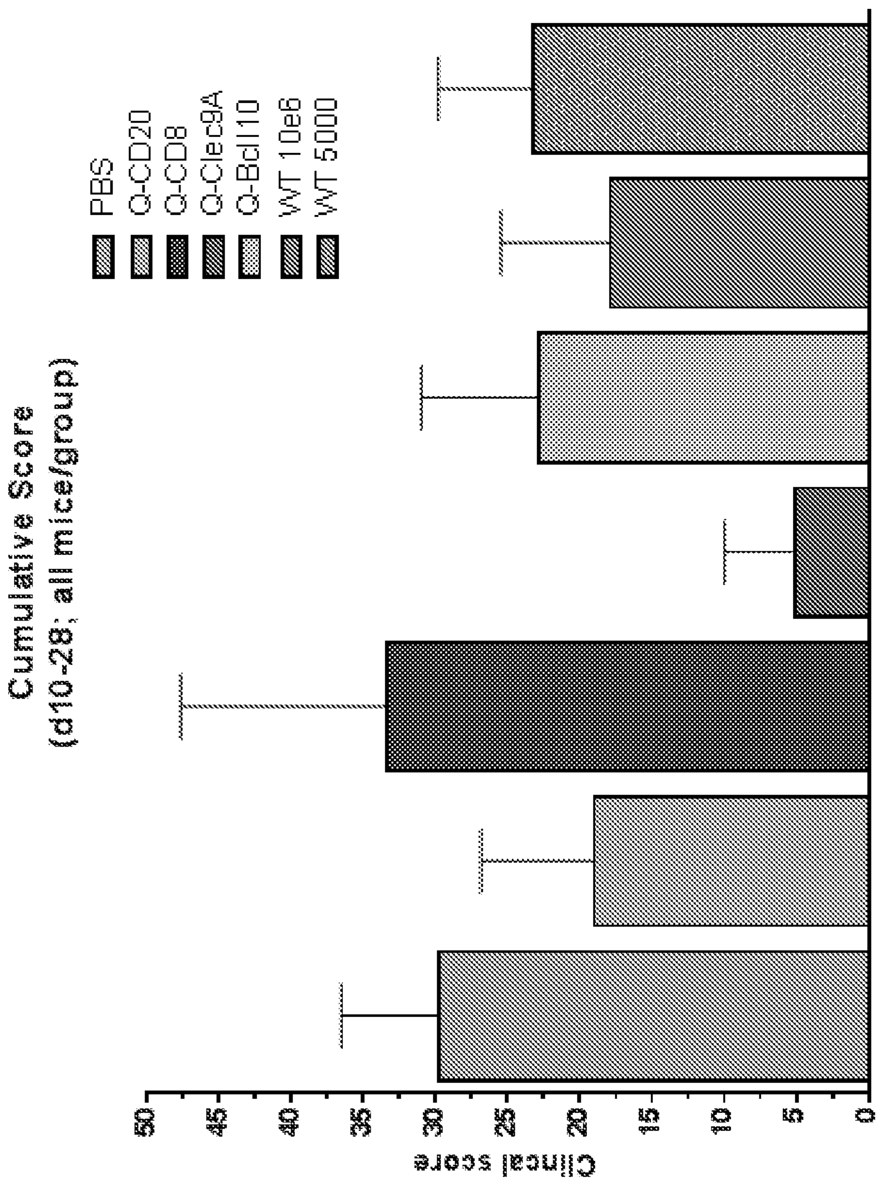
FIG. 11 shows the cumulative clinical score for various treatments; the histograms are (left to right: PBS (negative control), fusion of anti-CD20 and human IFN with a Q124R mutation ("Q-CD20"), fusion of anti-CD8 and human IFN with a Q124R mutation ("Q-CD8"), fusion of anti-Clec9A and human IFN with a Q124R mutation ("Q-Clec9A"), fusion of anti-BcII10 and human IFN with a Q124R mutation ("Q-BcII10," i.e. the untargeted control), and wild type IFN at two doses as indicated. Q124R is a human IFN mutation that is suitable for use in the mouse (i.e. it is a human mutant IFN that functions in mouse). See Nat. Comm. 2014; 5:3016. doi: 10.1038/ncomms4016, the entire contents of which are hereby incorporated by reference.
Figure 12:
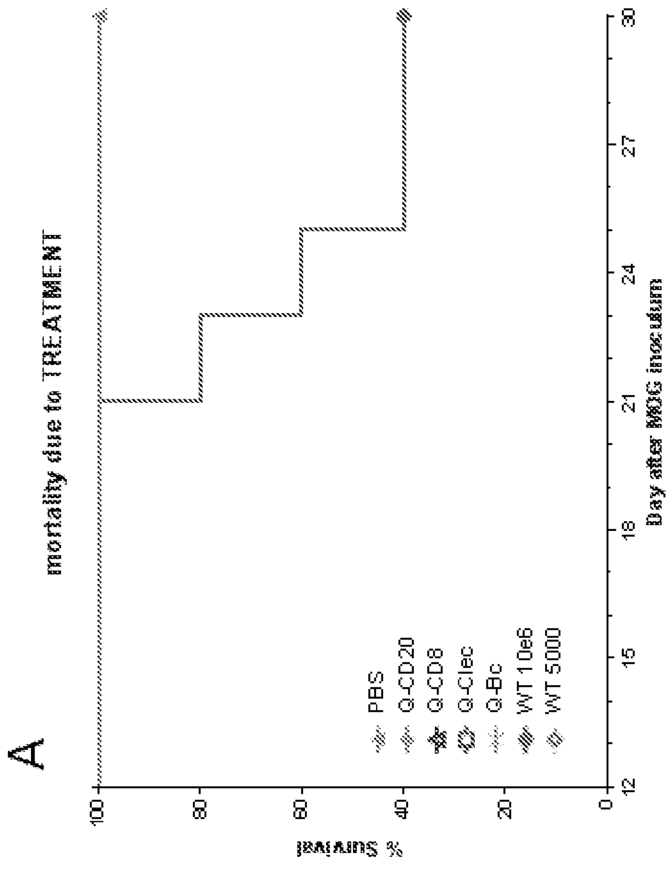
FIG. 12 shows various side effects in the treatments outlined in FIG. 11 above (same histogram order left to right for panels B-F).
Figure 12:
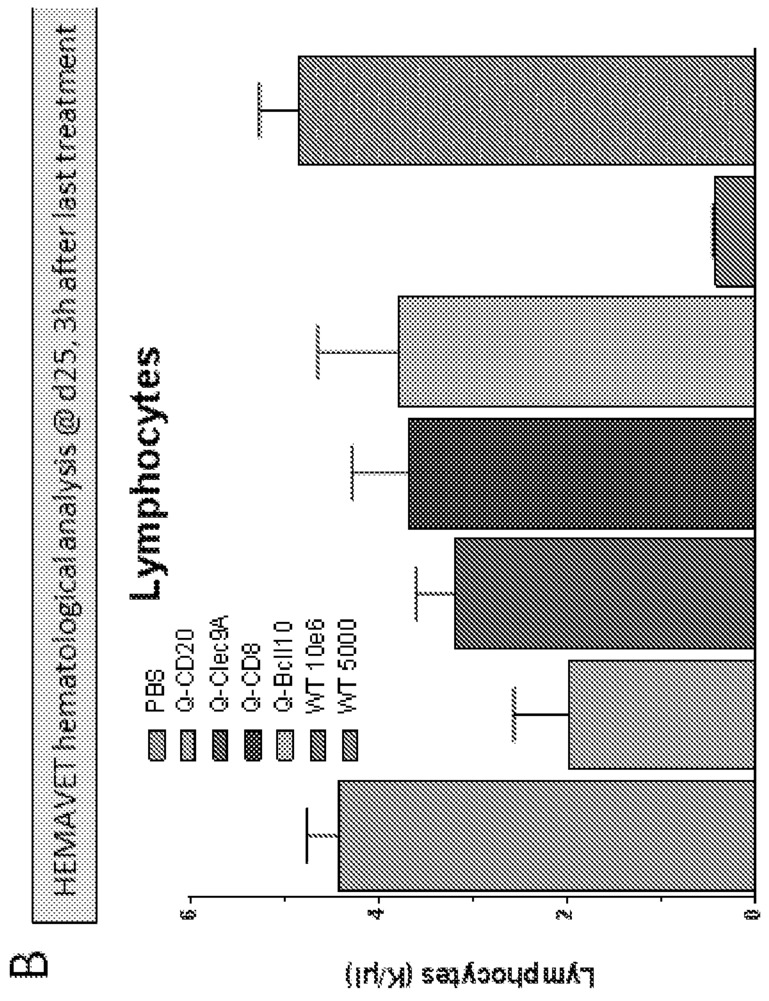
Figure 12:
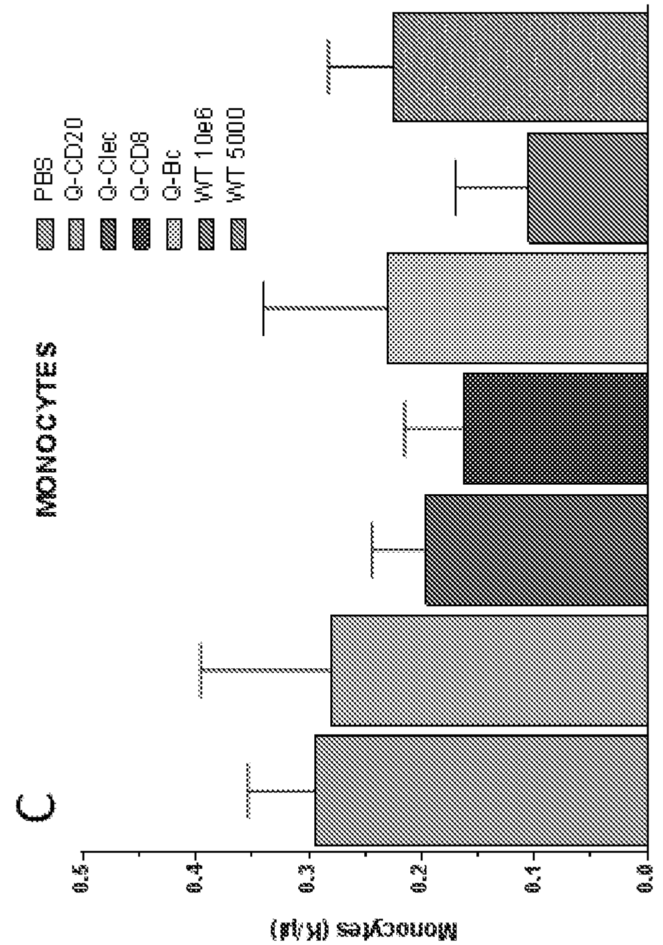
Figure 12:
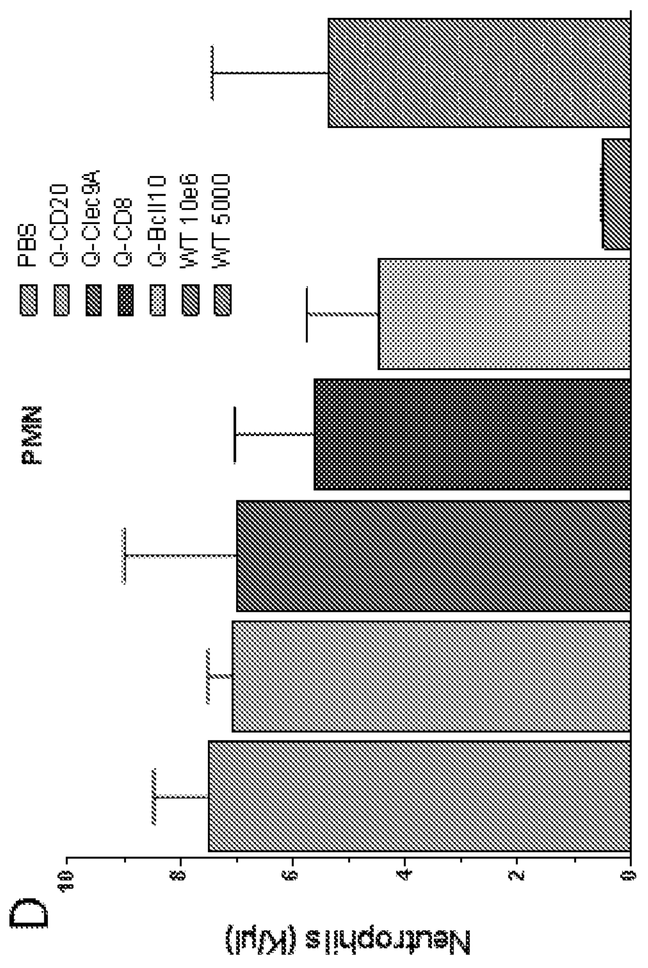
Figure 12:
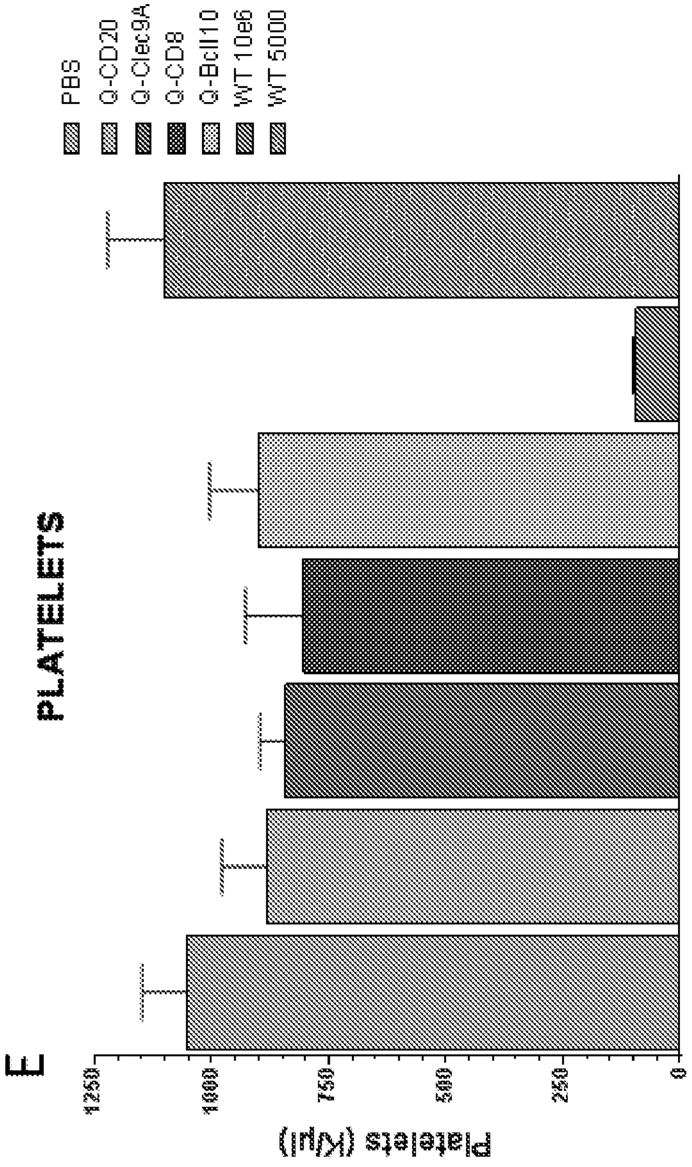
Figure 12:
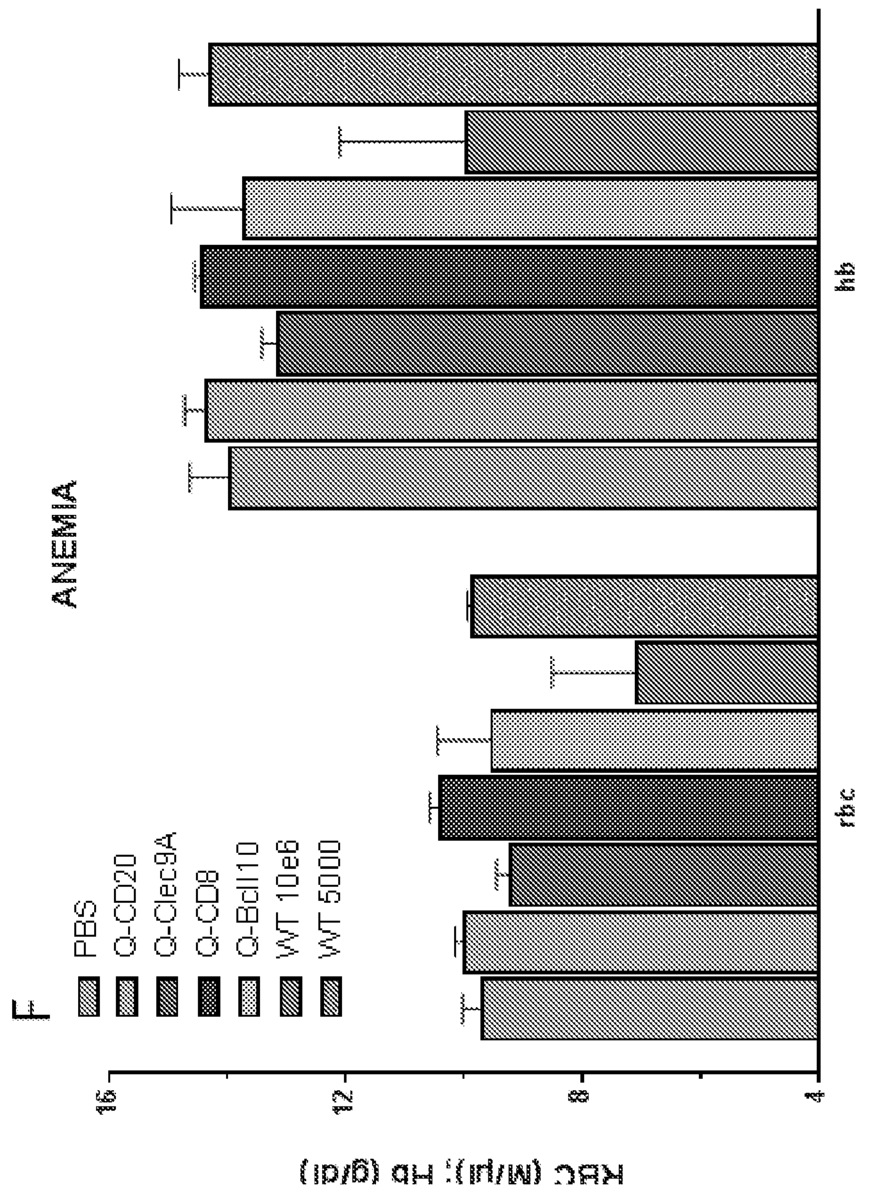

For FIGS. 10-12: various AcTaferons were used. In this context, these refer to attenuated interferon, i.e. hIFN Q124R ("Q") which was linked to various targeting domains that included VHHs against BcII10, mCD20, CD8, or Clec9A at 5000 IU. For comparison, wild type interferon was used ("WT mIFN" at either 5000 IU or 1,000,000 IU as noted. PBS buffer is a mock control (i.e. negative).

The treatment schedule for this study was as follows:

d0=sc injection MOG+CFA/mtb, +ip PT d2=ip PT d7=start daily treatments ip, and clinical scoring was as follows:

| | |
|---|---|
| 0-1 | varying degrees of less horizontal tail if mouse held by the neck |
| 1.5 | limp tail (totally vertical) but with still a tiny bit tension in it |
| 2 | totally limp tail |
| 2.5 | +hind paws closed (toes no longer spread open) |
| 3 | +waddled walk (but still using both hind paws) |
| 3.5 | one hind paw no longer used when walking |
| 4 | both hind paws . . . |
| 4.5 | +no longer able to turn if put on the back |
| 5 | moribund |
| 6 | dead. |

In FIG. 10, Panel A, male C57Bl/6J mice (8 wks old) were immunized s.c. with 2×100 p1 of an emulsion of myelin-specific peptide (Mouse Oligodendrocyte Glycoprotein amino acids 35-55 MEVGWYRSPFSRWHLYRNGK, (SEQ ID NO:296), 1 mg/ml) and Complete Freund's Adjuvant (5 mg/ml) at day 0, followed by an i.p. injection of 50 ng pertussis toxin. At day 2, a second pertussis toxin dose was inoculated i.p. Starting at day 7, mice were treated daily (i.p.) with 5000 IU of AcTaferon linked to a VHH binding to either BcII10 (i.e. an irrelevant target, thus the untargeted control), mCD8, mCD20 or mClec9A (n=5, except for mCD8-targeted AcTaferon, where n=4). As positive controls, untargeted wild type mIFN (linked to the BcII10 VHH) was injected either at 5,000 IU or 1,000,000 IU. Control mice received PBS treatments. Mice were scored daily for progressive paresis and paralysis. Scores between 0 and 2 were given for varying degrees of decreased tail tone, score 2 for a completely paralyzed tail; score 3 for hind limb weakness and starting paraplegia; score 4 for full paraplegia; score 5 for quadriplegia (at which stage the mice should be euthanized) and score 6 if the mouse died. Of note, if mice suddenly died with a score of less than 1, their death was attributed to toxicity of the treatment. These mice were not included for calculation of the mean clinical score (this was only the case for mice treated with high-dose wild type IFN). FIG. 10, Panel B, shows body weight change. Body weights were also measured daily. Mean weight was calculated including that of mice that died.

FIG. 11 shows the mean (±S.E.M.) cumulative clinical scores of days 10 to 28 after treatment. First signs of paralysis were visible from day 13 on (n=5, n=4 for mCD8-targeted AcTaferon). FIG. 12 shows an evaluation of the toxic side effects of daily treatments with the various AcTaferons. Shown are mortality during the course of the experiment (panel A) and leukocyte counts at day 25. Specifically, EDTA-treated blood was collected from the tail vein of mice 3 hours after the last treatment, and lymphocytes (panel B), monocytes (panel C), neutrophils (panel D), platelets (panel E) and red blood cells (panel F) were counted using a HEMAVET950FS hematological analyzer (Drew Scientific). Plotted are means±S.E.M. (n=5, n=4 for mCD8-targeted AcTaferon, n=2 for wild type mIFN 1.000.000 IU).

Example 8. Dendritic Cell Signaling Induced by Anti-human Clec9A VHH Chimeras

A dendritic cell pSTAT signaling assay was undertaken. Chimeras studied were anti-human Clec9A VHH//human IFN R149A and anti-human Clec9A VHH/human IFN R33A/E120R. Two doses of the agents were studied: 100 ng/ml and 500 ng/ml.

The anti-human Clec9A VHH used in this Example was R2CHCL24 (SEQ ID NO:63).

Briefly, human PBMCs were isolated from blood obtained from healthy donors. Approximately 120 ml of blood was collected from each donor using heparin coated tubes (12 tubes). The blood was kept at room temperature and processed immediately Briefly, blood was diluted 1:1 with DPBS and 25 ml was gently layered onto 15 ml of Lympholyte H. After centrifugation, the mononuclear cell rings were collected and cells were washed three times with DPBS (PBS Dulbecco's Phosphate Buffered Saline, Wisent, catalog #311-425-LL) and counted. Dendritic cells were enriched from the PBMC population using "DC-enrichment kit" containing a combination of lineage specific monoclonal antibodies in PBS and a suspension of magnetic particles (STEMCELL Technologies Catalogue number 19251), according to manufacturer's instructions.

Dendritic cells (DC) were stimulated for 15 minutes in the presence or absence of test items and controls (PBS) and the level of phosphorylated-STAT1 (pSTAT1, specifically pY701-STAT1) was determined in isolated DC cell populations (Lin-(CD14/CD16/CD20/CD56/CD3)/HLA-DR+) by flow cytometry. Post stimulation, cells were fixed (BD Cytofix fixation buffer, BD Bioscience, catalog #554655), then permeabilized with Perm buffer II (BD PhosFlow Perm Buffer, BD Bioscience, catalog #558052). Cells were then stained for phosphoSTAT1 and for DC surface markers (Lin-/HLA-DR+) (see table below). Both intra-cellular and surface staining were performed at the same time. Flow cytometry and data acquisition was performed after cell washing with DPBS.

Table showing list of antibodies for flow cytometry staining

| Marker/Product Name | Fluorochrome | Clone | Purpose | Supplier-Catalog Number |
|---|---|---|---|---|
| pSTAT1 | AlexaFluor647 | 4a | phospho-STAT1 | BD-562070 |
| Anti-human CD3 | PE | UC HT1 | T cells marker Lineage depletion | BD-561809 |
| Anti-human CD14 | PE | M5 E2 | Monocytes markers Lineage depletion | BD-555398 |
| anti-human CD16 | PE | 873.1 | NK, Neutrophils, Monocytes marker Lineage depletion | BD-561313 |
| anti-human CD19 | PE | HIB19 | B cells marker Lineage depletion | BD-555413 |
| anti-human CD56 | PE | B159 | NK cells marker Lineage depletion | BD-555516 |
| Anti-human HLA-DR | FITC | TU 36 | MHC II marker DC discrimination | BD-555560 |
| Anti-human CD11c | BV421 | B-Ly6 | DC discrimination | BD-562561 |
| LIVE/DEAD Fixable Aqua Dead Cell Stain | Aqua | N/Ap | Viability dye | ThermoFisher-L34957 |
| Normal mouse IgG | N/Ap | N/Ap | Fc receptor blocker Blocking agent | ThermoFisher-10400C |

Figure 13:
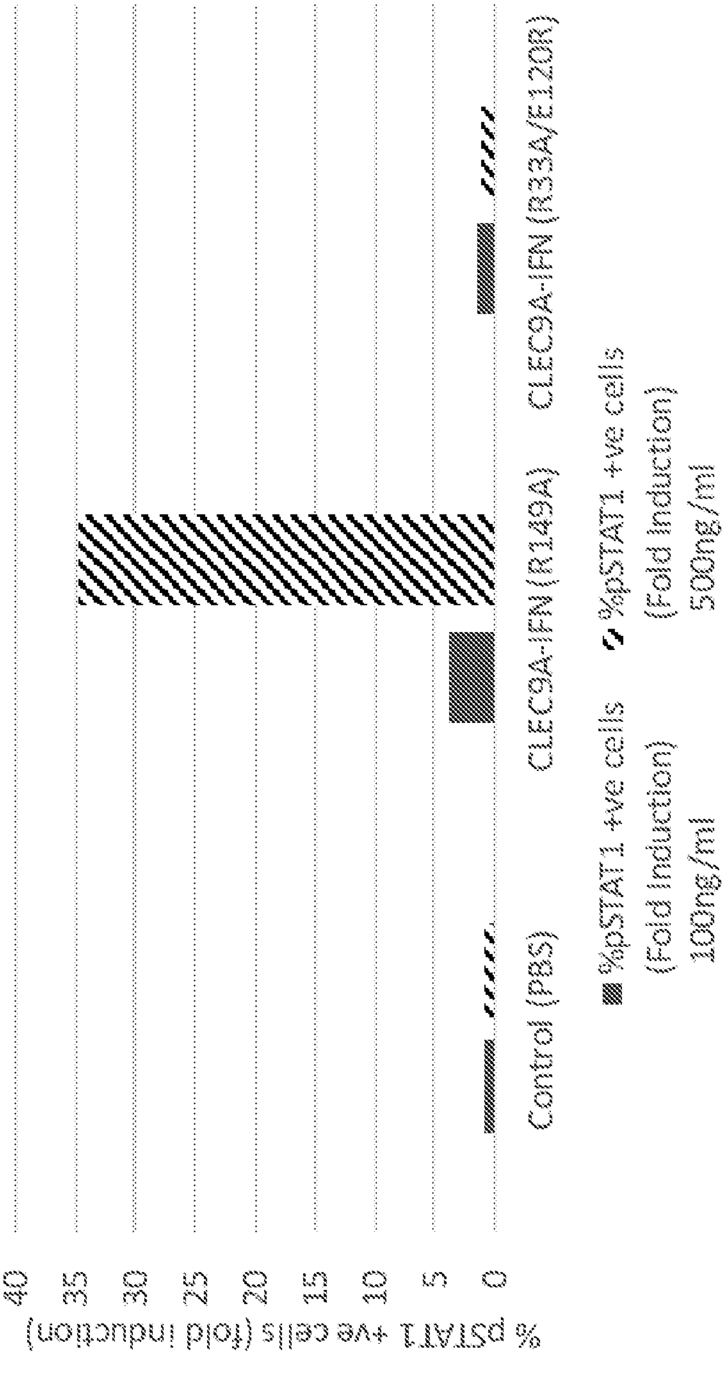
FIG. 13 shows a human dendritic cell pSTAT1 signaling assay. Chimeras studied were anti-human Clec9A VHH/human IFN R149A and anti-human Clec9A VHH/human IFN R33A/E120R. Two doses of the agents were studied: 100 ng/ml and 500 ng/ml. PBS was the control and the data are expressed as a fold change of the percentage of $pSTAT1^+$ dendritic cells (data is an average of a triplicate data set).

FIG. 13 shows the data, expressed as a fold change of the percentage of $pSTAT^{+}$ dendritic cells.

This study clearly shows that a human CLEC9A antigen-targeting construct comprising an IFN signaling agent whose activity is recoverable upon cell targeting (IFN R149A) promotes IFN signaling in human dendritic cells (as determined by pSTAT1 induction). In contrast, no IFN signaling activation is observed with a CLEC9A-targeting construct that incorporates an IFN signaling agent whose activity is not recoverable (IFN R33A/E120R). Thus, as observed for comparable IFN fusion constructs targeting mouse CLEC9A, targeting IFN to human dendritic cells using a targeting moiety directed at human CLEC9A antigen results in triggering of a pronounced IFN signal transduction.

Example 9. Modeled Human Anti-Tumor Effects

The Anti-Human Clec9A VHH Used in this Example was R2CHCL24 (SEQ ID NO:63).

Selection of Human Cord Blood

Stem cells were HLA-type matched with the expression of HLA-A2 by the tumor cells used during the experiments. To that end, only HLA-A2 positive cord bloods were selected to proceed with CD34 stem cell purification. Cells were stained with HLA-A2-FITC (BD Pharmingen) or HLA-ABC-PE (BD Pharmingen), the latter as a positive control. Samples were acquired on an Attune Nxt Acoustic Focusing Cytometer (Life Technologies).

Purification of $CD34^{+}$ Stem Cells from Human Cord Blood

Viable mononuclear cells from human cord bloods were isolated using Fycoll (Lymphoprep, Stemcell technologies) gradient separation prior to $CD34^{+}$ MACS isolation using a direct $CD34^{+}$ progenitor cell isolation kit (Miltenyi). Flow cytometric staining using human CD3-PE (BD Phamringen)/human-CD34-APC (BD Pharmingen) was used to evaluate purity of the isolated stem cells. Samples were acquired on an Attune Nxt Acoustic Focusing Cytometer (Life Technologies). Purity of injected cells reached 95-98%.

Generation of Humanized Mice

Newborn NSG mice (1-2 days of age) were sublethally irradiated with 100 cGy prior to intrahepatic delivery of $10^{5}$ $CD34^{+}$ human stem cells. At 6 weeks after cell transfer, peripheral blood was analyzed for the presence of both human and mouse CD45 (both BD) cells to analyze the effect of engraftment. Samples where acquired on a LSR flow cytometer (BD) and analyzed by FACS Diva software (BD).

The antitumor potential of chimeras was assessed in tumor-bearing humanized mice models. Newborn NSG mice (1-2 days of age) were sublethally irradiated with 100 cGy prior to intrahepatic delivery of $10^5$ $CD34^+$ human stem cells (from HLA-A2 positive cord bloods). At week 13 after stem cell transfer mice were s.c. inoculated with $2.5\times10^6$ human RL follicular lymphoma cells. Mice were treated i.p. daily starting at day 6 after tumor inoculation with 30 µl of Flt3L protein. Daily perilesional chimera delivery (30 µg) was started at day 10 after tumor inoculation, when a palpable tumor was reached. Treatment with the anti-human Clec9a VHH/anti-human PD-L1 VHH/human IFN-R149A bi-specific chimera resulted in stabilization of the tumor growth, which was even more pronounced when combined with Flt3L injections in contrast to injection of PBS. The graph shows tumor growth as mean±SEM.

Figure 14:
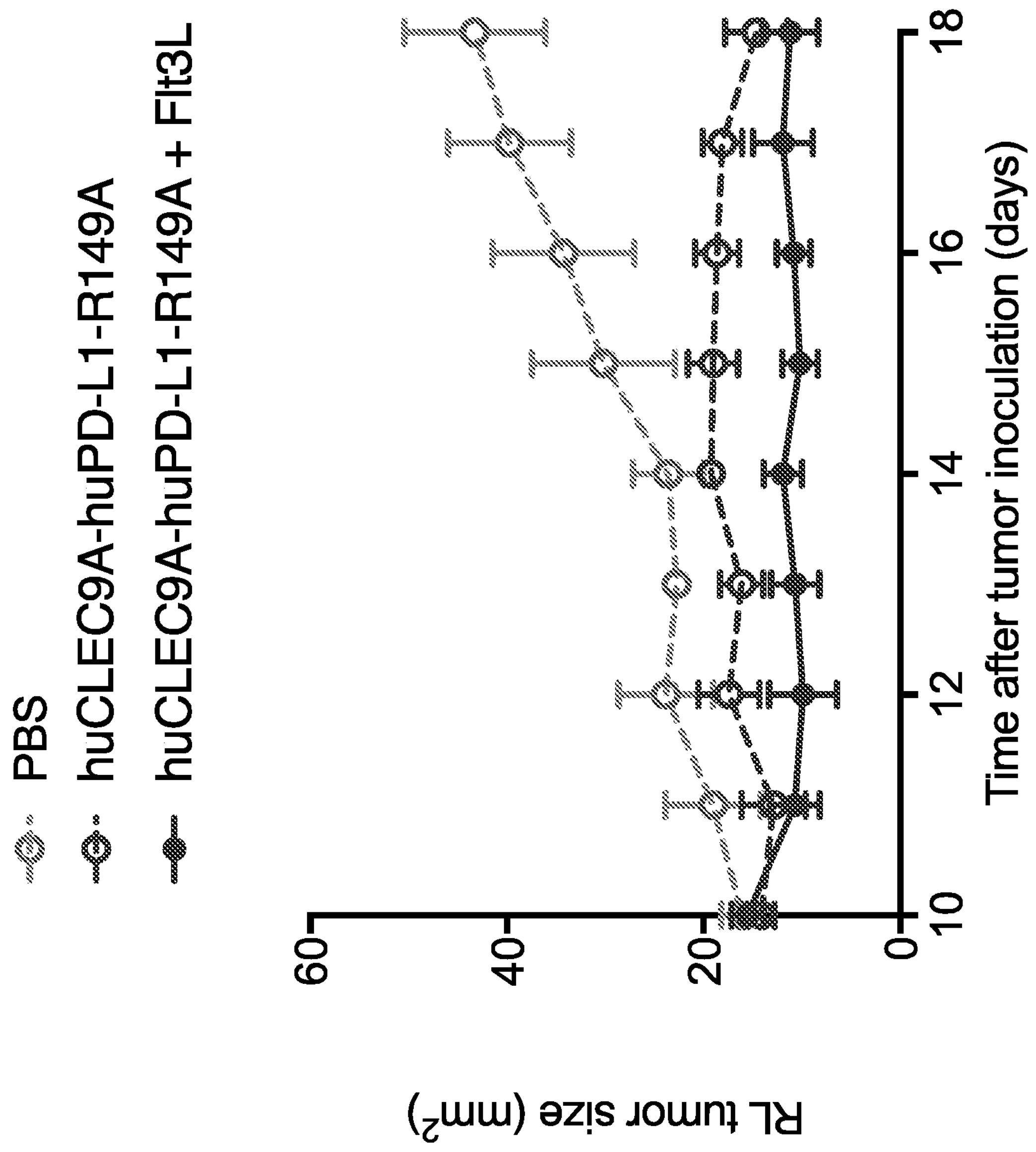
FIG. 14 shows anti-human Clec9a VHH/anti-human PD-L1 VHH/human IFN-R149A bi-specific chimera anti-tumor effects on a human tumor (RL) grown in humanized mice. With reference to day 18 on the X axis, the constructs studied were, from top to bottom: PBS (control); anti-human Clec9a VHH/anti-human PD-L1 VHH/human IFN-R149A bi-specific chimera; and anti-human Clec9a VHH/anti-human PD-L1 VHH/human IFN-R149A bi-specific chimera plus FMS-like tyrosine kinase 3 ligand (FLT3L).

Accordingly, the anti-human Clec9a VHH/anti-human PD-L1 VHH/human IFN-R149A bi-specific chimera showed clear antitumor effects on a human tumor (RL) grown in humanized mice (mice with a reconstituted human immune system). See FIG. 14.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

The following are hereby incorporated by reference in their entireties:

Hart D N (1997) Dendritic cells: unique leukocyte populations which control the primary immune response. *Blood* 90: 3245-3287

Banchereau J and Steinman R M (1998) Dendritic cells and the control of immunity. *Nature* 392: 245-252

Bell D, Young J W and Banchereau J (1999) Dendritic cells. *Advances in Immunology* 72: 255-324

Shortman K and Liu Y J (2002) Mouse and human dendritic cell subtypes. *Nature Reviews Immunology* 2: 151-161

Poulin L F, Salio M, Griessinger E, Anjos-Afonso F, Craciun L, Chen J L, Keller A M, Joffre O, Zelenay S, Nye E, Le Moine A, Faure F, Donckier V, Sancho D, Cerundolo V, Bonnet D and Reis e Sousa C (2010) Characterization of human DNGR-1+BDCA3+ leukocytes as putative equivalents of mouse CD8alpha+ dendritic cells. *The Journal of Experimental Medicine* 207: 1261-1271

Shortman K and Heath W R (2010) The CD8+ dendritic cell subset. *Immunological Reviews* 234: 18-31

Den Haan J M, Lehar S M and Bevan M J (2000) CD8(+) but not CD8(−) dendritic cells cross-prime cytotoxic T cells in vivo. *Journal of Experimental Medicine* 192: 1685-1696

Heath W R, Belz G T, Behrens G M, Smith C M, Forehan S P, Parish I A, Davey G M, Wilson N S, Carbone F R and Villadangos J A (2004) Cross-presentation, dendritic cell subsets, and the generation of immunity to cellular antigens. *Immunological Reviews* 199: 9-26

Dallal R M and Lotze M T (2000) The dendritic cell and human cancer vaccines. *Current Opinion in Immunology* 12: 583-588

Steinman R M and Dhodapkar M (2001) Active immunization against cancer with dendritic cells: the near future. *International Journal of Cancer* 94: 459-473

Hsu F J, Benike C, Fagnoni F, Liles T M, Czerwinski D, Taidi B, Engleman E G and Levy R (1996) Vaccination of patients with B-cell lymphoma using autologous antigen-pulsed dendritic cells. *Nature Medicine* 2: 52-58

Radford K J and Caminschi I (2013) New generation of dendritic cell vaccines. *Human Vaccines & Immunotherapeutics* 9: 259-264

Bozzacco L, Trumpfheller C, Siegal F P, Mehandru S, Markowitz M, Carrington M, Nussenzweig M C, Pipemo A G and Steinman R M (2007) DEC-205 receptor on dendritic cells mediates presentation of HIV gag protein to CD8+ T cells in a spectrum of human MHC I haplotypes. *Proceedings of the National Academy of Sciences of the United States of America* 104: 1289-1294

Birkholz K, Schwenkert M, Kellner C, Gross S, Fey G, Schuler-Thurner B, Schuler G, Schaft N and Dorrie J (2010) Targeting of DEC-205 on human dendritic cells results in efficient MHC class II-restricted antigen presentation. *Blood* 116: 2277-2285

Flynn B J, Kastenmuller K, Wille-Reece U, Tomaras G D, Alam M, Lindsay R W, Salazar A M, Perdiguero B, Gomez C E, Wagner R, Esteban M, Park C G, Trumpfheller C, Keler T, Pantaleo G, Steinman R M and Seder R (2011) Immunization with HIV Gag targeted to dendritic cells followed by recombinant New York vaccinia virus induces robust T-cell immunity in nonhuman primates. *Proceedings of the National Academy of Sciences of the United States of America* 108: 7131-7136

Idoyaga J, Lubkin A, Fiorese C, Lahoud M H, Caminschi I, Huang Y, Rodriguez A, Clausen B E, Park C G, Trumpfheller C and Steinman R M (2011) Comparable T helper 1 (Th1) and CD8 T-cell immunity by targeting HIV gag p24 to CD8 dendritic cells within antibodies to Langerin, DEC205, and Clec9A. *Proceedings of the National Academy of Sciences of the United States of America* 108: 2384-2389

Sancho D, Joffre O P, Keller A M, Rogers N C, Martinez D, Hernanz-Falcon P, Rosewell I and Reis e Sousa C (2009)

Identification of a dendritic cell receptor that couples sensing of necrosis to immunity. *Nature* 458: 899-903

Caminschi I, Proietto A I, Ahmet F, Kitsoulis S, Shin Teh J, Lo J C, Rizzitelli A, Wu L, Vremec D, van Dommelen S L, Campbell I K, Maraskovsky E, Braley H, Davey G M, Mottram P, van de Velde N, Jensen K, Lew A M, Wright M D, Heath W R, Shortman K and Lahoud M H (2008) The dendritic cell subtype-restricted C-type lectin Clec9A is a target for vaccine enhancement. *Blood* 112: 3264-3273

Sancho D, Mourao-Sa D, Joffre O P, Schulz O, Rogers N C, Pennington D J, Carlyle J R and Reis e Sousa C (2008) Tumor therapy in mice via antigen targeting to a novel, D C-restricted C-type lectin. *Journal of Clinical Investigation* 118: 2098-2110

Lahoud M H, Ahmet F, Kitsoulis S, Wan S S, Vremec D, Lee C N, Phipson B, Shi W, Smyth G K, Lew A M, Kato Y, Mueller S N, Davey G M, Heath W R, Shortman K and Caminschi I (2011) Targeting antigen to mouse dendritic cells via Clec9A induces potent CD4 T cell responses biased toward a follicular helper phenotype. *Journal of Immunology* 187: 842-850

Schreibelt G, Klinkenberg L J, Cruz L J, Tacken P J, Tel J, Kreutz M, Adema G J, Brown G D, Figdor C G and de Vries I J (2012) The C-type lectin receptor CLEC9A mediates antigen uptake and (cross-)presentation by human blood BDCA3+ myeloid dendritic cells. *Blood* 119: 2284-2292

Wesolowski J, Alzogaray V, Reyelt J, Unger M, Juarez K, Urrutia M, Cauerhff A, Danquah W, Rissiek B, Scheuplein F, Schwarz N, Adriouch S, Boyer O, Seman M, Licea A, Serreze D V, Goldbaum F A, Haag F and Koch-Nolte F (2009) Single domain antibodies: promising experimental and therapeutic tools in infection and immunity. *Medical Microbiology and Immunology* 198: 157-174

Harmsen M M and De Haard H J (2007) Properties, production, and applications of camelid single-domain antibody fragments. *Applied Microbiology and Biotechnology* 77: 13-22

Dolk E, van Vliet C, Perez J M, Vriend G, Darbon H, Ferrat G, Cambillau C, Frenken L G and Verrips T (2005) Induced refolding of a temperature denatured llama heavy-chain antibody fragment by its antigen. *Proteins* 59: 555-564

Muyldermans S (2013) Nanobodies: natural single-domain antibodies. *Annual Review of Biochemistry* 82: 775-797

Lesterhuis W J, Aarntzen E H, De Vries I J, Schuurhuis D H, Figdor C G, Adema G J and Punt C J (2008) Dendritic cell vaccines in melanoma: from promise to proof? *Critical Reviews in Oncology/Hematology* 66: 118-134

Vulink A, Radford K J, Melief C and Hart D N (2008) Dendritic cells in cancer immunotherapy. *Advances in Cancer Research* 99: 363-407

Luft T, Pang K C, Thomas E, Hertzog P, Hart D N, Trapani J and Cebon J (1998) Type I IFNs enhance the terminal differentiation of dendritic cells. *Journal of Immunology* 161: 1947-1953

Paquette R L, Hsu N C, Kiertscher S M, Park A N, Tran L, Roth M D and Glaspy J A (1998) Interferon-alpha and granulocyte-macrophage colony-stimulating factor differentiate peripheral blood monocytes into potent antigen-presenting cells. *Journal of Leukocyte Biology* 64: 358-367

Radvanyi L G, Banerjee A, Weir M and Messner H (1999) Low levels of interferon-alpha induce CD86 (B7.2) expression and accelerates dendritic cell maturation from human peripheral blood mononuclear cells. *Scandinavian Journal of Immunology* 50: 499-509

What is claimed is:

1. A composition comprising a targeting moiety that comprises a recognition domain that recognizes and binds to C-type lectin domain family 9 member A (Clec9A), wherein the targeting moiety comprises three complementarity determining regions (CDR1, CDR2, and CDR3) wherein:

(a) CDR1 comprises an amino acid sequence selected from any one of SEQ ID NOs: 2-21, and GSSDSINAMG (SEQ ID NO: 324);

(b) CDR2 comprises an amino acid sequence selected from any one of SEQ ID NOs: 22-43; and (c) CDR3 comprises an amino acid sequence selected from any one of SEQ ID NOs: 44-58, LGR, and VIK.

2. The composition of claim 1, wherein:

(i) CDR1 comprises the amino acid sequence of SEQ ID NO: 2; CDR2 comprises the amino acid sequence of SEQ ID NO: 22; CDR3 comprises the amino acid sequence of SEQ ID NO: 44;

(ii) CDR1 comprises the amino acid sequence of SEQ ID NO: 3; CDR2 comprises the amino acid sequence of SEQ ID NO: 23; CDR3 comprises the amino acid sequence of SEQ ID NO: 45;

(iii) CDR1 comprises the amino acid sequence of SEQ ID NO: 2; CDR2 comprises the amino acid sequence of SEQ ID NO: 25; CDR3 comprises the amino acid sequence of SEQ ID NO: 46;

(iv) CDR1 comprises the amino acid sequence of GSSDSINAMG (SEQ ID NO: 324); CDR2 comprises the amino acid sequence of SEQ ID NO: 26; CDR3 comprises the amino acid sequence of SEQ ID NO: 47;

(v) CDR1 comprises the amino acid sequence of SEQ ID NO: 8; CDR2 comprises the amino acid sequence of SEQ ID NO: 29; CDR3 comprises the amino acid sequence of SEQ ID NO: 50; or (vi) CDR1 comprises the amino acid sequence of SEQ ID NO: 14; CDR2 comprises the amino acid sequence of SEQ ID NO: 35; CDR3 comprises the amino acid sequence of SEQ ID NO: 57.

3. The composition of claim 1, wherein the targeting moiety comprises an amino acid sequence having at least 95% identity with a sequence selected from SEQ ID NOs: 59, 60, 62, 63, 66, and 75.

4. The composition of claim 3, wherein the targeting moiety comprises an amino acid sequence having at least 95% identity with SEQ ID NO: 60.

5. The composition of claim 1, wherein the targeting moiety is a full-length antibody, a single-domain antibody, a recombinant heavy-chain-only antibody (VHH), a single-chain antibody (scFv), a shark heavy-chain-only antibody (VNAR), a microprotein, a darpin, an anticalin, an adnectin, a Fv, a Fab, a Fab', or a $F(ab')_2$.

6. The composition of claim 5, wherein the targeting moiety comprises a VHH.

7. The composition of claim 2, wherein the targeting moiety is a full-length antibody, a single-domain antibody, a recombinant heavy-chain-only antibody (VHH), a single-chain antibody (scFv), a shark heavy-chain-only antibody (VNAR), a microprotein, a darpin, an anticalin, an adnectin, a Fv, a Fab, a Fab', or a $F(ab')_2$.

8. The composition of claim 2, wherein the targeting moiety comprises a VHH.

9. A pharmaceutical composition comprising the targeting moiety of claim 1 and pharmaceutically acceptable carrier.

10. A recombinant nucleic acid composition encoding the targeting moiety of claim 1.

11. An isolated host cell comprising a nucleic acid of claim 10.

* * * * *